(12) United States Patent
Stuible et al.

(10) Patent No.: US 9,493,562 B2
(45) Date of Patent: Nov. 15, 2016

(54) ANTI-SIGLEC-15 ANTIBODIES

(71) Applicant: ALETHIA BIOTHERAPEUTICS INC., Montréal (CA)

(72) Inventors: Matthew Stuible, Mont-Royal (CA); Gilles Bernard Tremblay, La Prairie (CA); Traian Sulea, Kirkland (CA); Anna N. Moraitis, Laval (CA); Mario Filion, Longueuil (CA)

(73) Assignee: Alethia Biotherapeutics Inc., Montreal (CA)

( * ) Notice: Subject to any disclaimer, the term of this patent is extended or adjusted under 35 U.S.C. 154(b) by 23 days.

(21) Appl. No.: 14/406,560

(22) PCT Filed: Jul. 17, 2013

(86) PCT No.: PCT/CA2013/000646
§ 371 (c)(1),
(2) Date: Dec. 9, 2014

(87) PCT Pub. No.: WO2014/012165
PCT Pub. Date: Jan. 23, 2014

(65) Prior Publication Data
US 2015/0139982 A1     May 21, 2015

Related U.S. Application Data

(60) Provisional application No. 61/673,442, filed on Jul. 19, 2012, provisional application No. 61/777,049, filed on Mar. 12, 2013, provisional application No. 61/810,415, filed on Apr. 10, 2013.

(51) Int. Cl.
| | |
|---|---|
| *A61K 39/00* | (2006.01) |
| *A61K 39/395* | (2006.01) |
| *C07K 16/00* | (2006.01) |
| *C07K 16/18* | (2006.01) |
| *C07K 16/22* | (2006.01) |
| *C07K 16/28* | (2006.01) |
| *A61K 47/48* | (2006.01) |

(52) U.S. Cl.
CPC ..... *C07K 16/2803* (2013.01); *A61K 47/48384* (2013.01); *A61K 47/48561* (2013.01); *A61K 2039/505* (2013.01); *C07K 2317/24* (2013.01); *C07K 2317/52* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,712,127 A | 1/1998 | Malek et al. | |
| 6,057,098 A | 5/2000 | Buechler et al. | |
| 6,451,555 B1 | 9/2002 | Duffy | |
| 6,498,024 B1 | 12/2002 | Malek et al. | |
| 6,617,434 B1 | 9/2003 | Duffy | |
| 7,357,929 B2 | 4/2008 | Carmeliet et al. | |
| 7,402,664 B2 | 7/2008 | Wolfgang et al. | |
| 7,407,940 B2 | 8/2008 | Falla et al. | |
| 7,411,051 B2 | 8/2008 | Rosen et al. | |
| 7,417,112 B2 | 8/2008 | Rathore et al. | |
| 7,425,612 B2 | 9/2008 | Nakamura et al. | |
| 7,432,065 B2 | 10/2008 | Lu et al. | |
| 7,449,320 B2 | 11/2008 | Miller et al. | |
| 7,459,539 B2 | 12/2008 | Challita-Eid et al. | |
| 7,485,327 B2 | 2/2009 | Kim et al. | |
| 7,488,590 B2 | 2/2009 | Feige et al. | |
| 7,501,391 B2 | 3/2009 | Khan et al. | |
| 7,501,557 B1 | 3/2009 | Wagner et al. | |
| 7,510,840 B1 | 3/2009 | Challita-Eid et al. | |
| 7,514,224 B2 | 4/2009 | Lu et al. | |
| 7,514,407 B2 | 4/2009 | Averback | |
| 7,517,529 B2 | 4/2009 | Khan et al. | |
| 7,524,513 B2 | 4/2009 | Hai-Quan et al. | |
| 7,528,232 B2 | 5/2009 | Wagner et al. | |
| 7,528,242 B2 | 5/2009 | Anderson et al. | |
| 7,534,579 B2 | 5/2009 | Glucksmann et al. | |
| 7,541,450 B2 | 6/2009 | Liu et al. | |
| 7,547,512 B2 | 6/2009 | Peiris et al. | |
| 7,560,433 B2 | 7/2009 | Khan et al. | |
| 7,566,685 B2 | 7/2009 | Kinsella | |
| 7,569,547 B2 | 8/2009 | Lindberg et al. | |
| 7,572,894 B2 | 8/2009 | Jin et al. | |
| 7,575,876 B2 | 8/2009 | Zhang | |
| 7,585,839 B2 | 9/2009 | Larsen et al. | |

(Continued)

FOREIGN PATENT DOCUMENTS

| | | |
|---|---|---|
| CA | 2439129 A1 | 8/2002 |
| CA | 2698326 A1 | 4/2009 |

(Continued)

OTHER PUBLICATIONS

Wells, 1990, Biochemistry 29:8509-8517.*

(Continued)

*Primary Examiner* — Elizabeth C Kemmerer

(74) *Attorney, Agent, or Firm* — Fangli Chen; Janique Forget

(57) ABSTRACT

Antibodies and antigen binding fragments that specifically binds to Siglec-15 are described herein. These antibodies or antigen binding fragments may have the ability of inhibiting differentiation of osteoclasts and/or the ability of inhibiting the bone resorption activity of osteoclasts. Compositions and cells expressing anti-Siglec-15 antibodies or antigen binding fragments are also disclosed herewith. Anti-Siglec-15 antibodies may also be useful for the treatment of bone loss, or bone diseases. Methods for the detection or diagnosis of bone loss or bone-related diseases are also described.

14 Claims, 24 Drawing Sheets

(56) References Cited

U.S. PATENT DOCUMENTS

| | | | |
|---|---|---|---|
| 7,585,849 B2 | 9/2009 | Liu et al. | |
| 7,585,937 B2 | 9/2009 | Kungl | |
| 7,601,807 B2 | 10/2009 | Kanayama et al. | |
| 7,608,704 B2 | 10/2009 | Yue et al. | |
| 7,625,996 B2 | 12/2009 | Fischer et al. | |
| 7,628,989 B2 | 12/2009 | Jakobovits et al. | |
| 7,635,681 B2 | 12/2009 | Bonny | |
| 7,635,755 B2 | 12/2009 | Kaplan et al. | |
| 7,641,905 B2 | 1/2010 | Jakobovits et al. | |
| 7,662,409 B2 | 2/2010 | Masters | |
| 7,662,776 B2 | 2/2010 | Khan et al. | |
| 7,671,011 B2 | 3/2010 | Shai et al. | |
| 7,691,977 B2 | 4/2010 | Fuh et al. | |
| 7,989,160 B2 | 8/2011 | Sooknanan et al. | |
| 8,147,829 B2 | 4/2012 | Hariharan et al. | |
| 8,168,181 B2 * | 5/2012 | Sooknanan | A61K 31/7088 424/130.1 |
| 8,431,126 B2 | 4/2013 | Sooknanan et al. | |
| 8,540,988 B2 | 9/2013 | Sooknanan et al. | |
| 8,900,579 B2 | 12/2014 | Tremblay et al. | |
| 9,067,984 B2 | 6/2015 | Sooknanan et al. | |
| 2003/0118592 A1 | 6/2003 | Ledbetter et al. | |
| 2003/0133939 A1 | 7/2003 | Ledbetter et al. | |
| 2004/0023313 A1 | 2/2004 | Boyle et al. | |
| 2004/0033535 A1 | 2/2004 | Boyle et al. | |
| 2004/0076992 A1 | 4/2004 | Nakamura et al. | |
| 2004/0082508 A1 | 4/2004 | Yue et al. | |
| 2005/0107588 A1 | 5/2005 | Duggan et al. | |
| 2005/0118625 A1 | 6/2005 | Mounts | |
| 2005/0153333 A1 | 7/2005 | Sooknanan | |
| 2005/0170450 A1 | 8/2005 | Durocher et al. | |
| 2006/0153867 A1 | 7/2006 | Li | |
| 2006/0240516 A1 | 10/2006 | Jalinot et al. | |
| 2008/0070232 A1 | 3/2008 | Durocher | |
| 2008/0171094 A1 | 7/2008 | Benner et al. | |
| 2008/0176243 A1 | 7/2008 | Khan et al. | |
| 2008/0176790 A1 | 7/2008 | DeFrees | |
| 2008/0178308 A1 | 7/2008 | Afar et al. | |
| 2008/0194489 A1 | 8/2008 | Khan et al. | |
| 2008/0199939 A1 | 8/2008 | Havenga et al. | |
| 2008/0206239 A1 | 8/2008 | Jones et al. | |
| 2008/0207502 A1 | 8/2008 | Rastelli et al. | |
| 2008/0207522 A1 | 8/2008 | Hancock et al. | |
| 2008/0213268 A1 | 9/2008 | Watts et al. | |
| 2008/0242618 A1 | 10/2008 | Khan et al. | |
| 2008/0242837 A1 | 10/2008 | Khan et al. | |
| 2008/0242847 A1 | 10/2008 | Liu et al. | |
| 2008/0248527 A1 | 10/2008 | Wolfgang et al. | |
| 2008/0254020 A1 | 10/2008 | Walker et al. | |
| 2008/0261819 A1 | 10/2008 | Lorens et al. | |
| 2008/0274979 A1 | 11/2008 | Ellis-Behnke et al. | |
| 2008/0275547 A1 | 11/2008 | Kanamaru et al. | |
| 2008/0279908 A1 | 11/2008 | Bertozzi et al. | |
| 2008/0286808 A1 | 11/2008 | Schellenberger et al. | |
| 2008/0287309 A1 | 11/2008 | Bowdish et al. | |
| 2008/0299111 A1 | 12/2008 | Delacourte et al. | |
| 2008/0299601 A1 | 12/2008 | Fike et al. | |
| 2008/0306001 A1 | 12/2008 | Liik et al. | |
| 2008/0306009 A1 | 12/2008 | Khan et al. | |
| 2008/0318871 A1 | 12/2008 | Khan et al. | |
| 2009/0004210 A1 | 1/2009 | Mattner et al. | |
| 2009/0005257 A1 | 1/2009 | Jespers et al. | |
| 2009/0005266 A1 | 1/2009 | Ostermeier et al. | |
| 2009/0005541 A1 | 1/2009 | Kungl | |
| 2009/0010983 A1 | 1/2009 | Melvik et al. | |
| 2009/0012032 A1 | 1/2009 | Nakamura et al. | |
| 2009/0017460 A1 | 1/2009 | Anderson et al. | |
| 2009/0019605 A1 | 1/2009 | Takagi et al. | |
| 2009/0023648 A1 | 1/2009 | Stredonsky et al. | |
| 2009/0028813 A1 | 1/2009 | Stedronsky et al. | |
| 2009/0028856 A1 | 1/2009 | Chen et al. | |
| 2009/0041671 A1 | 2/2009 | Young et al. | |
| 2009/0042769 A1 | 2/2009 | Maclean | |
| 2009/0047335 A1 | 2/2009 | Rastelli et al. | |
| 2009/0069259 A1 | 3/2009 | Collingwood | |
| 2009/0075377 A1 | 3/2009 | Lu et al. | |
| 2009/0081178 A1 | 3/2009 | Murray et al. | |
| 2009/0081457 A1 | 3/2009 | Nagarajan et al. | |
| 2009/0082551 A1 | 3/2009 | Zuckerman | |
| 2009/0088387 A1 | 4/2009 | Castillo et al. | |
| 2009/0092582 A1 | 4/2009 | Bogin et al. | |
| 2009/0093408 A1 | 4/2009 | Bridon et al. | |
| 2009/0093621 A1 | 4/2009 | Ferrari et al. | |
| 2009/0099031 A1 | 4/2009 | Stemmer et al. | |
| 2009/0099066 A1 | 4/2009 | Moulton et al. | |
| 2009/0117578 A1 | 5/2009 | Metz et al. | |
| 2009/0123412 A1 | 5/2009 | Healy et al. | |
| 2009/0130111 A1 | 5/2009 | Wu et al. | |
| 2009/0131265 A1 | 5/2009 | Zhang | |
| 2009/0136595 A1 | 5/2009 | Shah et al. | |
| 2009/0136912 A1 | 5/2009 | Kurokawa et al. | |
| 2009/0142280 A1 | 6/2009 | Zhang et al. | |
| 2009/0142828 A1 | 6/2009 | Bucciarelli et al. | |
| 2009/0142839 A1 | 6/2009 | Primiano | |
| 2009/0143567 A1 | 6/2009 | Rathore et al. | |
| 2009/0149339 A1 | 6/2009 | Lu et al. | |
| 2009/0169520 A1 | 7/2009 | Soreq et al. | |
| 2009/0170191 A1 | 7/2009 | Jakobovits et al. | |
| 2009/0175821 A1 | 7/2009 | Bridon et al. | |
| 2009/0176664 A1 | 7/2009 | Chu | |
| 2009/0180958 A1 | 7/2009 | Koivistoinen et al. | |
| 2009/0197812 A1 | 8/2009 | Kim et al. | |
| 2009/0214570 A1 | 8/2009 | Mrsny et al. | |
| 2009/0214582 A1 | 8/2009 | Dean | |
| 2009/0215667 A1 | 8/2009 | Wagner et al. | |
| 2009/0221505 A1 | 9/2009 | Kolonin et al. | |
| 2009/0226372 A1 | 9/2009 | Ruoslahti et al. | |
| 2009/0226374 A1 | 9/2009 | Hugli | |
| 2009/0226433 A1 | 9/2009 | Grandea, III et al. | |
| 2009/0227505 A1 | 9/2009 | Khan et al. | |
| 2009/0234026 A1 | 9/2009 | Kaplan et al. | |
| 2009/0252728 A1 | 10/2009 | Jakobovits et al. | |
| 2009/0258017 A1 | 10/2009 | Callahan et al. | |
| 2009/0264372 A1 | 10/2009 | Dal Farra et al. | |
| 2009/0270320 A1 | 10/2009 | Panjwani et al. | |
| 2009/0275050 A1 | 11/2009 | Glucksmann et al. | |
| 2009/0275503 A1 | 11/2009 | Shai et al. | |
| 2009/0281038 A1 | 11/2009 | Wagner et al. | |
| 2009/0298707 A1 | 12/2009 | Yarbrough et al. | |
| 2009/0304746 A1 | 12/2009 | Sette et al. | |
| 2009/0317420 A1 | 12/2009 | Telford et al. | |
| 2010/0004172 A1 | 1/2010 | Khan et al. | |
| 2010/0015664 A1 | 1/2010 | Kanayama et al. | |
| 2010/0016215 A1 | 1/2010 | Moulton et al. | |
| 2010/0016220 A1 | 1/2010 | Nakamura et al. | |
| 2010/0016697 A1 | 1/2010 | Spinale et al. | |
| 2010/0029005 A1 | 2/2010 | Kamiie et al. | |
| 2010/0035817 A1 | 2/2010 | Fischer et al. | |
| 2010/0041614 A1 | 2/2010 | Bussolino et al. | |
| 2010/0047163 A1 | 2/2010 | Forte et al. | |
| 2010/0055438 A1 | 3/2010 | Kaplan et al. | |
| 2010/0056457 A1 | 3/2010 | Barbas, III et al. | |
| 2010/0056459 A1 | 3/2010 | Bonny | |
| 2010/0076173 A1 | 3/2010 | Stephanopoulos et al. | |
| 2010/0080814 A1 | 4/2010 | Desjarlais et al. | |
| 2010/0080824 A1 | 4/2010 | Peiris et al. | |
| 2010/0086532 A1 | 4/2010 | Barbas, III et al. | |
| 2010/0104575 A1 * | 4/2010 | Sooknanan | A61K 31/7088 424/139.1 |
| 2010/0209428 A1 | 8/2010 | Hiruma et al. | |
| 2011/0268733 A1 | 11/2011 | Hiruma et al. | |
| 2011/0311526 A1 | 12/2011 | Sooknanan et al. | |
| 2013/0039915 A1 | 2/2013 | Tremblay et al. | |
| 2013/0303598 A1 | 11/2013 | Sooknanan et al. | |
| 2013/0330772 A1 | 12/2013 | Vincent et al. | |
| 2015/0110785 A1 | 4/2015 | Sooknanan et al. | |
| 2015/0139982 A1 | 5/2015 | Stuible et al. | |

FOREIGN PATENT DOCUMENTS

| | | |
|---|---|---|
| CA | 2753702 A1 | 9/2010 |
| CA | 2868959 A1 | 10/2013 |
| EP | 0911342 B2 | 4/1999 |
| EP | 1369479 A1 | 12/2003 |

(56) References Cited

FOREIGN PATENT DOCUMENTS

| | | |
|---|---|---|
| EP | 1544215 A1 | 6/2005 |
| EP | 1580263 A1 | 9/2005 |
| EP | 1715038 A1 | 10/2006 |
| EP | 1751179 A2 | 2/2007 |
| EP | 1874337 A2 | 1/2008 |
| EP | 1931198 A2 | 6/2008 |
| EP | 1934252 B1 | 6/2008 |
| EP | 1950221 A2 | 7/2008 |
| EP | 1953551 A2 | 8/2008 |
| EP | 1963499 A2 | 9/2008 |
| EP | 1970383 A1 | 9/2008 |
| EP | 1996609 A2 | 12/2008 |
| EP | 2002036 A2 | 12/2008 |
| EP | 2021467 A1 | 2/2009 |
| EP | 2032149 A2 | 3/2009 |
| EP | 2041569 A2 | 4/2009 |
| EP | 2046806 A2 | 4/2009 |
| EP | 2053406 A2 | 4/2009 |
| EP | 2057465 A2 | 5/2009 |
| EP | 2097094 A2 | 9/2009 |
| EP | 2105141 A1 | 9/2009 |
| EP | 2129682 A1 | 12/2009 |
| EP | 2130838 A2 | 12/2009 |
| EP | 2140005 B1 | 1/2010 |
| EP | 2168986 A2 | 3/2010 |
| EP | 2170363 A2 | 4/2010 |
| EP | 2206727 B1 | 7/2010 |
| EP | 2377932 A1 | 10/2011 |
| JP | 2003169687 A | 6/2003 |
| JP | 2003210166 | 7/2003 |
| JP | 2003210166 A | 7/2003 |
| JP | 2004107352 | 4/2004 |
| JP | 2004107352 A | 4/2004 |
| JP | 2004189848 | 7/2004 |
| JP | 2004189848 A | 7/2004 |
| JP | 2004533803 | 11/2004 |
| JP | 2004533803 A | 11/2004 |
| JP | 2004339189 | 12/2004 |
| JP | 2004339189 A | 12/2004 |
| JP | 2007020403 | 2/2007 |
| JP | 2007020403 A | 2/2007 |
| JP | 2008500267 | 1/2008 |
| JP | 2008500267 A | 1/2008 |
| JP | 2008504221 | 2/2008 |
| JP | 2008504221 A | 2/2008 |
| JP | 2008094822 | 4/2008 |
| JP | 2008094822 A | 4/2008 |
| JP | 2008111841 | 5/2008 |
| JP | 2008111841 A | 5/2008 |
| JP | 2008263955 | 11/2008 |
| JP | 2008263955 A | 11/2008 |
| JP | 200972081 | 4/2009 |
| JP | 200972081 A | 4/2009 |
| JP | 2009183293 | 8/2009 |
| JP | 2009183293 A | 8/2009 |
| JP | 2009528255 | 8/2009 |
| JP | 2009528255 A | 8/2009 |
| WO | WO-94/11014 A1 | 5/1994 |
| WO | WO-01/83560 A1 | 11/2001 |
| WO | WO-02/20723 A2 | 3/2002 |
| WO | WO-02/20822 A2 | 3/2002 |
| WO | WO-02/38602 A2 | 5/2002 |
| WO | WO-03/048305 A2 | 6/2003 |
| WO | WO-03/080671 A1 | 10/2003 |
| WO | WO-03/104275 A2 | 12/2003 |
| WO | WO-2004/064972 A2 | 8/2004 |
| WO | WO-2005/061546 A1 | 7/2005 |
| WO | WO-2005/078087 A1 | 8/2005 |
| WO | WO-2005/081628 A2 | 9/2005 |
| WO | WO-2006/063462 A1 | 6/2006 |
| WO | WO-2006/113311 A2 | 10/2006 |
| WO | WO-2007/038637 A2 | 4/2007 |
| WO | WO-2007/043059 A1 | 4/2007 |
| WO | WO-2007/062422 A2 | 5/2007 |
| WO | WO-2007/063300 A2 | 6/2007 |
| WO | WO-2007/093042 A1 | 8/2007 |
| WO | WO-2007/100524 A2 | 9/2007 |
| WO | WO-2007/104062 A2 | 9/2007 |
| WO | WO-2007/111952 A2 | 10/2007 |
| WO | WO-2007/128121 A1 | 11/2007 |
| WO | WO-2007/146319 A2 | 12/2007 |
| WO | WO-2008/006028 A2 | 1/2008 |
| WO | WO-2008/024105 A2 | 2/2008 |
| WO | WO-2008/063369 A2 | 5/2008 |
| WO | WO-2008/093982 A1 | 8/2008 |
| WO | WO-2008/101160 A2 | 8/2008 |
| WO | WO-2008/113185 A1 | 9/2008 |
| WO | WO-2008/116468 A2 | 10/2008 |
| WO | WO-2008/134544 A1 | 11/2008 |
| WO | WO-2008/148545 A1 | 12/2008 |
| WO | WO-2009/005793 A2 | 1/2009 |
| WO | WO-2009/008727 A2 | 1/2009 |
| WO | WO-2009/020101 A1 | 2/2009 |
| WO | WO-2009/023125 A1 | 2/2009 |
| WO | WO-2009/031835 A2 | 3/2009 |
| WO | WO-2009/031836 A1 | 3/2009 |
| WO | WO-2009/032158 A2 | 3/2009 |
| WO | WO-2009/038756 A2 | 3/2009 |
| WO | WO-2009/039854 A2 | 4/2009 |
| WO | WO-2009/048072 A1 | 4/2009 |
| WO | WO-2009/050453 A2 | 4/2009 |
| WO | WO-2009/059379 A1 | 5/2009 |
| WO | WO-2009/059972 A2 | 5/2009 |
| WO | WO-2009/061130 A2 | 5/2009 |
| WO | WO-2009/061890 A1 | 5/2009 |
| WO | WO-2009/090651 A2 | 7/2009 |
| WO | WO-2009/106715 A2 | 9/2009 |
| WO | WO-2009/108261 A2 | 9/2009 |
| WO | WO-2009/112645 A1 | 9/2009 |
| WO | WO-2009/132876 A1 | 11/2009 |
| WO | WO-2009/139599 A2 | 11/2009 |
| WO | WO-2009/146179 A1 | 12/2009 |
| WO | WO-2010/000794 A1 | 1/2010 |
| WO | WO-2010/033736 A1 | 3/2010 |
| WO | WO-2010/035504 A1 | 4/2010 |
| WO | WO-2010/037395 A2 | 4/2010 |
| WO | WO-2011/041894 A1 | 4/2011 |
| WO | WO-2012/045481 A2 | 4/2012 |
| WO | WO-2014/012165 A1 | 1/2014 |

OTHER PUBLICATIONS

Ngo et al., 1994, The Protein Folding Problem and Tertiary Structure Prediction, Merz et al., eds., Birkhauser, Boston, pp. 492-495.*

Tokuriki et al., 2009, Curr. Opin. Struc. Biol. 19:596-604.*

Agrawal, N., et al., RNA Interference: Biology, Mechanism, and Applications, Microbiology and Molecular Biology Reviews, 67(4):657-685 (2003).

Angata, T. et al., A second uniquely human mutation affecting sialic acid biology, J. Biol. Chem., 276(43):40282-7 (2001).

Angata, T. et al., Cloning and characterization of a novel mouse Siglec, mSiglec-F: differential evolution of the mouse and human (CD33) Siglec-3-related gene clusters, J. Biol. Chem., 276(48):45128-36 (2001).

Angata, T. et al., Siglec-15: an immune system Siglec conserved throughout vertebrate evolution, Glycobiology, 17(8):838-846 (2007).

Baron R., Anatomy and Biology of Bone Matrix and Cellular Elements, Primer on the Metabolic Bone Diseases and Disorders of Mineral Metabolism, Fifth Ed., American Society for Bone and Mineral Research, Washington DC, pp. 1-8 (2003).

Bespalov, I.A. et al., Preparation of single-chained antibodies to human ferritin in *Escherichia coli*, Molecular Biology (Mosk), 27(2):451-60 (English Abstract) (1993).

Bird, R.E., Single-Chain Antigen-Binding Proteins, Science, 242(4877):423-426 (1988).

Biskobing, D.M. et al., Acid pH increases Carbonic Anhydrase II and Calcitonin Receptor mRNA Expression in Mature Osteoclasts, Calcified Tissue International, 67(2):178-183 (2000).

Blasius, A.L. et al., Siglec-H is an IPC-specific receptor that modulates type I IFN secretion through DAP12, Blood, 107(6):2474-6 (2006).

(56) References Cited

OTHER PUBLICATIONS

Blixt, O. et al., Sialoside Specificity of the Siglec Family Assessed Using Novel Multivalent Probes, The Journal of Bilogical Chemistry, 278:31007-31019 (2003).
Boyle, W.J. et al., Osteoclast differentiation and activation, Nature, 423(6937):337-342 (2003).
Brage, M. et al., Different Cysteine Proteinases Involved in Bone Resorption and Osteoclast Formation, Calcified Tissue International, 76(6)439-447 (2005).
Brandenberger, R. et al., Transcriptome characterization elucidates signaling networks that control human ES cell growth and differentiation, Nature Biotechnology, 22(6):707-716 (2004).
Bregni, M. et al., B-Cell restricted saporin immunotoxins: activity against B-cell lines and chronic lymphocytic leukemia cells, Blood, 73:753-762 (1989).
Brown, M. et al., Tolerance to Single, but not multiple, Amino Acid Replacements in Antibody VH CDR2, The Journal of Immunology, 156(9):3285-3291 (1996).
Brummelkamp, T.R. et al., A System for Stable Expression of Short Interfering RNAs in Mammalian Cells, Science, 296(5567):550-553 (2002).
Buckley, K.A. et al., Human Osteoclast Culture from Peripheral Blood Monocytes: Phenotypica Characterization and Quantitation of Resorption, Methods in Molecular Medicine, 107:55-68 Human Cell Culture Protocols, Second edition (2005).
Cao, H. and Crocker, P.R., Evolution of CD33-related siglecs: regulating host immune functions and escaping pathogen exploitation?, Immunology, 132(1):18-26 (2011).
Carrier, A. et al. Recombinant antibody-alkaline phosphatase conjugates for diagnosis of human IgGs: application to anti-HBsAg detection, Journal of Immunological Methods, 26;181(2):177-86 (1995).
Casset, F. et al., A peptide mimetic of an anti-CD4; monoclonal antibody by rational design, Biochemical and Biophysical Research Communications, 18;307(1):198-205 (2003).
Clackson, T. et al., Making antibody fragments using phage display libraries, Nature, 352:624-628 (1991).
Collin-Osdoby, P. et al., RANKL-Mediated Osteoclast Formation from Murine RAW 264.7 Cells, Methods in Molecular Medicine, 80:153-66 Bone Research Protocols (2003).
Collins F. S. Generation and Initial Analysis of more than 15,00 Full-Length Human and Mouse cDNA Sequences, PNAS, Dec. 24, 2002,vol. 99 (26), pp. 16899-16903.
Communication Protesting the Granting of a Patent Pursuant to Section 10 of the Patent Rules for CA 2,822,302, 13 pages (Jan. 26, 2015).
Communication Protesting the Granting of a Patent Pursuant to Section 10 of the Patent Rules for CA Application No. 2,638,823, 38 pages (Nov. 20, 2014).
Communication Protesting the Granting of a Patent Pursuant to Section 10 of the Patent Rules for CA Application No. 2,638,823, 46 pages (Apr. 5, 2012).
Communication Protesting the Granting of a Patent Pursuant to Section 10 of the Patent Rules for CA Application No. 2,785,046, 61 pages (Apr. 15, 2014).
Communication Protesting the Granting of a Patent Pursuant to Section 10 of the Patent Rules for CA Application No. 2,785,046, 80 pages (May 10, 2013).
Communication Protesting the Granting of a Patent Pursuant to Section 10 of the Patent Rules for CA Application No. 2,822,302, 85 pages (Apr. 10, 2014).
Communication pursuant to Rule 114(2) EPC for EP 10821519.5 enclosing Third Party Observations under Article 115 EPC filed Mar. 9, 2015, 6 pages (Mar. 13, 2015).
Communication pursuant to Rule 114(2) EPC for EP 10821519.5 enclosing Third Party Observations under Article 115 EPC filed Apr. 15, 2016, 7 pages (Apr. 21, 2016).
Crocker, P.R. et al., Siglecs and their roles in the immune system, Nature Reviews Immunology, 7(4):255-266 (2007).

De Vernejoul, M.C., Dynamics of Bone Remodeling: Biochemical and Pathophysiological Basis, European Journal of Clinical Chemistry and Clinical Biochemistry, 34:729-734 (1996).
Elbashir, S.M. et al., Duplexes of 21-nucleotide RNAs mediate RNA interference in cultured mammalian cells, Nature, 411(6836):494-498 (2001).
Ellis, G.K. et al., Randomized Trial of Denosumab in Patients Receiving Adjuvant Aromatase Inhibitors for Nonmetastatic Breast Cancer, Journal of Clinical Oncology, 26(30):4875-4882 (2008).
ENSEMBL Protein ID: ENSBTAP00000016659, Jul. 19, 2010.
ENSEMBL Protein ID: ENSBTAP00000022107, Jul. 19, 2010.
ENSEMBL Protein ID: ENSCAFP00000026052, Jul. 19, 2010.
ENSEMBL Protein ID: ENSDNOP00000011608; Jul. 19, 2010.
ENSEMBL Protein ID: ENSECAP00000015632, Jul. 19, 2010.
ENSEMBL Protein ID: ENSFCAP00000009910, Jul. 19, 2010.
ENSEMBL Protein ID: ENSMICP00000015938, Jul. 19, 2010.
ENSEMBL Protein ID: ENSMLUP00000004457, Jul. 19, 2010.
ENSEMBL Protein ID: ENSMMUP00000004742, Jul. 19, 2010.
ENSEMBL Protein ID: ENSMUSP00000112309, Jul. 19, 2010.
ENSEMBL Protein ID: ENSOPRP00000004369, Jul. 19, 2010.
ENSEMBL Protein ID: ENSPPYP00000010254, Jul. 19, 2010.
ENSEMBL Protein ID: ENSPTRP00000042370, Jul. 19, 2010.
ENSEMBL Protein ID: ENSPTRP00000049394, Jul. 19, 2010.
ENSEMBL Protein ID: ENSRNOP00000041280, Jul. 19, 2010.
ENSEMBL Protein ID: ENSSARP00000011800, Jul. 19, 2010.
ENSEMBL Protein ID: ENSSTOP00000002285, Jul. 19, 2010.
ENSEMBL Protein ID:ENSP00000374125, Jul. 6, 2010.
Frost, H.M., Dynamics of Bone Remodeling. In: Bone Biodynamics, Little and Brown, Boston, MA, USA, pp. 315-333 (1964).
Gee, J.E. et al., Potential Therapeutic Usefulness of Intermolecular Triplex DNA. In: Huber BE Cancer Therapy in the Twenty-First Century, vol. 1: Molecular and Immunologic Approaches, Futura Publishing Co., Inc., Mt. Kisco, N.Y., pp. 163-177 (1994).
GenBank Accession No. AAB_34287, GI:957319, first referenced Aug. 26, 1995, updated Sep. 28, 1995 (2 pages).
GenBank Accession No. AAB_39983, GI:1769542, first referenced Jan. 9, 1997, updated Dec. 1, 1999 (1 page).
GenBank Accession No. AAC_60658, GI:385849, first referenced Aug. 25, 1993 (1 page).
GenBank Accession No. AAY40743, GI:63364962, 2007.
GenBank Accession No. AAY40744, GI:63364988, 2007.
GenBank Accession No. AF_019943, GI:2431979, first referenced Sep. 24, 1997, updated Nov. 13, 2001 (1 page).
GenBank Acc. No. AK172835, GI:47077862, 2004.
GenBank Acc. No. AL357873, GI:16972902, 2008.
GenBank Acc. No. AL645465, GI:18476850, 2008.
GenBank Accession No. BAD18800, GI:47077863, 2006.
GenBank Accession No. BAF83089, GI:158261823, 2008.
GenBank Accession No. BAF83091, GI:158261827, 2008.
GenBank Accession No. EAX01462.1, first reference 2005.
GenBank Acc. No. NM_000067, GI:157952216, first referenced 1976, updated 2008.
GenBank Acc. No. NM_000099, GI:19882253, first referenced 1990, updated 2008.
GenBank Acc. No. NM_000887, GI:34452172, first referenced 1987, updated 2008.
GenBank Acc. No. NM_001014433, GI:62526019 first referenced 2000, updated 2011.
GenBank Acc. No. NM_001014433, GI:62526019, first referenced 2000, updated 2008.
GenBank Acc. No. NM_001102, GI:194097348, first referenced 1989, updated 2008.
GenBank Acc. No. NM_001690, GI:19913423, first referenced 1993, updated 2007.
GenBank Acc. No. NM_001935, GI:47078262, first referenced 1991, updated 2008.
GenBank Acc. No. NM_002994, GI:41872613, first referenced 1991, updated 2008.
GenBank Acc. No. NM_003341, GI:33359692, first referenced 1993, updated 2008.
GenBank Acc. No. NM_004414, GI:44680111, first referenced 1995, updated 2008.

(56) References Cited

OTHER PUBLICATIONS

GenBank Acc. No. NM_004763, GI:115527101, first referenced 1997, updated 2007.
GenBank Acc. No. NM_004794, GI:34485717, first referenced 1993, updated 2005.
GenBank Acc. No. NM_005410, GI:62530390, first referenced 1991, updated 2008.
GenBank Acc. No. NM_005765, GI:15011917, first referenced 1998, updated 2007.
GenBank Acc. No. NM_006357, GI:33359695, first referenced 1997, updated 2008.
GenBank Acc. No. NM_006555, GI:34304384, first referenced 1997, updated 2007.
GenBank Acc. No. NM_006660, GI:12597621, first referenced 1999, updated 2008.
GeneBank Acc. No. NM_001771.3, first reference 1990.
GeneBank Acc. No. NM_001772.3, first reference 1988.
GenBank Acc. No. NM_013322, GI:23111022, first referenced 2001, updated 2006.
GenBank Acc. No. NM_014358, GI:90577173, first referenced 1999, updated 2003.
GenBank Acc. No. NM_014656, GI:7657258, 2006.
GenBank Acc. No. NM_015973, GI:88853582, first referenced 1990, updated 2008.
GenBank Acc. No. NM_018252, GI:149158718, 2006.
GenBank Acc. No. NM_018482, GI:46094080, first referenced 1998, updated 2008.
GenBank Acc. No. NM_021181, GI:19923571, first referenced 2001, updated 2008.
GenBank Acc. No. NM_030794, GI:13540575, first referenced 2000, updated 2008.
GenBank Acc. No. NM_032565, GI:141802977, first referenced 2003, updated 2007.
GenBank Acc. No. NM_032569, GI:190358483, first referenced 2005, updated 2006.
GenBank Acc. No. NM_032731, GI:153791420, first referenced 2004, updated 2008.
GenBank Acc. No. NM_054027, GI:170671715, first referenced 1995, updated 2008.
GenBank Acc. No. NM_138461, GI:115511027, 2004.
GenBank Acc. No. NM_145280, GI:188528683, 2004.
GenBank Acc. No. NM_178833, GI:196259823, first referenced 2007, updated 2008.
GenBank Acc. No. NM_182488, GI:209954829, first referenced 1998, updated 2004.
GenBank Acc. No. NM_213602, GI:47106068, 2007.
GenBank Accession No. NP_001094508, May 28, 2010.
GenBank Accession No. NP_998767, first referenced May 11, 2004, updated Mar. 5, 2010, Angata T. et al., J. Glycobiology 17(8):838-846, 2007.
GenBank Acc. No. XM_884636, GI:149270200, 2007.
GenBank Accession No. XP_889729; Dec. 1, 2005.
GenBank Accession No. XP_001056537, Apr. 2, 2010.
GenBank Accession No. XP_001089000, Jun. 1, 2010.
GenBank Accession No. XP_512109, Sep. 16, 2006.
GenBank Accession No. XP_512109.2, Oct. 25, 2012.
GenBank Accession No. XP_574176, Apr. 2, 2010.
GenBank Accession No. XP_574176.2, 2006.
GenBank Accession No. XP_601064, Jun. 3, 2010.
GenBank Accession No. XP_601064.4, 2008.
GenBank Accession No. XP_855238, Aug. 30, 2005.
GENESEQ Database (Online) Derwent; Human Siglec 15, SEQID2, XP002531845, from JP-2007020403-A (Nat. Inst. of Adv. Ind. & Technol.), Database accession No. AER31251 May 3, 2007.
GENESEQ Database [Online], Human protease/osteoarthritis gene-specific probe—SEQ ID 118248, Database accession No. AFV92822, Oct. 18, 2007.
GENESEQ Database [Online], Human protease/osteoarthritis gene-specific probe—SEQ ID 72066, Database accession No. AFV46640, Oct. 18, 2007.

Ghetie, M.A. et al., Evaluation of Ricin A Chain-containing Immunotoxins Directed Against CD19 and CD22 Antigens on Normal and Malignant Human B-Cells as Potential Reagents for in Vivo Therapy, Cancer Research, 48:2610-2617 (1988).
Hancock, D.C. and O'Rielly, N.J., Synthetic peptides as antigens for antibody production, Methods in Molecular Biology, vol. 295: Immunochemical Protocols, 3rd Edition (R. Burns, ed.), 13-25 (2005).
Hannon, G.J., RNA interference, Nature, 418(6894):244-251 (2002).
Hashimoto, T. et al., Biochemical Markers in Bone Metastasis, Jpn. J. Cancer Chemother, 31(7):1027-1033 (2004).
Henriksen, K. et al., Generation of human osteoclasts from peripheral blood, Methods Mol. Biol., 816:159-75 (2012).
Hiruma, Y. et al., Impaired osteoclast differentiation and function and mild osteopetrosis development in Siglec-15-deficient mice, Bone, 53:87-93, (2013).
Hiruma, Y. et al., Siglec-15, a member of the sialic acid-binding lectin, is a novel regulator for osteoclast differentiation, Biochemical and Biophysical Research Communications, 409(3):424-429 (2011).
Hsu, H. et al., Tumor necrosis factor receptor family member RANK mediates osteoclast differentiation and activation induced by osteoprotegerin ligand, Proceedings of the National Academy of Science, USA, 96:3540-3545 (1999).
Huston, J.S. et al., Protein engineering of antibody binding sites: Recovery of specific activity in an anti-digoxin single-chain Fv analogue produced in *Escherichia coli*, Proceedings of the National Academy of Sciences, 85:5879-5883 (1988).
Interlocutory decision in Opposition proceedings (Art. 101(3)(a) and 106(2) EPC), for EP 07 710 624.3 (Patent No. 1994155), 19 pages (Feb. 23, 2015).
International Search Report for PCT/CA2013/000646, 5 pages (Oct. 23, 2013).
IPI No. IPI00568858.4, sequence update Oct. 12, 2009.
IPI No. IPI00647937.1, Sep. 4, 2005.
IPI No. IPI00663527.4, sequence update Sep. 10, 2007.
IPI No. IPI00711850.4., sequence update Jun. 9, 2010.
IPI No. IPI00716135.2, 2007.
IPI No. IPI00796217.1, sequence update Oct. 31, 2006.
Ishida, N. et al., Large Scale Gene Expression Analysis of Osteoclastogenesis in Vitro and Elucidation of NFAT2 as a Key Regulator, The Journal of Biological Chemistry, 277(43):41147-41156 (2002).
Ishida-Kitagawa, N. et al., Siglec-15 Protein Regulates Formation of Functional Osteoclasts in Concert with DNAX-activating Protein of 12 kDa (DAP12), The Journal of Biological Chemistry, 287(21):17493-17502 (2012).
Ishii, M. et al, RANKL-Induced Expression of Tetraspanin CD9 in Lipid Raft Membrane Microdomain is Essential for Cell Fusion During Osteoclastogenesis, Journal of Bone and Mineral Research, 21(6):965-976 (2006).
Janeway Jr., C.A. et al., Immunobiology: The Immune System in Health and Disease, Part II. The Recognition of Antigen, Chapter 3. Antigen Recognition by B-cell and T-cell Receptors, 5th Edition, 35 pages (2001).
Janssen, E. et al., LAB: A new membrane-associated adaptor molecule in B cell activation, Nature Immunology, 4(2):117-123 (2003).
Jilka, R.L. et al., Increased Osteoclast Development After Estrogen Loss: Mediation by Interleukin-6, Science 257:88-91 (1992).
Jones, S. and Rappoport, J.Z., Interdependent epidermal growth factor receptor signalling and trafficking, Int. J. Biochem. Cell Biol., 51:23-8 (2014).
Kawai, J. et al., Functional annotation of a full-length mouse cDNA collection, Nature, 409(6821):685-690 (2001).
Kawaida, R. et al., Jun Dimerization Protein 2 (JDP2), a Member of the AP-1 Family of Transcription Factor, Mediates Osteoclast Differentiation Induced by RANKL, The Journal of Experimental Medicine, 197(8):1029-1035 (2003).
Kim, S.J. et al., Antibody engineering for the development of therapeutic antibodies, Mol. Cells., 20(1):17-29 (2005).

(56) References Cited

OTHER PUBLICATIONS

Kukita, T. et al., RANKL-induced DC-STAMP is Essential for Osteoclastogenesis, The Journal of Experimental Medicine, 200:941-946 (2004).
Lacey, D.L. et al., Bench to bedside: elucidation of the OPG-RANK-RANKL pathway and the development of denosumab, Nature Reviews Drug Discovery, 11:401-419 (2012).
Larkin, M.A. et al., Clustal W and Clustal X version 2.0, Bioinformatics, 23(21): 2947-2948 (2007).
Lee, J.S. et al., Stable gene silencing in human monocytic cell lines using lentiviral-delivered small interference RNA. Silencing of the p110α isoform of phosphoinositide 3-kinase reveals differential regulation of adherence induced by 1α,25-dihydroxycholecalciferol and bacterial lipopolysaccharide, The Journal of Biological Chemistry, 279(10):9379-9388 (2004).
Lee, S.W. et al., The anti-proliferative gene TIS21 is involved in osteoclast differentiation, J. Biochem. Mol. Biol., 35(6):609-14 (2002).
Li, C.H. et al., β-Endorphin omission analogs: Dissociation of immunoreactivity from other biological activities, Proceedings of the National Academy of Sciences, 77(6):3211-3214 (1980).
Ma, R. et al., Inhibition of osteoclastogenesis by RNA interference targeting RANK, BMC Musculoskeletal Disorders, 13:154 (2012).
Macauley, M.S. et al., Siglec-mediated regulation of immune cell function in disease, Nat. Rev. Immunol., 14(10):653-66 (2014).
Malkin, I. et al., Association of ANKH gene polymorphisms with radiographic hand bone size and geometry in a Chuvasha population, Bone, 36(2):365-373 (2005).
Martin, T.J. and Sims, N. A., Osteoclast-derived activity in the coupling of bone formation to resorption, Trends in Molecular Medicine, 11:76-81 (2005).
Martin, T.J., Bone Biology and Anabolic therapies for Bone: Current Status and Future Prospects, Journal of Bone Metabolism, 21:8-20 (2014).
Martin, T.J., Paracrine regulation of osteoclast formation and activity: milestones in discovery, J. Musculoskelet. Neuronal Interact., 4(3):243-53 (2004).
McMahon, C. et al. Bone marrow transplantation corrects osteopetrosis in the carbonic anhydrase II deficiency syndrome, Blood, 97(7):1947-1950 (2001).
McMillan, S.J. et al., CD33-related sialic-acid-binding immunoglobulin-like lectins in health and disease, Carbohydrate Research, 343(12):2050-2056 (2008).
Miyamoto, T. Regulators of osteoclast differentiation and cell-cell fusion, Keio J. Med., 60(4):101-5 (2011).
Morello, R. et al., cDNA cloning, characterization and chromosome mapping of *Crtap* encoding the mouse Cartilage Associated Protein, Matrix Biology, 18(3): 319-324 (1999).
Nagakawa, N. et al., RANK is the essential Signaling Receptor for Osteoclast Differentiation Factor in Osteoclastogenesis, Biochemical Biophysical Research Communications, 253:395-400 (1998).
Netzel-Arnett, S. et al., Member anchored serine proteases: A rapidly expanding group of cell surface proteolytic enzymes with potential roles in cancer, Cancer and Metastasis Reviews, 22(2-3):237-258 (2003).
Ngo, J.T. et al., Computational Complexity, Protein Structure Prediction, and the Levinthal Paradox in the Protein Folding Problem and Tertiary Structure Prediction, Birkhauser, Boston, pp. 491-495 (1994).
Nishi, T. et al., Expression and Function of the Mouse V-ATPase d Subunit Isoforms, The Journal of Biological Chemistry, 278(47): 46396-46402 (2003).
Nishi, T. et al., The vacuolar (H+)-ATPases-nature's most versatile protein pumps. Nature Reviews Molecular Cell Biology, 3(2):94-103 (2002).
Devita, V.T. et al., Biological Methods of Cancer Treatment, Moscow "Medicine," pp. 539-540 (2002).
Notice of Opposition against European Patent No. 1994155 including references D1-D12 (Jul. 30, 2013).
O'Reilly, M.K. et al., Siglecs as targets for therapy in immune cell mediated disease, Trends in Pharmacological Sciences, 30(5):240-248 (2009).
Opposition against European Patent No. 1994155 including declaration of Michael Clark, 16 pages (Dec. 22, 2014).
Ota, T. et al., Complete sequencing and characterization of 21,243 full-length human cDNAs, Nat. Genet., 36(1):40-5 (2004).
Patent Owner Preliminary Response for Inter Partes Review (No. IPR-2015-00291) for U.S. Pat. No. 8,168,181, with exhibits (Mar. 20, 2015).
Paul, W.E., editor, Structure and Function of Immunoglobulins, Fundamental Immunology, Third Edition, Raven Press, NY, pp. 292-295 (1993).
Pereira, B. et al., Cardiolipin binding a light chain from lupus-prone mice, Biochemistry, 37(5):1430-7 (1998).
Petition for Inter Partes Review (No. IPR2015-00291) for U.S. Pat. No. 8,168,181, 72 pages (Nov. 25, 2014), with exhibits.
Pisitkun, T. et al., NHLBI-AbDesigner: an online tool for design of peptide-directed antibodies, Am. J. Physiol. Cell Physiol., 302(1):C154-64 (2012).
Poli, V. et al., Interleukin-6 deficient mice are protected from bone loss caused by estrogen depletion, The EMBO Journal, 13(5):1189-1196 (1994).
Portolano, S. et al., Lack of Promiscuity in Autoantigen-Specific H and L Chain Combinations as Revealed by Human H and L Chain "Roulette", The Journal of Immunology, 150:880-887 (1993).
Roberts, S. et al., Generation of an antibody with enhanced affinity and specificity for its antigen by protein engineering, Nature, 328(6132):731-4 (1987).
Roitt, A., Immunology, pp. 110-111 (2000).
Roitt, A., Immunology, pp. 151-152 (2000).
Roovers, R.C. et al, High-affinity recombinant phage antibodies to the pan-carcinoma marker epithelial glycoprotein-2 for tumour targeting, British Journal of Cancer, 78(11):1407-16 (1998).
Rubinson, D.A. et al., A lentivirus-based system to functionally silence genes in primary mammalian cells, stem cells and transgenic mice by RNA interference, Nature Genetics, 33(3):401-406 (2003).
Rudikoff, S. et al., Single amino acid substitution altering antigen-binding specificity, Proc. Natl. Acad. Sci. U S A., 79(6):1979-83 (1982).
Sakharkar, M.K. et al., Huge proteins in the human proteome and their participation in hereditary diseases, in Silico Biology, 6, 0026, 5 pages (2006).
Shan, J. et al., TSP50, A Possible Protease in Human Testes, Is Activated in Breast Cancer Epithelial Cells, Cancer Research, 62(1):290-294 (2002).
Shankavaram, U.T. et al., Transcript and protein expression profiles of the NCI-60 cancer panel: an integromic microarray study, Molecular Cancer Therapies, 6(3):820-832 (2007).
Simmons, D. and Seed B., Isolation of a cDNA encoding CD33, a differentiation antigen of myeloid progenitor cells, J. Immunol., 141(8):2797-800 (1988).
Smith, A.N. et al., Mutations in *ATP6N1B*, encoding a new kidney vacuolar proton pump 116-kD subunit, cause recessive distal renal tubular acidosis with preserved hearing, Nature Genetics, 26(1):71-75 (2000).
Smith, A.N., et al. Vacuolar H+-ATPase d2 Subunit: Molecular Characterization, Development Regulation, and Localization to Specialized Proton Pumps in Kidney and Bone, Journal of the American Society of Nephrology, 16(5):1245-1256 (2005).
Song, E. et al., RNA interference targeting Fas protects mice from fulminant hepatitis, Nat. Med., 9(3):347-51 (2003).
Sooknanan, R. et al., Identification of Osteoclast-Specific Genes using Subtractive Transcription Amplification of mRNA (STAR), Journal of Bone and Mineral Research, 19:S415 (2004).
Sordillo, E.M. et al., RANK-FC: A Therapeutic Antagonist for RANK-L in Myeloma, Skeletal Complications of Malignancy, Cancer Supplement, 97(3):802-812 (2003).
Srivastava, S. et al., Estrogen Blocks M-CSF Gene Expression and Osteoclast Formation by Regulating Phosphorylation of Egr-1 and Its Interaction with Sp-1, The Journal of Clinical Investigation, 102(10):1850-1859 (1998).

(56) References Cited

OTHER PUBLICATIONS

Statement of Grounds and Particulars of Opposition for AU Application No. 2007215334 by Daiichi Sankyo Company Limited, 9 pages (May 21, 2014).
Stehberger, P.A. et al., Localization and Regulation of the ATP6V0A4 (a4) Vacuolar H+-ATPase Subunit Defective in an Inherited Form of Distal Renal Tubular Acidosis, Journal of the American Society of Nephrology,14(12):3027-3038 (2003).
Strausberg, R.L. et al., Generation and initial analysis of more than 15,000 full-length human and mouse cDNA sequences, Proceedings of the National Academy of Sciences, 99(26):16899-16903 (2002).
Strohl, W.R. and Strohl, L.M., Therapeutic Antibody Engineering: Current and future advances driving the strongest growth area in the pharmaceutical industry, 1st Edition, 21 pages (2012).
Stuible, M. et al., Abstract of Oral Presentation No. 1187, Targeting of the DAP12-associated, Osteoclast-specific, Receptor Siglec-15 by Antibody 25E9 inhibits Differentiation and Resorption Activity, The American Society for Bone and Mineral Research, San Diego Convention Center, Sep. 19, 2011.
Stuible, M. et al., Mechanism and function of monoclonal antibodies targeting siglec-15 for therapeutic inhibition of osteoclastic bone resorption, The Journal of Biological Chemistry, 289(10):6498-512, (2014).
Sugawara, K. et al., A Useful Method to Evaluate Bone Resorption Inhibitors, Using Osteoclast-like Multinucleated Cells, Analytical Biochemistry, 255:204-210 (1998).
Sun, M., TREM-2 promotes host resistance against Pseudomonas aeruginosa infection by suppressing corneal inflammation via a PI3K/Akt signaling pathway, Invest. Ophthalmol. Vis. Sci., 54(5):3451-62 (2013).
Supplementary European Search Report for EP07710624.3, 13 pages (Jul. 10, 2009).
Susa, M. et al., Human primary osteoclasts: in vitro generation and application as pharmacological and clinical assay, Journal of Translational Medicine, 2(6):1-12 (2004).
Tabares, P. et al., Human regulatory T cells are selectively activated by low-dose application of the CD28 superagonist TGN1412/TAB08, Eur. J. Immunol., 44(4):1225-36 (2014).
Takahata, M. et al., Sialylation of cell surface glycoconjugates is essential for osteoclastogenesis, Bone, 41(1):77-86 (2007).
Tatusova, T. et al., Blast 2 sequences, a new tool for comparing protein and nucleotide sequences, FEMS Microbiology Letters, 174:247-250 (1999).
Tokuriki, N. Stability effects of mutations and protein evolvability, Current Opinion in Structural Biology, 19:596-604, 2009.
Tonachini, L. et al., cDNA cloning, characterization and chromosome mapping of the gene encoding human cartilage associated protein (CRTAP), Cytogenetics and Cell Genetics, 87(3-4):191-194 (1999).

Tremblay, G.B. et al., Functional Validation of Osteoclast-Specific Genes in RAW264.7 Cells by RNA Interference, Journal of Bone and Mineral Research, 19:S414 (2004).
Trinquier, G. and Sanejouand, Y.H., Which effective property of amino acids is best preserved by the genetic code? Protein Eng., 11(3):153-69 (1998).
Tsuda, E. et al., Isolation of a novel cytokine from human fibroblasts that specifically inhibits osteoclastogenesis, Biochem. Biophys. Res. Commun., 234(1):137-42 (1997).
UniProtKB/Swiss-Prot A8K2Y5_Human, Jul. 13, 2010.
UniProtKB/Swiss-Prot Q6ZMC9 (SIG15_Human), Jun. 15, 2010.
UniProtKB/TrEMBL A7E1W7_Human, Mar. 2, 2010.
UniProtKB/TrEMBL A7E1W8_Mouse, Sep. 11, 2007.
Vajdos, F. et al., Comprehensive Functional Maps of the Antigen-binding Site of an Anti-ErbI32 Antibody Obtained with Shotgun Scanning Mutagenesis, Journal of Molecular Biology, 320(2):415-428 (2002).
Van Der Velden, V.H.J. et al., Targeting of the CD33-calicheamicin immunoconjugate Mylotarg (CMA-676) in acute myeloid leukemia: in vivo saturation and internalization by leukemic and normal myeloid cells, Blood, 97:3197-3204 (2001).
Walter, R.B. et al., ITIM-dependent endocytosis of CD33-related Siglecs: role of intracellular domain, tyrosine phosphorylation, and the tyrosine phosphatases, Shp1 and Shp2, J. Leukoc. Biol., 83(1):200-11 (2008).
Ward, E.S. et al., Binding activities of a repertoire of single immunoglobulin variable domains secreted from *Escherichia coli*, Nature, 341:544-546 (1989).
Wei, S. et al., Control of mouse graft-versus-host disease following allogeneic bone marrow transplantation by blocking the CD28/B7 signaling pathway with lentiviral vector-mediated RNA interference, Immunol. Lett., 136(2):194-202 (2011).
Wells, J.A., Additivity of Mutational Effects in Proteins, Biochemistry, 29(37):8509-8517 (1990).
Williams, E.L. et al., Development and characterization of monoclonal antibodies specific for the murine inhibitory FcγRIIB (CD32B), European Journal of Immunology, 42:2109-2120 (2012).
Written Opinion for PCT/CA2013/000646, 6 pages (Oct. 23, 2013).
Yang, M. et al., Osteoclast stimulatory transmembrane protein (OC-STAMP), a novel protein induced by RANKL that promotes osteoclast differentiation, Journal of Cell Physiology, 215(2):497-505 (2008).
Yavropoulou, M.P. and Yovos J.G., Osteoclastogenesis—current knowledge and future perspectives, J. Musculoskelet. Neuronal. Interact., 8(3):204-16 (2008).
Yuan, L. et al., Isolation of a Novel Gene, *TSP50*, by a Hypomethylated DNA Fragment in Human Breast Cancer, Cancer Research, 59(13):3215-3221 (1999).
Final Written Decision in *Inter Partes Review* of U.S. Pat. No. 8,168,181 (case IPR2015-00291), 26 pages, Jun. 14, 2016.

\* cited by examiner

Figure 2A- Sequence alignment of the mouse, humanized and selected human framework sequences for the variable light (VL) domain of the 25D8 antibody

```
D8-VL                1                   2                   3                   4                   5                   6                   7                   8                   9
             1234567890123456789012345678901234567890123456789012345678901234567890123456789012345678901234567890
Ag contact   11                      1113346416111              1113346416111                 111334641611        1  35113 111     1J11 1       364214
mouse        DIVMTQAAFSNPVTLTSASISCRSSKSLLHSNGITYLYWYLQRPGQSPQLLIYQMSNLASGVPDRFSSSGTDFTLRISRVEAEDVGVYYCAQNLELPYTFGGGTKLEIK    9/80 (88.8%) SEQ ID NO:22
               ||||||   ||| ||||||| ||| || ||||| ||||||||||||| ||||||  |||||||| |||||||  ||||||||||||||||||    |||| ||||||||||||| humanized    DIVMTQTPLSLPVTPGEPASISCRSSKSLLHSNGITYLYWYLQKPGQSPQLLIYQMSNLASGVPDRFSGSGSGTDFTLKISRVEAEDVGVYYCAQNLELPYTFGGGTKVEIK  SEQ ID NO:24 humanFRs     DIVMTQSPLSLPVTPGEPASISCRSSQSLLHSNGYNYLDWYLQKPGQSPQLLIYLGSNRASGVPDRFSSSGTDFTLRISRVEAEDVGVYYCMQSLQTPLTFGGGTKLEIK    0/80 (100%) SEQ ID NO:66
             DIVMTQSPLSLPVTPGEPASISCRASQSLLHSNGYNYLDWYLQKPGQSPQLLIYLGSNRASGVPDRFSSSGTDFTLRISRVEAEDVGVYYCMQGLQTPLTFGGGTKLEIK    1/80 (98.8%) SEQ ID NO:67
             DIVMTQSPLSLSVTPGQPASISCKSSQSLLHSDGKTYLYWYLQKPGQPPQLLIYEVSNRFSGVPDRFSGSGSGTDFTLRISRVEAEDVGVYYCMQSIQLPYTFGQGTKLEIK  4/80 (95%) SEQ ID NO:68
             DIVMTQSPLSLPVTLGEPASISCRSSQSLLHSNGYNYLDWYLQKPGQSPQLLIYLGSNRASGVPDRFSGSGSGTDFTLKISRVEAEDVGVYYCMQALQ              SEQ ID NO:69
             DIVMTQSPLSLPVTLGEPASISCRSSQSLLHSNGYNYLDWYLQKPGQSPQLLIYLGSNRASGVPDRFSGSGSGTDFTLKISRVEAEDVGVYYCMQALQ              SEQ ID NO:70
             DIVMTQSPLSLSVTPGQPASISCKSSQSLLHSDGKTYLYWYLQKPGQSPQLLIYEVSNRFSGVPDRFSGSGSGTDFTLKISRVEAEDVGVYYCMQSIQL             SEQ ID NO:71
             DIVMTQSPLSLPVTPGEPASISCRSSQSLLHSDGNYYLNWYLQKPGQSPQLLIYEVSNRASGVPDRFSGSGSGTDFTLRISRVEAEDVGVYYCMQALQPRYTFGQGTKVEIK  2/80 (97.5%) SEQ ID NO:72
                                                                                                    b
Back mut                                                                     ↑
                                                                             b
```

Human sequences:
gi|AB-74084.1
gi|AB-74076.1
dbj|BAC01740.1
>hurIGKV107 IGKV2-28*01, A3, A19, IGKV2D-28*01 297 bp
>hurIGKV125 297 bp
>hurIGKV033 IGKV2D-29*02 297 bp
>Consensus human kv2

Figure 2B- Sequence alignment of the mouse, humanized and selected human framework sequences for the variable heavy (VH) domain of the 25D8 antibody Figure 3A- Sequence alignment of the mouse, humanized and selected human framework sequences for the variable light (VL) domain of the 25E9 antibody Figure 3B- Sequence alignment of the mouse, humanized and selected human framework sequences for the variable heavy (VH) domain of the 25E9 antibody

Figure 4A

Humanized 25D8 Light (Kappa) Chain

MVLQTQVFISLLLLWISGAYGDIVMTQTPLSLPVTPGEPASISCRSSKSLLHSNGITYLYWYLQKPGQSPQLLIYQMSNLASGVPDRFSG
SGSGTDFTLKISRVEAEDVGVYYCAQNLELPYTFGGGTKVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

SEQ ID NO.:23

Humanized 25D8 Heavy (Igg2) Chain

MDWTWRILFLVAAATGTHAQVQLQQSGAEVKKPGSSVKVSCKASGYTFTSYWMHWVRQAPGQGLEWMGLINPSNARTNYNEKFNTRVTI
TADKSTSTAYMELSSLRSEDTAVYYCARGGDYFDYWGQGTTVTVSSASTKGPSVFPLAPCSRSTSESTAALGCLVKDYFPEPVTVSW
NSGALTSGVHTFPAVLQSSGLYSLSSVVTVPSSNFGTQTYTCNVDHKPSNTKVDKTVERKCCVECPPCPAPPVAGPSVFLFPPKPKDTL
MISRTPEVTCVVVDVSHEDPEVQFNWYVDGVEVHNAKTKPREEQFNSTFRVSVLTVVHQDWLNGKEYKCKVSNKGLPAPIEKTISKTK
GQPREPQVYTLPPSREEMTKNQVSLTCLVKGFYPSDIAVEWESNGQPENNYKTTPPMLDSDGSFFLYSKLTVDKSRWQQGNVFSCSVMH
EALHNHYTQKSLSLSPGK

SEQ ID NO.:27

Chimeric 25D8 Light (Kappa) Chain

MVLQTQVFISLLLLWISGAYGDIVMTQAAFSNPVTLGTSASISCRSSKSLLHSNGITYLYWYLQKPGQSPQLLIYQMSNLASGVPDRFSS
SGSGTDFTLRISRVEAEDVGVYYCAQNLELPYTFGGGTKLEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

SEQ ID NO.:21

Chimeric 25D8 Heavy (Igg2) Chain

MDWTWRILFLVAAATGTHAQVQVQQPGAELVKPGASVKLSCKASGYTFTSYWMHWKQRPGQGLEWIGLINPSNARTNYNEKFNTKATL
TVDKSSSTAYMQLSSLTSEDSAVYYCARGGDYFDYWGQGTTLTVSSASTKGPSVFPLAPCSRSTSESTAALGCLVKDYFPEPVTVSW
NSGALTSGVHTFPAVLQSSGLYSLSSVVTVPSSNFGTQTYTCNVDHKPSNTKVDKTVERKCCVECPPCPAPPVAGPSVFLFPPKPKDTL
MISRTPEVTCVVVDVSHEDPEVQFNWYVDGVEVHNAKTKPREEQFNSTFRVSVLTVVHQDWLNGKEYKCKVSNKGLPAPIEKTISKTK
GQPREPQVYTLPPSREEMTKNQVSLTCLVKGFYPSDIAVEWESNGQPENNYKTTPPMLDSDGSFFLYSKLTVDKSRWQQGNVFSCSVMH
EALHNHYTQKSLSLSPGK

SEQ ID NO.:25

Figure 4B

Humanized 25E9 Light (Kappa) Chain    (Variant 1)

MVLQTQVFISLLLWISGAYGDIVMTQSPLSLPVTPGEPASISCRSTKSLLHSNGNTYLYWYLQKPGQSPQLLIYRMSNLASGVPDRFSG
SGSGTDFTLKISRVEAEDVGVYYCMQHLEYPFTFGGGTKVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC    SEQ ID NO.:7

Humanized 25E9 Heavy (Igg2) Chain    (Variant 1)

MDWTWRILFLVAAATGTHAEIQLQQSGAEVKKPGSSVKVSCKASGYTFTDYDMHWVRQAPGQGLEWMGTIDPETGGTAYNQKFKGRVTI
TADKSTSTAYMELSSLRSEDTAVYYCTSFYYTYSNYDVGFAYWGQGTLVTVSSASTKGPSVFPLAPCSRSTSESTAALGCLVKDYFPEP
VTVSWNSGALTSGVHTFPAVLQSSGLYSLSSVVTVPSSNFGTQTYTCNVDHKPSNTKVDKTVERKCCVECPPCPAPPVAGPSVFLFPPK
PKDTLMISRTPEVTCVVVDVSHEDPEVQFNWYVDGVEVHNAKTKPREEQFNSTFRVVSVLTVVHQDWLNGKEYKCKVSNKGLPAPIEKT
ISKTKGQPREPQVYTLPPSREEMTKNQVSLTCLVKGFYPSDIAVEWESNGQPENNYKTTPPMLDSDGSFFLYSKLTVDKSRWQQGNVFS
CSVMHEALHNHYTQKSLSLSPGK    SEQ ID NO.:29

Chimeric 25E9 Light (Kappa) Chain

MVLQTQVFISLLLWISGAYGDIVMTQAAPSVPTPGESVSISCRSTKSLLHSNGNTYLYWFLQRPGQSPQLLIYRMSNLASGVPDRFSG
SGSGTAFTLRISRVEAEDVGVYYCMQHLEYPFTFGGGTKLEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC    SEQ ID NO.:5

Chimeric 25E9 Heavy (Igg2) Chain

MDWTWRILFLVAAATGTHAEIQLQQSGVELVRPGASVTLSCKASGYTFTDYDMHWVKQTPVHGLEWIGTIDPETGGTAYNQKFKGKATL
TADRSSTTAYMELSSLTSEDSAVYYCTSFYYTYSNYDVGFAYWGQGTLVTVSAASTKGPSVFPLAPCSRSTSESTAALGCLVKDYFPEP
VTVSWNSGALTSGVHTFPAVLQSSGLYSLSSVVTVPSSNFGTQTYTCNVDHKPSNTKVDKTVERKCCVECPPCPAPPVAGPSVFLFPPK
PKDTLMISRTPEVTCVVVDVSHEDPEVQFNWYVDGVEVHNAKTKPREEQFNSTFRVVSVLTVVHQDWLNGKEYKCKVSNKGLPAPIEKT
ISKTKGQPREPQVYTLPPSREEMTKNQVSLTCLVKGFYPSDIAVEWESNGQPENNYKTTPPMLDSDGSFFLYSKLTVDKSRWQQGNVFS
CSVMHEALHNHYTQKSLSLSPGK    SEQ ID NO.:30

Figure 6A

Alignment

```
SEQ ID NO:6   DIVMTQAAPSVPVTPGESVSISCRSTKSLLHSNGNTYLYWFLQRPGQSPQLLIYRMSNLA 60
SEQ ID NO:8   DIVMTQSPLSLPVTPGEPASISCRSTKSLLHSNGNTYLYWYLQKPGQSPQLLIYRMSNLA 60
              ******..*:******..*****************:**:*:*****************

SEQ ID NO:6   SGVPDRFSGSGSGTAFTLRISRVEAEDVGVYYCMQHLEYPFTFGGGTKLEIK 112
SEQ ID NO:8   SGVPDRFSGSGSGTDFTLKISRVEAEDVGVYYCMQHLEYPFTFGGGTKVEIK 112
              **************:***:*****************************:***
```

Figure 6B

Alignment

```
SEQ ID NO:12  EIQLQQSGVELVRPGASVTLSCKASGYTFTDYDMHWVKQTPVHGLEWIGTIDPETGGTAY 60
SEQ ID NO:14  EIQLQQSGAEVKKPGSSVKVSCKASGYTFTDYDMHWVRQAPGQGLEWMGTIDPETGGTAY 60
              ********.**::***:**:*****************:*.**:****:***********

SEQ ID NO:12  NQKFKGKATLTADRSSTTAYMELSSLTSEDSAVYYCTSFYYTYSNYDVGFAYWGQGTLVT 120
SEQ ID NO:14  NQKFKGRVTITADKSTSTAYMELSSLRSEDTAVYYCTSFYYTYSNYDVGFAYWGQGTLVT 120
              ******:.*:***:*:**********.***:*****************************

SEQ ID NO:12  VSA 123
SEQ ID NO:14  VSS 123
              **:
```

Figure 7A

```
Alignment
SEQ ID NO:22    DIVMTQAAFSNPVTLGTSASISCRSSKSLLHSNGITYLYWYLQKPGQSPQLLIYQMSNLA  60
SEQ ID NO:24    DIVMTQTPLSLPVTPGEPASISCRSSKSLLHSNGITYLYWYLQKPGQSPQLLIYQMSNLA  60
                ******:..:* *** *  .*****************************************

SEQ ID NO:22    SGVPDRFSSSGSGTDFTLRISRVEAEDVGVYYCAQNLELPYTFGGGTKLEIK  112
SEQ ID NO:24    SGVPDRFSGSGSGTDFTLKISRVEAEDVGVYYCAQNLELPYTFGGGTKVEIK  112
                ********.*********:****************************:***
```

Figure 7B

```
Alignment
SEQ ID NO:26    QVQVQQPGAELVKPGASVKLSCKASGYTFTSYWMHWVKQRPGQGLEWIGLINPSNARTNY  60
SEQ ID NO:28    QVQLQQSGAEVKKPGSSVKVSCKASGYTFTSYWMHWVRQAPGQGLEWMGLINPSNARTNY  60
                ***:**:.***:**:.***:*****************:*.*******:************

SEQ ID NO:26    NEKFNTKATLTVDKSSSTAYMQLSSLTSEDSAVYYCARGGDGDYFDYWGQGTTLTVSS   118
SEQ ID NO:28    NEKFNTRVTITADKSTSTAYMELSSLRSEDTAVYYCARGGDGDYFDYWGQGTTVTVSS   118
                ******:.*:*:***:*****:****:***:*****************************
```

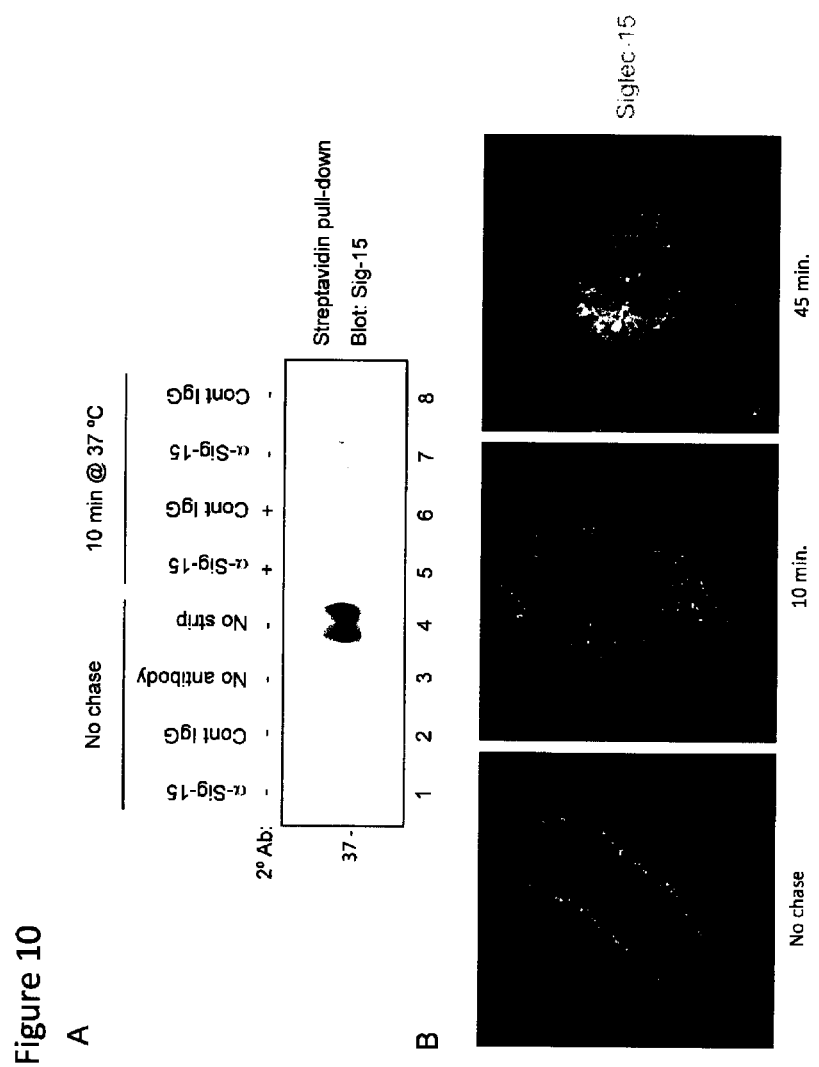

Figure 12
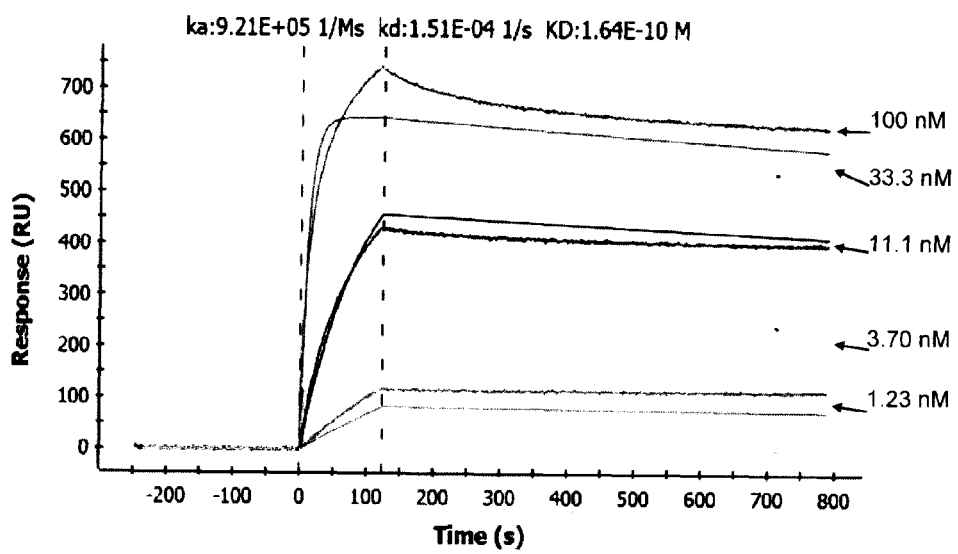
25E9 IgG1    $K_D$ = 0.164 nM
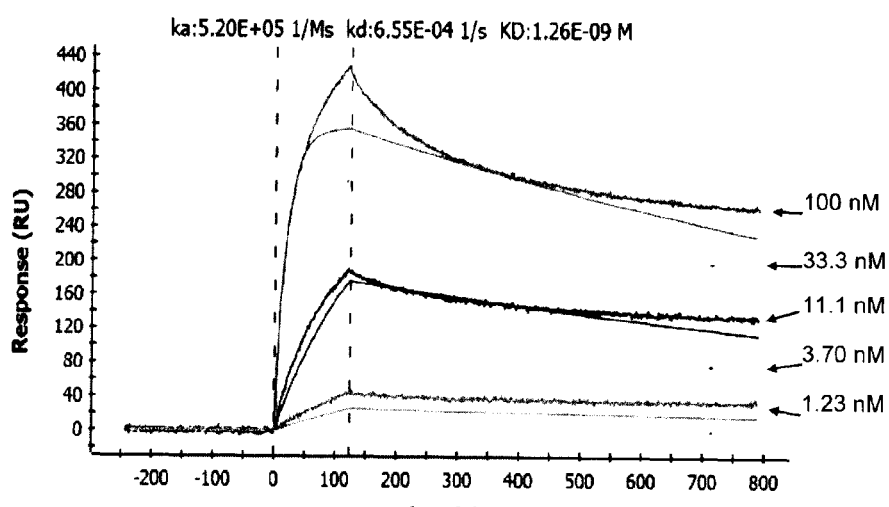
25E9 IgG2    $K_D$ = 1.26 nM

Figure 14A

Humanized 25D8 Light (Kappa) Chain

MVLQTQVFISLLLWISGAYGDIVMTQTPLSLPVTPGEPASISCRSSKSLLHSNGITYLYWYLQKPGQSPQLLIYQMSNLASGVPDRFSG SGSGTDFTLKISRVEAEDVGVYYCAQNLELPYTFGGGTKVEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPVTKSFNRGEC SEQ ID NO.:23

Humanized 25D8 Heavy (Igg1) Chain

MDWTWRILFLVAAATGTHAQVQLQQSGAEVKKPGSSVKVSCKASGYTFTSYWMHWVRQAPGQGLEWMGLINPSNARTNYNEKFNTRVTI TADKSTSTAYMELSSLRSEDTAVYYCARGGDGYFDYWGQGTTVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNGQPENNYKTTPPVLDSDGSFFLYSKLTVDKSRWQQGNVFSC SVMHEALHNHYTQKSLSLSPGK SEQ ID NO.:46

Chimeric 25D8 Light (Kappa) Chain

MVLQTQVFISLLLWISGAYGDIVMTQAAFSNPVTLGTSASISCRSSKSLLHSNGITYLYWYLQKPGQSPQLLIYQMSNLASGVPDRFSS SGSGTDFTLRISRVEAEDVGVYYCAQNLELPYTFGGGTKLEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPVTKSFNRGEC SEQ ID NO.:21

Chimeric 25D8 Heavy (Igg1) Chain

MDWTWRILFLVAAATGTHAQVQVQQPGAELVKPGASVKLSCKASGYTFTSYWMHWVKQRPGQGLEWIGLINPSNARTNYNEKFNTKATL TVDKSSSTAYMQLSSLTSEDSAVYYCARGGDGYFDYWGQGTTLTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNGQPENNYKTTPPVLDSDGSFFLYSKLTVDKSRWQQGNVFSC SVMHEALHNHYTQKSLSLSPGK SEQ ID NO.:45

Figure 14B

Humanized 25E9 Light (Kappa) Chain (Variant 1)

MVLQTQVFISLLLMISGAYGDIVMTQSPLSLPVTPGEPASISCRSTKSLLHSNGNTYLYWYLQKPGQSPQLLIYRMSNLASGVPDRFSG
SGSGTDFTLKISRVEAEDVGVYYCMQHLEYPFTFGGGTKVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC                    SEQ ID NO.:7

Humanized 25E9 Heavy (Igg1) Chain (Variant 1)

MDWTWRILFLVAAATGTHAEIQLQQSGAEVKKPGSSVKVSCKASGYTFTDYDMHWVRQAPGQGLEWMGTIDPETGGTAYNQKFKGRVTI
TADKSTSTAYMELSSLRSEDTAVYYCTSFYYTSNYDVGFAYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVLDSDGSFFLYSKLTVDKSRWQQG
NVFSCSVMHEALHNHYTQKSLSLSPGK                                                      SEQ ID NO.:13

Chimeric 25E9 Light (Kappa) Chain

MVLQTQVFISLLLMISGAYGDIVMTQAAPSVPVTPGESVSISCRSTKSLLHSNGNTYLYWFLQRPGQSPQLLIYRMSNLASGVPDRFSG
SGSGTAFTLRISRVEAEDVGVYYCMQHLEYPFTFGGGTKLEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC                    SEQ ID NO.:5

Chimeric 25E9 Heavy (Igg1) Chain

MDWTWRILFLVAAATGTHAEIQLQQSGVELVRPGASVTLSCKASGYTFTDYDMHWVKQTPVHGLEWIGTIDPETGGTAYNQKFKGKATL
TADRSSTAYMELSSLISEDSAVYYCTSFYYTSNYDVGFAYWGQGTLVTVSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLDSDGSFFLYSKLTVDKSRWQQGN
VFSCSVMHEALHNHYTQKSLSLSPGK                                                       SEQ ID NO.:11

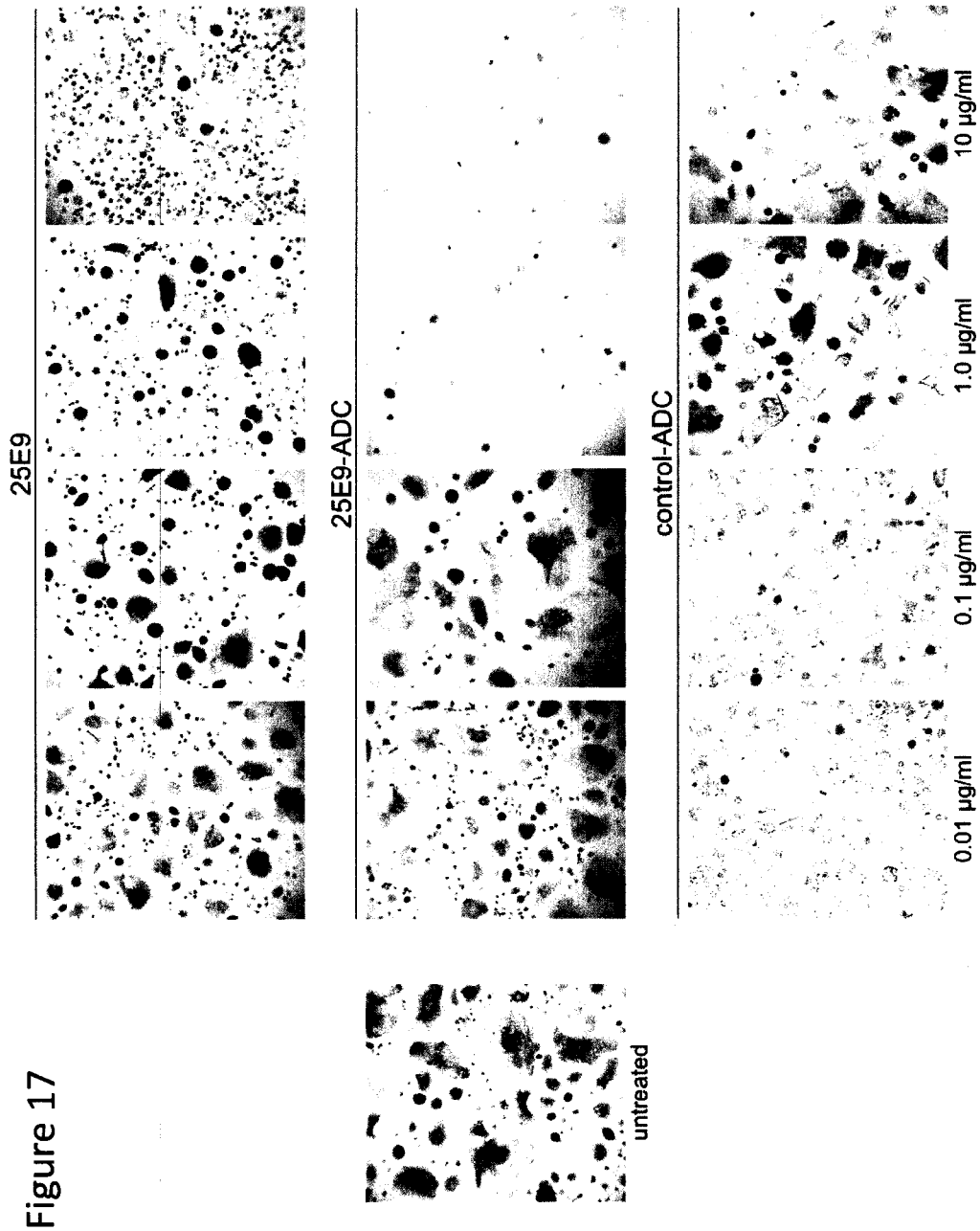

ANTI-SIGLEC-15 ANTIBODIES

PRIORITY CLAIM

This patent application is a national stage filing under 35 U.S.C. §371 of international application No. PCT/CA2013/000646 filed on Jul. 17, 2013, which claimed priority to U.S. provisional application No. 61/673,442 filed Jul. 19, 2012, U.S. provisional application No. 61/777,049 filed on Mar. 12, 2013 and U.S. provisional application No. 61/810,415 filed on Apr. 10, 2013. The entire contents of each of these priority applications are incorporated herein by reference.

SEQUENCE LISTING

In accordance with 37 C.F.R. §1,52(e)(5), a Sequence Listing in the form of a text file (entitled "Sequence Listing", created on Dec. 9, 2014 and of 168 kilobytes) is incorporated herein by reference in its entirety.

FIELD OF THE INVENTION

The present invention relates to antibodies and antigen binding fragments thereof that specifically bind to Siglec-15. The present invention particularly relates to anti-Siglec-15 antibodies adapted for administration to human and/or anti-Siglec-15 antibodies comprising amino acids of a human IgG1 constant region. The present invention also relates to the use of anti-Siglec-15 antibodies for treatment and/or diagnosis of diseases or conditions.

The antibodies of the present invention may be used, for example, to inhibit the activity or function of Siglec-15 or to deliver therapeutic agents to cells expressing the protein.

BACKGROUND OF THE INVENTION

Bone is a dynamic connective tissue comprised of functionally distinct cell populations required to support the structural, mechanical and biochemical integrity of bone and the human body's mineral homeostasis. The principal cell types involved include, osteoblasts responsible for bone formation and maintaining bone mass, and osteoclasts responsible for bone resorption. Osteoblasts and osteoclasts function in a dynamic process termed bone remodelling. The development and proliferation of these cells from their progenitors is governed by networks of growth factors and cytokines produced in the bone microenvironment as well as by systemic hormones. Bone remodelling is ongoing throughout the lifetime of the individual and is necessary for the maintenance of healthy bone tissue and mineral homeostasis. The process remains largely in equilibrium and is governed by a complex interplay of systemic hormones, peptides and downstream signalling pathway proteins, local transcription factors, cytokines, growth factors and matrix remodelling genes.

An interference or imbalance arising in the bone remodelling process can produce skeletal disease, with the most common skeletal disorders characterized by a net decrease in bone mass. A primary cause of this reduction in bone mass is an increase in osteoclast number and/or activity. The most common of such disease, and perhaps the best known, is osteoporosis occurring particularly in women after the onset of menopause. In fact osteoporosis is the most significant underlying cause of skeletal fractures in late middle-aged and elderly women. While estrogen deficiency has been strongly implicated as a factor in postmenopausal osteoporosis, there is longstanding evidence that remodelling is a locally controlled process being that it takes place in discrete packets throughout the skeleton as first described by Frost over forty years ago (Frost H. M. 1964).

Since bone remodelling takes place in discrete packets, locally produced hormones and enzymes may be more important than systemic hormones for the initiation of bone resorption and the normal remodelling process. Such local control is mediated by osteoblasts and osteoclasts in the microenvironment in which they operate. For example, osteoclasts attach to the bone matrix and form a separate compartment between themselves and the bone surface delimited by a sealing zone formed by a ring of actin surrounding the ruffled border. Multiple small vesicles transport enzymes toward the bone matrix and internalize partially digested bone matrix. The microenvironment within the sealing zone is rich with the presence of lysosomal enzymes and is highly acidic compared to the normal physiological pH of the body. The ruffled border membrane also expresses RANK, the receptor for RANKL, and macrophage-colony stimulating factor (MCSF) receptor, both of which are responsible for osteoclast differentiation, as well as the calcitonin receptor capable of rapidly inactivating the osteoclast (Baron, R. 2003).

In a complex pattern of inhibition and stimulation, growth hormone, insulin-like growth factor-1, the sex steroids, thyroid hormone, calciotrophic hormones such as PTH and prostaglandin E2, various cytokines, such as interleukin-1 beta, interleukin-6, and tumor necrosis factor-alpha, and 1,25-dihydroxyvitamin D (calcitriol) act coordinately in the bone remodelling process (Jilka et al. 1992; Poli et al. 1994; Srivastava et al. 1998; de Vemejoul 1996).

Thus, it stands to reason that the unique local environments created by these specialized cells is due to the expression of either unique genetic sequences not expressed in other tissues and/or splice variants of polynucleotides and polypeptides expressed in other tissues. The isolation and identification of polynucleotides, polypeptides and their variants and derivatives specific to osteoclast activity may permit a clearer understanding of the remodelling process and offer tissue specific therapeutic targets for the treatment of disease states related to bone remodelling.

Many diseases linked to bone remodelling are poorly understood, generally untreatable or treatable only to a limited extent. For example, osteoarthritis is difficult to treat as there is no cure and treatment focuses on relieving pain and preventing the affected joint from becoming deformed. Non-steroidal anti-inflammatory drugs (NSAIDs) are generally used to relieve pain.

Another example is osteoporosis where the only current medications approved by the FDA for use in the United States are the anti-resorptive agents that prevent bone breakdown. Estrogen replacement therapy is one example of an anti-resorptive agent. Others include alendronate (Fosamax—a biphosphonate anti-resorptive), risedronate (Actonel—a bisphosphonate anti-resorptive), raloxifene (Evista—selective estrogen receptor modulator (SERM)), calcitonin (Calcimar—a hormone), and parathyroid hormone/teriparatide (Forteo—a synthetic version of the human hormone, parathyroid hormone, which helps to regulate calcium metabolism).

Bisphosphonates such as alendronate and risedronate bind permanently to the surface of bone and interfere with osteoclast activity. This allows the osteoblasts to outpace the rate of resorption. The most common side effects are nausea, abdominal pain and loose bowel movements. However, alendronate is reported to also cause irritation and inflammation of the esophagus, and in some cases, ulcers of the esophagus. Risedronate is chemically different from alendronate and has less likelihood of causing esophagus irritation. However, certain foods, calcium, iron supplements, vitamins and minerals, or antacids containing calcium, magnesium, or aluminum can reduce the absorption of risedronate, thereby resulting in loss of effectiveness.

The most common side effect of Raloxifen and other SERMS (such as Tamoxifen) are hot flashes. However, Raloxifene and other hormone replacement therapies have been shown to increase the risk of blood clots, including deep vein thrombosis and pulmonary embolism, cardiovascular disease and cancer.

Calcitonin is not as effective in increasing bone density and strengthening bone as estrogen and the other antiresorptive agents. Common side effects of either injected or nasal spray calcitonin are nausea and flushing. Patients can develop nasal irritations, a runny nose, or nosebleeds. Injectable calcitonin can cause local skin redness at the site of injection, skin rash, and flushing.

A situation demonstrative of the link between several disorders or disease states involving bone remodelling is that of the use of etidronate (Didronel) first approved by the FDA to treat Paget's disease. Paget's disease is a bone disease characterized by a disorderly and accelerated remodelling of the bone, leading to bone weakness and pain. Didronel has been used 'off-label' and in some studies shown to increase bone density in postmenopausal women with established osteoporosis. It has also been found effective in preventing bone loss in patients requiring long-term steroid medications (such as Prednisone or Cortisone). However, high dose or continuous use of Didronel can cause another bone disease called osteomalacia. Like osteoporosis, osteomalacia can lead to weak bones with increased risk of fractures. Because of osteomalacia concerns and lack of enough studies yet regarding reduction in the rate of bone fractures, the United States FDA has not approved Didronel for the treatment of osteoporosis.

Osteoporosis therapy has been largely focused on antiresorptive drugs that reduce the rate of bone loss but emerging therapies show promise in increasing bone mineral density instead of merely maintaining it or slowing its deterioration. The osteoporosis early stage pipeline consists largely of drug candidates in new therapeutic classes, in particular cathepsin K inhibitors, osteoprotegerin and calcilytics as well as novel bisphosphonates. Some of these are examples where novel drugs exploiting genomics programs are being developed based on a deeper understanding of bone biology and have the potential to change the face of treatment of bone disorders in the long term.

The present invention particularly relates to anti-Siglec-15 antibodies adapted for administration to human. The present invention also particularly relates to anti-Siglec-15 antibodies comprising amino acids of a human IgG1 constant region (e.g., including humanized, chimeric or non-humanized antibodies). In some instances, the antibodies and antigen binding fragments of the present invention may bind to an epitope which is unique to a human Siglec-15 protein and which is not found in a corresponding Siglec-15 protein of other species (e.g., not found in Siglec-15 orthologs or putative orthologs). In other instances, the antibodies and antigen binding fragments of the present invention may bind to an epitope that is common to a human Siglec-15 protein and a mouse Siglec-15 protein. Yet in other instances, the antibodies and antigen binding fragments of the present invention may bind to an epitope that is common to human Siglec-15 and other orthologs or putative orthologs (see for example, Angata et al., 2007).

The present invention describes the use of antibodies specific for Siglec-15 for the diagnosis, prognosis, and treatment (including prevention) of cancer or bone loss (e.g., severe or excessive bone loss associated with bone-related disease or associated with an increase in osteoclast differentiation or activity). In particular, the present invention relates to the use of anti-Siglec-15 antibodies for inhibiting the differentiation of osteoclasts and/or for inhibiting bone resorption. The present invention also relates to the use of these antibodies for diagnosis, prevention and treatment of various other types of diseases where the activity of osteoclasts is increased.

Sialic-acid-binding immunoglobulin-like lectins (Siglecs) are members of the immunoglobulin (Ig) superfamily that have the ability to interact with sialic acids (McMillan and Crocker, 2008; Crocker et al., 2007). There are several Siglec family members that all share specific structural features, in particular, displaying an amino-terminal V-set Ig domain that binds to sialic acid and a variable number of C2-set Ig domains. These membrane receptors are generally expressed in highly specific manners and many of the family members are expressed in hematopoietic cells (McMillan and Crocker, 2008). These proteins are thought to promote cell-cell interactions, mediate signalling, and regulate immune functions through the recognition of glycans (Crocker et al., 2007). Sialic acids are nine-carbon sugars typically located at the ends of complex glycoconjugates on the surface of cells. They can be attached to a wide variety of proteins and lipids (McMillan and Crocker, 2008).

Siglec-15 is one of the most recently described Siglec family members that have a high homology to Siglec-14 (Angata et al., 2007). These authors reported that it preferentially binds to sialyl Tn structure and that it interacts with DAP12 and DAP10. The functional significance of these interactions is not known but it was proposed that Siglec-15 probably harbors an activating function (Angata et al., 2007). Despite these preliminary insights into a potential role in mammals of Siglec-15, important advances in the understanding of the biological function of the protein were contributed when the sequence was identified as part of a screen to discover novel regulators of osteoclast differentiation (Sooknanan et al. 2007). In this patent application, it was revealed that attenuation of the Siglec-15 transcript by RNA interference in a mouse model of osteoclastogenesis resulted in significant reduction of differentiation of precursors in response to RANKL treatment. Similar results were disclosed in human osteoclasts. Furthermore, the studies presented in this disclosure also showed that the localization of Siglec-15 at the cell membrane was necessary for its function in osteoclast differentiation. Furthermore, a recent publication showed that the presence of sialic acid at the end of surface glycoconjugates was required for proper osteoclast differentiation and were probably important for the fusion of osteoclast precursor cells (Takahata et al., 2007). This last observation creates a direct functional link between sialic acid binding and the expression of Siglec-15 in differentiating osteoclasts and strongly suggested that Siglec-15 plays a role in the early differentiation program of osteoclast precursors.

Thus, the expression profile of Siglec-15, its strong inducibility during osteoclast differentiation, its localization at the surface of the membrane, and its structural features all contribute to the feasibility of targeting this protein at the cell surface with monoclonal antibodies. The only other example of monoclonal antibody-based therapy that target osteoclasts is denosumab, a human monoclonal antibody that is specific for RANKL (Ellis et al. 2008). The present invention relates to the use of anti-Siglec-15 antibodies or antigen binding fragments as blockers of osteoclast differentiation and/or bone resorption, in the detection or treatment of bone loss, especially in the context of bone-related diseases or in the context of increased osteoclast differentiation or activity. The present invention also relates to the use of antibodies or antigen binding fragments in the detection or treatment of cancer.

SUMMARY OF THE INVENTION

This invention relates to antibodies and antigen binding fragments as well as kits useful for the treatment (including prevention), detection and diagnosis of bone loss or cancer. Humanized anti-Siglec-15 antibodies are particularly contemplated.

The antibodies or antigen binding fragments of the present invention may be useful for the treatment of bone loss or bone resorption.

The antibodies and antigen binding fragments may also be particularly be useful for detection of differentiated osteoclast or osteoclast undergoing differentiation. The antibodies and antigen binding fragments may additionally be useful for detection of and diagnosis of bone loss. The antibodies or antigen binding fragment of the present invention may also be useful for treating bone loss.

The antibodies and antigen binding fragments may also be particularly useful for detection or diagnosis of cancer cells expressing Siglec-15 and particularly cancers having a high expression of Siglec-15. The antibodies and antigen binding fragments may further be particularly be useful for detection of ovarian cancer, renal cancer, cancer of the central nervous system, prostate cancer, melanoma, breast cancer, lung cancer or colon cancer. The antibodies or antigen binding fragment of the present invention may further be useful for treating ovarian cancer, renal cancer, cancer of the central nervous system, prostate cancer, melanoma, breast cancer, lung cancer or colon cancer.

The antibodies or antigen-binding fragment of the present invention may bind to amino acids 20 to 259 of Siglec-15 (SEQ ID NO.:2) or to a corresponding region of a Siglec-15 variant (e.g., a variant having at least 80% sequence identity with SEQ ID NO.:12 including, for example, SEQ ID NO.:4). More particularly the antibodies or antigen-binding fragment of the present invention may bind to amino acids 49 to 165 of Siglec-15 (SEQ ID NO.:2) or to a corresponding region of a Siglec-15 variant (e.g., a variant having at least 80% sequence identity with SEQ ID NO.:12 including, for example, SEQ ID NO.:4). The antibodies or antigen binding fragment of the present invention include those which may bind to an epitope unique to human Siglec-15 including, for example, an epitope comprising the arginine located at position 99 (R99) of SEQ ID NO.:2.

The antibody or antigen binding fragment may be capable of inhibiting an osteoclast differentiation activity of the polypeptide and/or bone resorption.

It is to be understood herein that antibodies that preferably bind human Siglec-15 over mouse Siglec-15 may be more effective at inhibiting differentiation or activity of human osteoclasts than mouse osteoclasts. An antibody that binds an epitope found in human Siglec-15 and not in mouse Siglec-15, may inhibit differentiation or activity of human osteoclasts and not that of mouse osteoclasts. The Siglec-15 protein of cynomolgus monkeys is very similar to that of the human Siglec-15 amino acids. Potency of anti-Siglec-15 antibodies may thus be tested in monkeys or using cells isolated from monkeys. Therefore, potency assays may be adapted depending on the specificity of the antibody (e.g., towards human, monkey and/or mouse Siglec-15).

In accordance with an embodiment of the invention, the antibody or antigen binding fragment may interfere with the ability of the polypeptide to promote osteoclast differentiation and/or bone resorption. In accordance with another embodiment of the invention, the antibody or antigen binding fragment may interfere with the ability of the polypeptide to promote tumor growth.

The antibody or antigen binding fragment of the present invention may be capable of interfering with (inhibiting) differentiation of an osteoclast precursor cell into a differentiated osteoclast.

In accordance with the present invention, the antibody or antigen binding fragment may be, for example, a polyclonal antibody, a monoclonal antibody, a chimeric antibody, a humanized antibody, a human antibody, a hybrid antibody or a fragment thereof.

Particular examples of antibodies encompassed by the present invention include antibodies having at least one immunoglobulin chain (light chain or heavy chain) comprising a humanized variable domain while the other variable domains may be non-humanized (e.g., mouse variable domain) resulting in a hybrid antibody. Other example of antibodies encompassed by the present invention includes antibodies having heavy and light immunoglobulin chains comprising a humanized variable domain.

Other particular embodiments of the present invention include a humanized antibody where non-human amino acids (e.g., one or more amino acids from the mouse antibody counterpart) have been reintroduced.

The present invention therefore provides a humanized antibody of a non-human parent antibody (e.g., mouse antibody) that is capable of specific binding to Siglec-15.

In one embodiment, a hybrid antibody or fragment thereof may comprise, for example, a light chain variable region of a non-human antibody and a heavy chain variable region of a humanized antibody.

In another embodiment, a hybrid antibody or fragment thereof may comprise, for example, a heavy chain variable region of a non-human antibody and a light chain variable region of a humanized antibody.

A humanized or hybrid antibody of the present invention may comprise a heavy chain variable region which may include non-human complementarity determining region amino acid residues and human framework region amino acid residues of a natural human antibody and a complementary light chain.

A humanized or hybrid antibody of the present invention may comprise a light chain variable region which may include non-human complementarity determining region amino acid residues and human framework region amino acid residues of a natural human antibody and a complementary heavy chain.

The term "hybrid antibody" refers to an antibody comprising at least one humanized or human heavy or light chain variable region (having affinity for Siglec-15) and at least one non-human heavy or light chain variable region (e.g. from a mouse, rat, rabbit).

The natural human antibody that is selected for humanization of the non-human parent antibody may comprise a variable region having a three-dimensional structure similar to that of (superimposable to) a (modeled) variable region of the non-human parent antibody. As such, the humanized or hybrid antibody has a greater chance of having a three-dimensional structure similar to that of the non-human parent antibody.

In accordance with the present invention, the human framework region amino acid residues of the humanized or hybrid antibody light chain are from a natural human antibody light chain framework region. The light chain framework region of the natural human antibody selected for humanization purposes, may have, for example, at least 70% identity with a light chain framework region of the non-human parent antibody. Preferably, the natural human antibody selected for humanization purposes may have the same or substantially the same number of amino acids in its light chain complementarity determining region to that of a light chain complementarity determining region of the non-human parent antibody.

In other embodiments of the invention, the human framework region amino acid residues of the humanized or hybrid antibody light chain are from a natural human antibody light chain framework region having at least 70, 75, 80, 85% identity (or more) with the light chain framework region of the non-human parent antibody.

Also in accordance with the present invention, the human framework region amino acid residues of the humanized or hybrid antibody heavy chain are from a natural human antibody heavy chain framework region having at least 70% identity with a heavy chain framework region of the non-human parent antibody. Preferably, the natural human antibody selected for humanization purposes may have the same or substantially the same number of amino acids in its heavy chain complementarity determining region to that of a heavy chain complementarity determining region of the non-human parent antibody.

In other embodiments of the invention, the human framework region amino acid residues of the humanized or hybrid antibody heavy chain are from a natural human antibody heavy chain framework region having at least 70, 75, 80, 85% identity with the heavy chain framework region of the non-human parent antibody.

In an embodiment of the invention, the heavy chain variable region of the humanized or hybrid antibody may thus comprise at least one non-human complementarity determining region.

Alternatively, in other embodiments of the invention, the heavy chain variable region of the humanized or hybrid antibody may comprise at least two non-human complementarity determining regions or even three non-human complementarity determining regions.

In an additional embodiment of the invention, the light chain variable region may comprise at least one non-human complementarity determining region.

Alternatively, in yet additional embodiments of the invention, the light chain variable region comprise at least two non-human complementarity determining regions or even three non-human complementarity determining regions.

The humanized antibody may thus advantageously comprise all six CDRs of the non-human antibody. In the case of a divalent humanized antibody, all twelve CDRs may be from the non-human antibody.

The constant region or fragment thereof may be from an IgG1, IgG2, IgG3, or IgG4 and especially from a human IgG1, IgG2, IgG3, or IgG4. In a more specific embodiment, the constant region may be from an IgG2 (e.g., human IgG2). In a preferred embodiment the constant region may be from an IgG1 (e.g., human IgG1).

The constant region of the light chain may be a lambda constant region or a kappa constant region.

Antigen binding fragments which may be particularly useful include, for example, a FV (scFv), a Fab, a Fab' or a (Fab')$_2$.

The antibody or antigen binding fragment may be produced in or from an isolated mammalian cell (other than an hybridoma cell) or in an hybridoma cell. An exemplary embodiment of an isolated mammalian cell is a human cell.

In an aspect of the invention, the antibody or antigen binding fragment of the present invention may interfere (inhibit) with the differentiation of a human osteoclast precursor cell into a differentiated human osteoclast.

In an exemplary embodiment, the antibody or antigen binding fragment of the present invention may interfere (inhibit) with the differentiation of a primary human osteoclast precursor cell into a differentiated human osteoclast.

The antibodies and antigen binding fragments of the present invention may also be used to generally target cells expressing or overexpressing Siglec-15, including bone cells and breast, colon, lung, ovarian, prostate, and renal cancer cells as well as melanoma cells and cancer cells of the central nervous system.

More particularly, the antibodies and antigen binding fragments may be used to target osteoclasts cells undergoing differentiation.

The present invention provides in one aspect thereof, an antibody or antigen binding fragment (e.g., isolated or substantially purified) which may be capable of specific binding to SEQ ID NO:2.

As such, the present invention encompasses diagnostic and/or therapeutic antibodies or antigen binding fragments having specificity for SEQ ID NO:2. Also encompassed by the present invention are antibodies or antigen binding fragments having the same epitope specificity as the antibody of the present invention. A candidate antibody may be identified by determining whether it will bind to the epitope to which the antibodies described herein binds and/or by performing competition assays with antibodies or antigen binding fragments known to bind to the epitope.

Therefore, another aspect the present invention provides an isolated antibody or antigen binding fragment capable of competing with the antibody or antigen binding fragment described herein.

In further aspects, the present invention provides method of treatment and method of detection using the antibody or antigen binding fragment of the present invention.

The term "antibody" refers to intact antibody, monoclonal or polyclonal antibodies. The term "antibody" also encompasses, multispecific antibodies such as bispecific antibodies. Human antibodies are usually made of two light chains and two heavy chains each comprising variable regions and constant regions. The light chain variable region comprises 3 CDRs, identified herein as CDRL1, CDRL2 and CDRL3 flanked by framework regions. The heavy chain variable region comprises 3 CDRs, identified herein as CDRH1, CDRH2 and CDRH3 flanked by framework regions.

The term "antigen-binding fragment", as used herein, refers to one or more fragments of an antibody that retain the ability to bind to an antigen (e.g., SEQ ID NO:2 or variants thereof). It has been shown that the antigen-binding function of an antibody can be performed by fragments of an intact antibody. Examples of binding fragments encompassed within the term "antigen-binding fragment" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR), e.g., $V_H$ CDR3. Furthermore, although the two domains of the Fv fragment, $V_L$ and $V_H$, are coded for by separate genes, they can be joined, using recombinant methods, by a synthetic linker that enables them to be made as a single polypeptide chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. Furthermore, the antigen-binding fragments include binding-domain immunoglobulin fusion proteins comprising (i) a binding domain polypeptide (such as a heavy chain variable region, a light chain variable region, or a heavy chain variable region fused to a light chain variable region via a linker peptide) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The hinge region may be modified by replacing one or more cysteine residues with serine residues so as to prevent dimerization. Such binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

A typical antigen binding site is comprised of the variable regions formed by the pairing of a light chain immunoglobulin and a heavy chain immunoglobulin. The structure of the antibody variable regions is very consistent and exhibits very similar structures. These variable regions are typically comprised of relatively homologous framework regions (FR) interspaced with three hypervariable regions termed Complementarity Determining Regions (CDRs). The overall binding activity of the antigen binding fragment is often dictated by the sequence of the CDRs. The FRs often play a role in the proper positioning and alignment in three dimensions of the CDRs for optimal antigen binding.

Antibodies and/or antigen binding fragments of the present invention may originate, for example, from a mouse, a rat or any other mammal or from other sources such as through recombinant DNA technologies.

The antibodies or antigen binding fragments may have therapeutic uses in the treatment of bone loss.

Hormone ablative therapy (treatment with drugs that stop the production of specific hormones) increases the risk of fractures due to bone loss. Adjuvant hormonal therapies for women with breast cancer involve antiestrogens (e.g., tamoxifen) and aromatase inhibitors, which have been shown to accelerate bone loss and increase fracture risk due to estrogen suppression. Additionally, many men with prostate cancer are treated with androgen deprivation therapy (ADT) (e.g., gonadotropin-releasing hormone [GnRH] agonists) as their cancer progresses. GnRH agonists inhibit production of testosterone, which acts as a growth factor for prostate cancer cells. However, this treatment also leads to a decrease in bone mass, thus increasing the risk of fractures due to osteoporosis. Therefore, the antibodies or antigen binding fragment of the present invention may have therapeutic uses in the treatment of bone loss associated with cancer treatment.

The antibodies or antigen binding fragments may also have therapeutic uses in the treatment of cancer. In an exemplary embodiment, the antibodies or fragments may have therapeutic uses in cancer treatment-induced bone loss. In another exemplary embodiment, the antibodies or fragments may have therapeutic uses in bone loss associated with bone diseases such as conditions where there is an increase in the bone degradative activity of osteoclasts. In certain instances, the antibodies or antigen binding fragments may interact with cells that express SEQ ID NO:2 and induce an immunological reaction by mediating ADCC. In other instances, the antibodies and fragments may block the interaction of SEQ ID NO:2 with its natural ligands. In yet other instances, the antibodies and fragment may induce internalization of the protein and/or its degradation.

The antibody or antigen binding fragment of the invention may be administered (e.g., concurrently, sequentially) with another drug useful for the treatment of bone loss, bone resorption or useful for the treatment of a disease associated with bone loss or bone resorption.

Antibodies and antigen binding fragment capable of inhibiting bone loss have been described in international application Nos. PCT/CA2010/001586 published under No. WO2011/041894 on Apr. 14, 2011, and PCT/CA2007/000210 published under No. WO2007/093042 on Feb. 13, 2007, the entire content of which is incorporated herein by reference.

Antibody Conjugates

Although it is not always necessary, for detection or therapeutic purposes, the antibody or antigen binding fragment of the present invention may be conjugated with a detectable moiety (i.e., for detection or diagnostic purposes) or with a therapeutic moiety (for therapeutic purposes).

For detection purposes, an unconjugated antibody (primary antibody) may be used for binding to the antigen and a secondary antibody carrying a detectable moiety and capable of binding to the primary antibody may be added. However, as indicated above, the anti-SIGLEC 15 antibody may be conjugated with a detectable label and as such a secondary antibody may not be necessary, A "detectable moiety" is a moiety detectable by spectroscopic, photochemical, biochemical, immunochemical, chemical and/or other physical means. A detectable moiety may be coupled either directly and/or indirectly (for example via a linkage, such as, without limitation, a DOTA or NHS linkage) to antibodies and antigen binding fragments thereof of the present invention using methods well known in the art. A wide variety of detectable moieties may be used, with the choice depending on the sensitivity required, ease of conjugation, stability requirements and available instrumentation. A suitable detectable moiety include, but is not limited to, a fluorescent label, a radioactive label (for example, without limitation, 125I, $In^{111}$, $Tc^{99}$, $I^{131}$ and including positron emitting isotopes for PET scanner etc), a nuclear magnetic resonance active label, a luminescent label, a chemiluminescent label, a chromophore label, an enzyme label (for example and without limitation horseradish peroxidase, alkaline phosphatase, etc.), quantum dots and/or a nanoparticle. Detectable moiety may cause and/or produce a detectable signal thereby allowing for a signal from the detectable moiety to be detected.

In another exemplary embodiment of the invention, the antibody or antigen binding fragment thereof may be coupled (modified) with a therapeutic moiety (e.g., drug, cytotoxic moiety).

In some instances, for therapeutic purposes, an unconjugated antibody may by itself be capable of sequestering the antigen, may block an important interaction between the antigen and another binding partner, may recruit effector cells, etc. However, as indicated above, the antibody may be conjugated with a therapeutic moiety.

In an exemplary embodiment, the antibodies and antigen binding fragments may comprise a chemotherapeutic or cytotoxic agent. For example, the antibody and antigen binding fragments may be conjugated to the chemotherapeutic or cytotoxic agent. Such chemotherapeutic or cytotoxic agents include, but are not limited to, Yttrium-90, Scandium-47, Rhenium-186, Iodine-131, Iodine-125, and many others recognized by those skilled in the art (e.g., lutetium (e.g., $Lu^{177}$), bismuth (e.g., $Bi^{213}$), copper (e.g., $Cu^{67}$)). In other instances, the chemotherapeutic or cytotoxic agent may be comprised of, among others known to those skilled in the art, 5-fluorouracil, adriamycin, irinotecan, auristatins, taxanes, pseudomonas endotoxin, ricin, calicheamicin and other toxins. Exemplary cytotoxic agents may particularly comprise an agent, which is capable of killing non-proliferating cells.

The antibody or antigen binding fragment of the present invention may especially be conjugated with agents targeting DNA. Exemplary embodiments of agents targeting DNA includes for example, alkylating agents such as duocarmycins and duocarmycin derivatives such as adozelesin, bizelesin, carzelesin etc. Other exemplary embodiments of agents targeting DNA includes for example, calicheamicin, esperamicin and derivatives (see compounds disclosed for example in U.S. Pat. Nos. 5,264,586, 5,108,192, 4,970,198, 5,037,651, 5,079,233, 4,675,187, 4,539,203, 4,554,162, 4,837,206 and US2007213511, the entire content of each document is incorporated herein by reference).

A particular embodiment of the invention includes for example, an antibody or antigen binding fragment disclosed herein conjugated with duocarmycin. Another particular embodiment of the invention includes for example, an antibody or antigen binding fragment disclosed herein conjugated with calicheamicin.

Alternatively, in order to carry out the methods of the present invention and as known in the art, the antibody or antigen binding fragment of the present invention (conjugated or not) may be used in combination with a second molecule (e.g., a secondary antibody, etc.) which is able to specifically bind to the antibody or antigen binding fragment of the present invention and which may carry a desirable detectable, diagnostic or therapeutic moiety.

Pharmaceutical Compositions of the Antibodies and their Use

Pharmaceutical compositions of the antibodies (conjugated or not) are also encompassed by the present invention. The pharmaceutical composition may comprise an antibody or an antigen binding fragment and may also contain a pharmaceutically acceptable carrier.

Other aspects of the invention relate to a composition which may comprise the antibody or antigen binding fragment described herein and a carrier.

Yet other aspects of the invention relate to the use of the isolated antibody or antigen binding fragment described herein in the treatment or diagnosis of bone diseases or cancer.

In addition to the active ingredients, a pharmaceutical composition may contain pharmaceutically acceptable carriers comprising water, PBS, salt solutions, gelatins, oils, alcohols, and other excipients and auxiliaries that facilitate processing of the active compounds into preparations that may be used pharmaceutically. In other instances, such preparations may be sterilized.

As used herein, "pharmaceutical composition" usually comprises therapeutically effective amounts of the agent together with pharmaceutically acceptable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts). Solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions may influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal, oral, vaginal, rectal routes. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carrier" or "pharmaceutical carrier" are known in the art and include, but are not limited to, 0.01-0.1 M or 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's orfixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

For any compound, the therapeutically effective dose may be estimated initially either in cell culture assays or in animal models such as mice, rats, rabbits, dogs, or pigs. An animal model may also be used to determine the concentration range and route of administration. Such information may then be used to determine useful doses and routes for administration in humans. These techniques are well known to one skilled in the art and a therapeutically effective dose refers to that amount of active ingredient that ameliorates the symptoms or condition. Therapeutic efficacy and toxicity may be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the therapeutic compositions described above may be applied to any subject in need of such therapy, including, but not limited to, mammals such as dogs, cats, cows, horses, rabbits, monkeys, and humans.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

Pharmaceutical compositions of the present invention may further comprise for example, at least one drug member selected from the group consisting of bisphosphonates, active vitamin D3, calcitonin and derivatives thereof, hormone preparations such as estradiol, SERMs (selective estrogen receptor modulators), ipriflavone, vitamin K2 (menatetrenone), calcium preparations, PTH (parathyroid hormone) preparations, nonsteroidal anti-inflammatory agents, soluble TNF receptor preparations, anti-TNF-alpha antibodies or functional fragments of the antibodies, anti-PTHrP (parathyroid hormone-related protein) antibodies or functional fragments of the antibodies, IL-1 receptor antagonists, anti-IL-6 receptor antibodies or functional fragments of the antibodies, anti-RANKL antibodies or functional fragments of the antibodies and OCIF (osteoclastogenesis inhibitory factor).

The term "treatment" for purposes of this disclosure refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

The antibodies or antigen binding fragments may have therapeutic uses in the treatment of various bone loss or cancer. In an exemplary embodiment, the antibodies or fragments may have therapeutic uses in bone loss associated with bone diseases such as conditions where there is an increase in the bone degradative activity of osteoclasts.

In certain instances, the anti-Siglec-15 antibodies and fragments may interact with cells, such as osteoclasts or osteoclast precursors, that express Siglec-15. In certain instances, the antibodies or antigen binding fragments may interact with cells that express SEQ ID NO:2 and induce an immunological reaction by mediating ADCC. In other instances, the antibodies and fragments may block the interaction of SEQ ID NO:2 with its natural ligands.

The anti-Siglec-15 antibodies or antigen binding fragments may have therapeutic uses in the treatment of bone loss in the context of various bone-related diseases, including but not limited to osteoporosis, osteopenia, osteomalacia, hyperparathyroidism, hypothyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Turner's syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes. In the preferred embodiment, the antibodies and fragments have therapeutic uses in conditions where severe bone loss prevails, in particular metastatic cancer to the bone.

The anti-Siglec-15 antibodies and antigen binding fragments thereof may have therapeutic uses in the treatment of cancer or bone loss caused by or associated with various bone remodelling disorders. In particular, the anti-Siglec-15 antibodies and immunologically functional fragments therein have therapeutic uses in conditions where osteoclasts are hyperactive and contribute to the degradation of the bone surface. In certain instances, the anti-Siglec-15 antibodies and antigen binding fragment thereof may be administered concurrently in combination with other treatments given for the same condition. As such, the antibodies may be administered with anti-resorptives (e.g., bisphosphonates) that are known to those skilled in the art. Additionally, the antibodies may be administered with anti-mitotics (e.g., taxanes), platinum-based agents (e.g., cisplatin), DNA damaging agents (e.g. Doxorubicin), and other cytotoxic therapies that are known to those skilled in the art. In other instances, the anti-Siglec-15 antibodies and immunologically functional fragments therein may be administered with other therapeutic antibodies. These include, but are not limited to, antibodies that target RANKL, EGFR, CD-20, and Her2.

Further scope, applicability and advantages of the present invention will become apparent from the non-restrictive detailed description given hereinafter. It should be understood, however, that this detailed description, while indicating exemplary embodiments of the invention, is given by way of example only, with reference to the accompanying drawings.

BRIEF DESCRIPTION OF THE DRAWINGS

FIG. 2A. Sequence alignment of the mouse, humanized and selected human framework sequences for the variable light (VL) domain of the 25D8 antibody. The CDRs are highlighted in light grey and correspond to SEQ ID NOs. 53, 54 and 55.

FIG. 2B. Sequence alignment of the mouse, humanized and selected human framework sequences for the variable heavy (VH) domain of the 25D8 antibody. The CDRs are highlighted in light grey and correspond to SEQ ID NOs. 56, 57 and 58.

FIG. 3A. Sequence alignment of the mouse, humanized and selected human framework sequences for the variable light (VL) domain of the 25E9 antibody. The CDRs are highlighted in light grey and correspond to SEQ ID NOs. 47, 48 and 49.

FIG. 3B. Sequence alignment of the mouse, humanized and selected human framework sequences for the variable heavy (VH) domain of the 25E9 antibody. The CDRs are highlighted in light grey and correspond to SEQ ID NOs. 50, 51 and 52.

FIG. 4A. Assembled sequences of the humanized full-length IgG2 25D8 (SEQ ID NOs.:23 and 27) and chimeric full-length IgG2 (SEQ ID NOs.:21 and 25) 25D8 antibodies.

FIG. 4B. Assembled sequences of the humanized full-length IgG2 25E9 (SEQ ID NOs.:7 and 29) and chimeric full-length IgG2 25E9 (SEQ ID NOs.:5 and 30) antibodies.

FIG. 6A illustrates the alignment between 25E9 mouse light chain variable domain and 25E9 humanized light chain variable domain Variant 1. Alignment were done by using the ClustalW2 program; where "*" means that the residues in that column are identical in all sequences in the alignment, ":" means that conserved substitutions have been observed and "." means that semi-conserved substitutions are observed. (Larkin M. A., et al., (2007) ClustalW and ClustalX version 2. *Bioinformatics* 2007 23(21): 2947-2948). These alignments were used to generate the consensus sequences set forth in SEQ ID NOs.: 33, 34 and 35.

FIG. 6B illustrates the alignment between 25E9 mouse heavy chain variable domain and 25E9 humanized heavy chain variable domain Variant 1. Alignment were done by using the ClustalW2 program; where "*" means that the residues in that column are identical in all sequences in the alignment, ":" means that conserved substitutions have been observed and "." means that semi-conserved substitutions are observed. (Larkin M. A., et al., (2007) ClustalW and ClustalX version 2. *Bioinformatics* 2007 23(21): 2947-2948). These alignments were used to generate the consensus sequences set forth in SEQ ID NOs. 36, 37 and 38.

FIG. 7A illustrates the alignment between 25D8 mouse light chain variable domain and 25D8 humanized light chain variable domain. Alignment were done by using the ClustalW2 program; where "*" means that the residues in that column are identical in all sequences in the alignment, ":" means that conserved substitutions have been observed and "." means that semi-conserved substitutions are observed. (Larkin M. A., et al., (2007) ClustalW and ClustalX version 2. *Bioinformatics* 2007 23(21): 2947-2948). These alignments were used to generate the consensus sequences set forth in SEQ ID NOs.: 39, 40 and 41.

FIG. 7B illustrates the alignment between 25D8 mouse heavy chain variable domain and 25D8 humanized heavy chain variable domain. Alignment were done by using the ClustalW2 program; where "*" means that the residues in that column are identical in all sequences in the alignment, ":" means that conserved substitutions have been observed and "." means that semi-conserved substitutions are observed. (Larkin M. A., et al., (2007) ClustalW and ClustalX version 2. *Bioinformatics* 2007 23(21): 2947-2948). These alignments were used to generate the consensus sequences set forth in SEQ ID NOs.:42, 43 and 44.

FIG. 12. SPR chromatograms illustrating the differences in binding parameters between the humanized 25E9 L1H1 IgG1 (left panel) and the humanized 25E9 L1H1 IgG2 (right panel). Purified Fc-Siglec-15 was immobilized (150RU) and humanized 25E9 was injected at the indicated concentrations (100 nM, 33.3 nM, 11.1 nM, 3.70 nM and 1.23 nM). The curves were fit with a 1:1 ratio.

FIG. 14A. Assembled sequences of the humanized full-length IgG1 25D8 (SEQ ID NOs.:23 and 46) and chimeric full-length IgG1 25D8 (SEQ ID NO.: 21 and 45) antibodies.

FIG. 14B. Assembled sequences of the humanized full-length IgG1 25E9 (SEQ ID NOs:7 and 13) and chimeric full-length IgG1 25E9 (SEQ ID NOs.:5 and 11) antibodies.

FIG. 17 Shows images of TRAP stained osteoclasts to illustrate the cytotoxic effects of the 25E9-ADC against mature, multi-nucleated osteoclasts. The response is very different to the unconjugated 25E9, which strongly inhibits osteoclast activity without affecting their survival. A control-ADC has no effect against osteoclasts.

DETAILED DESCRIPTION OF THE INVENTION

Figure 1A:
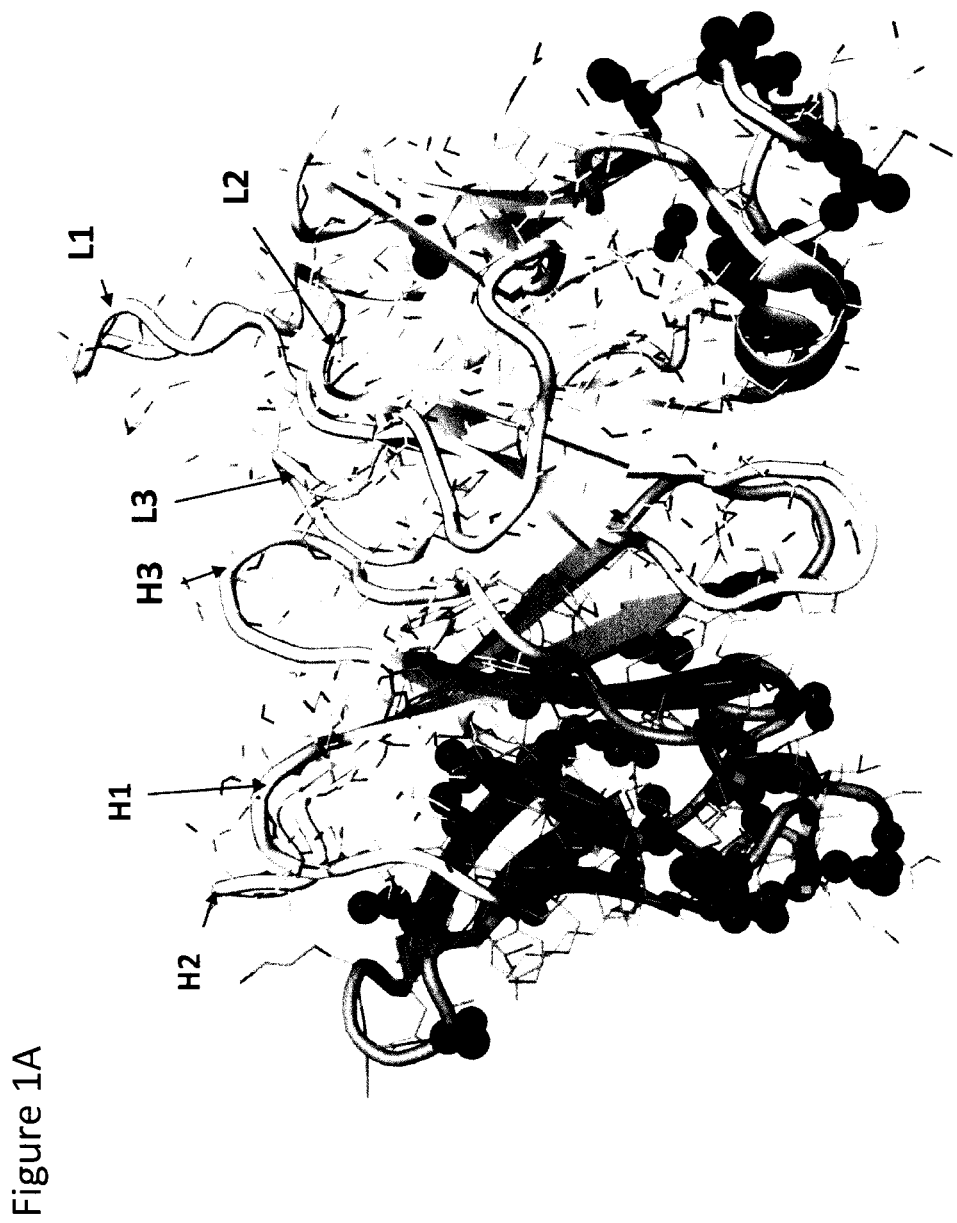
FIG. 1A. Molecular model of the murine 25D8 variable domain. CDR loops are indicated with arrows as L1, L2 and L3 in the light chain and H1, H2 and H3 in the heavy chain.

Variant antibodies or antigen binding fragments encompassed by the present invention are those, which may comprise an insertion, a deletion or an amino acid substitution (conservative or non-conservative). These variants may have at least one amino acid residue in its amino acid sequence removed and a different residue inserted in its place.

Sites of interest for substitutional mutagenesis include the hypervariable regions (CDRs), but modifications in the framework region or even in the constant region are also contemplated. Conservative substitutions may be made by exchanging an amino acid (of a CDR, variable chain, antibody, etc.) from one of the groups listed below (group 1 to 6) for another amino acid of the same group.

Generally, mutations in the CDRs may have a greater impact on the antigen binding activity of the antibody or antigen binding fragment than mutations in the framework region. Mutation in the framework region may be performed to increase the "humanness" of the antibody. Variant antibody or antigen binding fragments that are encompassed by the present invention are those which have a substantially identical antigen binding capacity (including similar, identical, or slightly less) to those presented herein or have a better antigen binding capacity than those presented herein.

Other exemplary embodiment of conservative substitutions are shown in Table 1A under the heading of "preferred substitutions". If such substitutions result in a undesired property, then more substantial changes, denominated "exemplary substitutions" in Table 1A, or as further described below in reference to amino acid classes, may be introduced and the products screened.

It is known in the art that variants may be generated by substitutional mutagenesis and retain the biological activity of the polypeptides of the present invention. These variants have at least one amino acid residue in the amino acid sequence removed and a different residue inserted in its place. For example, one site of interest for substitutional mutagenesis may include a site in which particular residues obtained from various species are identical. Examples of substitutions identified as "conservative substitutions" are shown in Table 1A. If such substitutions result in a change not desired, then other type of substitutions, denominated "exemplary substitutions" in Table 1A, or as further described herein in reference to amino acid classes, are introduced and the products screened.

Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(group 1) hydrophobic: norleucine, methionine (Met), Alanine (Ala), Valine (Val), Leucine (Leu), Isoleucine (Ile)
(group 2) neutral hydrophilic: Cysteine (Cys), Serine (Ser), Threonine (Thr)
(group 3) acidic: Aspartic acid (Asp), Glutamic acid (Glu)
(group 4) basic: Asparagine (Asn), Glutamine (Gln), Histidine (His), Lysine (Lys), Arginine (Arg)
(group 5) residues that influence chain orientation: Glycine (Gly), Proline (Pro); and
(group 6) aromatic: Tryptophan (Trp), Tyrosine (Tyr), Phenylalanine (Phe)

Non-conservative substitutions will entail exchanging a member of one of these classes for another.

TABLE 1A

Amino acid substitution

| Original residue | Exemplary substitution | Conservative substitution | Semi-conservative substitution |
| --- | --- | --- | --- |
| Ala (A) | Val, Leu, Ile | Val | N, V, P, (C) |
| Arg (R) | Lys, Gln, Asn | Lys | S, T, E, D, A |
| Asn (N) | Gln, His, Lys, Arg, Asp | Gln | K, R |
| Asp (D) | Glu, Asn | Glu | K, R, H, A |
| Cys (C) | Ser, Ala | Ser | F, G |
| Gln (Q) | Asn; Glu | Asn | M, L, K, R |
| Glu (E) | Asp, Gln | Asp | K, R, H, A |
| Gly (G) | Ala | Ala | — |
| His (H) | Asn, Gln, Lys, Arg | Arg | L, M, A, (C) |
| Ile (I) | Leu, Val, Met, Ala, Phe, norleucine | Leu | F, Y, W, G, (C) |
| Leu (L) | Norleucine, Ile, Val, Met, Ala, Phe | Ile | F, Y, W, H, (C) |
| Lys (K) | Arg, Gln, Asn | Arg | Q, N, S, T, D, E, A |
| Met (M) | Leu, Phe, Ile | Leu | Q, F, Y, W, (C), (R), (K), (E) |
| Phe (F) | Leu, Val, Ile, Ala, Tyr | Tyr | I, V, (C) |
| Pro (P) | Ala | Ala | A, (C), (D), (E), F, H, (K), L, M, N, Q, (R), S, T, W, Y |
| Ser (S) | Thr | Thr | D, E, R, K |
| Thr (T) | Ser | Ser | D, E, R, K, I |
| Trp (W) | Tyr, Phe | Tyr | L, M, I, V, (C) |

TABLE 1A-continued

Amino acid substitution

| Original residue | Exemplary substitution | Conservative substitution | Semi-conservative substitution |
| --- | --- | --- | --- |
| Tyr (Y) | Trp, Phe, Thr, Ser | Phe | L, M, I, V, (C) |
| Val (V) | Ile, Leu, Met, Phe, Ala, norleucine | Leu | P, (C) |

Changing from A, F, H, I, L, M, P, V, W, or Y to C is semi-conservative if the cysteine remains as a free thiol. Changing from M to E, R, K is semi-conservative if the ionic tip of the new side group may reach the protein surface while the methylene groups make hydrophobic contact. Changing from P to one of K, R, E or D is semi-conservative if the side group is on or near the surface of the protein.

Variation in the amino acid sequence of the variant antibody or antigen binding fragment may include an amino acid addition, deletion, insertion, substitution etc., one or more modification in the backbone or side-chain of one or more amino acid, or an addition of a group or another molecule to one or more amino acids (side-chains or backbone).

Variant antibody or antigen binding fragment may have substantial sequence similarity and/or sequence identity in its amino acid sequence in comparison with that of the original antibody or antigen binding fragment amino acid sequence. The degree of similarity between two sequences is based upon the percentage of identities (identical amino acids) and of conservative substitution.

Generally, the degree of similarity and identity between variable chains has been determined herein using the Blast2 sequence program (Tatiana A. Tatusova, Thomas L. Madden (1999), "Blast 2 sequences—a new tool for comparing protein and nucleotide sequences", FEMS Microbiol Lett. 174:247-250) using default settings, i.e., blastp program, BLOSUM62 matrix (open gap 11 and extension gap penalty 1; gapx dropoff 50, expect 10.0, word size 3) and activated filters.

Percent identity may therefore be indicative of amino acids which are identical in comparison with the original peptide and which may occupy the same or similar position.

Percent similarity may be indicative of amino acids which are identical and those which are replaced with conservative amino acid substitution in comparison with the original peptide at the same or similar position.

Variants (i.e., analogues) of the present invention (including VL variants, VH variants, CDR variants, antibody variants, polypeptide variants, etc.) therefore comprise those which may have at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with an original sequence or a portion of an original sequence.

In accordance with the present invention, a SEQ ID NO.:2 variant includes a polypeptide having a region at least 80% identical with amino acids 49-165 or with amino acids 20 to 259 of SEQ ID NO.:2. Variants of SEQ ID NO.:2 also include polypeptides having at least 80% sequence identity with SEQ ID NO.:2. Preferred variants of SEQ ID NO.:2 includes those that are able to inhibit osteoclast differentiation and/or bone resorption. Such variants may be identified, for example, by testing their osteoclast differentiation and/or bone resorption activity in vitro or in vivo. Examples of methods or assays that may be used to test the activity of Siglec-15 variants are described herein and have been provided in international application No. PCT/CA2007/001134. It is to be understood that the osteoclast used to perform the assays described herein may originate, for example, preferably from human but also from mouse. Preferred variants of SEQ ID NO.:2 may include, for example, those where an epitope comprising arginine 99 (R99) of SEQ ID NO.:2 is preserved.

Exemplary embodiments of variants are those having at least 81% sequence identity to a sequence described herein and 81%, 82%, 83%, 84%, 85%, 86%, 87%, 88%, 89%, 90%, 91%, 92%, 93%, 94%, 95%, 96%, 97%, 98%, 99% or 100% sequence similarity with an original sequence or a portion of an original sequence.

Other exemplary embodiments of variants are those having at least 82% sequence identity to a sequence described herein and 82%, 83%, 84%, 85%, 86%, 87%, 88%, 89%, 90%, 91%, 92%, 93%, 94%, 95%, 96%, 97%, 98%, 99% or 100% sequence similarity with an original sequence or a portion of an original sequence.

Further exemplary embodiments of variants are those having at least 85% sequence identity to a sequence described herein and 85%, 86%, 87%, 88%, 89%, 90%, 91%, 92%, 93%, 94%, 95%, 96%, 97%, 98%, 99% or 100% sequence similarity with an original sequence or a portion of an original sequence.

Other exemplary embodiments of variants are those having at least 90% sequence identity to a sequence described herein and 90%, 91%, 92%, 93%, 94%, 95%, 96%, 97%, 98%, 99% or 100% sequence similarity with an original sequence or a portion of an original sequence.

Additional exemplary embodiments of variants are those having at least 95% sequence identity to a sequence described herein and 95%, 96%, 97%, 98%, 99% or 100% sequence similarity with an original sequence or a portion of an original sequence.

Yet additional exemplary embodiments of variants are those having at least 97% sequence identity to a sequence described herein and 97%, 98%, 99% or 100% sequence similarity with an original sequence or a portion of an original sequence.

For a purpose of concision the applicant provides herein a Table 1B illustrating exemplary embodiments of individual variants encompassed by the present invention and comprising the specified % sequence identity and % sequence similarity. Each "X" is to be construed as defining a given variant.

TABLE 1B

| | | Percent (%) sequence identity | | | | | | | | | | | | | | | | | | | |
|---|---|---|---|---|---|---|---|---|---|---|---|---|---|---|---|---|---|---|---|---|---|
| | | 80 | 81 | 82 | 83 | 84 | 85 | 86 | 87 | 88 | 89 | 90 | 91 | 92 | 93 | 94 | 95 | 96 | 97 | 98 | 99 | 100 |
| Percent (%) sequence similarity | 80 | X | | | | | | | | | | | | | | | | | | | | |
| | 81 | X | X | | | | | | | | | | | | | | | | | | | |
| | 82 | X | X | X | | | | | | | | | | | | | | | | | | |
| | 83 | X | X | X | X | | | | | | | | | | | | | | | | | |
| | 84 | X | X | X | X | X | | | | | | | | | | | | | | | | |
| | 85 | X | X | X | X | X | X | | | | | | | | | | | | | | | |
| | 86 | X | X | X | X | X | X | X | | | | | | | | | | | | | | |
| | 87 | X | X | X | X | X | X | X | X | | | | | | | | | | | | | |
| | 88 | X | X | X | X | X | X | X | X | X | | | | | | | | | | | | |
| | 89 | X | X | X | X | X | X | X | X | X | X | | | | | | | | | | | |
| | 90 | X | X | X | X | X | X | X | X | X | X | X | | | | | | | | | | |
| | 91 | X | X | X | X | X | X | X | X | X | X | X | X | | | | | | | | | |
| | 92 | X | X | X | X | X | X | X | X | X | X | X | X | X | | | | | | | | |
| | 93 | X | X | X | X | X | X | X | X | X | X | X | X | X | X | | | | | | | |
| | 94 | X | X | X | X | X | X | X | X | X | X | X | X | X | X | X | | | | | | |
| | 95 | X | X | X | X | X | X | X | X | X | X | X | X | X | X | X | X | | | | | |
| | 96 | X | X | X | X | X | X | X | X | X | X | X | X | X | X | X | X | X | | | | |
| | 97 | X | X | X | X | X | X | X | X | X | X | X | X | X | X | X | X | X | X | | | |
| | 98 | X | X | X | X | X | X | X | X | X | X | X | X | X | X | X | X | X | X | X | | |
| | 99 | X | X | X | X | X | X | X | X | X | X | X | X | X | X | X | X | X | X | X | X | |
| | 100 | X | X | X | X | X | X | X | X | X | X | X | X | X | X | X | X | X | X | X | X | X |

As used herein, the term "identical" means that a sequence share 100% sequence identity with another sequence.

As used herein, the term "substantially identical" means that a sequence share 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity with another sequence or a portion of another sequence.

The present invention encompasses CDRs, light chain variable domains, heavy chain variable domains, light chains, heavy chains, antibodies and/or antigen binding fragments which comprise at least 70% identity (including any range between 70% and 99%) with the sequence described herein.

The present invention relates to the use of monoclonal antibodies to target osteoclasts found in various bone related disease where severe bone loss is observed due to increased activity of the osteoclasts. In order to direct the antibodies to the osteoclasts, the identification of osteoclast-specific antigens that are expressed at the cell surface of the cells must be carried out. There are several technologies that are available to identify cell-specific antigens and the method that was used to identify Siglec-15 in differentiating osteoclasts that were treated with RANKL, an innovative discovery platform called Subtractive Transcription-based Amplification of mRNA (STAR), is described in the published patent application No. PCT/CA2007/000210.

Analysis of the human osteoclast STAR libraries yielded many genes that encode secreted and cell surface proteins. One of these, termed 0326-SL109, contained an open reading frame that encoded a polypeptide of 328 amino acids, corresponding to SEQ ID NO:2 that was encoded by a cDNA of 987 base pairs with the nucleotide sequence shown in SEQ ID NO:1. A search of publicly available databases revealed that the 0326-SL109 nucleotide sequence was identical to that of a human gene called CD33 antigen-like 3 (CD33L3). CD33L3 was later found to be a member of the Siglec family of sialic acid binding proteins and was renamed Siglec-15 based on homology to other Siglecs (Crocker et al., 2007). Based on this information, the mouse orthologue was isolated and sequenced and found to be approximately 85% identical to the human sequence at the amino acid level. SEQ ID NO:3 and SEQ ID NO:4 show the sequences of cDNA and polypeptide of the murine Siglec-15, respectively. Bioinformatic analysis predicted a type I membrane-anchored protein that presents its functional domain to the extracellular compartment. As with other Siglec sequences, an amino-terminal signal peptide (located between amino acids 1 and 19 of SEQ ID NO:2) targets the protein to the membrane of cells and the final processed protein is anchored to the membrane via a single transmembrane helix located at the carboxy-terminus (located between amino acids 261 and 283 of SEQ ID NO:2). The V-set Ig domain is located between amino acids 49 and 165 of SEQ ID NO:2 whereas the C2-set Ig domain is located between amino acids 178 and 244 of SEQ ID NO:2.

Previous findings (Sooknanan et al. 2007) established that the transcript encoding human Siglec-15 was significantly upregulated in response to RANKL. This determination was performed on RNA macroarrays that contained spotted total RNA samples from several different human osteoclast differentiation experiments from different human PBMNC donors. Furthermore, these studies (Sooknanan et al. 2007) revealed that the Siglec-15 transcript was expressed in only one normal tissue among a vast panel of 30 human normal tissues indicating a very high osteoclast specificity of the Siglec-15 gene expression. Using more sensitive methods such as semi-quantitative RT-PCR, the expression of the Siglec-15 mRNA was stimulated within one day of RANKL treatment in many osteoclast samples indicating that the gene was expressed early in osteoclast precursor cells, prior to the commencement of cell fusion. Finally, the tissue expression profile of Siglec-15 was assessed by semi-quantitative RT-PCR and found to only be expressed in a single normal human tissue thus validating the macroarray results of Sooknanan et al. Taken together, these expression results underscore the strength of the Applicant's discovery approach in its ability to identify targets, as exemplified by Siglec-15, that are highly restricted to differentiating osteoclasts.

Based on the expression of Siglec-15 in the early stages of differentiation of osteoclasts, its limited expression in normal tissues, and a critical biological role for Siglec-15 in the activity of osteoclasts, Siglec-15 was chosen as a therapeutic target for the development of monoclonal antibodies for the detection, prevention, and treatment of bone resorption or bone-related diseases such as cancer-induced bone loss, osteoporosis, bone loss associate with cancer treatment.

Therefore, a variety of anti-Siglec-15 antibodies and immunologically functional fragments thereof, such as chimeric and humanized monoclonal antibodies, antibody fragments, single chain antibodies, domain antibodies, and polypeptides with an antigen-binding region, for targeting Siglec-15 are provided.

In accordance with the present invention, the antibodies or antigen binding fragment thereof may particularly be able to inhibit osteoclast differentiation.

Further in accordance with the present invention, the antibodies or antigen binding fragment thereof may be able to inhibit osteoclast formation.

Also in accordance with the present invention, the antibodies or antigen binding fragment thereof may be able to inhibit osteoclasts activity.

Further in accordance with the present invention, the antibodies or antigen binding fragment thereof may be able to inhibit bone resorption (e.g., bone resorption activity of osteoclasts).

Accordingly, the present invention provides in one aspect, an antibody or antigen binding fragment thereof capable of specific binding to Siglec-15 which may have a light chain variable region at least 80% identical to SEQ ID NO.:6 and/or a heavy chain variable region at least 80% identical to SEQ ID NO.:12. The antibody or antigen binding fragment thereof may also comprise at least one amino acid substitution in comparison with SEQ ID NO.:6 or SEQ ID NO.:12.

The present invention also provides in another aspect, an antibody or antigen binding fragment thereof which may have a light chain variable region at least 80% identical to SEQ ID NO.:22 and/or a heavy chain variable region at least 80% identical to SEQ ID NO.:26. The antibody or antigen binding fragment thereof may also comprise at least one amino acid substitution in comparison with SEQ ID NO.:22 or SEQ ID NO.:26.

In accordance with the present invention, the amino acid substitution may be an amino acid appearing at a corresponding position in a natural human antibody.

In accordance with an embodiment of the invention, the amino acid substitution may be outside of a complementarity determining region (CDR).

In accordance with an embodiment of the invention, the antibody the amino acid substitution may be located, for example, in the light chain variable region.

In accordance with an additional embodiment of the invention, the antibody or antigen binding fragment thereof may comprise at least two or at least three amino acid substitutions. Such amino acid substitutions may be located in the same variable region or may be located in distinct variable regions.

Further in accordance with the present invention, the antibody or antigen binding fragment thereof may comprise for example, from one to twenty-five amino acid substitutions in the light chain variable region and/or heavy chain variable region. More particularly, the antibody or antigen binding fragment thereof may have, for example, from one to twenty-two amino acid substitution in its light chain variable region and from one to twenty-five amino acid substitutions in its heavy chain variable region.

Antibodies or antigen binding fragments comprising the complementarity determining regions of SEQ ID NO.:6 and the complementarity determining regions of SEQ ID NO.:12 and comprising framework amino acids of a human antibody are particularly contemplated, such as, for example, humanized antibody.

Antibodies or antigen binding fragments comprising the complementarity determining regions of SEQ ID NO.:22 and the complementarity determining regions of SEQ ID NO.:26 and comprising framework amino acids of a human antibody are particularly contemplated.

Exemplary embodiments of the invention includes for example an antibody or an antigen binding fragment thereof having a light chain variable domain as set forth in SEQ ID NO.:33 (Generic 25E9 light chain variable domain (consensus 1)).

(SEQ ID NO.: 33)
DIVMTQXXXSXPVTPGEXXSISCRSTKSLLHSNGNTYLYWXLQXPGQSPQ

LLIYRMSNLASGVPDRFSGSGSGTXFTLXISRVEAEDVGVYYCMQHLEYP

FTFGGGTKXEIK;

wherein at least one of the amino acid identified by X may be an amino acid substitution in comparison with a corresponding amino acid in the polypeptide set forth in SEQ ID NO.:6 (the mouse VL). The amino acid substitution may be, for example conservative or non-conservative. In accordance with the invention, the amino acid substitution may be conservative.

Another exemplary embodiment of the invention includes for example an antibody or an antigen binding fragment thereof having a light chain variable domain as set forth in SEQ ID NO.:34 (Generic 25E9 light chain variable domain (consensus 2)).

(SEQ ID NO.: 34)
DIVMTQX$_{a1}$X$_{a2}$X$_{a3}$SX$_{a4}$PVTPGEX$_{a5}$X$_{a6}$SISCRSTKSLLHSNGNTYL

YWX$_{a7}$LQX$_{a8}$PGQSPQLLIYRMSNLASGVPDRFSGSGSGTX$_{a9}$FTLX$_{a10}$

ISRVEAEDVGVYYCMQHLEYPFTFGGGTKX$_{a11}$EIK;

wherein at least one of the amino acid identified by X may be an amino acid substitution in comparison with a corresponding amino acid in the polypeptide set forth in SEQ ID NO.:6 (the mouse VL) and;

wherein Xa1, Xa4, Xa7, Xa8, Xa10 and Xa11 may each independently be a conservative amino acid substitution in comparison with SEQ ID NO. 6;

wherein Xa2, Xa5, Xa6 may each independently be a semi-conservative amino acid substitution in comparison with SEQ ID NO. 6;

wherein Xa3 may be P or L; and wherein Xa9 may be A or D.

Yet another exemplary embodiment of the invention includes for example, an antibody or an antigen binding fragment thereof having a light chain variable domain as set forth in SEQ ID NO.:35 (Generic 25E9 light chain variable domain (consensus 3)).

(SEQ ID NO.: 35)
DIVMTQX$_{a1}$X$_{a2}$X$_{a3}$SX$_{a4}$PVTPGEX$_{a5}$X$_{a6}$SISCRSTKSLLHSNGNTYL

YWX$_{a7}$LQX$_{a8}$PGQSPQLLIYRMSNLASGVPDRFSGSGSGTX$_{a9}$FTLX$_{a10}$

ISRVEAEDVGVYYCMQHLEYPFTFGGGTKX$_{a11}$EIK;

wherein at least one of the amino acid identified by X (including Xa1 to Xa11) may be an amino acid substitution in comparison with a corresponding amino acid in the polypeptide set forth in SEQ ID NO.:6 (the mouse VL) and wherein Xa1 may be A or S;

wherein Xa2 may be A or P;

wherein Xa3 may be P or L;

wherein Xa4 may be a hydrophobic amino acid (e.g., V or L);

wherein Xa5 may be S or P;

wherein Xa6 may be a hydrophobic amino acid (e.g., V or A);

wherein Xa7 may be an aromatic amino acid (e.g. F or Y);

wherein Xa8 may be a basic amino acid (e.g., R or K);

wherein Xa9 may be A or D;

wherein Xa10 may be a basic amino acid (e.g., R or K); and wherein Xa11 may be a hydrophobic amino acid (e.g., L or V).

In a further embodiment, the present invention includes for example, an antibody or an antigen binding fragment thereof, having a heavy chain variable domain as set forth in SEQ ID NO.:36 (Generic 25E9 heavy chain variable domain (consensus 1)).

(SEQ ID NO.: 36)
EIQLQQSGXEXXXPGXSVXXSCKASGYTFTDYDMHVWXQXPXXGLEWXGT

IDPETGGTAYNQKFKGXXTXTADXSXXTAYMELSSLXSEDXAVYYCTSFY

YTYSNYDVGFAYWGQGTLVTVSX;

wherein at least one of the amino acid identified by X may be an amino acid substitution in comparison with a corresponding amino acid in the polypeptide set forth in SEQ ID NO.:12 (the mouse VH). The amino acid substitution may be, for example conservative or non-conservative. In accordance with the invention, the amino acid substitution may be conservative.

Yet a further embodiment of the present invention includes for example, an antibody or an antigen binding fragment thereof having a heavy chain variable domain as set forth in SEQ ID NO.:37 (Generic 25E9 heavy chain variable domain (consensus 2)).

(SEQ ID NO.: 37)
EIQLQQSGX$_{b1}$EX$_{b2}$X$_{b3}$X$_{b4}$PGX$_{b5}$SVX$_{b6}$X$_{b7}$SCKASGYTFTDYDMHW

VX$_{b8}$QX$_{b9}$PX$_{b10}$X$_{b11}$GLEWX$_{b12}$GTIDPETGGTAYNQKFKGX$_{b13}$

X$_{b14}$TX$_{b15}$TADX$_{b16}$SX$_{b17}$X$_{b18}$TAYMELSSLX$_{b19}$SEDX$_{b20}$AVYYC

TSFYYTYSNYDVGFAYWGQGTLVTVSX$_{b21}$;

wherein at least one of the amino acid identified by X (including Xb1 to Xb21) may be an amino acid substitution in comparison with a corresponding amino acid in the polypeptide set forth in SEQ ID NO.:12 (the mouse VH) and wherein Xb2, Xb4, Xb5, Xb7, Xb8, Xb9, Xb11, Xb12, Xb13, Xb15, Xb16, Xb17, Xb18, Xb20 and Xb21 may each independently be a conservative amino acid substitution in comparison with SEQ ID NO. 12;

wherein Xb1, Xb6, Xb14 may each independently be a semi-conserved amino acid substitution in comparison with SEQ ID NO.:12 (the mouse VH);

wherein Xb3 may be V or K;

wherein Xb10 may be V or G; and wherein Xb19 may be T or R.

Another embodiment of the invention includes, for example, an antibody or an antigen binding fragment having an heavy chain variable domain as set forth in SEQ ID NO.:38 (Generic 25E9 heavy chain variable domain (consensus 3)).

(SEQ ID NO.: 38)
EIQLQQSGX$_{b1}$EX$_{b2}$X$_{b3}$X$_{b4}$PGX$_{b5}$SVX$_{b6}$X$_{b7}$SCKASGYTFTDYDMHW

VX$_{b8}$QX$_{b9}$PX$_{b10}$X$_{b11}$GLEWX$_{b12}$GTIDPETGGTAYNQKFKGX$_{b13}$

X$_{b14}$TX$_{b15}$TADX$_{b16}$SX$_{b17}$X$_{b18}$TAYMELSSLX$_{b19}$SEDX$_{b20}$AVYYC

TSFYYTYSNYDVGFAYWGQGTLVTVSX$_{b21}$;

wherein at least one of the amino acid identified by X (including Xb1 to Xb21) may be an amino acid substitution in comparison with a corresponding amino acid in the polypeptide set forth in SEQ ID NO.:12 (the mouse VH) and;

wherein Xb1 may be a hydrophobic amino acid (e.g., V or A);

wherein Xb2 may be a hydrophobic amino acid (e.g., L or V);

wherein Xb3 may be V or K;

wherein Xb4 may be a basic amino acid (e.g., R or K);

wherein Xb5 may be A or S;

wherein Xb6 may be T or K;

wherein Xb7 may be a hydrophobic amino acid (e.g., L or V);

wherein Xb8 may be a basic amino acid (e.g., K or R);

wherein Xb9 may be T or A;

wherein Xb10 may be V or G;

wherein Xb11 may be a basic amino acid (e.g., H or Q);

wherein Xb12 may be a hydrophobic amino acid (e.g., I or M);

wherein Xb13 may be a basic amino acid (e.g., K or R);

wherein Xb14 may be a hydrophobic amino acid (e.g., A or V);

wherein Xb15 may be a hydrophobic amino acid (e.g., L or I);

wherein Xb16 may be a basic amino acid (e.g., R or K);

wherein Xb17 may be a neutral hydrophilic amino acid (e.g., S or T);

wherein Xb18 may be a neutral hydrophilic amino acid (e.g., T or S);

wherein Xb19 may be T or R;

wherein Xb20 may be a neutral hydrophilic amino acid (e.g., S or T); and wherein Xb21 may be A or S.

Other exemplary embodiments of the invention include, for example, an antibody or an antigen binding fragment thereof, having a light chain variable domain set forth in SEQ ID NO.: 39 (Generic 25D8 light chain variable domain (consensus 1)).

(SEQ ID NO.: 39)
DIVMTQXXXSXPVTXGXXASISCRSSKSLLHSNGITYLYWYLQKPGQSPQ

LLIYQMSNLASGVPDRFSXSGSGTDFTLXISRVEAEDVGVYYCAQNLELP

YTFGGGTKXEIK;

wherein at least one of the amino acid identified by X may be an amino acid substitution in comparison with a corresponding amino acid in the polypeptide set forth in SEQ ID NO.:22 (the mouse VL). The amino acid substitution may be, for example conservative or non-conservative. In accordance with the invention, the amino acid substitution may be conservative.

Yet another exemplary embodiment of the invention includes, for example, an antibody or antigen binding fragment thereof, having a light chain variable domain set forth in SEQ ID NO.: 40 (Generic 25D8 light chain variable domain (consensus 2)).

(SEQ ID NO.: 40)
DIVMTQX$_{c1}$X$_{c2}$X$_{c3}$SX$_{c4}$PVTX$_{c5}$GX$_{c6}$X$_{c7}$ASISCRSSKSLLHSNGIT

YLYWYLQKPGQSPQLLIYQMSNLASGVPDRFSX$_{c8}$SGSGTDFTLX$_{c9}$ISR

VEAEDVGVYYCAQNLELPYTFGGGTKX$_{c10}$EIK;

wherein at least one of the amino acid identified by X may be an amino acid substitution in comparison with a corresponding amino acid in the polypeptide set forth in SEQ ID NO.:22 (the mouse VL) and wherein Xc1, Xc3, Xc9 and Xc10 may each independently be a conservative amino acid substitution in comparison with SEQ ID NO.:22;

wherein Xc2, Xc7, Xc8 may each independently be a semi-conservative amino acid substitution in comparison with SEQ ID NO.: 22;

Wherein Xc4 may be N or L;

Wherein Xc5 may be L or P; and

Wherein Xc6 may be T or E.

An additional embodiment of the present invention includes for example, an antibody or antigen binding fragment thereof, having a light chain variable domain set forth in SEQ ID NO.: 41 (Generic 25D8 light chain variable domain (consensus 3)).

(SEQ ID NO.: 41)
DIVMTQX$_{c1}$X$_{c2}$X$_{c3}$SX$_{c4}$PVTX$_{c5}$GX$_{c6}$X$_{c7}$ASISCRSSKSLLHSNGIT

YLYWYLQKPGQSPQLLIYQMSNLASGVPDRFSX$_{c8}$SGSGTDFTLX$_{c9}$ISR

VEAEDVGVYYCAQNLELPYTFGGGTKX$_{c10}$EIK;

wherein at least one of the amino acid identified by X may be an amino acid substitution in comparison with a corresponding amino acid in the polypeptide set forth in SEQ ID NO.:22 (the mouse VL) and Wherein Xc1 may be A or T;

Wherein Xc2 may be A or P;

Wherein Xc3 may be F or L;

Wherein Xc4 may be N or L;

Wherein Xc5 may be L or P;

Wherein Xc6 may be T or E;

Wherein Xc7 may be S or P;

Wherein Xc8 may be S or G;

Wherein Xc9 may be a basic amino acid (e.g., R or K); and

Wherein Xc10 may be a hydrophobic amino acid (e.g., L or V).

Yet an additional embodiment of the present invention includes for example, an antibody or antigen binding fragment thereof, having a heavy chain variable domain set forth in SEQ ID NO.: 42 (Generic 25D8 heavy chain variable domain (consensus 1)).

(SEQ ID NO.: 42)
QVQXQQXGAEXXKPGXSVKXSCKASGYTFTSYWMHWVXQXPGQGLEWXGL

INPSNARTNYNEKFNTXXTXTXDKSXSTAYMXLSSLXSEDXAVYYCARGG

DGDYFDYWGQGTTXTVSS;

wherein at least one of the amino acid identified by X may be an amino acid substitution in comparison with a corresponding amino acid in the polypeptide set forth in SEQ ID NO.:26 (the mouse VH). The amino acid substitution may be, for example conservative or non-conservative. In accordance with the invention, the amino acid substitution may be conservative.

In a further embodiment, the present invention includes for example, an antibody or antigen binding fragment thereof, having a heavy chain variable domain set forth in SEQ ID NO.: 43 (Generic 25D8 heavy chain variable domain (consensus 2)).

(SEQ ID NO.: 43)
QVQX$_{d1}$QQX$_{d2}$GAEX$_{d3}$X$_{d4}$KPGX$_{d5}$SVKX$_{d6}$SCKASGYTFTSYWM

HWVX$_{d7}$QX$_{d8}$PGQGLEWX$_{d9}$GLINPSNARTNYNEKFNTX$_{d10}$X$_{d11}$

TX$_{d12}$TX$_{d13}$DKSX$_{d14}$STAYMX$_{d15}$LSSLX$_{d16}$SEDX$_{d17}$AVYYCAR

GGDGDYFDYWGQGTTX$_{d18}$TVSS;

wherein at least one of the amino acid identified by X may be an amino acid substitution in comparison with a corresponding amino acid in the polypeptide set forth in SEQ ID NO.:26 (the mouse VH) and;

wherein Xd1, Xd3, Xd5, Xd6, Xd7, Xd9, Xd10, Xd12, Xd14, Xd15, Xd17, Xd18 may each independently be a conservative amino acid substitution in comparison with SEQ ID NO.:26;

wherein Xd2, Xd11, Xd13, may each independently be a semi-conservative amino acid substitution in comparison with SEQ ID NO.:26;

wherein Xd4 may be V or K;

wherein Xd8 may be R or A; and;

wherein Xd16 may be T or R.

In yet a further embodiment, the present invention includes, for example, an antibody or antigen binding fragment thereof, having a heavy chain variable domain set forth in SEQ ID NO.: 44 (Generic 25D8 heavy chain variable domain (consensus 3)).

(SEQ ID NO.: 44)
QVQX$_{d1}$QQX$_{d2}$GAEX$_{d3}$X$_{d4}$KPGX$_{d5}$SVKX$_{d6}$SCKASGYTFTSYWM

HWVX$_{d7}$QX$_{d8}$PGQGLEWX$_{d9}$GLINPSNARTNYNEKFNTX$_{d10}$X$_{d11}$

TX$_{d12}$TX$_{d13}$DKSX$_{d14}$STAYMX$_{d15}$LSSLX$_{d16}$SEDX$_{d17}$AVYYCAR

GGDGDYFDYWGQGTTX$_{d18}$TVSS;

wherein at least one of the amino acid identified by X may be an amino acid substitution in comparison with a corresponding amino acid in the polypeptide set forth in SEQ ID NO.:26 (the mouse VH) and;

wherein Xd1 may be a hydrophobic amino acid (e.g., V or L);

wherein Xd2 may be P or S;

wherein Xd3 may be a hydrophobic amino acid (e.g., L or V);

wherein Xd4 may be V or K;

wherein Xd5 may be A or S;

wherein Xd6 may be a hydrophobic amino acid (e.g., L or V);

wherein Xd7 may be a basic amino acid (e.g., K or R);

wherein Xd8 may be R or A;

wherein Xd9 may be a hydrophobic amino acid (e.g., I or M);

wherein Xd10 may be a basic amino acid (e.g., K or R);

wherein Xd11 may be a hydrophobic amino acid (e.g., A or V);

wherein Xd12 may be a hydrophobic amino acid (e.g., L or I);

wherein Xd13 may be a hydrophobic amino acid (V or A);

wherein Xd14 may be a neutral hydrophilic amino acid (e.g., S or T);

wherein Xd15 may be Q or E;

wherein Xd16 may be T or R.

wherein Xd17 may be a neutral hydrophilic amino acid (e.g., S or T); and wherein Xd18 may be a hydrophobic amino acid (L or V).

The term "humanized antibody" encompasses fully humanized antibody (i.e., frameworks are 100% humanized) and partially humanized antibody (e.g., at least one variable domain contains one or more amino acids from a human antibody, while other amino acids are amino acids of a non-human parent antibody). Typically a "humanized antibody" contains CDRs of a non-human parent antibody (e.g., mouse, rat, rabbit, non-human primate, etc.) and frameworks that are identical to those of a natural human antibody or of a human antibody consensus. In such instance, those "humanized antibodies" are characterized as fully humanized. A "humanized antibody" may also contain one or more amino acid substitutions that have no correspondence to those of the human antibody or human antibody consensus. Such substitutions include, for example, back-mutations (e.g., re-introduction of non-human amino acids) that may preserve the antibody characteristics (e.g., affinity, specificity etc.). Such substitutions are usually in the framework region. A "humanized antibody" optionally also comprise at least a portion of a constant region (Fc) which is typically that of a human antibody. Typically, the constant region of a "humanized antibody" is identical to that of a human antibody.

Of course, any antibody, antigen binding fragment thereof or antibody portion (light chain or heavy chain variable regions), having an amino acid sequence identical to that described herein is encompassed by the present invention, irrelevant of whether it is obtained via humanization technology, hybridoma technology, transgenic mice technologies, or else.

It is to be understood herein that the framework amino acids of the antibodies of the present invention may be from 80% to 100% (e.g., 85 to 100%; 90 to 100%, 95 to 100%) identical to those of a natural human antibodies. Usually, when a framework amino acid is not identical to a corresponding amino acid of a natural antibody, such amino acid may remain identical to the original amino acid (e.g., a mouse amino acid).

As used herein the term "from one to twenty-five (1 to 25)" includes every individual values and ranges such as for example, 1, 2, 3, and up to 25; 1 to 25; 1 to 24, 1 to 23, 1 to 22, 1 to 21, 1 to 20, 1 to 19; 1 to 18; 1 to 17; 1 to 16; 1 to 15 and so on; 2 to 25, 2 to 24, 2 to 23, 2 to 22, 2 to 21, 2 to 20; 2 to 19; 2 to 18; 2 to 17 and so on; 3 to 25, 3 to 24, 3 to 23, 3 to 22, 3 to 21, 3 to 20; 3 to 19; 3 to 18 and so on; 4 to 25, 4 to 24, 4 to 23, 4 to 22, 4 to 21, 4 to 20; 4 to 19; 4 to 18; 4 to 17; 4 to 16 and so on; 5 to 25, 5 to 24, 5 to 23, 5 to 22, 5 to 21, 5 to 20; 5 to 19; 5 to 18; 5 to 17 and so on, etc.

Likewise, other ranges such as for example, "from one to twenty-two (1 to 22)" includes every individual values and ranges such as for example, 1, 2, 3, and up to 22; 1 to 22, 1 to 21, 1 to 20, 1 to 19, 1 to 18, 1 to 17, 1 to 16, 1 to 15; 1 to 14; 1 to 13; 1 to 12; 1 to 11; 1 to 10 and so on; 2 to 22, 2 to 21, 2 to 20, 2 to 19, 2 to 18, 2 to 17, 2 to 16, 2 to 15; 2 to 14; 2 to 13; 2 to 12 and so on; 3 to 22, 3 to 21, 3 to 20, 3 to 19, 3 to 18, 3 to 17, 3 to 16, 3 to 15; 3 to 14; 3 to 13 and so on; 4 to 22, 4 to 21, 4 to 20, 4 to 19, 4 to 18, 4 to 17, 4 to 16, 4 to 15; 4 to 14; 4 to 13; 4 to 12; 4 to 11 and so on; 5 to 22, 5 to 21, 5 to 20, 5 to 19, 5 to 18, 5 to 17, 5 to 16, 5 to 15; 5 to 14; 5 to 13; 5 to 12 and so on, etc.

In a more specific embodiment of the invention, the number of amino acid substitutions that may be made in a light chain variable region derived from SEQ ID NO.:6 may be for example, from 1 to 11 amino acid substitutions.

In yet a more specific embodiment of the invention, the number of amino acid substitutions that may be made in a heavy chain variable region derived from SEQ ID NO.:12 may be for example, from 1 to 21 amino acid substitutions. In some instances, when considering SEQ ID NO.:12, it may be useful to have at least three amino acid substitutions.

In a further more specific embodiment of the invention, the number of amino acid substitutions that may be made in a light chain variable region derived from SEQ ID NO.:22 may be for example, from 1 to 10 amino acid substitutions.

In yet a further more specific embodiment of the invention, the number of amino acid substitutions that may be made in a heavy chain variable region of SEQ ID NO.:26 may be for example, from 1 to 18 amino acid substitutions.

In accordance with an embodiment of the invention, the acid substitutions may be for example, in the light chain variable region.

In accordance with an embodiment of the invention, the amino acid substitutions may be for example, in the heavy chain variable region.

An antibody or antigen binding fragment may therefore have a light chain variable region having up to twenty-two amino acid substitutions in comparison with SEQ ID NO.:6 or SEQ ID NO.:22 and may have a heavy chain variable region having up to twenty-five amino acid substitutions in comparison with SEQ ID NO.:12 or SEQ ID NO.:26. It is to be understood herein that when the antibody or antigen binding fragment has two light chain variable regions and two heavy chain variable regions, each one of the light chain variable regions may independently have up to twenty amino acid substitutions and each one of the heavy chain variable regions may have up to twenty amino acid substitutions.

As discussed herein the amino acid substitutions may be conservative or non-conservative. In an exemplary embodiment the amino acid substitutions may be conservative.

It is to be understood herein that the antibody or antigen binding fragment of the invention may if desired have a light chain variable region and/or heavy chain variable region showing a deletion in comparison with SEQ ID NO.:6, SEQ ID NO.:12, SEQ ID NO.:22 and/or SEQ ID NO.:26. Such deletion may be found, for example, at an amino- or carboxy-terminus of the light chain variable region and/or heavy chain variable region.

Another exemplary embodiment of the antibody or antigen binding fragment of the present invention includes for example, an antibody or antigen binding fragment having a light chain variable region which may comprise at least 90 consecutive amino acids of any of SEQ ID NO.:33, SEQ ID NO.:34, SEQ ID NO.:35, SEQ ID NO.:8 or SEQ ID NO.:10.

As used herein the term "at least 90 consecutive amino acids of SEQ ID NO.:33" also includes the terms "at least 91, 92, 93, 94, 95, 96, 97, 98, 99, 100, 101, 102, 103, 104, 105, 106, 107, 108, 109, 110, 111, or at least 112 consecutive amino acids". The term "at least 90 consecutive amino acids of SEQ ID NO.:33" encompasses any possible sequence of at least 90 consecutive amino acids found in SEQ ID NO.:33 and especially those sequences which include the 3 CDRs of SEQ ID NO.:33, such as, for example a sequence comprising amino acids 6 to 108, 5 to 109, 13 to 103, 14 to 111 of SEQ ID NO.:33 and so on.

As used herein the term "at least 90 consecutive amino acids of SEQ ID NO.:34" also includes the terms "at least 91, 92, 93, 94, 95, 96, 97, 98, 99, 100, 101, 102, 103, 104, 105, 106, 107, 108, 109, 110, 111, or at least 112 consecutive amino acids". The term "at least 90 consecutive amino acids of SEQ ID NO.:34" encompasses any possible sequence of at least 90 consecutive amino acids found in SEQ ID NO.:34 and especially those sequences which include the 3 CDRs of SEQ ID NO.:34, such as, for example a sequence comprising amino acids 7 to 109, 12 to 104, 22 to 112, 18 to 112 of SEQ ID NO.:34 and so on.

The terms "at least 90 consecutive amino acids of SEQ ID NO.:35", "at least 90 consecutive amino acids of SEQ ID NO.:8" or "at least 90 consecutive amino acids of SEQ ID NO.:10" have similar meanings.

In accordance with the present invention, the antibody or antigen binding fragment of the present invention may have, for example, a light chain variable region as set forth in SEQ ID NO.:8 or in SEQ ID NO.:10.

The antibody or antigen binding fragment of the invention includes (or further includes) for example, a heavy chain variable region which may comprise at least 90 consecutive amino acids of any of SEQ ID NOs.:36, 37, 38, 14, 16, 18 or 20.

As used herein the term "at least 90 consecutive amino acids of SEQ ID NO.:36" also includes the terms "at least 91, 92, 93, 94, 95, 96, 97, 98, 99, 100, 101, 102, 103, 104, 105, 106, 107, 108, 109, 110, 111, or at least 123 consecutive amino acids". The term "at least 90 consecutive amino acids of SEQ ID NO.:36" encompasses any possible sequence of at least 90 consecutive amino acids found in SEQ ID NO.:36 and especially those sequences which include the 3 CDRs of SEQ ID NO.:36, such as, for example a sequence comprising amino acids 1 to 106, 2 to 112, 11 to 113, 7 to 102 of SEQ ID NO.:36 and so on.

As used herein the term "at least 90 consecutive amino acids of SEQ ID NO.:37" also includes the terms "at least 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122 or at least 123 consecutive amino acids". The term "at least 90 consecutive amino acids of SEQ ID NO.:37" encompasses any possible sequence of at least 90 consecutive amino acids found in SEQ ID NO.:37 and especially those sequences which include the 3 CDRs of SEQ ID NO.:37, for example a sequence comprising amino acids 6 to 109, 8 to 113, 1 to 102, 2 to 105 of SEQ ID NO.:37 and so on.

The terms "at least 90 consecutive amino acids of SEQ ID NO.:38", "at least 90 consecutive amino acids of SEQ ID NO.:14, "at least 90 consecutive amino acids of SEQ ID NO.:16", "at least 90 consecutive amino acids of SEQ ID NO.:18" or "at least 90 consecutive amino acids of SEQ ID NO.:20" have similar meanings.

In accordance with the present invention, the antibody or antigen binding fragment of the present invention may have, for example, a heavy chain variable region as set forth in SEQ ID NO.:14, 16, 18 or 20.

In accordance with the present invention the antibody or antigen binding fragment may comprise, for example,
  a) a light chain variable region which may comprise at least 90 consecutive amino acids of SEQ ID NO.:33 and a heavy chain variable region which may comprise at least 90 consecutive amino acids of any of SEQ ID NO.:36, SEQ ID NO.:37, SEQ ID NO.:38, SEQ ID NO.:14, SEQ ID NO.:16, SEQ ID NO.:18 or SEQ ID NO.:20;
  b) a light chain variable region which may comprise at least 90 consecutive amino acids of SEQ ID NO.:34 and a heavy chain variable region which may comprise at least 90 consecutive amino acids of any of SEQ ID NO.:36, SEQ ID NO.:37, SEQ ID NO.:38, SEQ ID NO.:14, SEQ ID NO.:16, SEQ ID NO.:18 or SEQ ID NO.:20;

c) a light chain variable region which may comprise amino acids at least 90 consecutive amino acids of SEQ ID NO.:35 and a heavy chain variable region which may comprise at least 90 consecutive amino acids of any of SEQ ID NO.:36, SEQ ID NO.:37, SEQ ID NO.:38, SEQ ID NO.:14, SEQ ID NO.:16, SEQ ID NO.:18 or SEQ ID NO.:20;

d) a light chain variable region which may comprise at least 90 consecutive amino acids of SEQ ID NO.:8 and a heavy chain variable region which may comprise at least 90 consecutive amino acids of any of SEQ ID NO.:36, SEQ ID NO.:37, SEQ ID NO.:38, SEQ ID NO.:14, SEQ ID NO.:16, SEQ ID NO.:18 or SEQ ID NO.:20; or e) a light chain variable region which may comprise at least 90 consecutive amino acids of SEQ ID NO.:10 and a heavy chain variable region which may comprise at least 90 consecutive amino acids of any of SEQ ID NO.:36, SEQ ID NO.:37, SEQ ID NO.:38, SEQ ID NO.:14, SEQ ID NO.:16, SEQ ID NO.:18 or SEQ ID NO.:20.

In accordance with a more specific embodiment of the invention, the light chain variable region may comprise at least 90 consecutive amino acids of SEQ ID NO.:8 or 10 and the heavy chain variable region may comprise at least 90 consecutive amino acids of SEQ ID NO.:14, 16, 18 or 20.

In accordance with an even more specific embodiment of the invention, the light chain variable region may be as set forth in SEQ ID NO.:8 or 10 and the heavy chain variable region may be as set forth in SEQ ID NO.:14, 16, 18 or 20.

More particularly, antibodies comprising the light chain variable region set fort in SEQ ID NO.: 8 and the heavy chain variable region set forth in SEQ ID NO.:14 are contemplated.

Other exemplary embodiments of the antibodies or antigen binding fragments of the invention are those which may comprise a light chain variable region which may comprise at least 90 consecutive amino acids of any of SEQ ID Nos. 39, 40, 41, or 24.

As used herein the term "at least 90 consecutive amino acids of SEQ ID NO.:39" also includes the terms "at least 91, 92, 93, 94, 95, 96, 97, 98, 99, 100, 101, 102, 103, 104, 105, 106, 107, 108, 109, 110 111 or at least 112, consecutive amino acids". The term "at least 90 consecutive amino acids of SEQ ID NO.:39" encompasses any possible sequence of at least 90 consecutive amino acids found in SEQ ID NO.:39 and especially those sequences which include the 3 CDRs of SEQ ID NO.:39, for example a sequence comprising amino acids 6 to 102, 11 to 106, 1 to 106, 3 to 95, 5 to 95 of SEQ ID NO.:39 and so on.

As used herein the term "at least 90 consecutive amino acids of SEQ ID NO.:40" also includes the terms "at least 91, 92, 93, 94, 95, 96, 97, 98, 99, 100, 101, 102, 103, 104, 105, 106, 107, 108, 109, 110, 111 or at least 112, consecutive amino acids". The term "at least 90 consecutive amino acids of SEQ ID NO.:40" encompasses any possible sequence of at least 90 consecutive amino acids found in SEQ ID NO.:40 and especially those sequences which include the 3 CDRs of SEQ ID NO.:40, for example a sequence comprising amino acids 9 to 106, 10 to 101, 1 to 98, 3 to 99, 7 to 107 of SEQ ID NO.:40 and so on.

The terms "at least 90 consecutive amino acids of SEQ ID NO.:41" or "at least 90 consecutive amino acids of SEQ ID NO.:24" have similar meanings.

In accordance with the present invention, the antibody or antigen binding fragment of the present invention may have, for example, a light chain variable region as set forth in SEQ ID NO.:24.

The antibody or antigen binding fragment of the invention includes (or further includes) for example, a heavy chain variable region which may comprise at least 90 consecutive amino acids of any of SEQ ID NOs.:42, 43, 44 or 26.

As used herein the term "at least 90 consecutive amino acids of SEQ ID NO.:42" also includes the terms "at least 91, 92, 93, 94, 95, 96, 97, 98, 99, 100, 101, 102, 103, 104, 105, 106, 107, 108, 109, 110, 111, 112, 113, 114, 115, 116, 117 or at least 118 consecutive amino acids". The term "at least 90 consecutive amino acids of SEQ ID NO.:42" encompasses any possible sequence of at least 90 consecutive amino acids found in SEQ ID NO.:42 and especially those sequences which include the 3 CDRs of SEQ ID NO.:42, such as, for example a sequence comprising amino acids 6 to 111, 1 to 106, 2 to 104, 5 to 106, 10 to 107 of SEQ ID NO.:42 and so on.

As used herein the term "at least 90 consecutive amino acids of SEQ ID NO.:43" also includes the terms "at least 91, 92, 93, 94, 95, 96, 97, 98, 99, 100, 101, 102, 103, 104, 105, 106, 107, 108, 109, 110, 111, 112, 113, 114, 115, 116, 117 or at least 118 consecutive amino acids". The term "at least 90 consecutive amino acids of SEQ ID NO.:43" encompasses any possible sequence of at least 90 consecutive amino acids found in SEQ ID NO.:43 and especially those sequences which include the 3 CDRs of SEQ ID NO.:43, such as, for example a sequence comprising amino acids 3 to 107, 1 to 115, 1 to 110, 22 to 116, 20 to 115 of SEQ ID NO.:43 and so on.

The terms "at least 90 consecutive amino acids of SEQ ID NO.:44" or "at least 90 consecutive amino acids of SEQ ID NO.:26" has a similar meaning.

In accordance with the present invention, the antibody or antigen binding fragment of the present invention may have, for example, a heavy chain variable region as set forth in SEQ ID NO.:26.

In accordance with the present invention the antibody or antigen binding fragment may comprise, for example, a) a light chain variable region which may comprise at least 90 consecutive amino acids of SEQ ID NO.:39 and a heavy chain variable region which may comprise at least 90 consecutive amino acids of any of SEQ ID NO.:42, SEQ ID NO.:43, SEQ ID NO.:44 or SEQ ID NO.:26;

b) a light chain variable region which may comprise at least 90 consecutive amino acids of SEQ ID NO.:40 and a heavy chain variable region which may comprise at least 90 consecutive amino acids of any of SEQ ID NO.:42, SEQ ID NO.:43, SEQ ID NO.:44 or SEQ ID NO.:26;

c) a light chain variable region which may comprise amino acids at least 90 consecutive amino acids of SEQ ID NO.:41 and a heavy chain variable region which may comprise at least 90 consecutive amino acids of any of SEQ ID NO.:42, SEQ ID NO.:43, SEQ ID NO.:44 or SEQ ID NO.:26 or;

d) a light chain variable region which may comprise at least 90 consecutive amino acids of SEQ ID NO.:24 and a heavy chain variable region which may comprise at least 90 consecutive amino acids of any of SEQ ID NO.:42, SEQ ID NO.:43, SEQ ID NO.:44 or SEQ ID NO.:26.

In accordance with a more specific embodiment of the invention, the light chain variable region may have at least 90 consecutive amino acids of SEQ ID NO.:24 and the heavy chain variable region may have at least 90 consecutive amino acids of SEQ ID NO.:26.

In accordance with an even more specific embodiment of the invention, the light chain variable region may be as set forth in SEQ ID NO.:24 and the heavy chain variable region may be as set forth in SEQ ID NO.:26.

Embodiments of the invention more particularly comprises an antibody or antigen binding fragment selected from the group consisting of:

a. an antibody comprising a light chain as set forth in SEQ ID NO.:7 and a heavy chain as set forth in SEQ ID NO.:13 or an antigen binding fragment thereof;
b. an antibody comprising a light chain as set forth in SEQ ID NO.:7 and a heavy chain as set forth in SEQ ID NO.:15 or an antigen binding fragment thereof;
c. an antibody comprising a light chain as set forth in SEQ ID NO.:7 and a heavy chain as set forth in SEQ ID NO.:17 or an antigen binding fragment thereof;
d. an antibody comprising a light chain as set forth in SEQ ID NO.:7 and a heavy chain as set forth in SEQ ID NO.:19 or an antigen binding fragment thereof;
e. an antibody comprising a light chain as set forth in SEQ ID NO.:7 and a heavy chain as set forth in SEQ ID NO.:29 or an antigen binding fragment thereof;
f. an antibody comprising a light chain as set forth in SEQ ID NO.:7 and a heavy chain as set forth in SEQ ID NO.:59 or an antigen binding fragment thereof;
g. an antibody comprising a light chain as set forth in SEQ ID NO.:7 and a heavy chain as set forth in SEQ ID NO.:60 or an antigen binding fragment thereof;
h. an antibody comprising a light chain as set forth in SEQ ID NO.:7 and a heavy chain as set forth in SEQ ID NO.:61 or an antigen binding fragment thereof;
i. an antibody comprising a light chain as set forth in SEQ ID NO.:9 and a heavy chain as set forth in SEQ ID NO.:13 or an antigen binding fragment thereof;
j. an antibody comprising a light chain as set forth in SEQ ID NO.:9 and a heavy chain as set forth in SEQ ID NO.:15 or an antigen binding fragment thereof;
k. an antibody comprising a light chain as set forth in SEQ ID NO.:9 and a heavy chain as set forth in SEQ ID NO.:17 or an antigen binding fragment thereof;
l. an antibody comprising a light chain as set forth in SEQ ID NO.:9 and a heavy chain as set forth in SEQ ID NO.:19 or an antigen binding fragment thereof;
m. an antibody comprising a light chain as set forth in SEQ ID NO.:9 and a heavy chain as set forth in SEQ ID NO.:29 or an antigen binding fragment thereof;
n. an antibody comprising a light chain as set forth in SEQ ID NO.:9 and a heavy chain as set forth in SEQ ID NO.:59 or an antigen binding fragment thereof;
o. an antibody comprising a light chain as set forth in SEQ ID NO.:9 and a heavy chain as set forth in SEQ ID NO.:60 or an antigen binding fragment thereof;
p. an antibody comprising a light chain as set forth in SEQ ID NO.:9 and a heavy chain as set forth in SEQ ID NO.:61 or an antigen binding fragment thereof;
q. an antibody comprising a light chain as set forth in SEQ ID NO.:23 and a heavy chain as set forth in SEQ ID NO.:27 or an antigen binding fragment thereof;
r. an antibody comprising a light chain as set forth in SEQ ID NO.:23 and a heavy chain as set forth in SEQ ID NO.:46 or an antigen binding fragment thereof.

Other embodiments of the invention comprises an antibody or antigen binding fragment selected from the group consisting of:

a. an antibody comprising a light chain as set forth in SEQ ID NO.:5 and a heavy chain as set forth in SEQ ID NO.:13 or an antigen binding fragment thereof;
b. an antibody comprising a light chain as set forth in SEQ ID NO.:5 and a heavy chain as set forth in SEQ ID NO.:15 or an antigen binding fragment thereof;
c. an antibody comprising a light chain as set forth in SEQ ID NO.:5 and a heavy chain as set forth in SEQ ID NO.:17 or an antigen binding fragment thereof;
d. an antibody comprising a light chain as set forth in SEQ ID NO.:5 and a heavy chain as set forth in SEQ ID NO.:19 or an antigen binding fragment thereof;
e. an antibody comprising a light chain as set forth in SEQ ID NO.:5 and a heavy chain as set forth in SEQ ID NO.:29 or an antigen binding fragment thereof;
f. an antibody comprising a light chain as set forth in SEQ ID NO.:5 and a heavy chain as set forth in SEQ ID NO.:59 or an antigen binding fragment thereof;
g. an antibody comprising a light chain as set forth in SEQ ID NO.:5 and a heavy chain as set forth in SEQ ID NO.:60 or an antigen binding fragment thereof;
h. an antibody comprising a light chain as set forth in SEQ ID NO.:5 and a heavy chain as set forth in SEQ ID NO.:61 or an antigen binding fragment thereof;
i. an antibody comprising a light chain as set forth in SEQ ID NO.:7 and a heavy chain as set forth in SEQ ID NO.:11 or an antigen binding fragment thereof;
j. an antibody comprising a light chain as set forth in SEQ ID NO.:7 and a heavy chain as set forth in SEQ ID NO.:30 or an antigen binding fragment thereof;
k. an antibody comprising a light chain as set forth in SEQ ID NO.:9 and a heavy chain as set forth in SEQ ID NO.:11 or an antigen binding fragment thereof; and
l. an antibody comprising a light chain as set forth in SEQ ID NO.:9 and a heavy chain as set forth in SEQ ID NO.:30 or an antigen binding fragment thereof.

The antibody or antigen binding fragment of the present invention may have a light chain variable region and/or heavy chain variable region as described above and may further comprise amino acids of a constant region, such as, for example, amino acids of a constant region of a human antibody.

In an exemplary embodiment, the antibody or antigen binding fragment of the present invention may comprise, for example, a human IgG1 constant region.

Anti-Siglec-15 antibodies of the IgG1 subtypes, which have, for example, an increase in activity of at least 10 fold in comparison with corresponding IgG2 subtypes *or other subtypes) are particularly contemplated.

An increase in the potency of the IgG1-based anti-Siglec-15 antibody of at least 2, 3, 4, 5, 6, 7, 8, 9, 10, 20, 30, 40, 50, 60, 70, 80, 90, 95, 100 fold or more or an increase in its affinity of at least 2, 3, 4, 5, 6, 7, 8, 9, 10, 20, 30, 40, 50, 60, 70, 80, 90, 95, 100 fold or more may be particularly useful.

The increased in potency or affinity may be measured by the ability of the IgG1-based anti-Siglec-15 antibody to inhibit osteoclast differentiation or osteoclast activity in comparison with a different antibody subtype having identical or substantially identical CDRs or variable regions. In some circumstances, it may be possible to consider using an IgG1 antibody concentration as low as 10 ng/ml or 100 ng/ml for attempting to inhibit osteoclast differentiation and/or bone resorption in vitro. It may be understood herein that lower dosage of IgG1-based anti-Siglec-15 antibodies may achieve a desired therapeutic effect when compared, for example, with a corresponding IgG2-based anti-Siglec-15.

Particularly contemplated antibodies include those having a kappa light chain constant region and an IgG1 heavy chain constant region.

Antibodies and antigen binding fragments of the invention include for example, monoclonal antibodies, polyclonal antibodies, human antibodies, humanized antibodies, chimeric antibodies having the amino acid sequence described herein. Human and humanized antibodies having the amino acid sequences identified herewith are particularly contemplated.

It is to be understood herein that the sequences of antibodies or antigen binding fragments thereof made of a) a light chain variable region set forth in SEQ ID NO.:6 and a heavy chain variable region set forth in SEQ ID NO.:12 or b) a light chain variable region set forth in SEQ ID NO.:22 and a heavy chain variable region set forth in SEQ ID NO.: 26 are considered of mouse origin (i.e., a non-human antibody).

As indicated herein, humanization of a non-human antibody may be performed for example, by substitution of framework amino acids for corresponding amino acids of a natural human antibody. Substitutions are usually made in a manner that does not negatively affect antigen binding.

In accordance with another exemplary embodiment of the invention, the antigen binding fragment may be, for example, a scFv, a Fab, a Fab' or a (Fab')$_2$.

EXAMPLES

Based on binding assays to recombinant Siglec-15 and evaluation of their ability to inhibit the differentiation and activity of human osteoclasts, candidate lead antibodies 25D8 and 25E9 were selected for humanization. This experimental report describes the in silico humanization procedure and the resulting humanized versions of the antibodies.

Example 1

3D Modeling of the Variable Regions of the Mouse 25D8 and 25E9 Monoclonal Antibodies This task was accomplished by homology modeling. The most similar template structures to the murine 25D8 (SEQ ID NO.:22 and SEQ ID NO.:26) and 25E9 (SEQ ID NO.:6 and SEQ ID NO.:12) variable sequences were identified by a blast searches against PDB. To build an initial model of the mouse 25D8 variable region the following template structures were used (PDB codes): 3CFC for the light chain, and 1NGQ for the heavy chain. To build an initial model of the mouse 25E9 variable region the following template structures were used: 1AE6 for the light chain, and 1NMC for the heavy chain. Mutations were operated on these template structures according to the murine 25D8 and 25E9 sequences: 3 mutations in 3CFC light chain (all in CDRs), 17 mutations in 1NGQ heavy chain (3 in the framework, 14 in CDRs), 7 mutations in 1AE6 light chain (4 in the framework, 3 in CDRs), and 34 mutations in 1NMC heavy chain (17 in the framework, 17 in CDRs). The CDR loops did not appear to require any adjustment in length except for the CDR-H3 loop in each antibody (2-residue deletion was made from 1NGQ to 25D8, and 1-residue insertion from 1NMC to 25E9). The mutated structures corresponding to the heavy and light chains of the murine 25D8 and 25E9 variable domains were virtually assembled into two-chain antibody structures by superimposing the heavy and light chains of the respective template structures. The resulting structures of assembled 25D8 and 25E9 variable domains were first refined by energy minimization with the AMBER force-field and a stepwise release of constraints, ranging from the CDR loops that were relaxed first, to the backbone heavy atoms of the framework region that were fully relaxed only in the last stage. The CDR-H3 loop in each antibody variable domain structure was then refined by Monte-Carlo-minimization (MCM) conformational sampling, in which dihedral angles in the CDR-H3 region were sampled in each MCM cycle followed by energy minimization of a pre-defined region extending 10 Å around the initial conformation of the CDR-H3 loop.

Figure 1B:
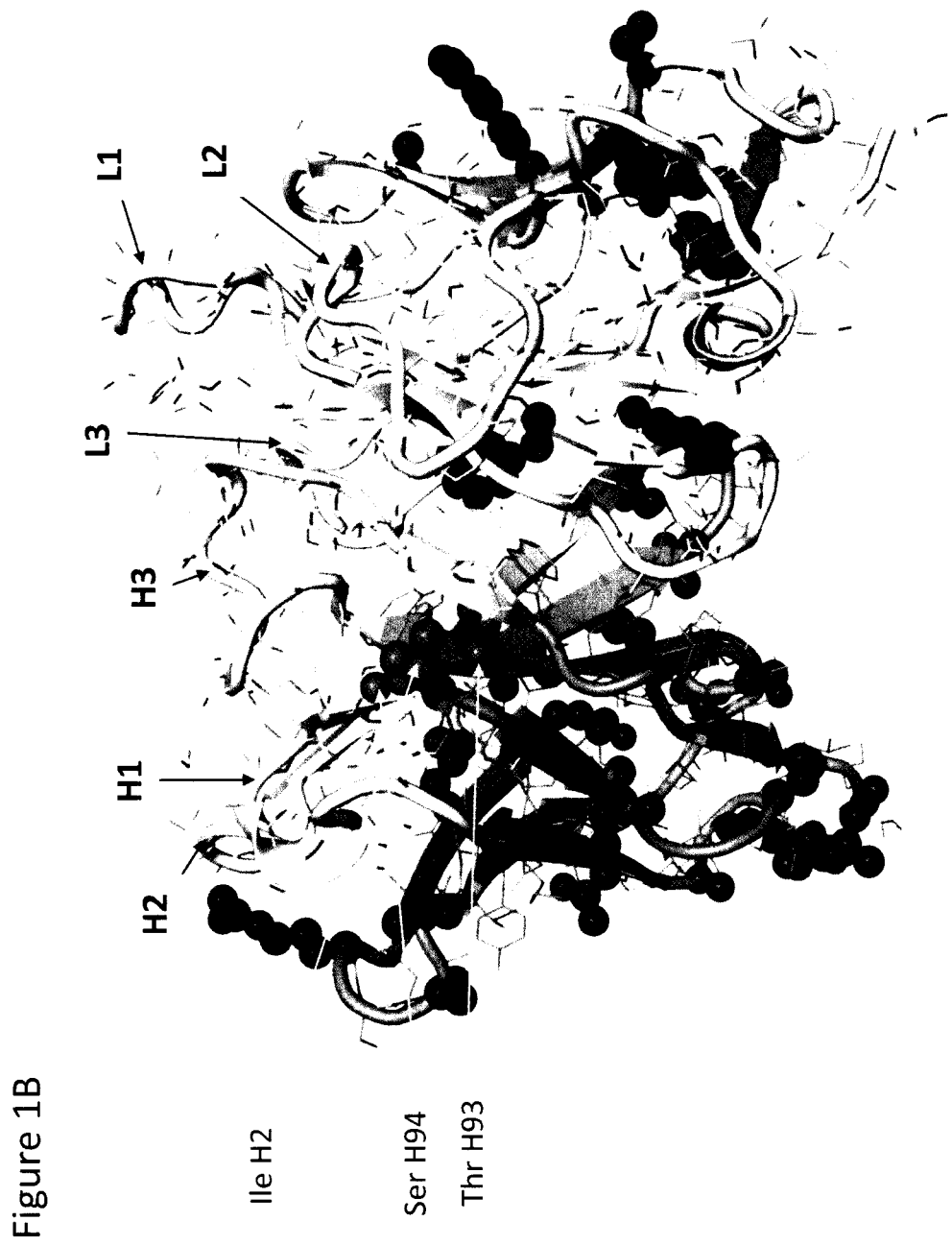
FIG. 1B. Molecular model of the murine 25E9 variable domain. CDR loops are indicated with arrows as L1, L2 and L3 in the light chain and H1, H2 and H3 in the heavy chain.

Representations of the modeled variable regions of the mouse 25D8 and 25E9 antibodies are given in FIGS. 1A and 1B, respectively. Homology 3D-models of the variable region of the mouse 25D8 (FIG. 1A) and mouse 25E9 (FIG. 1B) antibodies. CDRs are labeled (L1, L2, L3 in the light chain, and H1, H2, H3 in the heavy chain). Mouse framework residues replaced by human framework residues are indicated as blue sphere models. Retained mouse residues in the 25E9 heavy chain are represented by red sphere models and labeled.

The structures of the human or humanized variable sequences most similar to each of the 25D8 and 25E9 variable sequences were also identified from PDB, and then superimposed onto the modeled structures of the murine 25D8 and 25E9 variable domains. This assisted the modeling of side-chain mutations in the framework region in order to build the humanized 3D-structure starting from the modeled murine 3D-structures.

Example 2

Characterization of the Mouse 25D8 and 25E9 Amino-Acid Sequences and Modeled Structure This step was carried out to estimate the humanness index, antigen contact propensity index, to delineate the CDRs, canonical residues, inter-chain packing (VHNL interface residues), variable-/constant-region packing (VH/CH and VL/CL interface residues), unusual framework residues, potential N- and O-glycosylation sites, buried residues, Vernier zone residues, and proximity to CDRs. Internet-available resources and local software were used to assess these properties.

Example 3

Selection of the Best Human Light-Chain and Heavy-Chain Frameworks for the Mouse CDRs This was done by standard sequence homology comparison against a local copy of human germline databases (VBASE), against other sequence libraries (Genbank and SwissProt), as well as the set of human framework consensus sequences. BLAST searches were conducted to retrieve sequence matches with highest homology in the framework region only (thus excluding CDRs) while matching the length of the CDR loops. The human frameworks identified for the heavy and light chains correspond to the k2 and h1 classes, respectively, for both 25D8 and 25E9 antibodies. Several highly similar human framework sequences were retained in order to assess the amino-acid variability at candidate positions for mutation, as well as to provide a pool of suitable framework sequences as backup in the event of affinity loss upon humanization.

These homologous human framework sequences are aligned to the murine 25D8 and 25E9 sequences in FIGS. 2 and 3, respectively. Kabat numbering and antigen contact propensity scores are shown at the top. CDRs are highlighted in grey. Candidate residues for back-mutations are highlighted below the sequence alignment according to proximity to CDRs, surface exposure, and contact with the pairing variable domain. Primary candidate positions for back-mutations are indicated by arrows.

Example 4

Identifying Mouse Framework Residues that can Influence Conformation and Antigen Binding This is an important step that flags amino-acid residues that should be mutated to the corresponding human sequences with particular care. These residues represent primary candidates for back-mutations to the mouse sequences in case of affinity loss. It is the most difficult and unpredictable step of humanization by design, particularly in the absence of an experimental structure of the antibody-antigen complex. It relies on the identification of residues in one or more of the following categories: canonical, CDR-H3, Vernier zone, unusual, CDR-proximal (within 5 Å), inter-chain packing, and glycosylation-site residues. Such residues might affect antigen-binding site and affinity directly or indirectly. The antigen contact propensity index as well as amino-acid occurrence in human germline databases at each position are also extremely important in deciding whether a certain residue can be safely mutated from the mouse sequence to the human sequence. The proposed humanized sequences of the 25D8 and 25E9 light and heavy variable sequences are shown in FIGS. 2 and 3, respectively. The number of framework mutations between each humanized sequence and their donor mouse sequence and several aligned candidate acceptor human sequences are also listed (given as percentage of the framework in parentheses). Mutated residues and candidate residues for back-mutations are also indicated in FIGS. 1, 2 and 3. As it can be seen, the light chains of the 25D8 and 25E9 antibodies appear to require 9 and 11 mutations to their respective proposed humanized framework, respectively. This represents a 100% framework humanization attempt for the light chains. The heavy chain of each antibody appears to require substantially more mutations than their light chains for humanization, 18 in the case of 25D8 and 17 in the case of 25E9. In addition, the humanized sequences for the heavy chains do not correspond fully (100%) to human framework sequences. Particularly in the case of the 25E9 heavy chain, the highest level of framework humanization proposed is 94% in a first attempt, which translates into 5 residues differing in the humanized sequence from the closest human framework sequence. The decision to retain 4 of these residues from the 25E9 mouse sequence was based on careful structural and comparative sequence analyses that indicated a high probability of altering antigen-binding affinity if mutations are to be introduced at these positions: GluH1, IleH2, ThrH93, and SerH94 due to proximity to antigen-binding CDRs (see FIG. 1*b*). It must be noted that Glu is a common residue found at the H1 position in human framework sequences (see FIG. 3). A fifth residue differing in the humanized sequence from the closest human framework is His H43 in the mouse sequence, that was mutated to GlnH43 in the humanized sequence (Gln is common at this position while His is rare). In the case of humanization of the 25D8 variable heavy chain framework, that reached 99%, i.e., one residue difference in the framework of the proposed humanized sequence relative to the closest human framework sequence: GluH81 in the humanized sequences replaced GlnH81 of the mouse sequence instead of AspH81 that appears in the closest human framework. The decision to mutate to Glu instead of Asp at position H81 was based on the relative occurrence of these two possible substitutions in human frameworks (see FIG. 2). Overall, it can be concluded that humanization of the 25D8 antibody is easier than that of the 25E9 antibody.

Example 5

Additional Structural Analysis

Prior to submitting the humanized sequence for recombinant expression, additional structural analysis included selection of signal peptide, selection of isotype, and analysis of structural compatibility at the variable-/constant-region junctions. In addition, a comparative analysis of inter-chain packing and variable-/constant-region packing between mouse and humanized antibodies indicated that in the case of 25D8 and 25E9 humanizations it may be feasible to generate hybrid antibodies combining humanized and chimeric (mouse variable region) chains, i.e., mouse/mouse (M/M), mouse/humanized (M/H), humanized/mouse (H/M) and humanized/humanized (H/H) as light-chain/heavy-chain pairing. Assembled humanized and chimeric sequences for the 25D8 and 25E9 full-length $IgG_2$ antibodies are shown in FIGS. 4A and 4B, respectively. Assembled humanized and chimeric sequences for the 25D8 and 25E9 full-length IgG1 antibodies are shown in FIGS. 12A and 12B, respectively.

Other exemplary embodiments of antibodies may be generated, for example, by mixing each of the light chains disclosed herein with each of the heavy chain variants disclosed herein. For example, antibodies may be generated by the association of a light chain and heavy chain comprising respectively the 25E9 light chain humanized variant 2 variable domain (SEQ ID NO.:10) and the 25E9 heavy chain humanized variable domain variants 1, 2, 3 or 4 (SEQ ID NO.:14, 16, 18 or 20). Antibodies generated by the association of a light chain and heavy chain comprising respectively, the 25E9 light chain humanized variant 1 variable domain (SEQ ID NO.:8) and the 25E9 heavy chain humanized variable domain variants 1, 2, 3 or 4 (SEQ ID NO.:14, 16, 18 or 20) are particularly contemplated. Humanized 25E9 antibodies comprising the light chain humanized variant 1 variable domain (SEQ ID NO.:8) and the heavy chain humanized variable domain variant 1 (SEQ ID NO.: 14) (a.k.a., the L1H1 IgG2 variant (SEQ ID NOs.:7 and 29) or the L1H1 IgG1 variant (SEQ ID NOs.:7 and 13)) have been selected for further experimentation. However, based on experiments disclosed herewith, it appears that antibodies having a kappa light chain constant region and an IgG1 heavy chain constant region have interesting characteristics (e.g., L1H1 IgG1 variant (SEQ ID NOs. 7 and 13)).

Antibodies or antigen binding fragments made by the association of the light chain of SEQ ID NO.:7 with any of the heavy chains set forth in SEQ ID NOs. 13, 15, 17, 19, 29, 59, 60 or 61 or by the association of the light chain of SEQ ID NO.:9 with any of the heavy chains set forth in SEQ ID NOs. 13, 15, 17, 19, 29, 59, 60, or 61 are contemplated.

Example 6

Analysis of the Binding Parameters of Humanized Siglec-15 Antibodies

Small lots of the mouse and selected humanized or chimeric 25D8 IgG2 and humanized 25E9 (the L1H1 IgG2, L1H1 IgG1, L1H2 IgG1, L1H3 IgG and L1H1 IgG1 variants) antibodies were produced by transient transfection and purified to allow some comparative analyses to be conducted. A Surface Plasmon Resonance (SPR) method was used to measure the direct binding of recombinant Siglec-15 with the different antibodies. As with the ELISA methods, Siglec-15 that was used in the SPR experiments was expressed as a Fc-Siglec-15 fusion protein in 293-6E cells. It should be noted that as a Fc conjugate, the protein may be expressed as dimer by virtue of the homodimeric interaction in the Fc region. This occurrence could produce avidity effects during the binding that did not allow a direct determination of affinity constants. In addition, the presence of the Fc region in both the antibodies and the Siglec-15 protein does not permit direct affinity determinations. Thus, the binding results of each antibody sample are presented only in relation to each other.

Figure 5A:
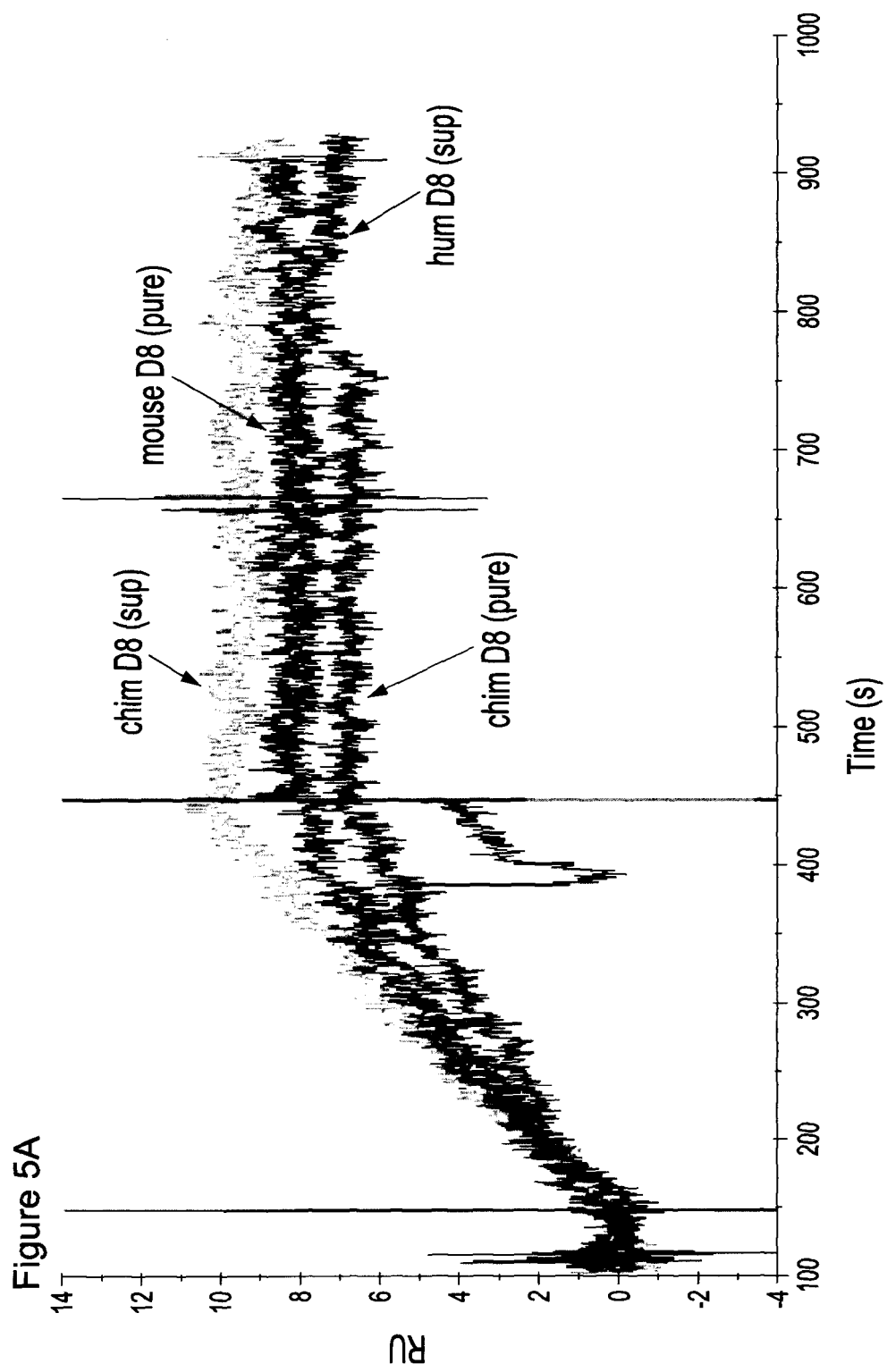
FIG. 5A. SPR chromatograms of the mouse and humanized 25D8 IgG2 antibodies.
Figure 5B:
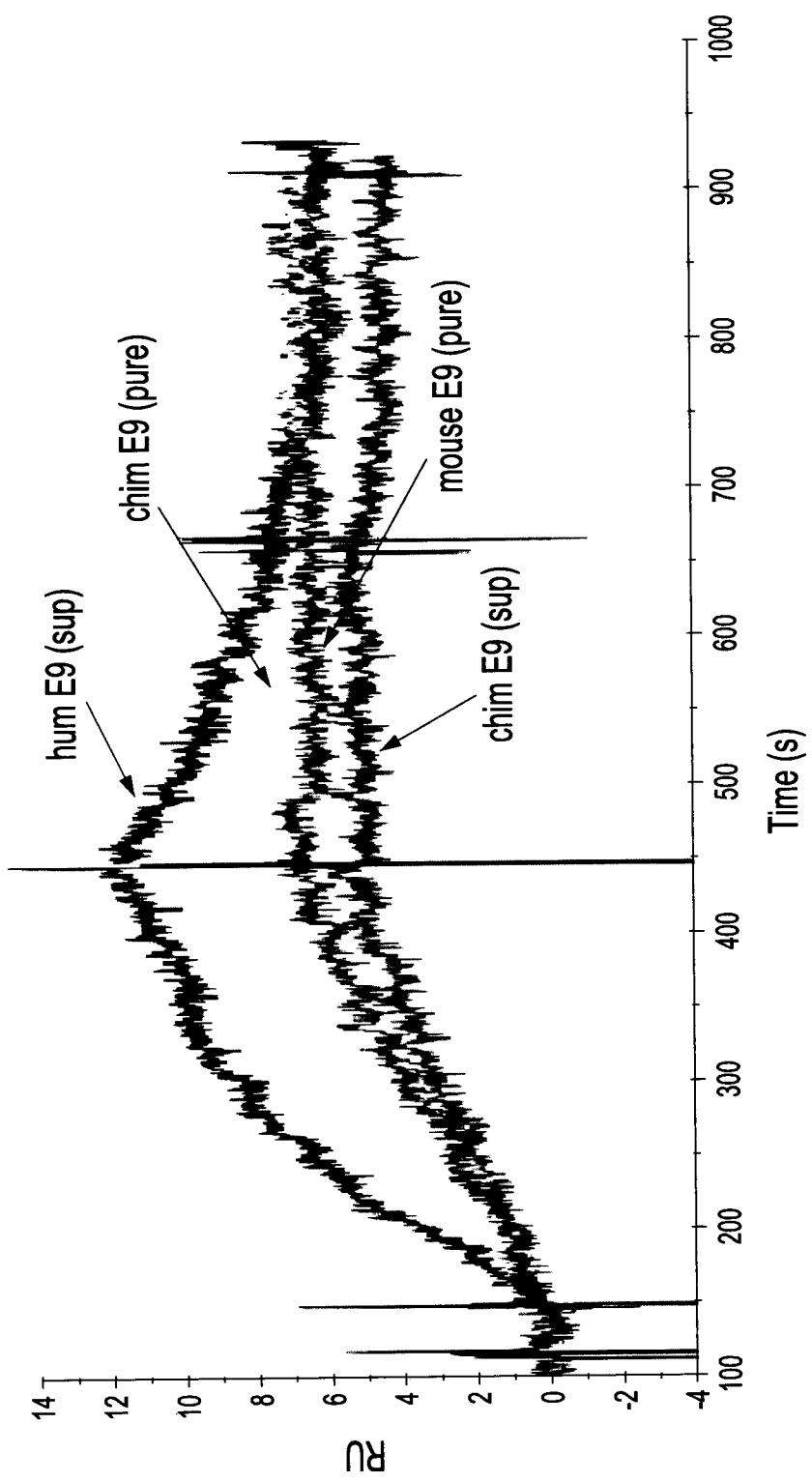
FIG. 5B. SPR chromatograms of the mouse and humanized 25E9 IgG2 antibodies.

To conduct the study, the heavy and light immunoglobulin chains from either chimeric (mouse variable regions) 25D8 IgG2, chimeric 25E9 IgG2, humanized 25D8 IgG2 or the humanized 25E9 L1H1 IgG2 variant were used directly. For comparison, purified preparations of full mouse antibodies were also tested. In the case of the purified batches of antibodies, size-exclusion chromatography was applied to all protein samples to reduce the proportion of aggregates in the preparations. For SPR, the Fc-Siglec-15 was immobilized on the sensor chip and antibody dilutions were injected (flowed) over the chips. Representative scans for the 25D8 and the 25E9 antibodies are shown in FIGS. 5A and 5B, respectively.

For the 25D8 antibody, the scans were very similar between the mouse, chimeric and humanized versions of the antibody. This showed that the kinetic parameters were not significantly altered during the humanization of this antibody. Although there are slight differences between the chromatograms, this was to be expected given the fact that the comparison was conducted between purified antibodies and cell supernatants.

In the case of the 25E9 antibody, the chromatograms for the chimeric and mouse antibodies were very similar. For the humanized 25E9 L1H1 IgG2 variant, the on and off rates appeared to be slightly different compared to the other versions. This was likely due to interference from the cell supernatants. Despite this difference, the actual affinity constant of the humanized 25E9 L1H1 IgG2 variant was expected to be very similar to that of the mouse antibody.

Figure 8:
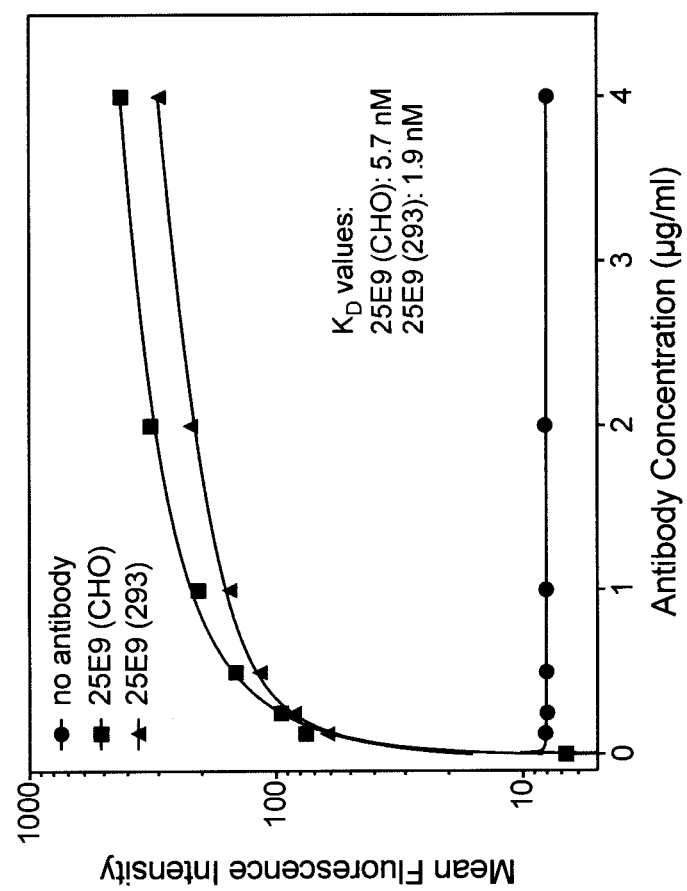
FIG. 8. Flow cytometry results indicating that 25E9 specifically binds to human Siglec-15 expressed on the surface of cells in a concentration dependent manner.

We tested the ability of the humanized antibodies to interact with human Siglec-15 expressed on the surface of cultured cells. Human 293-6E cells were grown to a cell density of approximately $1.5 \times 10^6$ cells/ml and transfected with an expression plasmid that encodes the entire human Siglec-15 cDNA. Twenty-four hours later, the cells were harvested, counted and $1 \times 10^5$ cells were incubated with increasing concentrations of the humanized IgG1 variant of 25E9 for 1 hour at 4 C. Following a washing step with cold PBS, bound 25E9 was detected with an anti-human kappa light chain IgG conjugated to FITC. Fluorescently labeled cells were injected into a flow cytometer to measure the fluorescence signal on the surface of intact cells. As shown in FIG. 8, the humanized 25E9 L1H1 IgG1 variant binds to cells expressing human Siglec-15 in a concentration dependent manner. The average $K_D$ was in the low nanomolar range. Furthermore, the binding parameters were very similar in the presence of the humanized 25E9 L1H1 IgG1 variant produced in either CHO cells or 293 cells. As a control, transfected cells incubated with either PBS, a control IgG or untransfected 293 cells resulted in no fluorescence signal indicating the specificity of the interaction between Siglec-15 and the humanized 25E9 L1H1 IgG1 variant. Similar results were obtained with other 25E9 humanized IgG1 antibody variants (the L1H2 IgG1, the L1H3 IgG1, the L1H4 IgG1 and, the L1H1 IgG2) or with the humanized 25D8 IgG2 antibody.

Example 7

Antibody Testing

Cell Culture

To induce osteoclast differentiation, mouse RAW264.7 cells (ATCC, Manassas, Va.), grown in DMEM containing 10% fetal calf serum (Gibco) and 1 mM sodium pyruvate, were scraped and resuspended in PBS. Cells were plated at $2 \times 10^4$ cells/cm$^2$ in media containing 100 ng/ml mouse RANKL (R&D Systems, Minneapolis, Minn.). Cells were allowed to differentiate for 3 days (for immunofluorescence microscopy) or 4 days (for all other experiments). Human osteoclast precursors (CD14+ peripheral blood mononuclear cells (PBMCs)) were isolated from normal human PBMCs (AllCells, Emeryville, Calif.) using CD14 microbeads and MS columns (Miltenyi Biotec, Cologne, Germany) following the manufacturer's instructions. Cells were plated at $3.1 \times 10^5$ cells/cm$^2$ in Alpha-MEM (Gibco) containing 10% fetal calf serum (HyClone), 1 mM sodium pyruvate (HyClone), 25 ng/ml human MCSF and 30 ng/ml human RANKL (R&D Systems). Cells were allowed to differentiate for 7 days, with half of the media replaced on Day 4.

Cell Stimulation

For cell stimulation with single antibodies, differentiation media was replaced with fresh growth media (without RANKL) containing the indicated antibody concentrations before lysing the cells at various times. For stimulations with primary and secondary (crosslinking) antibodies, differentiation media was replaced with cold growth media containing the primary antibody at 10 ug/ml, and cells were incubated 20 min at 4 C. Media was then replaced with warm growth media containing goat anti-human IgG polyclonal antibody (Jackson Immunoresearch, West Grove, Pa.) and cells were incubated for the indicated times at 37 C before lysis.

Osteoclast TRAP Staining and In Vitro Functional Assays

Figure 9:
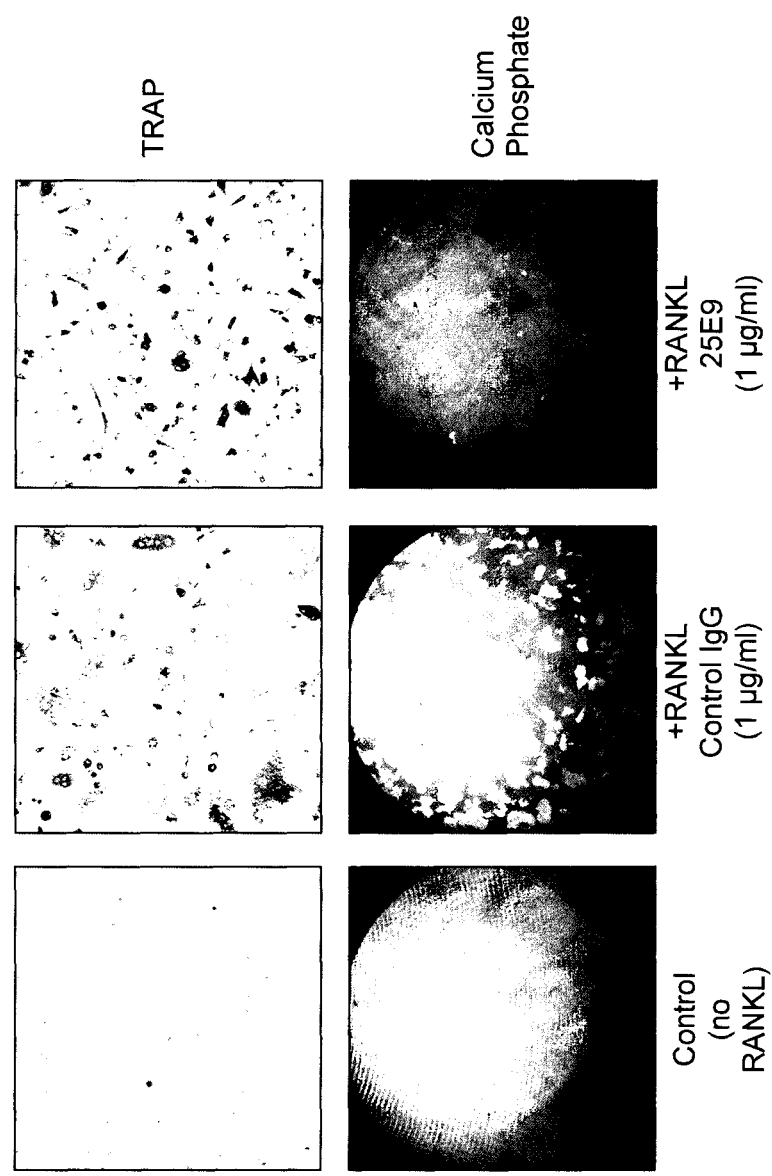
FIG. 9. Images showing the ability of 25E9 to inhibit the differentiation and resorptive activity of human osteoclasts.

To test the effect of antibodies on osteoclast differentiation and function, cells were induced to differentiate, as described above, in media containing indicated concentrations of antibodies. Osteoclasts were visualized after four days in culture by TRAP staining: briefly, cells were fixed in 3.7% formaldehyde, permeabilized with 0.2% Triton X-100/PBS, and incubated in TRAP staining buffer (100 mM sodium acetate, pH 5.2, 50 mM sodium tartrate, 0.01% Naphthol ASMX and 0.06% Fast Red Violet) for approximately 30 min at 37 C. The TRAP enzyme generates a red reaction product in osteoclasts. To test osteoclast resorption activity, cells were seeded in wells coated with a calcium phosphate substrate (Osteologic, BD BioSciences or OsteoAssay, Corning) and induced to differentiate as above. After 7 days, wells were treated with bleach to remove cells, and areas of substrate resorption were observed by light microscopy. Antibodies that are able to block the activity of Siglec-15 (in osteoclast or in osteoclast precursor cells) may show, for example, fewer TRAP-positive multinucleated cells or may result in an altered morphology of the TRAP-positive multinucleated cells. This is illustrated in FIG. 9. As shown in the upper panels, human osteoclasts exposed to 1 µg/ml of the humanized 25E9 antibody (the L1H1 IgG1 variant) (upper right panel) were unable to properly form mature multinucleated osteoclasts. By contrast, human osteoclasts treated with an equal quantity of a control antibody differentiated normally (upper middle panel). As osteoclasts actively digest mineralized substrate, antibodies that are able to block the activity of Siglec-15 (in osteoclast or in osteoclast precursor cells) may show, for example, fewer areas where the calcium substrate has been digested (denuded area) in comparison with a control (e.g., antibodies that do not bind to Siglec-15, absence of antibodies etc.). When the human osteoclasts were differentiated on a calcium phosphate substrate (see FIG. 9), which acts as a bone-like surface, cells treated with the control antibody (lower middle panel) generated large areas of denuded calcium phosphate indicating that the osteoclasts exhibited resorptive activity. By contrast, cells treated with 1 µg/ml 25E9 (the L1H1 IgG1 variant) (lower right panel) were unable to resorb the substrate, which was comparable to the undifferentiated precursor cells (lower left panel).

The ability of the 25D8 antibody to inhibit osteoclasts was also preserved after humanization, although its potency always remained lower than that of the 25E9 antibodies (whether humanized or chimeric 25E9).

Another technique involves CD14+ PBMCs that are differentiated into osteoclasts and plated on bovine cortical bone slices (differentiation may be done before plating, upon plating or after plating). The anti-Siglec-15 is added and resorption pits generated on the bone slice surface are observed by reflected light microscopy. Antibodies that are able to block the activity of Siglec-15 (in osteoclast or in osteoclast precursor cells) may result, for example, in fewer or smaller resorption pits.

Our results indicate that anti-Siglec-15 humanized antibodies are able to inhibit osteoclast differentiation and/or bone resorption.

Internalization Assay

To biotinylate cell-surface proteins, differentiated RAW264.7-derived osteoclasts were rinsed twice with cold PBS containing 1 mM $CaCl_2$ and 1 mM $MgCl_2$ (PBS/Ca/Mg, HyClone) and incubated with the biotinylation reagent sulfo-NHS-SS-biotin (Pierce), diluted to 1 mg/ml in PBS/Ca/Mg for 1 h at 4 C. The reaction was stopped by quenching unreacted biotinylation reagent with glycine (100 mM in PBS/Ca/Mg). To induce Siglec-15 internalization, cells were treated with anti-Siglec-15 antibody or a control human IgG alone or in combination with a secondary crosslinking antibody, as described in "Cell stimulations", above. Following antibody treatments, cells were rinsed twice with cold NT buffer (20 mM Tris/HCl, pH 8.6, 150 mM NaCl, 1 mM EDTA and 0.2% BSA) and incubated 2×25 min with sodium-2-mercaptoethane sulfonate (MesNa), prepared at 25 mM in cold NT buffer, to reduce the disulfide bond of sulfo-NHS-SS-biotin and thereby remove any remaining cell-surface biotin. To gauge the maximum possible level of Siglec-15 biotinylation, this MesNa treatment was omitted for one control (these control cells were incubated 2×25 min with NT buffer alone). The remaining MesNa was then quenched with iodoacetamide, diluted to 5 mg/ml in PBS/Ca/Mg, for 15 min.

To evaluate the amount of biotinylated Siglec-15 that had been internalized by the osteoclasts, cells were lysed in mRIPA. Biotinylated proteins were collected by streptavidin pull-down: 250 µg of lysate was incubated overnight with 50 µl of Dynal MyOne streptavidin beads (Invitrogen), rotating at 4 C. After extensive washing, Siglec-15 was detected in the precipitated material by western blotting.

Siglec-15 is Internalized and Degraded Following Antibody Ligation

The ability to mediate endocytosis of bound ligands and antibodies has been demonstrated for some members of the Siglec family; indeed, the cellular uptake of therapeutic antibodies is a critical aspect of the mechanism of action of antibody-drug conjugates targeting the CD22 and CD33 Siglecs (O'Reilly and Paulson, 2009). Interestingly, Siglec-15 also contains a Yxxϕ sequence in its cytoplasmic domain (this tyrosine, Y309, is also part of a putative ITIM motif); Yxxf motifs can interact with the clathrin adapter AP-2 to regulate receptor internalization (Angata et al., 2007; Bonifacino and Traub, 2003). Thus, we investigated the effect of antibody ligation on Siglec-15 endocytosis in osteoclasts.

Figure 10:
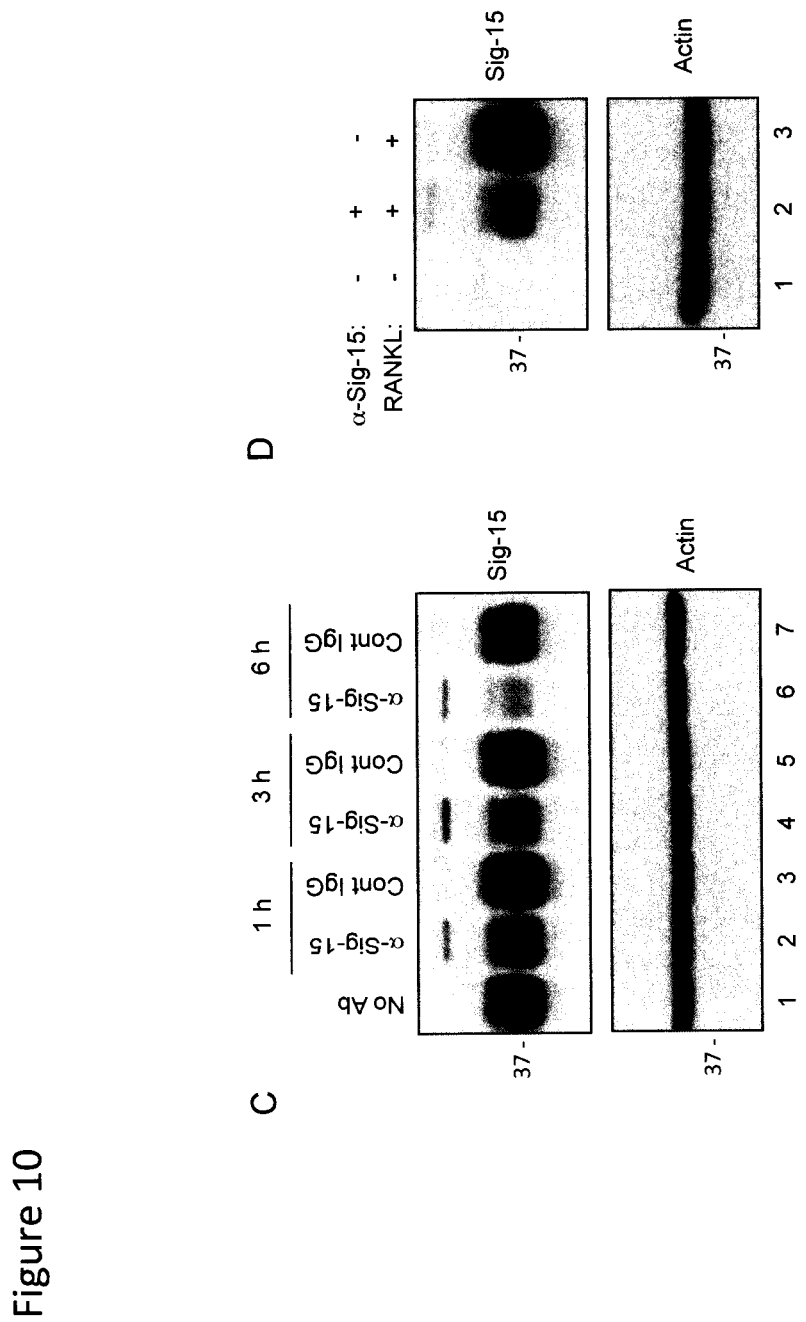
FIG. 10A. Western blot showing internalization of biotinylated Siglec-15 in the presence of anti-Siglec-15 antibody.
FIG. 10B. Characterization of Siglec-15 endocytosis by confocal microscopy.
FIG. 10C. Western blot showing Siglec-15 protein levels
FIG. 10D. Western blot showing Siglec-15 protein expression in RAW264.7 following RANKl stimulation in the presence or absence of anti-Siglec-15 antibody.

We first tested whether a Siglec-15 antibody, either alone or in combination with a secondary crosslinking antibody, could induce internalization of Siglec-15, labeled with biotin, from the surface of RAW264.7-derived osteoclasts. After the antibody stimulation, any remaining cell-surface biotin was released by treatment with a reducing agent. Cells were then lysed, and internalized, and biotinylated proteins were collected with streptavidin beads. Siglec-15 was detected in the precipitated material by western blotting. Interestingly, we found that treatment with Siglec-15 antibody alone induced substantial internalization compared to a control human IgG (FIG. 10A, compare lances 7 and 8), while addition of a secondary antibody to induce receptor clustering had less of an effect than the single antibody (FIG. 10A, lane 5).

We proceeded to characterize the antibody-induced endocytosis of Siglec-15 by immunofluorescence microscopy. RAW264.7-derived osteoclasts, growing on glass coverslips, were "cold-loaded" with anti-Siglec-15 diluted in normal growth media at 4 C, conditions that should permit antibody binding but not endocytosis. Cells were then fixed immediately or incubated in antibody-free warm media for different times prior to fixation. As expected based on the distribution of Siglec-15 in fixed, permeabilized osteoclasts, in intact osteoclasts, cold-loaded Siglec-15 antibodies bound strongly at the cell surface. After a 10-min incubation at 37 C, the staining pattern was clearly altered: Siglec-15 antibodies were present in internal punctae that are likely endosomes (FIG. 10B, center panel). While after 10 min the Siglec-15 signal was still near the plasma membrane, after 45-min it became mostly perinuclear, which is a typical lysosomal staining pattern (Toyomura et al., 2003). This was confirmed by co-staining these cells for the lysosome marker LAMP-2. Indeed, at 45 min there was substantial co-localization of Siglec-15 and LAMP-2 in perinuclear regions, whereas at earlier time points, the staining patterns were clearly divergent (FIG. 10B).

Lysosomes are principal sites of receptor degradation following endocytosis. To determine whether this is the fate of Siglec-15, we treated RAW264.7-derived osteoclasts with antibodies over a prolonged time course and analyzed total protein extracts by western blotting. Our results indicate that there was a clear decrease in Siglec-15 protein levels beginning within 3 h of addition of anti-Siglec-15 (FIG. 10C, lanes 4 and 6). In contrast, exposure of the osteoclasts with a control IgG did not cause this reduction in signal. Notably, a similar reduction in Siglec-15 protein levels was detected in RAW264.7 cells differentiated with RANKL (for 4 d) in the presence of anti-Siglec-15 (FIG. 10D). Together, these results demonstrated that bivalent anti-Siglec-15 antibodies induce rapid internalization of the receptor, which is then targeted to lysosomes for degradation.

Example 8

Preparation of Cell Lysates and Immunoprecipitation

Cell lysates were prepared using mRIPA lysis buffer (50 mM Tris/HCl pH 7.4, 1% NP-40, 0.25% deoxycholate, 150 mM NaCl) containing protease and phosphatase inhibitors (50 mM NaF, 1 mM NaVO$_4$ and 1× Roche Complete EDTA-free phosphatase inhibitors). Lysate protein concentrations were measured by BCA assay (Pierce). For western blotting of total cell lysates, equal amounts of protein (10-15 ug) were heat-denatured in SDS sample buffer containing β-mercaptoethanol, separated on a 10 or 12% SDS-PAGE gel, transferred to PVDF and probed with the indicated antibodies. For immunoprecipitations, 2 mg or 1 mg of total lysates were incubated with 4 μg antibody and 15 μl of Protein G-Sepharose beads for 4 h, rotating at 4 C. After washing the beads 4× with mRIPA, half of the precipitated material was analyzed by western blotting, as above.
Interaction Between Siglec-15 and DAP12 and Multimerization of Siglec-15

A recent study demonstrated that upon co-overexpression of epitope-tagged forms of Siglec-15 and DAP12 in 293T cells, a complex could be detected, which was dependent on the presence of K273 (Angata et al., 2007). We were also able to detect this complex under similar overexpression conditions (data not shown), and we proceeded to determine whether the complex is also present at endogenous expression levels in osteoclasts. Protein lysates were prepared from differentiated RAW264.7-derived osteoclasts as well as from non-differentiated control cells, and immunoprecipitations were performed using Siglec-15 and DAP12 antibodies. DAP12 was readily detected in protein complexes precipitated with anti-Siglec-15, and likewise, anti-DAP12 precipitated abundant Siglec-15. As expected, based on Siglec-15 protein expression levels, this complex was highly osteoclast-specific and was not detected in non-differentiated cells. Notably, DAP12 expression was not dramatically altered during RAW264.7 osteoclast differentiation.

Figure 11:
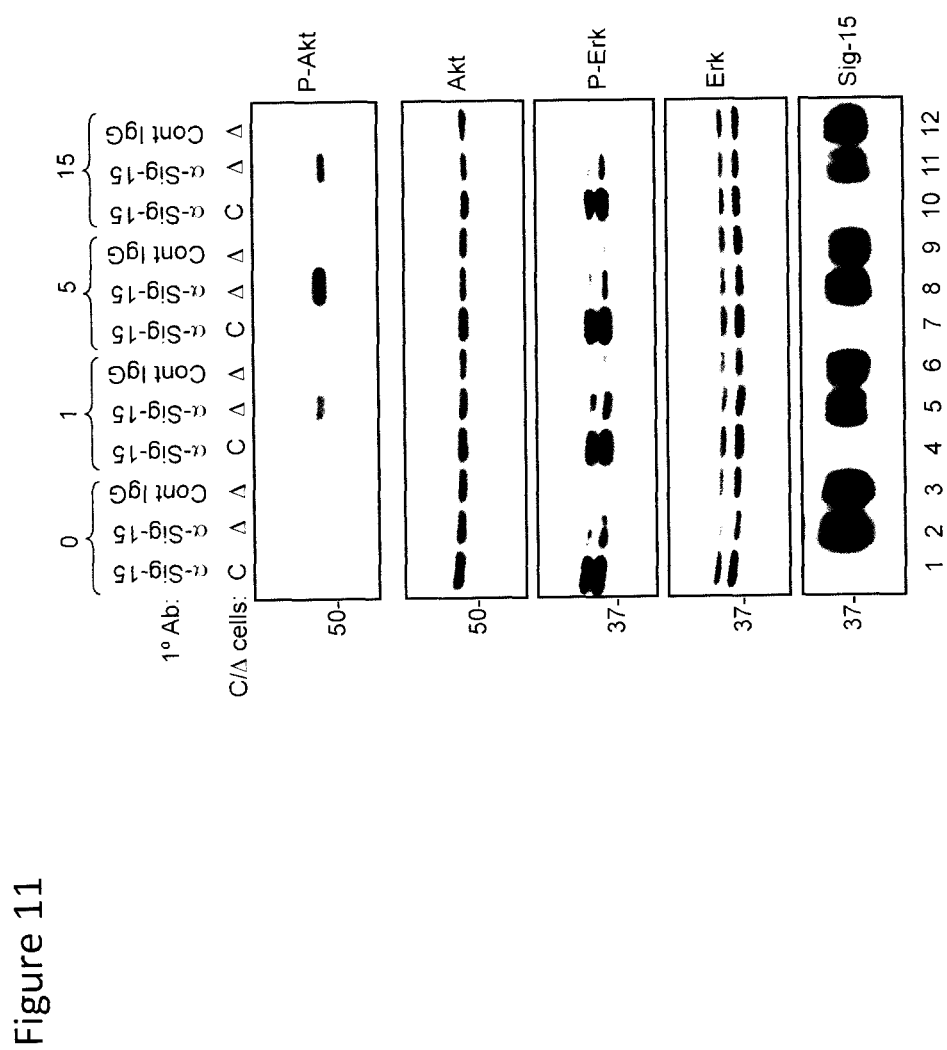
FIG. 11. Analysis of cell signaling induced by Siglec-15 clustering. Control (C) or differentiated (Δ) RAW264.7 cells were treated with primary antibody (anti-Siglec-15 or control human IgG) at 4 C followed by a secondary crosslinking antibody for the indicated times at 37 C. Total lysates were analyzed by western blotting with the indicated antibodies.

Previous studies showed that when phosphorylated on its ITAM motif, DAP12 is capable of activating a number of signaling pathways, including the PI3K-Akt, PLCg and Grb2-Ras-Erk cascades (Turnbull and Colonna, 2007). However, the signaling output of DAP12 in specific contexts is highly dependent on its associated receptor (Turnbull and Colonna, 2007). In the absence of an identified natural ligand or molecular partner for Siglec-15, we used an antibody cross-linking approach to evaluate the ability of Siglec-15 to activate intracellular signaling. Initially, we treated RAW-derived osteoclasts with anti-Siglec-15 for multiple time points up to 30 min but failed to observe any activation of Akt, PLCg, or Erk (data not shown). However, for several other DAP12-associated receptors, higher-order clustering of the receptor, rather than bivalent antibody-induced dimerization, is required to induce ITAM-dependent signaling (Turnbull and Colonna, 2007; Underhill and Goodridge, 2007). To induce multimerization, we treated cells with a primary Siglec-15 antibody followed by a secondary, crosslinking antibody. Under these conditions, we observed a signaling effect (FIG. 11, lanes 5, 8 and 11), with Akt becoming strongly phosphorylated within minutes of secondary antibody crosslinking. Maximum phosphorylation of Akt was achieved after 5 min of treatment with anti-Siglec-15 (FIG. 11, lane 8). In contrast, phospho-Erk (FIG. 11) and phospho-PLCg (not shown) were not modulated. Consistent with the lack of expression of Siglec-15, there was no activation of Akt in non-differentiated RAW264.7 cells under the same conditions. Likewise, substitution of the primary Siglec-15 antibody with a control human IgG eliminated the signaling response (FIG. 11, see lanes 3, 6, 9 and 12). These results demonstrated that Siglec-15 crosslinking specifically activates Akt without affecting Erk or PLCg, two other pathways commonly downstream of DAP12 (Turnbull and Colonna, 2007; Underhill and Goodridge, 2007).

If induction of cell signaling by Siglec-15 is dependent on the DAP12 ITAM motif, tyrosine phosphorylation of DAP12 should be detectable upon Siglec-15 clustering. To test this, we immunoprecipitated DAP12 and evaluated its phosphorylation by western blotting. In RAW264.7-derived osteoclasts stimulated with primary/secondary antibodies to crosslink Siglec-15 (as described above), we detected a tyrosine-phosphorylated band at 12 kDa that is very likely DAP12. In non-differentiated cells treated in the same manner or osteoclasts treated with a control human IgG, little or no DAP12 phosphorylation was detected. Notably, although abundant Siglec-15 was co-precipitated with DAP12 from the differentiated osteoclasts (as expected), no phosphotyrosine signal was detected at its molecular weight (37 kDa), indicating that phosphorylation of the cytoplasmic tyrosine residue of Siglec-15, part of its putative ITIM motif, is not involved in the signaling response (data not shown). Thus, our results are consistent with DAP12 acting as a signaling module for Siglec-15; DAP12 becomes phosphorylated following Siglec-15 clustering, likely leading to recruitment of signaling molecules to its ITAM motif and activation of the Akt pathway.

Anti-Siglec-15 antibodies capable of inhibiting dimerization or multimerization of Siglec-15 may thus inhibit Siglec-15 activity in osteoclasts or in osteoclast precursors. For example, in order to determine the ability of an antibody to inhibit dimerization or multimerization of Siglec-15, the level of activation of DAP12 (e.g., DAP12 phosphorylation) and/or of its downstream effectors (Akt pathway) may be tested.

Example 9

Comparison of IgG1 and IgG2 Antibody Variants

We proceeded to compare humanized anti-Siglec-15 IgG1 antibody variants with corresponding humanized anti-Siglec-15 IgG2 antibody variants (i.e., the antibodies have the same variable domains but the human constant region of the heavy chain differs) and found that, in the in vitro experiments described below, IgG1s are much more active than the corresponding IgG2s.

More particularly, we compared the binding activity of the humanized 25E9 L1H1 IgG1 (the L1H1 IgG1 variant) with the humanized 25E9 L1H1 IgG2 (the L1H1 IgG2 variant) using SPR. The analysis was conducted using methods similar to what was described above (see Example 6). In this instance, Fc-Siglec-15 was immobilized on the chip and decreasing concentrations of the 25E9 antibody variants were injected (100 nM, 33.3 nM, 11.1 nM, 3.70 nM and 1.23 nM). The result showed that the affinity of the humanized 25E9 L1H1 IgG1 variant for Siglec-15 was almost 10-fold higher than the humanized 25E9 L1H1 IgG2 variant with comparative KD values of 0.164 nM and 1.26 nM, respectively (see FIG. 12). The difference in binding was mostly contributed by a slower off-rate (kd) of the IgG1 compared to the IgG2.

Figure 13:
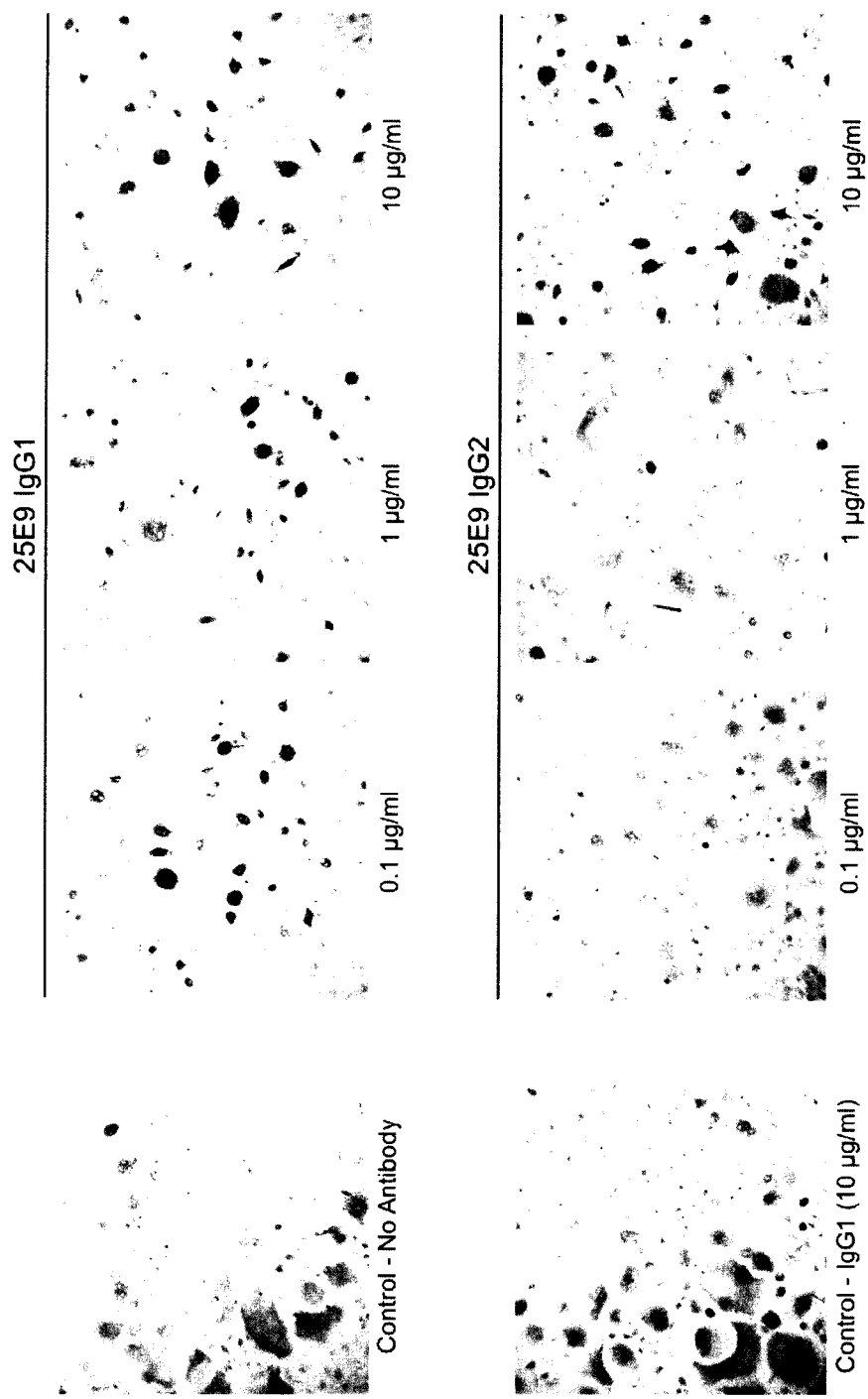
FIG. 13. Representative images showing the increased potency of the humanized 25E9 L1H1 IgG1 compared to the humanized 25E9 IgG2 for inhibiting the differentiation of osteoclasts.

The ability to inhibit human osteoclast differentiation of the humanized 25E9 L1H1 IgG1 variant (the L1H1 IgG1 variant) and IgG2 (the L1H1 IgG2 variant) was also examined. Human osteoclast precursor cells were enriched and differentiated as described above in the presence of increasing concentrations of the antibodies (see FIG. 13). In the presence of the humanized 25E9 L1H1 IgG1 variant, less than 100 ng/ml of antibody is required to completely inhibit the differentiation of osteoclasts in this assay. By contrast, 10 µg/ml of the humanized 25E9 L1H1 IgG2 variant is required to obtain the same degree of inhibition. This represents an almost 100-fold difference in potency of the humanized 25E9 L1H1 IgG1 variant versus the corresponding IgG2 variant. In control samples, the differentiation of osteoclasts exposed to either the vehicle or a control IgG at 10 µg/ml was unaffected. Although the increase in potency of IgG1-based antibodies was demonstrated for the L1H1 variant, such increase is also expected for the other 25E9 humanized variants, hybrid or mouse antibodies.

In fact, we also observed that the potency of another Siglec-15 humanized antibody, 25D8, was highly augmented as an IgG1 versus and IgG2. It is expected that other anti-Siglec-15 antibodies may benefit from having a human IgG1 constant region instead of other types of constant region. Such antibodies may be identified by measuring an increase in affinity of the IgG1-based anti-Siglec-15 antibody towards cells expressing Siglec-15 or towards recombinant Siglec-15, or testing the ability of the IgG1-based antibody to inhibit osteoclast differentiation or activity (in vitro or in vivo).

Based on these results, human IgG1-based anti-Siglec-15 antibodies may advantageously be administered at lower dosage in human.

Example 10

Antibody-Drug Conjugates (ADC) that Target Siglec-15

Figure 15:
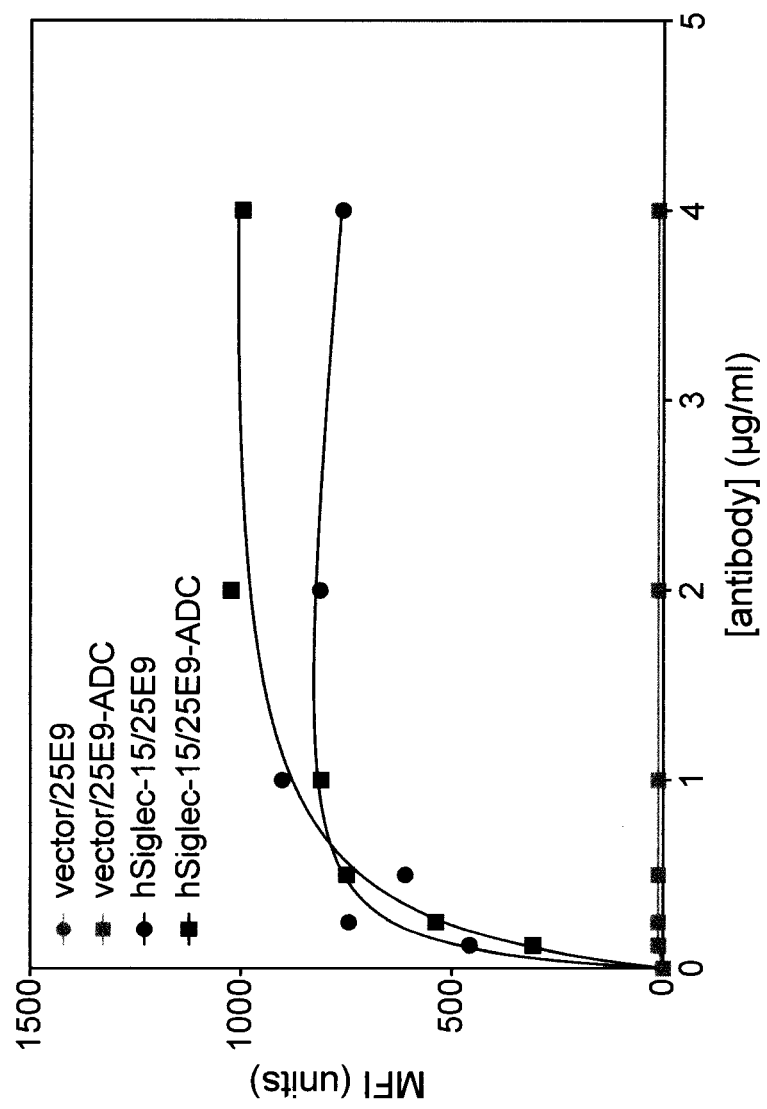
FIG. 15. Flow cytometry results indicating that 25E9-ADC specifically binds to human Siglec-15 expressed on the surface of cells in a manner very similar to the unconjugated antibody.

The Applicant demonstrated that binding of an antibody to Siglec-15 expressed on the surface of osteoclasts was efficiently internalized and degraded. Additional studies also indicated that the internalization followed the endosomal pathway and the Siglec-15/antibody complex could be co-localized with LAMP2, a marker of late-endosomes/lysosomes. Experiments were undertaken to examine the feasibility of targeting Siglec-15-expressing cells with an ADC. The humanized 25E9 L1H1 IgG1 variant was conjugated to a payload that is toxic to proliferating cells as well as non-proliferating or fully differentiated cells, in particular osteoclasts. The humanized 25E9 L1H1 IgG1 conjugated antibody was designated 25E9-ADC. Since the conjugation might affect the ability of 25E9 to interact with native Siglec-15, flow cytometry was conducted to measure the binding of the 25E9-ADC to Siglec-15 expressing cells. The experiments were performed as described above using 293-6E cells transfected with a cDNA encoding the human Siglec-15. As illustrated in FIG. 15, unconjugated 25E9 and the 25E9-ADC interacted with the Siglec-15-transfected cells with very similar affinities (see black curves, h-Siglec-15). This indicated that the conjugation reaction did not alter the ability of the 25E9-ADC to bind to Siglec-15. As a control, cells transfected with the plasmid not containing the Siglec-15 cDNA (see FIG. 15 grey curves, vector) did not bind to 25E9 indicating that the antibodies do not bind to the cells non-specifically.

Figure 16:
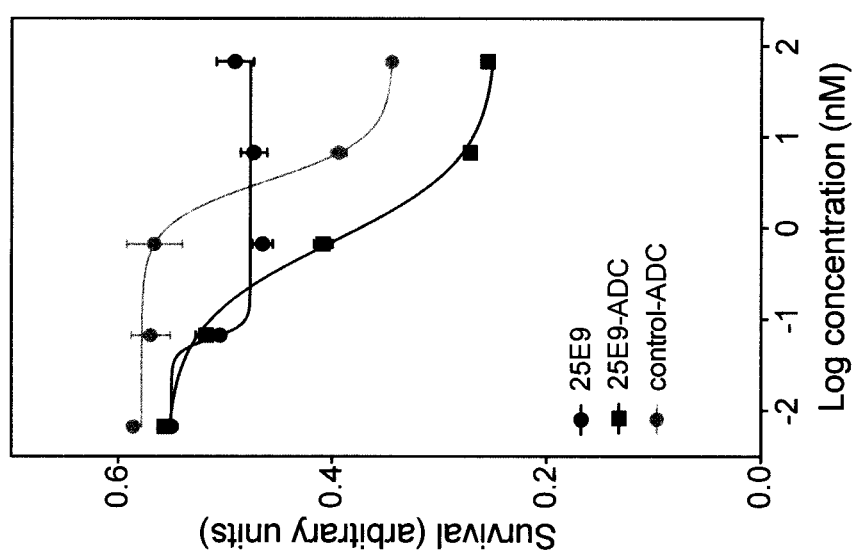
FIG. 16. Shows the survival curves of the 25E9-ADC against mature, multi-nucleated osteoclasts. The response is very different to the unconjugated 25E9, which strongly inhibits osteoclast activity without affecting their survival.

The cytotoxic activity of the antibodies was examined next. Human osteoclast precursor cells were isolated and seeded in 96-well plates in the presence of M-SCF and RANKL, in a manner similar to what was described previously. The osteoclasts were allowed to differentiate for 7 days in order to become fully mature, multi-nucleated TRAP-positive osteoclasts. Following differentiation, the cells were treated with unconjugated 25E9, 25E9-ADC or the control-ADC for 4 days. The remaining cell number (% survival) was determined using standard calorimetric methods. As expected, unconjugated 25E9 had no effect on the survival of human osteoclasts (see FIG. 16). This result was in agreement with previous results showing that despite potent inhibition of osteoclast differentiation by 25E9, the antibody does not kill the cells. By contrast, the 25E9-ADC showed dose-dependent decrease in the number of surviving cells (FIG. 16), a result consistent with cytotoxicity of the delivered toxin. The $IC_{50}$ value of this cytotoxicity was in the sub-nanomolar range. The control ADC, which does not bind to human Siglec-15, showed mild non-specific activity in this assay. At the end of the study, the cells were fixed and stained for TRAP activity using methods that were described in Example 7 in order to visually inspect the effect of the antibodies on the osteoclasts. As shown in FIG. 17, treatment with unconjugated 25E9 (upper panels) had a severe effect on the morphology of the osteoclasts resulting in small, intensely-TRAP stained cells, which we have previously shown are non-functional and completely devoid of resorptive activity (see FIG. 9). Treatment with the 25E9-ADC resulted in death of the osteoclasts and virtually all of the cells were gone at 1 µg/ml (see FIG. 17, middle panels), a result that was in agreement with the cell number determinations shown in FIG. 16. Finally, the control-ADC did not show any toxic effects on the mature osteoclasts (see FIG. 17, lower panels) and the number of osteoclasts, even at 10 µg/ml, was similar to the number observed with the untreated cells. These results indicate that the cytotoxicity observed with the 25E9-ADC was specific to Siglec-15-positive osteoclasts.

Taken together, these results show that ADCs that target Siglec-15 expressed on the surface of osteoclasts have cytotoxic activity.

Example 11

In Vivo Functional Assay—Mouse

Evaluation of in vivo efficacy was adapted from the methods described by Schenk (Muhlbauer et al., 1991) using very young mice that have rapidly growing bones. Briefly, 3-4 week-old male mice (5 animals/group) were treated with either, PBS, a control mouse IgG or an anti-Siglec-15 antibody capable of binding to mouse Siglec-15. The antibodies were administered intra-peritoneally twice per week for four weeks using 26G needles. The mice were sacrificed, and bones were dissected and fixed in 4% paraformaldehyde for 24 h. After washing in PBS, the bones were scanned using a PIXImus Densitometer (GE Medical Systems) to determine the bone mineral density (BMD) of the femurs, the tibias and the vertebrae. Three-dimensional images of the bones were generated with a SkyScan high resolution microCT (SkyScan Inc., Kontich, Belgium).

For these experiments, 3-4 week old mice were treated with an anti-Siglec-15 antibody for four weeks and assessed the effects of this treatment on the long bones and the vertebrae. Since young mice have rapidly growing bones at this age, the perturbation of osteoclast activity by anti-resorptives can provoke a rapid, dramatic increase in bone mineral density (BMD) in a relatively short period of time. Following the treatment period, the animals were euthanized, the bones were dissected and scanned by densitometry to calculate the BMD. Compared to a control mouse IgG, treatment with the anti-Siglec-15 monoclonal antibody resulted in a considerable, dose-dependent increase in BMD in the femur, tibia and vertebra of these mice. In order to further examine the changes in BMD, selected bone samples were scanned using X-ray microtomography (MicroCT) to analyze their microarchitecture. In agreement with the densitometry result, we observed a marked increase in trabecular volume in the femurs and the vertebra of the mice treated with the anti-Siglec-15 antibody compared with the control IgG-treated mice and the L5 vertebra. In agreement with these qualitative observations, quantitative measurements of the microCT scans confirmed the increase in bone mineral density in the animals treated with the Siglec-15 antibody. In particular, there were statistically significant increases in bone volume, bone surface, trabecular number and connectivity density. Conversely, the trabecular separation was significantly decreased, a change that was in line with the increased density of trabecular structures.

The objective of the following study was to determine the effect of an antibody targeting Siglec-15 in the rat ovariectomy (OVX) model.

Thirty-two Sprague-Dawley rats were sham operated or ovariectomized and treated 12 weeks later with PBS (q28d), Siglec-15 antibody (an anti-mouse Siglec-15 antibody, 10 mg/kg, q28d) or zoledronic acid (ZOL, 0.1 mg/kg, single injection). After a twelve-week treatment, bones were analyzed by densitometry, microCT, histomorphometry, 3-point bending (femur) and axial compression (LV4) and serum was analyzed for TRAP 5b and ALP levels.

As expected, bone mineral density (BMD) was reduced dramatically in the OVX-PBS group compared to the sham operated animals, while ZOL treatment increased BMD. Administration of 25B2 caused a significant increase in BMD at all sites. These changes were confirmed by microCT analyses, which showed significant increases in bone volume, trabecular (Tb) number and corresponding decreases in Tb separation compared to control group. Correspondingly, improvements in bone strength in animals treated with the anti-mouse Siglec-15 antibody were observed by biomechanical analysis: maximum load, stiffness and energy-to-failure parameters were all increased. Examination of tibial sections showed that the number of osteoclasts was significantly increased by the anti-mouse Siglec-15 antibody treatment, but the TRAP-positive cells were smaller and more intensely stained. Serum TRAP 5b was decreased in the anti-mouse Siglec-15 antibody group consistent with a decrease in secretion of this enzyme by osteoclasts. Interestingly, the serum level and the histological staining of ALP were unchanged in the antibody-treated animals. This contrasts with the effect of ZOL treatment, which caused a significant decrease in ALP staining. Dynamic histomorphometry analysis using dual-calcein labeling indicated that the endosteal mineral apposition rate was greater in the antibody-treated group compared to both the vehicle and ZOL treated groups, suggesting stimulation of new bone formation by the anti-Siglec-15 antibody.

Taken together, our results reveal that targeting Siglec-15 with a monoclonal antibody in a pathologic bone loss model improves bone quality and strength, likely due to combined inhibition of osteoclast function and maintenance of osteoblast activity.

In Vivo Functional Assay—Monkeys

To explore the effects of Siglec-15 inhibition on bone biomarkers in primates, we administered the humanized monoclonal antibody targeting Siglec-15, 25E9, to estrogen-deficient female cynomolgus monkeys.

Two intravenous injections of vehicle (PBS) or 25E9 at 10 mg/kg were administered to two groups at an 8-week interval with a follow-up period of 6 months. Estrogen deficiency was induced by the repeated subcutaneous administration of a gonadotropin-releasing hormone agonist every 4 weeks starting 3 months prior to administering 25E9 and throughout the follow-up period. Serum and urine samples were collected weekly to evaluate the bone resorption and formation biomarkers, determine the PK profile of AB-25E9 and monitor for the presence of antibody-drug antibodies (ADA).

Treatment with 25E9 rapidly decreased bone resorption biomarkers (urinary NTx, serum CTx and TRAP5b) by 30% to 45% demonstrating the anti-resorptive properties of 25E9. Strikingly, the bone formation biomarkers (osteocalcin and BSAP) did not rapidly decrease and were minimally affected. The decrease in the levels of bone resorption biomarkers began to attenuate at approximately Week 6, which coincided with the appearance of ADAs. Interestingly, this attenuation was not observed before Week 20 in animals where little or no ADAs were detected. In agreement with these findings, the decline in AB-25E9 serum concentrations was faster in animals in which ADAs were detected. In monkeys that were negative for ADAs, the terminal elimination half-life of 25E9 ranged between 5-12 days.

Taken together, the biomarker profiles presented here show that 25E9 has anti-resorptive activity and maintains bone formation estrogen-deficient cynomolgus monkeys. These results underscore the novel mechanism of action of 25E9 and highlight its potential for osteoclast-targeted therapy of bone-related diseases.

Our experiments in mice or monkeys also included groups treated with 30 mg/kg of the anti-Siglec-15 antibody. Surprisingly, this increase in dosage was not associated with added benefit. To the contrary, in some instances there was a decrease in the effect of the antibody at this dose compared to a dosage of 10 mg/kg.

REFERENCES

The entire content of the references listed in the present application is incorporated herein by reference.

Stuible M. et al., U.S. Provisional application No. 61/673, 442 filed on Jul. 19, 2012.

Stuible M. et al., U.S. Provisional application No. 61/777, 049 filed on Mar. 12, 2013.

Stuible M. et al., U.S. Provisional application No. 61/810, 415 filed on Apr. 10, 2013.

Sooknanan, R. R. et al., "Polynucleotides and polypeptide sequences involved in the process of bone remodelling", international application No. PCT/CA2007/000210 (published on Aug. 23, 2007 under No. WO2007/093042).

Tremblay, G. B. et al. "Siglec 15 Antibodies in Treating Bone Loss-Related Disease", international application No. PCT/CA2010/001586 (published on Apr. 14, 2011 under No. WO2011/041894);

Hiruma Y. et al., "Antibody Targeting Osteoclast-Related Protein Siglec-15"; U.S. Ser. No. 12/677,621 published on Aug. 19, 2010 under US2010/0209428A1;

Hiruma Y. et al., "Anti-Siglec-15 Antibody", U.S. Ser. No. 13/143,253 published on Nov. 3, 2011 under No. US2011/0268733A1;

Watanabe, I. et al., "Antibody Targeting Osteoclast-Related Protein Siglec-15", international application No. PCT/EP2011/005219 published on Apr. 12, 2012 under No. WO2012045481A2.

Angata, T., T. Hayakawa, M. Yamanaka, A. Varki, and M. Nakamura. 2006. Discovery of Siglec-14, a novel sialic acid receptor undergoing concerted evolution with Siglec-5 in primates. *FASEB J* 20:1964-1973.

Angata, T., Y. Tabuchi, K. Nakamura, and M. Nakamura. 2007. Siglec-15: an immune system Siglec conserved throughout vertebrate evolution. *Glycobiology* 17:838-846.

Baron, R., S. Ferrari, and R. G. Russell. 2011. Denosumab and bisphosphonates: different mechanisms of action and effects. *Bone* 48:677-692.

Blasius, A. L., M. Cella, J. Maldonado, T. Takai, and M. Colonna. 2006. Siglec-His an IPC-specific receptor that modulates type I IFN secretion through DAP12. *Blood* 107:2474-2476.

Blasius, A. L., and M. Colonna. 2006. Sampling and signaling in plasmacytoid dendritic cells: the potential roles of Siglec-H. *Trends Immunol* 27:255-260.

Bonifacino, J. S., and L. M. Traub. 2003. Signals for sorting of transmembrane proteins to endosomes and lysosomes. *Annu Rev Biochem* 72:395-447.

Boyle, W. J., W. S. Simonet, and D. L. Lacey. 2003. Osteoclast differentiation and activation. *Nature* 423:337-342.

Crocker, P. R., J. C. Paulson, and A. Varki. 2007. Siglecs and their roles in the immune system. *Nat Rev Immunol* 7:255-266.

Crocker, P. R., and P. Redelinghuys. 2008. Siglecs as positive and negative regulators of the immune system. *Biochem Soc Trans* 36:1467-1471.

Hiruma, Y., T. Hirai, and E. Tsuda. 2011. Siglec-15, a member of the sialic acid-binding lectin, is a novel regulator for osteoclast differentiation. *Biochem Biophys Res Commun* 409:424-429.

Humphrey, M. B., M. R. Daws, S. C. Spusta, E. C. Niemi, J. A. Torchia, L. L. Lanier, W. E. Seaman, and M. C. Nakamura. 2006. TREM2, a DAP12-associated receptor, regulates osteoclast differentiation and function. *J Bone Miner Res* 21:237-245.

Ishida-Kitagawa, N., K. Tanaka, X. Bao, T. Kimura, T. Miura, Y. Kitaoka, K. Hayashi, M. Sato, M. Maruoka, T. Ogawa, J. Miyoshi, and T. Takeya. 2012. Siglec-15 regulates the formation of functional osteoclasts in concert with DNAX-activating protein of 12 KDa (DAP12). *J Biol Chem*

Kaifu, T., J. Nakahara, M. Inui, K. Mishima, T. Momiyama, M. Kaji, A. Sugahara, H. Koito, A. Ujike-Asai, A. Nakamura, K. Kanazawa, K. Tan-Takeuchi, K. Iwasaki, W. M. Yokoyama, A. Kudo, M. Fujiwara, H. Asou, and T. Takai. 2003. Osteopetrosis and thalamic hypomyelinosis with synaptic degeneration in DAP12-deficient mice. *J Clin Invest* 111:323-332.

Lanier, L. L. 2009. DAP10- and DAP12-associated receptors in innate immunity. *Immunol Rev* 227:150-160.

Law, C. L., S. P. Sidorenko, K. A. Chandran, Z. Zhao, S. H. Shen, E. H. Fischer, and E. A. Clark. 1996. CD22 associates with protein tyrosine phosphatase 1C, Syk, and phospholipase C-gamma (1) upon B cell activation. *J Exp Med* 183:547-560.

Liu, Q. Y., R. R. Sooknanan, L. T. Malek, M. Ribecco-Lutkiewicz, J. X. Lei, H. Shen, B. Lach, P. R. Walker, J. Martin, and M. Sikorska. 2006. Novel subtractive transcription-based amplification of mRNA (STAR) method and its application in search of rare and differentially expressed genes in AD brains. *BMC Genomics* 7:286.

Mao, D., H. Epple, B. Uthgenannt, D. V. Novack, and R. Faccio. 2006. PLCgamma2 regulates osteoclastogenesis via its interaction with ITAM proteins and GAB2. *J Clin Invest* 116:2869-2879.

Muhlbauer, R. C., F. Bauss, R. Schenk, M. Janner, E. Bosies, K. Strein, and H. Fleisch. 1991. BM 21.0955, a potent new bisphosphonate to inhibit bone resorption. *J Bone Miner Res* 6:1003-1011.

O'Reilly, M. K., and J. C. Paulson. 2009. Siglecs as targets for therapy in immune-cell-mediated disease. *Trends Pharmacol Sci* 30:240-248.

Paloneva, J., M. Kestila, J. Wu, A. Salminen, T. Bohling, V. Ruotsalainen, P. Hakola, A. B. Bakker, J. H. Phillips, P. Pekkarinen, L. L. Lanier, T. Timonen, and L. Peltonen. 2000. Loss-of-function mutations in TYROBP (DAP12) result in a presenile dementia with bone cysts. *Nat Genet.* 25:357-361.

Park-Wyllie, L. Y., M. M. Mamdani, D. N. Juurlink, G. A. Hawker, N. Gunraj, P. C. Austin, D. B. Whelan, P. J. Weiler, and A. Laupacis. 2011. Bisphosphonate use and the risk of subtrochanteric or femoral shaft fractures in older women. *JAMA* 305:783-789.

Raggatt, L. J., and N. C. Partridge. 2010. Cellular and molecular mechanisms of bone remodeling. *J Biol Chem* 285:25103-25108.

Reid, I. R., and J. Cornish. 2011. Epidemiology and pathogenesis of osteonecrosis of the jaw. *Nat Rev Rheumatol* 8:90-96.

Roelofs, A. J., K. Thompson, S. Gordon, and M. J. Rogers. 2006. Molecular mechanisms of action of bisphosphonates: current status. *Clin Cancer Res* 12:6222s-6230s.

Sooknanan, R. R., G. B. Tremblay, and M. Filion. 2011. Polynucleotides and polypeptide sequences involved in the process of bone remodeling. U.S. Pat. No. 7,989,160.

Takahata, M., N. Iwasaki, H. Nakagawa, Y. Abe, T. Watanabe, M. Ito, T. Majima, and A. Minami. 2007. Sialylation of cell surface glycoconjugates is essential for osteoclastogenesis. *Bone* 41:77-86.

Taylor, V. C., C. D. Buckley, M. Douglas, A. J. Cody, D. L. Simmons, and S. D. Freeman. 1999. The myeloid-specific sialic acid-binding receptor, CD33, associates with the protein-tyrosine phosphatases, SHP-1 and SHP-2. *J Biol Chem* 274:11505-11512.

Tomasello, E., and E. Vivier. 2005. KARAP/DAP12/TYROBP: three names and a multiplicity of biological functions. *Eur J Immunol* 35:1670-1677.

Toyomura, T., Y. Murata, A. Yamamoto, T. Oka, G. H. Sun-Wada, Y. Wada, and M. Futai. 2003. From lysosomes to the plasma membrane: localization of vacuolar-type H+-ATPase with the a3 isoform during osteoclast differentiation. *J Biol Chem* 278:22023-22030.

Turnbull, I. R., and M. Colonna. 2007. Activating and inhibitory functions of DAP12. *Nat Rev Immunol* 7:155-161.

Underhill, D. M., and H. S. Goodridge. 2007. The many faces of ITAMs. *Trends Immunol* 28:66-73.

Walker, J. A., and K. G. Smith. 2008. CD22: an inhibitory enigma. *Immunology* 123:314-325.

Walsh, M. C., and Y. Choi. 2003. Biology of the TRANCE axis. *Cytokine Growth Factor Rev* 14:251-263.

Sequences

Note: Underlined sequences represent the constant region, twice-underlined sequences represent the signal sequence and sequences in bold represent complementarity determining regions.

(human Siglec-15 cDNA)

SEQ ID NO: 1

```
ATGGAAAAGTCCATCTGGCTGCTGGCCTGCTTGGCGTGGGTTCTCCCGACAGGCTCATTTGTGAGA
ACTAAAATAGATACTACGGAGAACTTGCTCAACACAGAGGTGCACAGCTCGCCAGCGCAGCGCTGG
TCCATGCAGGTGCCACCCGAGGTGAGCGCGGAGGCAGGCGACGCGGCAGTGCTGCCCTGCACCTTC
ACGCACCCGCACCGCCACTACGACGGGCCGCTGACGGCCATCTGGCGCGCGGGCGAGCCCTATGCG
GGCCCGCAGGTGTTCCGCTGCGCTGCGGCGCGGGCAGCGAGCTCTGCCAGACGGCGCTGAGCCTG
CACGGCCGCTTCCGGCTGCTGGGCAACCCGCGCCGCAACGACCTCTCGCTGCGCGTCGAGCGCCTC
GCCCTGGCTGACGACCGCCGCTACTTCTGCCGCGTCGAGTTCGCCGGCGACGTCCATGACCGCTAC
GAGAGCCGCCACGGCGTCCGGCTGCACGTGACAGCCGCGCCGCGGATCGTCAACATCTCGGTGCTG
CCCAGTCCGGCTCACGCCTTCCGCGCGCTCTGCACTGCCGAAGGGGAGCCGCCGCCCGCCCTCGCC
TGGTCCGGCCCGGCCCTGGGCAACAGCTTGGCAGCCGTGCGGAGCCCGCGTGAGGGTCACGGCCAC
CTAGTGACCGCCGAACTGCCCGCACTGACCCATGACGGCCGCTACACGTGTACGGCCGCCAACAGC
CTGGGCCGCTCCGAGGCCAGCGTCTACCTGTTCCGCTTCCATGGCGCCAGCGGGGCCTCGACGGTC
GCCCTCCTGCTCGGCGCTCTCGGCTTCAAGGCGCTGCTGCTGCTCGGGGTCCTGGCCGCCCGCGCT
GCCCGCCGCCGCCCAGAGCATCTGGACACCCCGGACACCCCACCACGGTCCCAGGCCCAGGAGTCC
AATTATGAAAATTTGAGCCAGATGAACCCCCGGAGCCCACCAGCCACCATGTGCTCACCGTGA
```

(Human Siglec-15 polypeptide: 1-328)

SEQ ID NO: 2

```
MEKSIWLLACLAWVLPTGSFVRTKIDTTENLLNTEVHSSPAQRWSMQVPPEVSAEAGDAAVLPCTF
THPHRHYDGPLTAIWRAGEPYAGPQVFRCAAARGSELCQTALSLHGRFRLLGNPRRNDLSLRVERL
ALADDRRYFCRVEFAGDVHDRYESRHGVRLHVTAAPRIVNISVLPSPAHAFRALCTAEGEPPPALA
WSGPALGNSLAAVRSPREGHGHLVTAELPALTHDGRYTCTAANSLGRSEASVYLFRFHGASGASTV
ALLLGALGFKALLLLGVLAARAARRRPEHLDTPDTPPRSQAQESNYENLSQMNPRSPPATMCSP
```

(mouse Siglec-15 cDNA)

SEQ ID NO: 3

```
ATGGAGGGGTCCCTCCAACTCCTGGCCTGCTTGGCCTGTGTGCTCCAGATGGGATCCCTTGTGAAA
ACTAGAAGAGACGCTTCGGGGGATCTGCTCAACACAGAGGCGCACAGTGCCCCGGCGCAGCGCTGG
TCCATGCAGGTGCCCGCGGAGGTGAACGCGGAGGCTGGCGACGCGGCGGTGCTGCCCTGCACCTTC
ACGCACCCGCACCGCCACTACGACGGGCCGCTGACGGCCATCTGGCGCTCGGGCGAGCCGTACGCG
GGCCCGCAGGTGTTCCGCTGCACCGCGGCGCCGGGCAGCGAGCTGTGCCAGACGGCGCTGAGCCTG
CACGGCCGCTTCCGCCTGCTGGGCAACCCGCGCCGCAACGACCTGTCCCTGCGCGTCGAGCGCCTC
GCCCTGGCGGACAGCGGCCGCTACTTCTGCCGCGTGGAGTTCACCGGCGACGCCCACGATCGCTAT
GAGAGTCGCCATGGGGTCCGTCTGCGCGTGACTGCAGCTGCGCCGCGGATCGTCAACATCTCGGTG
CTGCCGGGCCCCGCGCACGCCTTCCGCGCGCTCTGCACCGCCGAGGGGAGCCCCGCCCGCCCTC
GCCTGGTCGGGTCCCGCCCCAGGCAACAGCTCCGCTGCCCTGCAGGGCCAGGGTCACGGCTACCAG
GTGACCGCCGAGTTGCCCGCGCTGACCCGCGACGGCCGCTACACGTGCACGGCGGCCAATAGCCTG
GGCCGCGCCGAGGCCAGCGTCTACCTGTTCCGCTTCCACGGCGCCCCCGGAACCTCGACCCTAGCG
CTCCTGCTGGGCGCGCTGGGCCTCAAGGCCTTGCTGCTGCTTGGCATTCTGGGAGCGCGTGCCACC
CGACGCCGACTAGATCACCTGGTCCCCCAGGACACCCCTCCACGGTCTCAGGCTCAGGAGTCCAAT
```

-continued

TATGAAAATTTGAGCCAGATGAGTCCTCCAGGCCACCAGCTGCCACGTGTTTGCTGTGAGGAACTC

CTCAGCCATCACCATCAGTCATTCACCATGAGAAATAA (mouse Siglec-15 polypeptide)
SEQ ID NO: 4
MEGSLQLLACLACVLQMGSLVKTRRDASGDLLNTEAHSAPAQRWSMQVPAEVNAEAGDAAVLPCTF

THPHRHYDGPLTAIWRSGEPYAGPQVFRCTAAPGSELCQTALSLHGRFRLLGNPRRNDLSLRVERL

ALADSGRYFCRVEFTGDAHDRYESRHGVRLRVTAAAPRIVNISVLPGPAHAFRALCTAEGEPPPAL

AWSGPAPGNSSAALQGQGHGYQVTAELPALTRDGRYTCTAANSLGRAEASVYLFRFHGAPGTSTLA

LLLGALGLKALLLLGILGARATRRRLDHLVPQDTPPRSQAQESNYENLSQMSPPGHQLPRVCCEEL

LSHHHLVIHHEK

25E9 Light (Kappa) Chain Chimeric (mouse variable domain and human
constant region)
SEQ ID No.: 5
<u>MVLQTQVFISLLLWISGAYG</u>DIVMTQAAPSVPVTPGESVSISCRSTKSLLHSNGNTYLYWFLQRPG

QSPQLLIYRMSNLASGVPDRFSGSGSGTAFTLRISRVEAEDVGVYYCMQHLEYPFTFGGGTKLEIK

<u>RTVAAPSVFIFPPSDEQLKSGTASVVCLLNNFYPREAKVQWKVDNALQSGNSQESVTEQDSKDSTY</u>

<u>SLSSTLTLSKADYEKHKVYACEVTHQGLSSPVTKSFNRGEC</u>

25E9 Light Chain mouse variable domain (illustrated without signal
sequence: CDRs are in bold)
SEQ ID No.: 6
DIVMTQAAPSVPVTPGESVSISCRSTKSLLHSNGNTYLYWFLQRPGQSPQLLIYRMSNLASGVPDR

FSGSGSGTAFTLRISRVEAEDVGVYYCMQHLEYPFTFGGGTKLEIK

25E9 Light (Kappa) Chain Humanized Variant 1 (a.k.a.: L1)
(humanized variable domain and human constant region)
SEQ ID NO.: 7
<u>MVLQTQVFISLLLWISGAYG</u>DIVMTQSPLSLPVTPGEPASISCRSTKSLLHSNGNTYLYWYLQKPG

QSPQLLIYRMSNLASGVPDRFSGSGSGTDFTLKISRVEAEDVGVYYCMQHLEYPFTFGGGTKVEIK

<u>RTVAAPSVFIFPPSDEQLKSGTASVVCLLNNFYPREAKVQWKVDNALQSGNSQESVTEQDSKDSTY</u>

<u>SLSSTLTLSKADYEKHKVYACEVTHQGLSSPVTKSFNRGEC</u>

25E9 Light Chain Humanized Variant 1 variable domain (a.k.a.: VL1)
(illustrated without signal sequence)
SEQ ID NO.: 8
DIVMTQSPLSLPVTPGEPASISCRSTKSLLHSNGNTYLYWYLQKPGQSPQLLIYRMSNLASGVPDR

FSGSGSGTDFTLKISRVEAEDVGVYYCMQHLEYPFTFGGGTKVEIK

25E9 Light (Kappa) Chain Humanized Variant 2 (a.k.a.: L2)
(humanized variable domain and human constant region)
SEQ ID NO.: 9
<u>MVLQTQVFISLLLWISGAYG</u>DIVMTQSPLSLPVTPGEPASISCRSTKSLLHSNGNTYLYWFLQKPG

QSPQLLIYRMSNLASGVPDRFSGSGSGTDFTLKISRVEAEDVGVYYCMQHLEYPFTFGGGTKVEIK

<u>RTVAAPSVFIFPPSDEQLKSGTASVVCLLNNFYPREAKVQWKVDNALQSGNSQESVTEQDSKDSTY</u>

<u>SLSSTLTLSKADYEKHKVYACEVTHQGLSSPVTKSFNRGEC</u>

25E9 Light Chain Humanized Variant 2 variable domain (a.k.a.: VL2)
(illustrated without signal sequence)
SEQ ID NO.: 10
DIVMTQSPLSLPVTPGEPASISCRSTKSLLHSNGNTYLYWFLQKPGQSPQLLIYRMSNLASGVPDR

FSGSGSGTDFTLKISRVEAEDVGVYYCMQHLEYPFTFGGGTKVEIK

25E9 Heavy (Igg1) Chain Chimeric (mouse variable domain and human
constant region)
SEQ ID NO.: 11
<u>MDWTWRILFLVAAATGTHA</u>EIQLQQSGVELVRPGASVTLSCKASGYTFTDYDMHWVKQTPVHGLEW

IGTIDPETGGTAYNQKFKGKATLTADRSSTTAYMELSSLTSEDSAVYYCTSFYYTYSNYDVGFAYW

GQGTLVTVSA<u>ASTKGPSVFPLAPSSKSTSGGTAALGCLVKDYFPEPVTVSWNSGALTSGVHTFPAV</u>

-continued

LQSSGLYSLSSVVTVPSSSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHYT

QKSLSLSPGK

25E9 Heavy Chain mouse variable domain (illustrated without signal
sequence: CDRs are in bold)
SEQ ID NO.: 12
EIQLQQSGVELVRPGASVTLSCKASGYTFTDIDMHWVKQTPVHGLEWIGTIDPETGGTAYNQKFKG

KATLTADRSSTTAYMELSSLTSEDSAVYYCTSFYYTYSNYDVGFAYWGQGTLVTVSA

25E9 Heavy (Igg1) Chain Humanized Variant 1 (a.k.a.: H1)
(humanized variable domain and human constant region)
SEQ ID NO.: 13
MDWTWRILFLVAAATGTHAEIQLQQSGAEVKKPGSSVKVSCKASGYTFTDYDMHWVRQAPGQGLEW

MGTIDPETGGTAYNQKFKGRVTITADKSTSTAYMELSSLRSEDTAVYYCTSFYYTYSNYDVGFAYW

GQGTLVTVSSASTKGPSVFPLAPSSKSTSGGTAALGCLVKDYFPEPVTVSWNSGALTSGVHTFPAV

LQSSGLYSLSSVVTVPSSSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHYT

QKSLSLSPGK

25E9 Heavy Chain Humanized Variant 1 variable domain (a.k.a., VH1)
(illustrated without signal sequence)
SEQ ID NO.: 14
EIQLQQSGAEVKKPGSSVKVSCKASGYTFTDYDMHWVRQAPGQGLEWMGTIDPETGGTAYNQKFKG

RVTITADKSTSTAYMELSSLRSEDTAVYYCTSFYYTYSNYDVGFAYWGQGTLVTVSS

25E9 Heavy (Igg1) Chain Humanized Variant 2 (a.k.a.: H2)
(humanized variable domain and human constant region)
SEQ ID NO.: 15
MDWTWRILFLVAAATGTHAEIQLQQSGAEVKKPGSSVKVSCKASGYTFTDYDMHWVRQAPGQGLEW

IGTIDPETGGTAYNQKFKGRATLTADRSTSTAYMELSSLRSEDTAVYYCTSFYYTYSNYDVGFAYW

GQGTLVTVSSASTKGPSVFPLAPSSKSTSGGTAALGCLVKDYFPEPVTVSWNSGALTSGVHTFPAV

LQSSGLYSLSSVVTVPSSSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHYT

QKSLSLSPGK

25E9 Heavy Chain Humanized Variant 2 variable domain (a.k.a., VH2)
(illustrated without signal sequence)
SEQ ID NO.: 16
EIQLQQSGAEVKKPGSSVKVSCKASGYTFTDYDMHWVRQAPGQGLEWIGTIDPETGGTAYNQKFKG

RATLTADRSTSTAYMELSSLRSEDTAVYYCTSFYYTYSNYDVGFAYWGQGTLVTVSS

25E9 Heavy (Igg1) Chain Humanized Variant 3 (a.k.a.: H3) (humanized
variable domain and human constant region)
SEQ ID NO.: 17
MDWTWRILFLVAAATGTHAEIQLQQSGAEVKKPGSSVKVSCKASGYTFTDYDMHWVKQAPGQGLEW

IGTIDPETGGTAYNQKFKGKATLTADRSTSTAYMELSSLRSEDTAVYYCTSFYYTYSNYDVGFAYW

GQGTLVTVSSASTKGPSVFPLAPSSKSTSGGTAALGCLVKDYFPEPVTVSWNSGALTSGVHTFPAV

LQSSGLYSLSSVVTVPSSSLGTQTYICNVNHKPSNTKVDKKVEPKSCDKTHTCPPCPAPELLGGPS

-continued

VFLFPPKPKDTLMISRTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVESCSVMHEALHNHYT

QKSLSLSPGK

```
25E9 Heavy Chain Humanized Variant 3 variable domain (a.k.a.: VH3)
(illustrated without signal sequence)
                                           SEQ ID NO.: 18
```
EIQLQQSGAEVKKPGSSVKVSCKASGYTFTDYDMHWVKQAPGQGLEWIGTIDPETGGTAYNQKFKG

KATLTADRSTSTAYMELSSLRSEDTAVYYCTSFYYTYSNYDVGFAYWGQGTLVTVSS

```
25E9 Heavy (Igg1) Chain Humanized Variant 4 (a.k.a.: H4) (humanized
variable domain and human constant region)
                                           SEQ ID NO.: 19
```
MDWTWRILFLVAAATGTHAEIQLQQSGAEVKKPGSSVKVSCKASGYTFTDYDMHWVKQAPGHGLEW

IGTIDPETGGTAYNQKFKGKATLTADRSTSTAYMELSSLTSEDTAVYYCTSFYYTYSNYDVGFAYW

GQGTLVTVSSASTKGPSVFPLAPSSKSTSGGTAALGCLVKDYFPEPVTVSWNSGALTSGVHTFPAV

LQSSGLYSLSSVVTVPSSSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHYT

QKSLSLSPGK

```
25E9 Heavy Chain Humanized Variant 4 variable domain (a.k.a.: VH4)
(illustrated without signal sequence)
                                           SEQ ID NO.: 20
```
EIQLQQSGAEVKKPGSSVKVSCKASGYTFTDYDMHWVKQAPGHGLEWIGTIDPETGGTAYNQKFKG

KATLTADRSTSTAYMELSSLTSEDTAVYYCTSFYYTYSNYDVGFAYWGQGTLVTVSS

```
Chimeric 25D8 Light (Kappa) Chain (mouse variable domain and human
constant region)
                                           SEQ ID NO.: 21
```
MVLQTQVFISLLLWISGAYGDIVMTQAAFSNPVTLGTSASISCRSSKSLLHSNGITYLYWYLQKPG

QSPQLLIYQMSNLASGVPDRFSSSGSGTDFTLRISRVEAEDVGVYYCAQNLELPYTFGGGTKLEIK

RTVAAPSVFIFPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC

```
25D8 Light Chain mouse variable domain (illustrated without signal
sequence)
                                           SEQ ID NO.: 22
```
DIVMTQAAFSNPVTLGTSASISCRSSKSLLHSNGITYLYWYLQKPGQSPQLLIYQMSNLASGVPDR

FSSSGSGTDFTLRISRVEAEDVGVYYCAQNLELPYTFGGGTKLEIK

```
Humanized 25D8 Light (Kappa) Chain (humanized variable domain and
human constant region)
                                           SEQ ID NO.: 23
```
MVLQTQVFISLLLWISGAYGDIVMTQTPLSLPVTPGEPASISCRSSKSLLHSNGITYLYWYLQKPG

QSPQLLIYQMSNLASGVPDRFSGSGSGTDFTLKISRVEAEDVGVYYCAQNLELPYTFGGGTKVEIK

RTVAAPSVFIFPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC

```
Humanized 25D8 Light Chain variable domain (illustrated without
signal sequence)
                                           SEQ ID NO.: 24
```
DIVMTQTPLSLPVTPGEPASISCRSSKSLLHSNGITYLYWYLQKPGQSPQLLIYQMSNLASGVPDR

FSGSGSGTDFTLKISRVEAEDVGVYYCAQNLELPYTFGGGTKVEIK

```
Chimeric 25D8 Heavy (Igg2) Chain (mouse variable domain and human
constant region)
                                           SEQ ID NO.: 25
```
MDWTWRILFLVAAATGTHAQVQVQQPGAELVKPGASVKLSCKASGYTFTSYWMHWVKQRPGQGLEW -continued

IGLINPSNARTNYNEKENTKATLTVDKSSSTAYMQLSSLTSEDSAVYYCARGGDGDYFDYWGQGTT

LTVSSASTKGPSVFPLAPCSRSTSESTAALGCLVKDYFPEPVTVSWNSGALTSGVHTFPAVLQSSG

LYSLSSVVTVPSSNFGTQTYTCNVDHKPSNTKVDKTVERKCCVECPPCPAPPVAGPSVFLFPPKPK

DTLMISRTPEVTCVVVDVSHEDPEVQFNWYVDGVEVHNAKTKPREEQFNSTFRVVSVLTVVHQDWL

NGKEYKCKVSNKGLPAPIEKTISKTKGQPREPQVYTLPPSREEMTKNQVSLTCLVKGFYPSDIAVE

WESNGQPENNYKTTPPMLDSDGSFFLYSKLTVDKSRWQQGNVESCSVMHEALHNHYTQKSLSLSPG

K

25D8 Heavy Chain mouse variable domain (illustrated without signal
sequence)
SEQ ID NO.: 26
QVQVQQPGAELVKPGASVKLSCKASGYTFTSYWMHWVKQRPGQGLEWIGLINPSNARTNYNEKFNT

KATLTVDKSSSTAYMQLSSLTSEDSAVYYCARGGDGDYFDYWGQGTTLTVSS

Humanized 25D8 Heavy (Igg2) Chain (humanized variable domain and
human constant region)
SEQ ID NO.: 27
MDWTWRILFLVAAATGTHAQVQLQQSGAEVKKPGSSVKVSCKASGYTFTSYWMHWVRQAPGQGLEW

MGLINPSNARTNYNEKENTRVTITADKSTSTAYMELSSLRSEDTAVYYCARGGDGDYFDYWGQGTT

VTVSSASTKGPSVFPLAPCSRSTSESTAALGCLVKDYFPEPVTVSWNSGALTSGVHTFPAVLQSSG

LYSLSSVVTVPSSNFGTQTYTCNVDHKPSNTKVDKTVERKCCVECPPCPAPPVAGPSVFLFPPKPK

DTLMISRTPEVTCVVVDVSHEDPEVQFNWYVDGVEVHNAKTKPREEQFNSTFRVVSVLTVVHQDWL

NGKEYKCKVSNKGLPAPIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHEALHNHYTQKSLSLSPG

K

Humanized 25D8 Heavy Chain variable domain (illustrated without
signal sequence)
SEQ ID NO.: 28
QVQLQQSGAEVKKPGSSVKVSCKASGYTFTSYWMHWVRQAPGQGLEWMGLINPSNARTNYNEKFNT

RVTITADKSTSTAYMELSSLRSEDTAVYYCARGGDGDYFDYWGQGTTVTVSS

25E9 Heavy (Igg2) Chain Humanized Variant 1 (humanized variable
domain and human constant region)
SEQ ID NO. 29
MDWTWRILFLVAAATGTHAEIQLQQSGAEVKKPGSSVKVSCKASGYTFTDYDMHWVRQAPGQGLEW

MGTIDPETGGTAYNQKFKGRVTITADKSTSTAYMELSSLRSEDTAVYYCTSFYYTYSNYDVGFAYW

GQGTLVTVSSASTKGPSVFPLAPCSRSTSESTAALGCLVKDYFPEPVTVSWNSGALTSGVHTFPAV

LQSSGLYSLSSVVTVPSSNFGTQTYTCNVDHKPSNTKVDKTVERKCCVECPPCPAPPVAGPSVFLF

PPKPKDTLMISRTPEVTCVVVDVSHEDPEVQFNWYVDGVEVHNAKTKPREEQFNSTFRVVSVLTVV

HQDWLNGKEYKCKVSNKGLPAPIEKTISKTKGQPREPQVYTLPPSREEMTKNQVSLTCLVKGFYPS

DIAVEWESNGQPENNYKTTPPMLDSDGSFFLYSKLTVDKSRWQQGNVFSCSVMHEALHNHYTQKSL

SLSPGK

25E9 Heavy (Igg2) Chain Chimeric (mouse variable domain and human
constant region)
SEQ ID No.: 30
MDWTWRILFLVAAATGTHAEIQLQQSGVELVRPGASVTLSCKASGYTFTDYDMHWVKQTPVHGLEW

IGTIDPETGGTAYNQKFKGKATLTADRSSTTAYMELSSLTSEDSAVYYCTSFYYTYSNYDVGFAYW

GQGTLVTVSAASTKGPSVFPLAPCSRSTSESTAALGCLVKDYFPEPVTVSWNSGALTSGVHTFPAV

LQSSGLYSLSSVVTVPSSNFGTQTYTCNVDHKPSNTKVDKTVERKCCVECPPCPAPPVAGPSVFLF

PPKPKDTLMISRTPEVTCVVVDVSHEDPEVQFNWYVDGVEVHNAKTKPREEQFNSTFRVVSVLTVV

HQDWLNGKEYKCKVSNKGLPAPIEKTISKTKGQPREPQVYTLPPSREEMTKNQVSLTCLVKGFYPS

```
DIAVEWESNGQPENNYKTTPPMLDSDGSFFLYSKLTVDKSRWQQGNVFSCSVMHEALHNHYTQKSL

SLSPGK (human IgG1 constant region)
                                                   SEQ ID NO.: 31
ASTKGPSVFPLAPSSKSTSGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSPGK (human IgG2 constant region)
                                                   SEQ ID NO.: 32
ASTKGPSVFPLAPCSRSTSESTAALGCLVKDYFPEPVTVSWNSGALTSGVHTFPAVLQSSGLYSLS

SVVTVPSSNFGTQTYTCNVDHKPSNTKVDKTVERKCCVECPPCPAPPVAGPSVFLFPPKPKDTLMI

SRTPEVTCVVVDVSHEDPEVQFNWYVDGVEVHNAKTKPREEQFNSTFRVVSVLTVVHQDWLNGKEY

KCKVSNKGLPAPIEKTISKTKGQPREPQVYTLPPSREEMTKNQVSLTCLVKGFYPSDIAVEWESNG

QPENNYKTTPPMLDSDGSFFLYSKLTVDKSRWQQGNVFSCSVMHEALHNHYTQKSLSLSPGK

Generic 25E9 light chain variable domain (consensus 1)
                                                   SEQ ID No. 33
DIVMTQXXXSXPVTPGEXXSISCRSTKSLLHSNGNTYLYWXLQXPGQSPQLLIYRMSNLASGVPDR

FSGSGSGTXFTLXISRVEAEDVGVYYCMQHLEYPFTFGGGTKXEIK
``` wherein at least one of the amino acid identified by X may be an amino acid substitution in comparison with a corresponding amino acid in the polypeptide set forth in SEQ ID NO.:6 (the mouse VL). The amino acid substitution may be, for example conservative or non-conservative. In accordance with the invention, the amino acid substitution may be conservative.

```
Generic 25E9 light chain variable
domain (consensus 2)
                                                   SEQ ID No. 34
DIVMTQX_{a1}X_{a2}X_{a3}SX_{a4}PVTPGEX_{a5}X_{a6}SISCRSTKSLLHSNG NTYLYWX_{a7}LQX_{a8}PGQSPQLLIYRMSNLASGVPDRFSGSGSG TX_{a9}FTLX_{a10}ISRVEAEDVGVYYCMQHLEYPFTFGGGTKX_{a11}

EIK
``` wherein at least one of the amino acid identified by X may be an amino acid substitution in comparison with a corresponding amino acid in the polypeptide set forth in SEQ ID NO.:6 (the mouse VL) and Wherein Xa1, Xa4, Xa7, Xa8, Xa10 and Xa11 may each independently be a conservative amino acid substitution in comparison with SEQ ID NO. 6; Wherein Xa2, Xa5, Xa6 may each independently be a semi-conservative amino acid substitution in comparison with SEQ ID NO. 6;
Wherein Xa3 may be P or L; and
Wherein Xa9 may be A or D.

```
Generic 25E9 light chain variable
domain (consensus 3)
                                                   SEQ ID NO. 35
DIVMTQX_{a1}X_{a2}X_{a3}SX_{a4}PVTPGEX_{a5}X_{a6}SISCRSTKSLLHSNG NTYLYWX_{a7}LQX_{a8}PGQSPQLLIYRMSNLASGVPDRFSGSGSG TX_{a9}FTLX_{a10}ISRVEAEDVGVYYCMQHLEYPFTFGGGTKX_{a11}

EIK
``` wherein at least one of the amino acid identified by X (including Xa1 to Xa11) may be an amino acid substitution in comparison with a corresponding amino acid in the polypeptide set forth in SEQ ID NO.:6 (the mouse VL) and
Wherein Xa1 may be A or S;
Wherein Xa2 may be A or P;
Wherein Xa3 may be P or L;
Wherein Xa4 may be a hydrophobic amino acid (e.g., V or L);
Wherein Xa5 may be S or P;
Wherein Xa6 may be a hydrophobic amino acid (e.g., V or A);
Wherein Xa7 may be an aromatic amino acid (e.g. F or Y);
Wherein Xa8 may be a basic amino acid (e.g., R or K);
Wherein Xa9 may be A or D;
Wherein Xa10 may be a basic amino acid (e.g., R or K);
and wherein Xa11 may be a hydrophobic amino acid (e.g., L or V).

```
Generic 25E9 heavy chain variable
domain (consensus 1)
                                                   SEQ ID NO. 36
EIQLQQSGXEXXXPGXSVXXSCKASGYTFTDYDMHWVXQXPX

XGLEWXGTIDPETGGTAYNQKFKGXXTXTADXSXXTAYMELS

SLXSEDXAVYYCTSFYYTYSNYDVGFAYWGQGTLVTVSX
``` wherein at least one of the amino acid identified by X may be an amino acid substitution in comparison with a corresponding amino acid in the polypeptide set forth in SEQ ID NO.:12 (the mouse VH). The amino acid substitution may be, for example conservative or non-conservative. In accordance with the invention, the amino acid substitution may be conservative.

Generic 25E9 heavy chain variable
domain (consensus 2)
                                    SEQ ID NO. 37
EIQLQQSGX$_{b1}$EX$_{b2}$X$_{b3}$X$_{b4}$PGX$_{b5}$SVX$_{b6}$X$_{b7}$SCKASGYTFTDY DMHWVX$_{b8}$QX$_{b9}$PX$_{b10}$X$_{b11}$GLEWX$_{b12}$GTIDPETGGTAYNQKFK GX$_{b13}$X$_{b14}$TX$_{b15}$TADX$_{b16}$SX$_{b17}$X$_{b18}$TAYMELSSLX$_{b19}$SEDX$_{b20}$ AVYYCTSFYYTYSNYDVGFAYWGQGTLVTVSX$_{b21}$ wherein at least one of the amino acid identified by X (including Xb1 to Xb21) may be an amino acid substitution in comparison with a corresponding amino acid in the polypeptide set forth in SEQ ID NO.:12 (the mouse VH) and wherein Xb2, Xb4, Xb5, Xb7, Xb8, Xb9, Xb11, Xb12, Xb13, Xb15, Xb16, Xb17, Xb18, Xb20 and Xb21 may each independently be a conservative amino acid substitution in comparison with SEQ ID NO. 12;
wherein Xb1, Xb6, Xb14 may each independently be a semi-conserved amino acid substitution in comparison with SEQ ID NO.:12 (the mouse VH)
wherein Xb3 may be V or K;
wherein Xb10 may be V or G; and
wherein Xb19 may be T or R.

Generic 25E9 heavy chain variable
domain (consensus 3)
                                    SEQ ID NO. 38
EIQLQQSGX$_{b1}$EX$_{b2}$X$_{b3}$X$_{b4}$PGX$_{b5}$SVX$_{b6}$X$_{b7}$SCKASGYTFTDY DMHWVX$_{b8}$QX$_{b9}$PX$_{b10}$X$_{b11}$GLEWX$_{b12}$GTIDPETGGTAYNQKFK GX$_{b13}$X$_{b14}$TX$_{b15}$TADX$_{b16}$SX$_{b17}$X$_{b18}$TAYMELSSLX$_{b19}$SEDX$_{b20}$ AVYYCTSFYYTYSNYDVGFAYWGQGTLVTVSX$_{b21}$ wherein at least one of the amino acid identified by X (including Xb1 to Xb21) may be an amino acid substitution in comparison with a corresponding amino acid in the polypeptide set forth in SEQ ID NO.:12 (the mouse VH) and
wherein Xb1 may be a hydrophobic amino acid (e.g., V or A);
wherein Xb2 may be a hydrophobic amino acid (e.g., L or V);
wherein Xb3 may be V or K;
wherein Xb4 may be a basic amino acid (e.g., R or K);
Wherein Xb5 may be A or S;
Wherein Xb6 may be T or K;
Wherein Xb7 may be a hydrophobic amino acid (e.g., L or V);
Wherein Xb8 may be a basic amino acid (e.g., K or R);
Wherein Xb9 may be T or A;
wherein Xb10 may be V or G;
Wherein Xb11 may be a basic amino acid (e.g., H or Q);
Wherein Xb12 may be a hydrophobic amino acid (e.g., I or M);
Wherein Xb13 may be a basic amino acid (e.g., K or R);
Wherein Xb14 may be a hydrophobic amino acid (e.g., A or V);
Wherein Xb15 may be a hydrophobic amino acid (e.g., L or I);
Wherein Xb16 may be a basic amino acid (e.g., R or K);
Wherein Xb17 may be a neutral hydrophilic amino acid (e.g., S or T);
Wherein Xb18 may be a neutral hydrophilic amino acid (e.g., T or S);
wherein Xb19 may be T or R;
Wherein Xb20 may be a neutral hydrophilic amino acid (e.g., S or T); and
Wherein Xb21 may be A or S.

Generic 25D8 light chain variable
domain (consensus 1)
                                    SEQ ID No.: 39
DIVMTQXXXSXPVTXGXXASISCRSSKSLLHSNGITYLYWY

LQKPGQSPQLLIYQMSNLASGVPDRFSXSGSGTDFTLXISR

VEAEDVGVYYCAQNLELPYTFGGGTKXEIK wherein at least one of the amino acid identified by X may be an amino acid substitution in comparison with a corresponding amino acid in the polypeptide set forth in SEQ ID NO.:22 (the mouse VL). The amino acid substitution may be, for example conservative or non-conservative. In accordance with the invention, the amino acid substitution may be conservative.

Generic 25D8 light chain variable
domain (consensus 2)
                                    SEQ ID NO.: 40
DIVMTQX$_{c1}$X$_{c2}$X$_{c3}$SX$_{c4}$PVTX$_{c5}$GX$_{c6}$X$_{c7}$ASISCRSSKSLLHS NGITYLYWYLQKPGQSPQLLIYQMSNLASGVPDRFSX$_{c8}$SGS GTDFTLX$_{c9}$ISRVEAEDVGVYYCAQNLELPYTFGGGTKX$_{c10}$E

IK wherein at least one of the amino acid identified by X may be an amino acid substitution in comparison with a corresponding amino acid in the polypeptide set forth in SEQ ID NO.:22 (the mouse VL) and
wherein Xc1, Xc3, Xc9 and Xc10 may each independently be a conservative amino acid substitution in comparison with SEQ ID NO.:22;
wherein Xc2, Xc7, Xc8 may each independently be a semi-conservative amino acid substitution in comparison with SEQ ID NO.: 22;
Wherein Xc4 may be N or L;
Wherein Xc5 may be L or P; and
Wherein Xc6 may be T or E.

Generic 25D8 light chain variable
domain (consensus 3)
                                    SEQ ID NO.: 41
DIVMTQX$_{c1}$X$_{c2}$X$_{c3}$SX$_{c4}$PVTX$_{c5}$GX$_{c6}$X$_{c7}$ASISCRSSKSLLHS NGITYLYWYLQKPGQSPQLLIYQMSNLASGVPDRFSX$_{c8}$SGS GTDFTLX$_{c9}$ISRVEAEDVGVYYCAQNLELPYTFGGGTKX$_{c10}$E

IK wherein at least one of the amino acid identified by X may be an amino acid substitution in comparison with a corresponding amino acid in the polypeptide set forth in SEQ ID NO.:22 (the mouse VL) and
Wherein Xc1 may be A or T;
Wherein Xc2 may be A or P;
Wherein Xc3 may be F or L;
Wherein Xc4 may be N or L;
Wherein Xc5 may be L or P;
Wherein Xc6 may be T or E;
Wherein Xc7 may be S or P;
Wherein Xc8 may be S or G;
Wherein Xc9 may be a basic amino acid (e.g., R or K); and Wherein Xc10 may be a hydrophobic amino acid (e.g., L or V).

```
Generic 25D8 heavy chain variable
domain (consensus 1)
                                    SEQ ID NO.: 42
QVQXQQXGAEXXKPGXSVKXSCKASGYTFTSYWMHWVXQXP

GQGLEWXGLINPSNARTNYNEKFNTXXTXTXDKSXSTAYMX

LSSLXSEDXAVYYCARGGDGDYFDYWGQGTTXTVSS
``` wherein at least one of the amino acid identified by X may be an amino acid substitution in comparison with a corresponding amino acid in the polypeptide set forth in SEQ ID NO.:26 (the mouse VH). The amino acid substitution may be, for example conservative or non-conservative. In accordance with the invention, the amino acid substitution may be conservative.

```
Generic 25D8 heavy chain variable
domain (consensus 2)
                                    SEQ ID NO.: 43
QVQX_{d1}QQX_{d2}GAEX_{d3}X_{d4}KPGX_{d5}SVKX_{d6}SCKASGYTFTSYWM HWVX_{d7}QX_{d8}PGQGLEWX_{d9}GLINPSNARTNYNEKFNTX_{d10}X_{d11}

TX_{d12}TX_{d13}DKSX_{d14}STAYMX_{d15}LSSLX_{d16}SEDX_{d17}AVYYCAR

GGDGDYFDYWGQGTTX_{d18}TVSS
``` wherein at least one of the amino acid identified by X may be an amino acid substitution in comparison with a corresponding amino acid in the polypeptide set forth in SEQ ID NO.:26 (the mouse VH) and;
wherein Xd1, Xd3, Xd5, Xd6, Xd7, Xd9, Xd10, Xd12, Xd14, Xd15, Xd17, Xd18 may each independently be a conservative amino acid substitution in comparison with SEQ ID NO.:26;
wherein Xd2, Xd11, Xd13, may each independently be a semi-conservative amino acid substitution in comparison with SEQ ID NO.:26;
wherein Xd4 may be V or K;
wherein Xd8 may be R or A; and;
wherein Xd16 may be T or R.

```
Generic 25D8 heavy chain variable
domain (consensus 3)
                                    SEQ ID NO.: 44
QVQX_{d1}QQX_{d2}GAEX_{d3}X_{d4}KPGX_{d5}SVKX_{d6}SCKASGYTFTSYWM HWVX_{d7}QX_{d8}PGQGLEWX_{d9}GLINPSNARTNYNEKFNTX_{d10}X_{d11}

TX_{d12}TX_{d13}DKSX_{d14}STAYMX_{d15}LSSLX_{d16}SEDX_{d17}AVYYCAR

GGDGDYFDYWGQGTTX_{d18}TVSS
``` wherein at least one of the amino acid identified by X may be an amino acid substitution in comparison with a corresponding amino acid in the polypeptide set forth in SEQ ID NO.:26 (the mouse VH) and;
wherein Xd1 may be a hydrophobic amino acid (e.g., V or L);
wherein Xd2 may be P or S;
wherein Xd3 may be a hydrophobic amino acid (e.g., L or V);
wherein Xd4 may be V or K;
wherein Xd5 may be A or S;
wherein Xd6 may be a hydrophobic amino acid (e.g., L or V);
wherein Xd7 may be a basic amino acid (e.g., K or R);
wherein Xd8 may be R or A;
wherein Xd9 may be a hydrophobic amino acid (e.g., I or M);
wherein Xd10 may be a basic amino acid (e.g., K or R);
wherein Xd11 may be a hydrophobic amino acid (e.g., A or V);
wherein Xd12 may be a hydrophobic amino acid (e.g., L or I);
wherein Xd13 may be a hydrophobic amino acid (V or A);
wherein Xd14 may be a neutral hydrophilic amino acid (e.g., S or T);
wherein Xd15 may be Q or E;
wherein Xd16 may be T or R.
wherein Xd17 may be a neutral hydrophilic amino acid (e.g., S or T); and
wherein Xd18 may be a hydrophobic amino acid (L or V).

```
Chimeric 25D8 Heavy (Igg1) Chain (mouse variable domain and human
constant region)
                                                      SEQ ID NO.: 45
MDWTWRILFLVAAATGTHAQVQVQQPGAELVKPGASVKLSCKASGYTFTSYWMHWVKQRPGQGLEW

IGLINPSNARTNYNEKFNTKATLTVDKSSSTAYMQLSSLTSEDSAVYYCARGGDGDYFDYWGQGTT

LTVSSASTKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCSVMHEALHNHYTQKSLS

LSPGK

Humanized 25D8 Heavy (Igg1) Chain (humanized variable domain and
human constant region)
                                                      SEQ ID NO.: 46
MDWTWRILFLVAAATGTHAQVQLQQSGAEVKKPGSSVKVSCKASGYTFTSYWMHWVRQAPGQGLEW

MGLINPSNARTNYNEKFNTRVTITADKSTSTAYMELSSLRSEDTAVYYCARGGDGDYFDYWGQGTT

VTVSSASTKGPSVFPLAPSSKSTSGGTAALGCLVKDYFPEPVTVSWNSGALTSGVHTFPAVLQSSG
```

-continued

LYSLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCSVMHEALHNHYTQKSLS

LSPGK

CDR1 of the 25E9 light chain mouse variable domain
SEQ ID NO.: 47
RSTKSLLHSEGNTYLY

CDR2 of the 25E9 light chain mouse variable domain
SEQ ID NO.: 48
RMSNLAS

CDR3 of the 25E9 light chain mouse variable domain
SEQ ID NO.: 49
MQHLEYPFT

CDR1 of the 25E9 heavy chain mouse variable domain
SEQ ID NO.: 50
GYTFTDYDMH

CDR2 of the 25E9 heavy chain mouse variable domain
SEQ ID NO.: 51
TIDPETGGTAYNQKFKG

CDR3 of the 25E9 heavy chain mouse variable domain
SEQ ID NO.: 52
FYYTYSNYDVGFAY

CDR1 of the 25D8 light chain mouse variable domain
SEQ ID NO.: 53
RSSKSLLHSNGITYLY

CDR2 of the 25D8 light chain mouse variable domain
SEQ ID NO.: 54
QMSNLASG

CDR3 of the 25D8 light chain mouse variable domain
SEQ ID NO.: 55
AQNLELPYT

CDR1 of the 25D8 heavy chain mouse variable domain
SEQ ID NO.: 56
GYTFTSYWMH

CDR2 of the 25D8 heavy chain mouse variable domain
SEQ ID NO.: 57
LINPSNARTNYNEKFNT

CDR3 of the 25D8 heavy chain mouse variable domain
SEQ ID NO.: 58
GGDGDYFDY

25E9 Heavy (Igg2) Chain Humanized Variant 2 (a.k.a.: H2)
(humanized variable domain and human constant region)
SEQ ID NO.: 59
<u>MDWTWRILFLVAAATGTHA</u>EIQLQQSGAEVKKPGSSVKVSCKASGYTFTDYDMHWVRQAPGQGLEW

IGTIDPETGGTAYNQKFKGRATLTADRSTSTAYMELSSLRSEDTAVYYCTSFYYTYSNYDVGFAYW

GQGTLVTVSS<u>ASTKGPSVFPLAPCSRSTSESTAALGCLVKDYFPEPVTVSWNSGALTSGVHTFPAV</u>

<u>LQSSGLYSLSSVVTVPSSNFGTQTYTCNVDHKPSNTKVDKTVERKCCVECPPCPAPPVAGPSVFLF</u>

<u>PPKPKDTLMISRTPEVTCVVVDVSHEDPEVQFNWYVDGVEVHNAKTKPREEQFNSTFRVVSVLTVV</u>

<u>HQDWLNGKEYKCKVSNKGLPAPIEKTISKTKGQPREPQVYTLPPSREEMTKNQVSLTCLVKGFYPS</u>

<u>DIAVEWESNGQPENNYKTTPPMLDSDGSFFLYSKLTVDKSRWQQGNVFSCSVMHEALHNHYTQKSL</u>

<u>SLSPGK</u>

25E9 Heavy (Igg2) Chain Humanized Variant 3 (a.k.a.: H3)
(humanized variable domain and human constant region)
SEQ ID NO.: 60
<u>MDWTWRILFLVAAATGTHA</u>EIQLQQSGAEVKKPGSSVKVSCKASGYTFTDYDMHWVKQAPGQGLEW -continued

IGTIDPETGGTAYNQKFKGKATLTADRSTSTAYMELSSLRSEDTAVYYCTSFYYTYSNYDVGFAYW

GQGTLVTVSSASTKGPSVFPLAPCSRSTSESTAALGCLVKDYFPEPVTVSWNSGALTSGVHTFPAV

LQSSGLYSLSSVVTVPSSNFGTQTYTCNVDHKPSNTKVDKTVERKCCVECPPCPAPPVAGPSVFLF

PPKPKDTLMISRTPEVTCVVVDVSHEDPEVQFNWYVDGVEVHNAKTKPREEQFNSTFRVVSVLTVV

HQDWLNGKEYKCKVSNKGLPAPIEKTISKTKGQPREPQVYTLPPSREEMTKNQVSLTCLVKGFYPS

DIAVEWESNGQPENNYKTTPPMLDSDGSFFLYSKLTVDKSRWQQGNVFSCSVMHEALHNHYTQKSL

SLSPGK

25E9 Heavy (Igg2) Chain Humanized Variant 4 (a.k.a.: H4)
(humanized variable domain and human constant region)
SEQ ID NO.: 61
MDWTWRILFLVAAATGTHAEIQLQQSGAEVKKPGSSVKVSCKASGYTFTDYDMHWVKQAPGHGLEW

IGTIDPETGGTAYNQKFKGKATLTADRSTSTAYMELSSLTSEDTAVYYCTSFYYTYSNYDVGFAYW

GQGTLVTVSSASTKGPSVFPLAPCSRSTSESTAALGCLVKDYFPEPVTVSWNSGALTSGVHTFPAV

LQSSGLYSLSSVVTVPSSNFGTQTYTCNVDHKPSNTKVDKTVERKCCVECPPCPAPPVAGPSVFLF

PPKPKDTLMISRTPEVTCVVVDVSHEDPEVQFNWYVDGVEVHNAKTKPREEQFNSTFRVVSVLTVV

HQDWLNGKEYKCKVSNKGLPAPIEKTISKTKGQPREPQVYTLPPSREEMTKNQVSLTCLVKGFYPS

DIAVEWESNGQPENNYKTTPPMLDSDGSFFLYSKLTVDKSRWQQGNVFSCSVMHEALHNHYTQKSL

SLSPGK (nucleotide sequence of the 25E9 Light Chain mouse variable domain)
SEQ ID No.: 62
GATATTGTGATGACCCAGGCTGCACCCTCTGTACCTGTCACTCCTGGAGAGTCAGTATCCATCTCC

TGCAGGTCTACTAAGAGTCTCCTGCATAGTAATGGCAACACTTACTTGTATTGGTTCCTGCAGAGG

CCAGGCCAGTCTCCTCAGCTCCTGATATATCGGATGTCCAACCTTGCCTCAGGAGTCCCAGACAGG

TTCAGTGGCAGTGGGTCAGGAACTGCTTTCACACTGAGAATCAGTAGAGTGGAGGCTGAGGATGTG

GGTGTTTATTACTGTATGCAACATCTAGAATATCCTTTCACGTTCGGAGGGGGGACCAAGCTGGAA

ATAAAA (nucleotide sequence of the 25E9 heavy Chain mouse variable domain)
SEQ ID NO: 63
GAGATCCAGCTGCAGCAGTCTGGAGTTGAGCTGGTGAGGCCTGGGGCTTCAGTGACGCTGTCCTGC

AAGGCTTCGGGCTACACATTTACTGACTATGACATGCACTGGGTGAAGCAGACACCTGTTCATGGC

CTGGAATGGATTGGAACTATTGATCCTGAAACTGGTGGTACTGCCTACAATCAGAAGTTCAAGGGC

AAGGCCACACTGACTGCGGACAGATCCTCCACCACAGCCTACATGGAGCTCAGCAGCCTGACATCT

GAGGACTCTGCCGTCTATTACTGTACAAGTTTCTACTATACTTACTCTAATTACGACGTGGGGTTT

GCTTACTGGGGCCAAGGGACTCTGGTCACTGTCTCTGCA (nucleotide sequence of the humanized 25E9 light
chain variable domain-variant 1- illustrated without the portion
coding for the signal sequence)
SEQ ID NO.:64
gacatcgtgatgacccagtcccccctgtccctgcctgtgacacctggcgagcccgcctccatctcc tgccggtccaccaagtccctgctgcactccaacggcaacacctacctgtactggtatctgcagaag cccggccagtcccctcagctgctgatctaccggatgtccaacctggcctccggcgtgcccgacaga ttctccggctctggctccggcaccgacttcaccctgaagatctcccgggtggaagccgaggacgtg ggcgtgtactactgcatgcagcacctggaataccccttcaccttcggcggaggcaccaaggtggaa atcaag (nucleotide sequence of the humanized 25E9 heavy
chain variable domain-variant 1- illustrated without the portion
coding for the signal sequence)

```
gagattcagctgcagcagtcaggagccgaagtgaagaaacccggctccagcgtcaaggtgagttgc aaggcctccggatacactttcaccgactatgatatgcactgggtgagacaggcacctgggcaggt ctggagtggatggggaccatcgatccagaaaccggcggaacagcctacaaccagaagtttaaaggt cgagtgacaattactgctgacaagtccaccagcacagcatatatggagctgtctagtctgcgttct gaagatacagccgtctactattgcacttctttctactacacctacagtaactacgacgtggggttt gcttactggggccagggaactctggtcaccgtgtcatcc
```

SEQ ID NO.: 66: candidate human model for 25D8 light chain variable
domain
DIVMTQTPLSLPVTPGEPASISCRSSQSLLHSEGYNYLDWYLQKPGQSPQLLIYLGSNRASGVPDR
FSGSGSGTDFTLKISRVEAEDVGVYYCMQGLQTPLTFGGGTKVEIK SEQ ID NO.: 67: candidate human model for 25D8 light chain variable
domain
DIVMTQTPLSLPVTPGEPASISCRASQSLLHSNGYNYLDWYLQKPGQSPQLLIYLGSNRASGVPDR
FSGSGSGTDFTLRISRVEAEDVGVYYCMQGLQTPLTFGGGTKVEIK SEQ ID NO.: 68: candidate human model for 25D8 light chain variable
domain
DIVMTQSPLSLSVTPGQPASISCKSSQSLLHSDGKTYLYWYLQKPGQPPQLLIYEVSNRFSGVPDR
FSGSGSGTDFTLKISRVEAEDVGVYYCMQSIQLPYTFGQGTKLEIK SEQ ID NO.: 69: human model for 25D8 light chain variable domain
DIVMTQSPLSLPVTPGEPASISCRSSQSLLHSNGYNYLDWYLQKPGQSPQLLIYLGSNRASGVPDR
FSGSGSGTDFTLKISRVEAEDVGVYYCMQALQ

SEQ ID No.: 70: candidate human model for 25D8 light chain variable
domain
DIVMTQPPLSLPVTPGEPASISCRSSQSLLHSEGYNYLDWYLQKPGQSPQLLIYLGSNRASGVPDR
FSGSGSGTDFTLKISRVEAEDVGVYYCMQALQ

SEQ ID NO.: 71: candidate human model for 25D8 light chain variable
domain
DIVMTQTPLSLSVTPGQPASISCKSSQSLLHSDGKTYLYWYLQKPGQSPQLLIYEVSNRFSGVPDR
FSGSGSGTDFTLKISRVEAEDVGVYYCMQSIQL

SEQ ID NO.: 72: candidate human model for 25D8 light chain variable
domain
DIVMTQSPLSLPVTPGEPASISCRSSQSLLHSDGNNYLNWYLQKPGQSPQLLIYLVSNRASGVPDR
FSGSGSGTDFTLKISRVEAEDVGVYYCMQALQPRXTFGQGTKVEIK SEQ ID NO.: 73: candidate human model for 25D8 heavy chain variable
domain
QVQLQQSGAEVKKPGSSVKVSCKASGGTFGSYAISWVRQAPGQGLEWMGRIIPILGIATYAQKFQG
RVTITADKSTSTAYMDLSSLRSEDTAVYYCARGKGEFEGMDVWGQGTTVTVSS SEQ ID NO.: 74: candidate human model for 25D8 heavy chain variable
domain
QVQLQQSGAEVKKPGSSVKVSCKASGGTFSSYAISWVRQAPGQGLEWMGRIIPILGIANYAQKFQG
RVTITADKSTSTAYMELSSLRSEDTAVYYCARDTHSWFAFDIWGQGTMVTVSS SEQ ID NO.: 75: candidate human model for 25D8 heavy chain variable
domain
EVQLVQSGAEMKKPGASVKVSCKASGYSFSIYNIHWVRQAPGQGLEWMGWIHAGTGNRKYSQVFQD
RVTITRDTSASTSYMELSSLTSEDTAVYYCARDPNFGDFDSWGQGTLVTVSS SEQ ID NO.: 76: candidate human model for 25D8 heavy chain variable
domain
QVQLVQSGAEVKKPGSSVKVSCKASGGTFSSYAISWVRQAPGQGLEWMGGIIPIFGTANYAQKFQG
RVTITADESTSTAYMELSSLRSEDTAVYYCARMYNWNFFDYWGQGTLVTVSS SEQ ID NO.: 77: candidate human model for 25D8 heavy chain variable
domain
QVQLVQSGAEVKKPGASVKVSCKASGYTFTSYYMHWVRQAPGQGLEWMGIINPSGGSTSYAQKFQG
RVTMTRDTSTSTVYMELSSLRSEDTAVYYCAREGDGYIQAFDYWGQGTLVTVSS SEQ ID NO.: 78: candidate human model for 25D8 heavy chain variable
domain
QVQLVQSGAEVKKPGSSVKVSCKASGGTFSSYAISWVRQAPGQGLEWMGGIIPIFGTANYAQKFQG
RVTITADKSTSTAYMELSSLRSEDTAVYYCAR SEQ ID NO.: 79: candidate human model for 25D8 heavy chain variable
domain
QVQLVQSGAEVKKPGASVKVSCKASGYTFTSYYMHWVRQAPGQGLEWMGIINPSGGSTSYAQKFQG
RVTMTRDTSTSTVYMELSSLRSEDTAVYYCAR SEQ ID NO.: 80: candidate human model for 25D8 heavy chain variable
domain
QVQLVQSGAEVKKPGASVKVSCKASGYTFTSYAISWVRQAPGQGLEWMGWINPGNGDTNYAQKFQG
RVTITADTSTSTAYMELSSLRSEDTAVYYCARGGRGDYFDYWGQGTLVTVSS SEQ ID NO.: 81: candidate human model for 25E9 light chain variable
domain
DIVMTQSPLSLPVTPGEPASISCRSSQSLLHSTGNNYLDWYLQKPGQSPQLLIYLGSNRASGVPDR
FSGSGSGTDFTLKISRVEAEDVGVYYCMQFLQTPLTFGGGTKVEIK SEQ ID NO.: 82: candidate human model for 25E9 light chain variable
domain
DIVMTQTPLSLPVTPGEPASISCRASQSLLHSNGYNYLDWYLQKPGQSPQLLIYLGSNRASGVPDR
FSGSGSGTDFTLRISRVEAEDVGVYYCMQGLQTPLTFGGGTKVEIK SEQ ID NO.: 83: candidate human model for 25E9 light chain variable
domain
DIVMTQSPLSLPVTPGEPASISCRSSQSLLHSNGYNYLDWYLQKPGQSPQLLIYLGSNRASGVPDR
FSGSGSGTDFTLKISRVEAEDVGVYYCMQALQ

SEQ ID NO.: 84: candidate human model for 25E9 light chain variable
domain
DIVMTQPPLSLPVTPGEPASISCRSSQSLLHSNGYNYLDWYLQKPGQSPQLLIYLGSNRASGVPDR
FSGSGSGTDFTLKISRVEAEDVGVYYCMQALQ

SEQ ID NO.: 85: candidate human model for 25E9 light chain variable
domain
DIVMTQSPLSLPVTPGEPASISCRSSQSLLHSDGNNYLNWYLQKPGQSPQLLIYLVSNRASGVPDR
FSGSGSGTDFTLKISRVEAEDVGVYYCMQALQPRXTFGGGTKVEIK SEQ ID NO.: 86: candidate human model for 25E9 heavy chain variable
domain
QVQLQQSGAEVKKPGSSVKVSCKASGGTFSTYSISWVRQAPGHGLEWMGRIFPLLGVAKYAQKFQG
RVTITADKSTSTAYMELSSLRSEDTAVYYCAVPRSSSYWFDPWGQGTLVTVSS 5

SEQ ID NO.: 87: candidate human model for 25E9 heavy chain variable
domain
EVQLVQSGAEVKKPGSSVKVSCKASGGTFSSYAISWVRQAPGQGLEWMGGIIPIFGTANYAQKFQG
RVTITADESTSTAYMELSSLRSEDTAVYYCARGNYDSSGYDDAFDIWGQGTMVTVSS SEQ ID NO.: 88: candidate human model for 25E9 heavy chain variable
domain
EVQLVQSGAEVKKPGSSVKLSCKASGDTFSSRPVSWVRQAPGQGLEWMGGIIPIFRTTNYAQKFQG
RVTITADESMTTAYLELRGLTSDDTAVYYCATTRMKITVFASTFDYWGQGTLVTVSS SEQ ID NO.: 89: candidate human model for 25E9 heavy chain variable
domain
QVQLVQSGAEVKKPGSSVKVSCKASGGTFSSYAISWVRQAPGQGLEWMGGIIPIFGTANYAQKFQG
RVTITADKSTSTAYMELSSLRSEDTAVYYC SEQ ID NO.: 90: candidate human model for 25E9 heavy chain variable
domain
QVQLVQSGAEVKKPGASVKVSCKASGYTFTSYYMHWVRQAPGQGLEWMGIINPSGGSTSYAQKFQG
RVTMTRDTSTSTVYMELSSLRSEDTAVYYC SEQ ID NO.: 91: candidate human model for 25E9 heavy chain variable
domain
EVQLVQSGAEVKKPGATVKISCKVSGYTFTDYYMHWVQQAPGKGLEWMGLVDPEDGETIYAEKFQG
RVTITADTSTDTAYMELSSLRSEDTAVYYCAT SEQ ID NO.: 92: candidate human model for 25E9 heavy chain variable
domain
QVQLVQSGAEVKKPGASVKVSCKASGYTFTSYAISWVRQAPGQGLEWMGWINPGNGDTNYAQKFQG
RVTITADTSTSTAYMELSSLRSEDTAVYYCARAPGYGSRGDYXFDYWGQGTLVTVSS

---

The invention claimed is:

1. An antibody or an antigen binding fragment thereof capable of specific binding to the Siglec-15 protein consisting of the amino acid sequence set forth in SEQ ID NO.:2 and wherein the antibody or antigen binding fragment thereof comprises a light chain variable domain as set forth in SEQ ID NO.: 8 or SEQ ID NO.:10 and a heavy chain variable domain as set forth in SEQ ID NO.:14, SEQ ID NO.:16, SEQ ID NO.:18 or SEQ ID NO.:20.

2. The antibody or antigen binding fragment thereof of claim 1, wherein said antibody or antigen binding fragment thereof comprises the light chain variable domain set forth in SEQ ID NO.:8 and the heavy chain variable domain set forth in SEQ ID NO.:14.

3. The antibody or antigen binding fragment thereof of claim 2, wherein said antibody or antigen binding fragment thereof comprises a human IgG1 constant region.

4. The antibody or antigen binding fragment thereof of claim 2, wherein said antibody or antigen binding fragment thereof is conjugated with a therapeutic moiety.

5. The antibody or antigen binding fragment thereof of claim 4, wherein the therapeutic moiety comprises a cytotoxic moiety.

6. The antibody or antigen binding fragment thereof of claim 3, wherein said antibody or antigen binding fragment thereof is conjugated with a therapeutic moiety.

7. The antibody or antigen binding fragment thereof of claim 6, wherein the therapeutic moiety comprises a cytotoxic moiety.

8. A pharmaceutical composition comprising the antibody or antigen binding fragment thereof of claim 1 and a pharmaceutically acceptable carrier.

9. A pharmaceutical composition comprising the antibody or antigen binding fragment thereof of claim 2 and a pharmaceutically acceptable carrier.

10. A pharmaceutical composition comprising the antibody or antigen binding fragment thereof of claim 3 and a pharmaceutically acceptable carrier.

11. A pharmaceutical composition comprising the antibody or antigen binding fragment thereof of claim 4 and a pharmaceutically acceptable carrier.

12. A pharmaceutical composition comprising the antibody or antigen binding fragment thereof of claim 5 and a pharmaceutically acceptable carrier.

13. A pharmaceutical composition comprising the antibody or antigen binding fragment thereof of claim 6 and a pharmaceutically acceptable carrier.

14. A pharmaceutical composition comprising the antibody or antigen binding fragment thereof of claim 7 and a pharmaceutically acceptable carrier.

* * * * *

SEQUENCE LISTING

<160> NUMBER OF SEQ ID NOS: 92

<210> SEQ ID NO 1
<211> LENGTH: 987
<212> TYPE: DNA
<213> ORGANISM: Homo sapiens

<400> SEQUENCE: 1

```
atggaaaagt ccatctggct gctggcctgc ttggcgtggg ttctcccgac aggctcattt      60
gtgagaacta aaatagatac tacggagaac ttgctcaaca cagaggtgca cagctcgcca     120
gcgcagcgct ggtccatgca ggtgccaccc gaggtgagcg cggaggcagg cgacgcggca     180
gtgctgccct gcaccttcac gcacccgcac cgccactacg acgggccgct gacggccatc     240
tggcgcgcgg gcgagcccta tgcgggcccg caggtgttcc gctgcgctgc ggcgcggggc     300
agcgagctct gccagacggc gctgagcctg cacggccgct tccggctgct gggcaacccg     360
cgccgcaacg acctctcgct gcgcgtcgag cgcctcgccc tggctgacga ccgccgctac     420
ttctgccgcg tcgagttcgc cggcgacgtc catgaccgct acgagagccg ccacggcgtc     480
cggctgcacg tgacagccgc gccgcggatc gtcaacatct cggtgctgcc cagtccggct     540
cacgccttcc gcgcgctctg cactgccgaa ggggagccgc cgcccgccct cgcctggtcc     600
ggcccggccc tgggcaacag cttggcagcc gtgcggagcc cgcgtgaggg tcacggccac     660
ctagtgaccg ccgaactgcc cgcactgacc catgacggcc gctacacgtg tacggccgcc     720
aacagcctgg gccgctccga ggccagcgtc tacctgttcc gcttccatgg cgccagcggg     780
gcctcgacgg tcgccctcct gctcggcgct ctcggcttca aggcgctgct gctgctcggg     840
gtcctggccg cccgcgctgc ccgccgccgc ccagagcatc tggacacccc ggacacccca     900
ccacggtccc aggcccagga gtccaattat gaaaatttga ccagatgaa ccccggagc      960
ccaccagcca ccatgtgctc accgtga                                          987
```

<210> SEQ ID NO 2
<211> LENGTH: 328
<212> TYPE: PRT
<213> ORGANISM: Homo sapiens

<400> SEQUENCE: 2

```
Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Asp Arg Arg Tyr Phe Cys Arg Val
    130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
                165                 170                 175

Pro Ser Pro Ala His Ala Phe Arg Ala Leu Cys Thr Ala Glu Gly Glu
            180                 185                 190
```

```
Pro Pro Pro Ala Leu Ala Trp Ser Gly Pro Ala Leu Gly Asn Ser Leu
            195                 200                 205

Ala Ala Val Arg Ser Pro Arg Glu Gly His Gly His Leu Val Thr Ala
210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
                245                 250                 255

Gly Ala Ser Gly Ala Ser Thr Val Ala Leu Leu Gly Ala Leu Gly
            260                 265                 270

Phe Lys Ala Leu Leu Leu Gly Val Leu Ala Ala Arg Ala Ala Arg
        275                 280                 285

Arg Arg Pro Glu His Leu Asp Thr Pro Asp Thr Pro Pro Arg Ser Gln
290                 295                 300

Ala Gln Glu Ser Asn Tyr Glu Asn Leu Ser Gln Met Asn Pro Arg Ser
305                 310                 315                 320

Pro Pro Ala Thr Met Cys Ser Pro
            325

<210> SEQ ID NO 3
<211> LENGTH: 1029
<212> TYPE: DNA
<213> ORGANISM: Mus musculus

<400> SEQUENCE: 3 atggagggt ccctccaact cctggcctgc ttggcctgtg tgctccagat gggatccctt      60
gtgaaaacta aagagacgc ttcggggat ctgctcaaca cagaggcgca cagtgccccg     120
gcgcagcgct ggtccatgca ggtgcccgcg gaggtgaacg cggaggctgg cgacgcggcg     180
gtgctgccct gcaccttcac gcacccgcac cgccactacg acgggccgct gacggccatc     240
tggcgctcgg gcgagccgta cgcgggcccg caggtgttcc gctgcaccgc ggcgccgggc     300
agcgagctgt gccagacggc gctgagcctg cacggccgct ccgcctgct gggcaacccg     360
cgccgcaacg acctgtccct gcgcgtcgag cgcctcgccc tggcggacag cggccgctac     420
ttctgccgcg tggagttcac cggcgacgcc acgatcgct atgagagtcg ccatgggtc     480
cgtctgcgcg tgactgcagc tgcgccgcgg atcgtcaaca tctcggtgct gccgggcccc     540
gcgcacgcct tccgcgcgct ctgcaccgcc gaggggagc cccgccgc ctcgcctgg     600
tcgggtcccg ccccaggcaa cagctccgct gccctgcagg gccagggtca cggctaccag     660
gtgaccgccg agttgcccgc gctgacccgc gacggccgct acacgtgcac ggcggccaat     720
agcctgggcc gcgccgaggc cagcgtctac ctgttccgct ccacggcgc ccccggaacc     780
tcgaccctag cgctcctgct gggcgcgctg ggctcaagg ccttgctgct gcttggcatt     840
ctgggagcgc gtgccacccg acgccgacta gatcacctgg tcccccagga caccctcca     900
cggtctcagg ctcaggagtc caattatgaa aattgagcc agatgagtcc tccaggccac     960
cagctgccac gtgttgctg tgaggaactc ctcagccatc accatctagt cattcaccat    1020
gagaaataa                                                           1029

<210> SEQ ID NO 4
<211> LENGTH: 342
<212> TYPE: PRT
<213> ORGANISM: Mus musculus

<400> SEQUENCE: 4
```

Met Glu Gly Ser Leu Gln Leu Leu Ala Cys Leu Ala Cys Val Leu Gln
1               5                   10                  15

Met Gly Ser Leu Val Lys Thr Arg Arg Asp Ala Ser Gly Asp Leu Leu
            20                  25                  30

Asn Thr Glu Ala His Ser Ala Pro Ala Gln Arg Trp Ser Met Gln Val
            35                  40                  45

Pro Ala Glu Val Asn Ala Glu Ala Gly Asp Ala Ala Val Leu Pro Cys
        50                  55                  60

Thr Phe Thr His Pro His Arg His Tyr Asp Gly Pro Leu Thr Ala Ile
65                  70                  75                  80

Trp Arg Ser Gly Glu Pro Tyr Ala Gly Pro Gln Val Phe Arg Cys Thr
                85                  90                  95

Ala Ala Pro Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Ser Gly Arg Tyr Phe Cys Arg Val
    130                 135                 140

Glu Phe Thr Gly Asp Ala His Asp Arg Tyr Glu Ser Arg His Gly Val
145                 150                 155                 160

Arg Leu Arg Val Thr Ala Ala Pro Arg Ile Val Asn Ile Ser Val
                165                 170                 175

Leu Pro Gly Pro Ala His Ala Phe Arg Ala Leu Cys Thr Ala Glu Gly
                180                 185                 190

Glu Pro Pro Pro Ala Leu Ala Trp Ser Gly Pro Ala Pro Gly Asn Ser
                195                 200                 205

Ser Ala Ala Leu Gln Gly Gln Gly His Gly Tyr Gln Val Thr Ala Glu
            210                 215                 220

Leu Pro Ala Leu Thr Arg Asp Gly Arg Tyr Thr Cys Thr Ala Ala Asn
225                 230                 235                 240

Ser Leu Gly Arg Ala Glu Ala Ser Val Tyr Leu Phe Arg Phe His Gly
                245                 250                 255

Ala Pro Gly Thr Ser Thr Leu Ala Leu Leu Leu Gly Ala Leu Gly Leu
            260                 265                 270

Lys Ala Leu Leu Leu Leu Gly Ile Leu Gly Ala Arg Ala Thr Arg Arg
        275                 280                 285

Arg Leu Asp His Leu Val Pro Gln Asp Thr Pro Pro Arg Ser Gln Ala
    290                 295                 300

Gln Glu Ser Asn Tyr Glu Asn Leu Ser Gln Met Ser Pro Pro Gly His
305                 310                 315                 320

Gln Leu Pro Arg Val Cys Cys Glu Glu Leu Leu Ser His His Leu
                325                 330                 335

Val Ile His His Glu Lys
            340

<210> SEQ ID NO 5
<211> LENGTH: 239
<212> TYPE: PRT
<213> ORGANISM: Artificial Sequence
<220> FEATURE:
<223> OTHER INFORMATION: 25E9 light chain (kappa) chimeric

<400> SEQUENCE: 5

Met Val Leu Gln Thr Gln Val Phe Ile Ser Leu Leu Leu Trp Ile Ser
1               5                   10                  15

-continued

```
Gly Ala Tyr Gly Asp Ile Val Met Thr Gln Ala Ala Pro Ser Val Pro
             20                  25                  30

Val Thr Pro Gly Glu Ser Val Ser Ile Ser Cys Arg Ser Thr Lys Ser
         35                  40                  45

Leu Leu His Ser Asn Gly Asn Thr Tyr Leu Tyr Trp Phe Leu Gln Arg
 50                  55                  60

Pro Gly Gln Ser Pro Gln Leu Leu Ile Tyr Arg Met Ser Asn Leu Ala
 65                  70                  75                  80

Ser Gly Val Pro Asp Arg Phe Ser Gly Ser Gly Ser Gly Thr Ala Phe
                 85                  90                  95

Thr Leu Arg Ile Ser Arg Val Glu Ala Glu Asp Val Gly Val Tyr Tyr
            100                 105                 110

Cys Met Gln His Leu Glu Tyr Pro Phe Thr Phe Gly Gly Gly Thr Lys
            115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
            165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 6
<211> LENGTH: 112
<212> TYPE: PRT
<213> ORGANISM: Artificial Sequence
<220> FEATURE:
<223> OTHER INFORMATION: 25E9 light chain mouse variable domain

<400> SEQUENCE: 6

Asp Ile Val Met Thr Gln Ala Ala Pro Ser Val Pro Val Thr Pro Gly
1               5                  10                  15

Glu Ser Val Ser Ile Ser Cys Arg Ser Thr Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110

<210> SEQ ID NO 7
<211> LENGTH: 239
<212> TYPE: PRT
<213> ORGANISM: Artificial Sequence
<220> FEATURE:
```

<223> OTHER INFORMATION: 25E9 light chain (kappa) humanized variant 1

<400> SEQUENCE: 7

```
Met Val Leu Gln Thr Gln Val Phe Ile Ser Leu Leu Leu Trp Ile Ser
1               5                   10                  15
Gly Ala Tyr Gly Asp Ile Val Met Thr Gln Ser Pro Leu Ser Leu Pro
            20                  25                  30
Val Thr Pro Gly Glu Pro Ala Ser Ile Ser Cys Arg Ser Thr Lys Ser
        35                  40                  45
Leu Leu His Ser Asn Gly Asn Thr Tyr Leu Tyr Trp Tyr Leu Gln Lys
    50                  55                  60
Pro Gly Gln Ser Pro Gln Leu Leu Ile Tyr Arg Met Ser Asn Leu Ala
65                  70                  75                  80
Ser Gly Val Pro Asp Arg Phe Ser Gly Ser Gly Ser Gly Thr Asp Phe
                85                  90                  95
Thr Leu Lys Ile Ser Arg Val Glu Ala Glu Asp Val Gly Val Tyr Tyr
            100                 105                 110
Cys Met Gln His Leu Glu Tyr Pro Phe Thr Phe Gly Gly Gly Thr Lys
        115                 120                 125
Val Glu Ile Lys Arg Thr Val Ala Ala Pro Ser Val Phe Ile Phe Pro
    130                 135                 140
Pro Ser Asp Glu Gln Leu Lys Ser Gly Thr Ala Ser Val Val Cys Leu
145                 150                 155                 160
Leu Asn Asn Phe Tyr Pro Arg Glu Ala Lys Val Gln Trp Lys Val Asp
                165                 170                 175
Asn Ala Leu Gln Ser Gly Asn Ser Gln Glu Ser Val Thr Glu Gln Asp
            180                 185                 190
Ser Lys Asp Ser Thr Tyr Ser Leu Ser Ser Thr Leu Thr Leu Ser Lys
        195                 200                 205
Ala Asp Tyr Glu Lys His Lys Val Tyr Ala Cys Glu Val Thr His Gln
    210                 215                 220
Gly Leu Ser Ser Pro Val Thr Lys Ser Phe Asn Arg Gly Glu Cys
225                 230                 235
```

<210> SEQ ID NO 8
<211> LENGTH: 112
<212> TYPE: PRT
<213> ORGANISM: Artificial Sequence
<220> FEATURE:
<223> OTHER INFORMATION: 25E9 light chain humanized variant 1 variable domain

<400> SEQUENCE: 8

```
Asp Ile Val Met Thr Gln Ser Pro Leu Ser Leu Pro Val Thr Pro Gly
1               5                   10                  15
Glu Pro Ala Ser Ile Ser Cys Arg Ser Thr Lys Ser Leu Leu His Ser
            20                  25                  30
Asn Gly Asn Thr Tyr Leu Tyr Trp Tyr Leu Gln Lys Pro Gly Gln Ser
        35                  40                  45
Pro Gln Leu Leu Ile Tyr Arg Met Ser Asn Leu Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln His
                85                  90                  95
```

Leu Glu Tyr Pro Phe Thr Phe Gly Gly Gly Thr Lys Val Glu Ile Lys
            100                 105                 110

<210> SEQ ID NO 9
<211> LENGTH: 239
<212> TYPE: PRT
<213> ORGANISM: Artificial Sequence
<220> FEATURE:
<223> OTHER INFORMATION: 25E9 light chain (kappa) humanized variant 2

<400> SEQUENCE: 9

Met Val Leu Gln Thr Gln Val Phe Ile Ser Leu Leu Trp Ile Ser
1               5                   10                  15

Gly Ala Tyr Gly Asp Ile Val Met Thr Gln Ser Pro Leu Ser Leu Pro
            20                  25                  30

Val Thr Pro Gly Glu Pro Ala Ser Ile Ser Cys Arg Ser Thr Lys Ser
        35                  40                  45

Leu Leu His Ser Asn Gly Asn Thr Tyr Leu Tyr Trp Phe Leu Gln Lys
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln His Leu Glu Tyr Pro Phe Thr Phe Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 10
<211> LENGTH: 112
<212> TYPE: PRT
<213> ORGANISM: Artificial Sequence
<220> FEATURE:
<223> OTHER INFORMATION: 25E9 light chain humanized variant 2 variable
      domain

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Thr Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Val Glu Ile Lys
            100                 105                 110

<210> SEQ ID NO 11
<211> LENGTH: 472
<212> TYPE: PRT
<213> ORGANISM: Artificial Sequence
<220> FEATURE:
<223> OTHER INFORMATION: 25E9 heavy chain (IgG1) chimeric

<400> SEQUENCE: 11

Met Asp Trp Thr Trp Arg Ile Leu Phe Leu Val Ala Ala Ala Thr Gly
1               5                   10                  15

Thr His Ala Glu Ile Gln Leu Gln Gln Ser Gly Val Glu Leu Val Arg
            20                  25                  30

Pro Gly Ala Ser Val Thr Leu Ser Cys Lys Ala Ser Gly Tyr Thr Phe
        35                  40                  45

Thr Asp Tyr Asp Met His Trp Val Lys Gln Thr Pro Val His Gly Leu
50                  55                  60

Glu Trp Ile Gly Thr Ile Asp Pro Glu Thr Gly Gly Thr Ala Tyr Asn
65                  70                  75                  80

Gln Lys Phe Lys Gly Lys Ala Thr Leu Thr Ala Asp Arg Ser Ser Thr
                85                  90                  95

Thr Ala Tyr Met Glu Leu Ser Ser Leu Thr Ser Glu Asp Ser Ala Val
            100                 105                 110

Tyr Tyr Cys Thr Ser Phe Tyr Tyr Thr Tyr Ser Asn Tyr Asp Val Gly
        115                 120                 125

Phe Ala Tyr Trp Gly Gln Gly Thr Leu Val Thr Val Ser Ala Ala Ser
130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
290                 295                 300

```
Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
            325                 330                 335

Asp Trp Leu Asn Gly Lys Glu Tyr Lys Cys Lys Val Ser Asn Lys Ala
        340                 345                 350

Leu Pro Ala Pro Ile Glu Lys Thr Ile Ser Lys Ala Lys Gly Gln Pro
    355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Pro Pro Val Leu Asp Ser Asp Gly Ser Phe Phe Leu Tyr
        420                 425                 430

Ser Lys Leu Thr Val Asp Lys Ser Arg Trp Gln Gln Gly Asn Val Phe
    435                 440                 445

Ser Cys Ser Val Met His Glu Ala Leu His Asn His Tyr Thr Gln Lys
450                 455                 460

Ser Leu Ser Leu Ser Pro Gly Lys
465                 470

<210> SEQ ID NO 12
<211> LENGTH: 123
<212> TYPE: PRT
<213> ORGANISM: Artificial Sequence
<220> FEATURE:
<223> OTHER INFORMATION: 25E9 heavy chain mouse variable domain

<400> SEQUENCE: 12

Glu Ile Gln Leu Gln Gln Ser Gly Val Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Asp Met His Trp Val Lys Gln Thr Pro Val His Gly Leu Glu Trp Ile
        35                  40                  45

Gly Thr Ile Asp Pro Glu Thr Gly Gly Thr Ala Tyr Asn Gln Lys Phe
    50                  55                  60

Lys Gly Lys Ala Thr Leu Thr Ala Asp Arg Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Thr Ser Phe Tyr Tyr Thr Tyr Ser Asn Tyr Asp Val Gly Phe Ala Tyr
            100                 105                 110

Trp Gly Gln Gly Thr Leu Val Thr Val Ser Ala
        115                 120

<210> SEQ ID NO 13
<211> LENGTH: 472
<212> TYPE: PRT
<213> ORGANISM: Artificial Sequence
<220> FEATURE:
<223> OTHER INFORMATION: 25E9 heavy chain (IgG1) humanized variant 1

<400> SEQUENCE: 13

Met Asp Trp Thr Trp Arg Ile Leu Phe Leu Val Ala Ala Ala Thr Gly
1               5                   10                  15
```

-continued

Thr His Ala Glu Ile Gln Leu Gln Gln Ser Gly Ala Glu Val Lys Lys
                20                  25                  30

Pro Gly Ser Ser Val Lys Val Ser Cys Lys Ala Ser Gly Tyr Thr Phe
            35                  40                  45

Thr Asp Tyr Asp Met His Trp Val Arg Gln Ala Pro Gly Gln Gly Leu
    50                  55                  60

Glu Trp Met Gly Thr Ile Asp Pro Glu Thr Gly Thr Ala Tyr Asn
65                  70                  75                  80

Gln Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Ser Phe Tyr Tyr Thr Tyr Ser Asn Tyr Asp Val Gly
        115                 120                 125

Phe Ala Tyr Trp Gly Gln Gly Thr Leu Val Thr Val Ser Ser Ala Ser
130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

```
Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
        450                 455                 460

Ser Leu Ser Leu Ser Pro Gly Lys
465                 470

<210> SEQ ID NO 14
<211> LENGTH: 123
<212> TYPE: PRT
<213> ORGANISM: Artificial Sequence
<220> FEATURE:
<223> OTHER INFORMATION: 25E9 heavy chain humanized variant 1 variable
      domain

<400> SEQUENCE: 14

Glu Ile Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asp Met His Trp Val Arg Gln Ala Pro Gly Gln Gly Leu Glu Trp Met
        35                  40                  45

Gly Thr Ile Asp Pro Glu Thr Gly Gly Thr Ala Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Phe Tyr Tyr Thr Tyr Ser Asn Tyr Asp Val Gly Phe Ala Tyr
            100                 105                 110

Trp Gly Gln Gly Thr Leu Val Thr Val Ser Ser
        115                 120

<210> SEQ ID NO 15
<211> LENGTH: 472
<212> TYPE: PRT
<213> ORGANISM: Artificial Sequence
<220> FEATURE:
<223> OTHER INFORMATION: 25E9 heavy chain (IgG1) humanized variant 2

<400> SEQUENCE: 15

Met Asp Trp Thr Trp Arg Ile Leu Phe Leu Val Ala Ala Ala Thr Gly
1               5                   10                  15

Thr His Ala Glu Ile Gln Leu Gln Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asp Tyr Asp Met His Trp Val Arg Gln Ala Pro Gly Gln Gly Leu
    50                  55                  60

Glu Trp Ile Gly Thr Ile Asp Pro Glu Thr Gly Gly Thr Ala Tyr Asn
65                  70                  75                  80

Gln Lys Phe Lys Gly Arg Ala Thr Leu Thr Ala Asp Arg Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Ser Phe Tyr Tyr Thr Tyr Ser Asn Tyr Asp Val Gly
        115                 120                 125
```

```
Phe Ala Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
450                 455                 460

Ser Leu Ser Leu Ser Pro Gly Lys
465                 470

<210> SEQ ID NO 16
<211> LENGTH: 123
<212> TYPE: PRT
<213> ORGANISM: Artificial Sequence
<220> FEATURE:
<223> OTHER INFORMATION: 25E9 heavy chain humanized variant 2 variable
      domain

<400> SEQUENCE: 16

Glu Ile Gln Leu Gln Gln Ser Gly Ala Glu Val Lys Lys Pro Gly Ser
1               5                   10                  15
```

-continued

Ser Val Lys Val Ser Cys Lys Ala Ser Gly Tyr Thr Phe Thr Asp Tyr
            20                  25                  30

Asp Met His Trp Val Arg Gln Ala Pro Gly Gln Gly Leu Glu Trp Ile
        35                  40                  45

Gly Thr Ile Asp Pro Glu Thr Gly Gly Thr Ala Tyr Asn Gln Lys Phe
    50                  55                  60

Lys Gly Arg Ala Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Phe Tyr Tyr Thr Tyr Ser Asn Tyr Asp Val Gly Phe Ala Tyr
            100                 105                 110

Trp Gly Gln Gly Thr Leu Val Thr Val Ser Ser
            115                 120

<210> SEQ ID NO 17
<211> LENGTH: 472
<212> TYPE: PRT
<213> ORGANISM: Artificial Sequence
<220> FEATURE:
<223> OTHER INFORMATION: 25E9 heavy chain (IgG1) humanized variant 3

<400> SEQUENCE: 17

Met Asp Trp Thr Trp Arg Ile Leu Phe Leu Val Ala Ala Ala Thr Gly
1               5                   10                  15

Thr His Ala Glu Ile Gln Leu Gln Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asp Tyr Asp Met His Trp Val Lys Gln Ala Pro Gly Gln Gly Leu
    50                  55                  60

Glu Trp Ile Gly Thr Ile Asp Pro Glu Thr Gly Gly Thr Ala Tyr Asn
65                  70                  75                  80

Gln Lys Phe Lys Gly Lys Ala Thr Leu Thr Ala Asp Arg Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Ser Phe Tyr Tyr Thr Tyr Ser Asn Tyr Asp Val Gly
            115                 120                 125

Phe Ala Tyr Trp Gly Gln Gly Thr Leu Val Thr Val Ser Ser Ala Ser
        130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

```
Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 18
<211> LENGTH: 123
<212> TYPE: PRT
<213> ORGANISM: Artificial Sequence
<220> FEATURE:
<223> OTHER INFORMATION: 25E9 heavy chain humanized variant 3 variable
      domain

<400> SEQUENCE: 18

Glu Ile Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asp Met His Trp Val Lys Gln Ala Pro Gly Gln Gly Leu Glu Trp Ile
        35                  40                  45

Gly Thr Ile Asp Pro Glu Thr Gly Gly Thr Ala Tyr Asn Gln Lys Phe
    50                  55                  60

Lys Gly Lys Ala Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Phe Tyr Tyr Thr Tyr Ser Asn Tyr Asp Val Gly Phe Ala Tyr
            100                 105                 110

Trp Gly Gln Gly Thr Leu Val Thr Val Ser Ser
        115                 120
```

```
<210> SEQ ID NO 19
<211> LENGTH: 472
<212> TYPE: PRT
<213> ORGANISM: Artificial Sequence
<220> FEATURE:
<223> OTHER INFORMATION: 25E9 heavy chain (IgG1) humanized variant 4

<400> SEQUENCE: 19

Met Asp Trp Thr Trp Arg Ile Leu Phe Leu Val Ala Ala Thr Gly
1               5                   10                  15

Thr His Ala Glu Ile Gln Leu Gln Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asp Tyr Asp Met His Trp Val Lys Gln Ala Pro Gly His Gly Leu
    50                  55                  60

Glu Trp Ile Gly Thr Ile Asp Pro Glu Thr Gly Gly Thr Ala Tyr Asn
65                  70                  75                  80

Gln Lys Phe Lys Gly Lys Ala Thr Leu Thr Ala Asp Arg Ser Thr Ser
                85                  90                  95

Thr Ala Tyr Met Glu Leu Ser Ser Leu Thr Ser Glu Asp Thr Ala Val
            100                 105                 110

Tyr Tyr Cys Thr Ser Phe Tyr Tyr Thr Tyr Ser Asn Tyr Asp Val Gly
        115                 120                 125

Phe Ala Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365
```

```
Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
450                 455                 460

Ser Leu Ser Leu Ser Pro Gly Lys
465                 470

<210> SEQ ID NO 20
<211> LENGTH: 123
<212> TYPE: PRT
<213> ORGANISM: Artificial Sequence
<220> FEATURE:
<223> OTHER INFORMATION: 25E9 heavy chain humanized variant 4 variable
      domain

<400> SEQUENCE: 20

Glu Ile Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Asp Met His Trp Val Lys Gln Ala Pro Gly His Gly Leu Glu Trp Ile
            35                  40                  45

Gly Thr Ile Asp Pro Glu Thr Gly Gly Thr Ala Tyr Asn Gln Lys Phe
        50                  55                  60

Lys Gly Lys Ala Thr Leu Thr Ala Asp Arg Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Ser Phe Tyr Tyr Thr Tyr Ser Asn Tyr Asp Val Gly Phe Ala Tyr
                100                 105                 110

Trp Gly Gln Gly Thr Leu Val Thr Val Ser Ser
        115                 120

<210> SEQ ID NO 21
<211> LENGTH: 239
<212> TYPE: PRT
<213> ORGANISM: Artificial Sequence
<220> FEATURE:
<223> OTHER INFORMATION: chimeric 25D8 light chain (kappa)

<400> SEQUENCE: 21

Met Val Leu Gln Thr Gln Val Phe Ile Ser Leu Leu Leu Trp Ile Ser
1               5                   10                  15

Gly Ala Tyr Gly Asp Ile Val Met Thr Gln Ala Ala Phe Ser Asn Pro
                20                  25                  30

Val Thr Leu Gly Thr Ser Ala Ser Ile Ser Cys Arg Ser Ser Lys Ser
            35                  40                  45

Leu Leu His Ser Asn Gly Ile Thr Tyr Leu Tyr Trp Tyr Leu Gln Lys
        50                  55                  60
```

```
Pro Gly Gln Ser Pro Gln Leu Leu Ile Tyr Gln Met Ser Asn Leu Ala
65                  70                  75                  80

Ser Gly Val Pro Asp Arg Phe Ser Ser Gly Ser Gly Thr Asp Phe
            85                  90                  95

Thr Leu Arg Ile Ser Arg Val Glu Ala Glu Asp Val Gly Val Tyr Tyr
            100                 105                 110

Cys Ala Gln Asn Leu Glu Leu Pro Tyr Thr Phe Gly Gly Gly Thr Lys
            115                 120                 125

Leu Glu Ile Lys Arg Thr Val Ala Ala Pro Ser Val Phe Ile Phe Pro
            130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 22
<211> LENGTH: 112
<212> TYPE: PRT
<213> ORGANISM: Artificial Sequence
<220> FEATURE:
<223> OTHER INFORMATION: 25D8 light chain mouse variable domain

<400> SEQUENCE: 22

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
            50                  55                  60

Asp Arg Phe Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
            85                  90                  95

Leu Glu Leu Pro Tyr Thr Phe Gly Gly Gly Thr Lys Leu Glu Ile Lys
            100                 105                 110

<210> SEQ ID NO 23
<211> LENGTH: 239
<212> TYPE: PRT
<213> ORGANISM: Artificial Sequence
<220> FEATURE:
<223> OTHER INFORMATION: humanized 25D8 light chain (kappa)

<400> SEQUENCE: 23

Met Val Leu Gln Thr Gln Val Phe Ile Ser Leu Leu Leu Trp Ile Ser
1               5                   10                  15

Gly Ala Tyr Gly Asp Ile Val Met Thr Gln Thr Pro Leu Ser Leu Pro
            20                  25                  30
```

```
Val Thr Pro Gly Glu Pro Ala Ser Ile Ser Cys Arg Ser Lys Ser
        35                  40                  45

Leu Leu His Ser Asn Gly Ile Thr Tyr Leu Tyr Trp Tyr Leu Gln Lys
 50                  55                  60

Pro Gly Gln Ser Pro Gln Leu Leu Ile Tyr Gln Met Ser Asn Leu Ala
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Val Tyr Tyr
                100                 105                 110

Cys Ala Gln Asn Leu Glu Leu Pro Tyr Thr Phe Gly Gly Gly Thr Lys
                115                 120                 125

Val Glu Ile Lys Arg Thr Val Ala Ala Pro Ser Val Phe Ile Phe Pro
        130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
                180                 185                 190

Ser Lys Asp Ser Thr Tyr Ser Leu Ser Ser Thr Leu Thr Leu Ser Lys
                195                 200                 205

Ala Asp Tyr Glu Lys His Lys Val Tyr Ala Cys Glu Val Thr His Gln
        210                 215                 220

Gly Leu Ser Ser Pro Val Thr Lys Ser Phe Asn Arg Gly Glu Cys
225                 230                 235

<210> SEQ ID NO 24
<211> LENGTH: 112
<212> TYPE: PRT
<213> ORGANISM: Artificial Sequence
<220> FEATURE:
<223> OTHER INFORMATION: humanized 25D8 light chain variable domain

<400> SEQUENCE: 24

Asp Ile Val Met Thr Gln Thr Pro Leu Ser Leu Pro Val Thr Pro Gly
 1               5                  10                  15

Glu Pro Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
                100                 105                 110

<210> SEQ ID NO 25
<211> LENGTH: 463
<212> TYPE: PRT
<213> ORGANISM: Artificial Sequence
<220> FEATURE:
<223> OTHER INFORMATION: Chimeric 25D8 heavy chain (IgG2)
```

<400> SEQUENCE: 25

```
Met Asp Trp Thr Trp Arg Ile Leu Phe Leu Val Ala Ala Ala Thr Gly
1               5                   10                  15

Thr His Ala Gln Val Gln Val Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Leu Ile Asn Pro Ser Asn Ala Arg Thr Asn Tyr Asn
65              70                  75                  80

Glu Lys Phe Asn Thr Lys Ala Thr Leu Thr Val Asp Lys Ser Ser
                85                  90                  95

Thr Ala Tyr Met Gln Leu Ser Ser Leu Thr Ser Glu Asp Ser Ala Val
                100                 105                 110

Tyr Tyr Cys Ala Arg Gly Gly Asp Gly Asp Tyr Phe Asp Tyr Trp Gly
            115                 120                 125

Gln Gly Thr Thr Leu Thr Val Ser Ser Ala Ser Thr Lys Gly Pro Ser
130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415
```

-continued

```
Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 26
<211> LENGTH: 118
<212> TYPE: PRT
<213> ORGANISM: Artificial Sequence
<220> FEATURE:
<223> OTHER INFORMATION: 25D8 heavy chain mouse variable domain

<400> SEQUENCE: 26

Gln Val Gln Val Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Leu Ile Asn Pro Ser Asn Ala Arg Thr Asn Tyr Asn Glu Lys Phe
    50                  55                  60

Asn Thr Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Asp Gly Asp Tyr Phe Asp Tyr Trp Gly Gln Gly Thr
            100                 105                 110

Thr Leu Thr Val Ser Ser
        115

<210> SEQ ID NO 27
<211> LENGTH: 463
<212> TYPE: PRT
<213> ORGANISM: Artificial Sequence
<220> FEATURE:
<223> OTHER INFORMATION: humanized 25D8 heavy chain (IgG2)

<400> SEQUENCE: 27

Met Asp Trp Thr Trp Arg Ile Leu Phe Leu Val Ala Ala Ala Thr Gly
1               5                   10                  15

Thr His Ala Gln Val Gln Leu Gln Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Ser Tyr Trp Met His Trp Val Arg Gln Ala Pro Gly Gln Gly Leu
    50                  55                  60

Glu Trp Met Gly Leu Ile Asn Pro Ser Asn Ala Arg Thr Asn Tyr Asn
65                  70                  75                  80

Glu Lys Phe Asn Thr Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Gly Asp Gly Asp Tyr Phe Asp Tyr Trp Gly
        115                 120                 125
```

```
Gln Gly Thr Thr Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 28
<211> LENGTH: 118
<212> TYPE: PRT
<213> ORGANISM: Artificial Sequence
<220> FEATURE:
<223> OTHER INFORMATION: humanized 25D8 heavy chain variable domain

<400> SEQUENCE: 28

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30
```

```
Trp Met His Trp Val Arg Gln Ala Pro Gly Gln Gly Leu Glu Trp Met
         35                  40                  45

Gly Leu Ile Asn Pro Ser Asn Ala Arg Thr Asn Tyr Asn Glu Lys Phe
 50                  55                  60

Asn Thr Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Asp Gly Asp Tyr Phe Asp Tyr Trp Gly Gln Gly Thr
                100                 105                 110

Thr Val Thr Val Ser Ser
            115

<210> SEQ ID NO 29
<211> LENGTH: 468
<212> TYPE: PRT
<213> ORGANISM: Artificial Sequence
<220> FEATURE:
<223> OTHER INFORMATION: 25E9 heavy chain (Igg2) humanized variant 1

<400> SEQUENCE: 29

Met Asp Trp Thr Trp Arg Ile Leu Phe Leu Val Ala Ala Thr Gly
 1               5                  10                  15

Thr His Ala Glu Ile Gln Leu Gln Gln Ser Gly Ala Glu Val Lys Lys
                 20                  25                  30

Pro Gly Ser Ser Val Lys Val Ser Cys Lys Ala Ser Gly Tyr Thr Phe
             35                  40                  45

Thr Asp Tyr Asp Met His Trp Val Arg Gln Ala Pro Gly Gln Gly Leu
 50                  55                  60

Glu Trp Met Gly Thr Ile Asp Pro Glu Thr Gly Gly Thr Ala Tyr Asn
 65                  70                  75                  80

Gln Lys Phe Lys Gly Arg Val Thr Ile Thr Ala Asp Lys Ser Thr Ser
                 85                  90                  95

Thr Ala Tyr Met Glu Leu Ser Ser Leu Arg Ser Glu Asp Thr Ala Val
                100                 105                 110

Tyr Tyr Cys Thr Ser Phe Tyr Tyr Thr Tyr Ser Asn Tyr Asp Val Gly
            115                 120                 125

Phe Ala Tyr Trp Gly Gln Gly Thr Leu Val Thr Val Ser Ser Ala Ser
130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
            195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270
```

```
Met Ile Ser Arg Thr Pro Glu Val Thr Cys Val Val Asp Val Ser
              275                 280                 285
His Glu Asp Pro Glu Val Gln Phe Asn Trp Tyr Val Asp Gly Val Glu
    290                 295                 300
Val His Asn Ala Lys Thr Lys Pro Arg Glu Glu Gln Phe Asn Ser Thr
305                 310                 315                 320
Phe Arg Val Val Ser Val Leu Thr Val His Gln Asp Trp Leu Asn
                325                 330                 335
Gly Lys Glu Tyr Lys Cys Lys Val Ser Asn Lys Gly Leu Pro Ala Pro
                340                 345                 350
Ile Glu Lys Thr Ile Ser Lys Thr Lys Gly Gln Pro Arg Glu Pro Gln
                355                 360                 365
Val Tyr Thr Leu Pro Pro Ser Arg Glu Glu Met Thr Lys Asn Gln Val
    370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Met Leu Asp Ser Asp Gly Ser Phe Phe Leu Tyr Ser Lys Leu Thr
                420                 425                 430
Val Asp Lys Ser Arg Trp Gln Gln Gly Asn Val Phe Ser Cys Ser Val
                435                 440                 445
Met His Glu Ala Leu His Asn His Tyr Thr Gln Lys Ser Leu Ser Leu
                450                 455                 460
Ser Pro Gly Lys
465

<210> SEQ ID NO 30
<211> LENGTH: 468
<212> TYPE: PRT
<213> ORGANISM: Artificial Sequence
<220> FEATURE:
<223> OTHER INFORMATION: 25E9 heavy chain (IgG2) chimeric

<400> SEQUENCE: 30

Met Asp Trp Thr Trp Arg Ile Leu Phe Leu Val Ala Ala Ala Thr Gly
1               5                   10                  15
Thr His Ala Glu Ile Gln Leu Gln Gln Ser Gly Val Glu Leu Val Arg
                20                  25                  30
Pro Gly Ala Ser Val Thr Leu Ser Cys Lys Ala Ser Gly Tyr Thr Phe
            35                  40                  45
Thr Asp Tyr Asp Met His Trp Val Lys Gln Thr Pro Val His Gly Leu
50                  55                  60
Glu Trp Ile Gly Thr Ile Asp Pro Glu Thr Gly Gly Thr Ala Tyr Asn
65                  70                  75                  80
Gln Lys Phe Lys Gly Lys Ala Thr Leu Thr Ala Asp Arg Ser Ser Thr
                85                  90                  95
Thr Ala Tyr Met Glu Leu Ser Ser Leu Thr Ser Glu Asp Ser Ala Val
                100                 105                 110
Tyr Tyr Cys Thr Ser Phe Tyr Tyr Thr Tyr Ser Asn Tyr Asp Val Gly
            115                 120                 125
Phe Ala Tyr Trp Gly Gln Gly Thr Leu Val Thr Val Ser Ala Ala Ser
    130                 135                 140
Thr Lys Gly Pro Ser Val Phe Pro Leu Ala Pro Cys Ser Arg Ser Thr
145                 150                 155                 160
```

Ser Glu Ser Thr Ala Ala Leu Gly Cys Leu Val Lys Asp Tyr Phe Pro
            165                 170                 175

Glu Pro Val Thr Val Ser Trp Asn Ser Gly Ala Leu Thr Ser Gly Val
        180                 185                 190

His Thr Phe Pro Ala Val Leu Gln Ser Ser Gly Leu Tyr Ser Leu Ser
            195                 200                 205

Ser Val Val Thr Val Pro Ser Ser Asn Phe Gly Thr Gln Thr Tyr Thr
        210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
        290                 295                 300

Val His Asn Ala Lys Thr Lys Pro Arg Glu Glu Gln Phe Asn Ser Thr
305                 310                 315                 320

Phe Arg Val Val Ser Val Leu Thr Val His Gln Asp Trp Leu Asn
                325                 330                 335

Gly Lys Glu Tyr Lys Cys Lys Val Ser Asn Lys Gly Leu Pro Ala Pro
            340                 345                 350

Ile Glu Lys Thr Ile Ser Lys Thr Lys Gly Gln Pro Arg Glu Pro Gln
        355                 360                 365

Val Tyr Thr Leu Pro Pro Ser Arg Glu Glu Met Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Met Leu Asp Ser Asp Gly Ser Phe Phe Leu Tyr Ser Lys Leu Thr
        420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
        450                 455                 460

Ser Pro Gly Lys
465

<210> SEQ ID NO 31
<211> LENGTH: 330
<212> TYPE: PRT
<213> ORGANISM: Artificial Sequence
<220> FEATURE:
<223> OTHER INFORMATION: Human IgG1 constant region

<400> SEQUENCE: 31

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 32
<211> LENGTH: 326
<212> TYPE: PRT
<213> ORGANISM: Artificial Sequence
<220> FEATURE:
<223> OTHER INFORMATION: Human IgG2 constant region

<400> SEQUENCE: 32

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80
```

```
Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 33
<211> LENGTH: 112
<212> TYPE: PRT
<213> ORGANISM: Artificial Sequence
<220> FEATURE:
<223> OTHER INFORMATION: Generic 25E9 light chain variable domain
      (consensus 1)
<220> FEATURE:
<221> NAME/KEY: MISC_FEATURE
<222> LOCATION: (7)..(7)
<223> OTHER INFORMATION: Xaa may be an amino acid substitution in
      comparison with SEQ ID NO.:6
<220> FEATURE:
<221> NAME/KEY: MISC_FEATURE
<222> LOCATION: (8)..(8)
<223> OTHER INFORMATION: Xaa may be an amino acid substitution in
      comparison with SEQ ID NO.:6
<220> FEATURE:
<221> NAME/KEY: MISC_FEATURE
<222> LOCATION: (9)..(9)
<223> OTHER INFORMATION: Xaa may be an amino acid substitution in
      comparison with SEQ ID NO.:6
<220> FEATURE:
<221> NAME/KEY: MISC_FEATURE
<222> LOCATION: (11)..(11)
<223> OTHER INFORMATION: Xaa may be an amino acid substitution in
      comparison with SEQ ID NO.:6
<220> FEATURE:
<221> NAME/KEY: MISC_FEATURE
<222> LOCATION: (18)..(18)
```

```
<223> OTHER INFORMATION: Xaa may be an amino acid substitution in
      comparison with SEQ ID NO.:6
<220> FEATURE:
<221> NAME/KEY: MISC_FEATURE
<222> LOCATION: (19)..(19)
<223> OTHER INFORMATION: Xaa may be an amino acid substitution in
      comparison with SEQ ID NO.:6
<220> FEATURE:
<221> NAME/KEY: MISC_FEATURE
<222> LOCATION: (41)..(41)
<223> OTHER INFORMATION: Xaa may be an amino acid substitution in
      comparison with SEQ ID NO.:6
<220> FEATURE:
<221> NAME/KEY: MISC_FEATURE
<222> LOCATION: (44)..(44)
<223> OTHER INFORMATION: Xaa may be an amino acid substitution in
      comparison with SEQ ID NO.:6
<220> FEATURE:
<221> NAME/KEY: MISC_FEATURE
<222> LOCATION: (75)..(75)
<223> OTHER INFORMATION: Xaa may be an amino acid substitution in
      comparison with SEQ ID NO.:6
<220> FEATURE:
<221> NAME/KEY: MISC_FEATURE
<222> LOCATION: (79)..(79)
<223> OTHER INFORMATION: Xaa may be an amino acid substitution in
      comparison with SEQ ID NO.:6
<220> FEATURE:
<221> NAME/KEY: MISC_FEATURE
<222> LOCATION: (109)..(109)
<223> OTHER INFORMATION: Xaa may be an amino acid substitution in
      comparison with SEQ ID NO.:6

<400> SEQUENCE: 33

Asp Ile Val Met Thr Gln Xaa Xaa Xaa Ser Xaa Pro Val Thr Pro Gly
1               5                   10                  15

Glu Xaa Xaa Ser Ile Ser Cys Arg Ser Thr Lys Ser Leu Leu His Ser
            20                  25                  30

Asn Gly Asn Thr Tyr Leu Tyr Trp Xaa Leu Gln Xaa Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Xaa Phe Thr Leu Xaa Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Xaa Glu Ile Lys
            100                 105                 110

<210> SEQ ID NO 34
<211> LENGTH: 112
<212> TYPE: PRT
<213> ORGANISM: Artificial Sequence
<220> FEATURE:
<223> OTHER INFORMATION: Generic 25E9 light chain variable domain
      (consensus 2)
<220> FEATURE:
<221> NAME/KEY: MISC_FEATURE
<222> LOCATION: (7)..(7)
<223> OTHER INFORMATION: Xaa may be a conservative amino acid
      substitution in comparison with SEQ ID NO.:6
<220> FEATURE:
<221> NAME/KEY: MISC_FEATURE
<222> LOCATION: (8)..(8)
<223> OTHER INFORMATION: Xaa may be a semi-conservative amino acid
      substitution in comparison with SEQ ID NO.:6
<220> FEATURE:
<221> NAME/KEY: MISC_FEATURE
<222> LOCATION: (9)..(9)
<223> OTHER INFORMATION: Xaa may be P or L
<220> FEATURE:
```

<220> FEATURE:
<221> NAME/KEY: MISC_FEATURE
<222> LOCATION: (11)..(11)
<223> OTHER INFORMATION: Xaa may be a conservative amino acid
      substitution in comparison with SEQ ID NO.:6
<220> FEATURE:
<221> NAME/KEY: MISC_FEATURE
<222> LOCATION: (18)..(18)
<223> OTHER INFORMATION: Xaa may be a semi-conservative amino acid
      substitution in comparison with SEQ ID NO.:6
<220> FEATURE:
<221> NAME/KEY: MISC_FEATURE
<222> LOCATION: (19)..(19)
<223> OTHER INFORMATION: Xaa may be a semi-conservative amino acid
      substitution in comparison with SEQ ID NO.:6
<220> FEATURE:
<221> NAME/KEY: MISC_FEATURE
<222> LOCATION: (41)..(41)
<223> OTHER INFORMATION: Xaa may be a conservative amino acid
      substitution in comparison with SEQ ID NO.:6
<220> FEATURE:
<221> NAME/KEY: MISC_FEATURE
<222> LOCATION: (44)..(44)
<223> OTHER INFORMATION: Xaa may be a conservative amino acid
      substitution in comparison with SEQ ID NO.:6
<220> FEATURE:
<221> NAME/KEY: MISC_FEATURE
<222> LOCATION: (75)..(75)
<223> OTHER INFORMATION: Xaa may be A or D
<220> FEATURE:
<221> NAME/KEY: MISC_FEATURE
<222> LOCATION: (79)..(79)
<223> OTHER INFORMATION: Xaa may be a conservative amino acid
      substitution in comparison with SEQ ID NO.:6
<220> FEATURE:
<221> NAME/KEY: MISC_FEATURE
<222> LOCATION: (109)..(109)
<223> OTHER INFORMATION: Xaa may be a conservative amino acid
      substitution in comparison with SEQ ID NO.:6

<400> SEQUENCE: 34

Asp Ile Val Met Thr Gln Xaa Xaa Xaa Ser Xaa Pro Val Thr Pro Gly
1               5                   10                  15

Glu Xaa Xaa Ser Ile Ser Cys Arg Ser Thr Lys Ser Leu Leu His Ser
            20                  25                  30

Asn Gly Asn Thr Tyr Leu Tyr Trp Xaa Leu Gln Xaa Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Xaa Phe Thr Leu Xaa Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Xaa Glu Ile Lys
            100                 105                 110

<210> SEQ ID NO 35
<211> LENGTH: 112
<212> TYPE: PRT
<213> ORGANISM: Artificial Sequence
<220> FEATURE:
<223> OTHER INFORMATION: Generic 25E9 light chain variable domain
      (consensus 3)
<220> FEATURE:
<221> NAME/KEY: MISC_FEATURE
<222> LOCATION: (7)..(7)
<223> OTHER INFORMATION: Xaa may be A or S
<220> FEATURE:
<221> NAME/KEY: MISC_FEATURE
<222> LOCATION: (8)..(8)
<223> OTHER INFORMATION: Xaa may be A or P
<220> FEATURE:

```
<221> NAME/KEY: MISC_FEATURE
<222> LOCATION: (9)..(9)
<223> OTHER INFORMATION: Xaa may be P or L
<220> FEATURE:
<221> NAME/KEY: MISC_FEATURE
<222> LOCATION: (11)..(11)
<223> OTHER INFORMATION: Xaa may be a hydrophobic amino acid
<220> FEATURE:
<221> NAME/KEY: MISC_FEATURE
<222> LOCATION: (18)..(18)
<223> OTHER INFORMATION: Xaa may be S or P
<220> FEATURE:
<221> NAME/KEY: MISC_FEATURE
<222> LOCATION: (19)..(19)
<223> OTHER INFORMATION: Xaa may be a hydrophobic amino acid
<220> FEATURE:
<221> NAME/KEY: MISC_FEATURE
<222> LOCATION: (41)..(41)
<223> OTHER INFORMATION: Xaa may be an aromatic amino acid
<220> FEATURE:
<221> NAME/KEY: MISC_FEATURE
<222> LOCATION: (44)..(44)
<223> OTHER INFORMATION: Xaa may be a basic amino acid
<220> FEATURE:
<221> NAME/KEY: MISC_FEATURE
<222> LOCATION: (75)..(75)
<223> OTHER INFORMATION: Xaa may be A or D
<220> FEATURE:
<221> NAME/KEY: MISC_FEATURE
<222> LOCATION: (79)..(79)
<223> OTHER INFORMATION: Xaa may be a basic amino acid
<220> FEATURE:
<221> NAME/KEY: MISC_FEATURE
<222> LOCATION: (109)..(109)
<223> OTHER INFORMATION: Xaa may be a hydrophobic amino acid

<400> SEQUENCE: 35

Asp Ile Val Met Thr Gln Xaa Xaa Xaa Ser Xaa Pro Val Thr Pro Gly
1               5                   10                  15

Glu Xaa Xaa Ser Ile Ser Cys Arg Ser Thr Lys Ser Leu Leu His Ser
            20                  25                  30

Asn Gly Asn Thr Tyr Leu Tyr Trp Xaa Leu Gln Xaa Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Xaa Phe Thr Leu Xaa Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Xaa Glu Ile Lys
            100                 105                 110

<210> SEQ ID NO 36
<211> LENGTH: 123
<212> TYPE: PRT
<213> ORGANISM: Artificial Sequence
<220> FEATURE:
<223> OTHER INFORMATION: Generic 25E9 heavy chain variable domain
      (consensus 1)
<220> FEATURE:
<221> NAME/KEY: MISC_FEATURE
<222> LOCATION: (9)..(9)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (11)..(11)
<223> OTHER INFORMATION: Xaa may be an amino acid substitution in
      comparison with SEQ ID NO.:12
<220> FEATURE:
<221> NAME/KEY: MISC_FEATURE
```

```
<222> LOCATION: (12)..(12)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (13)..(13)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (16)..(16)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (19)..(19)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (20)..(20)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (38)..(38)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (40)..(40)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (42)..(42)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (43)..(43)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (48)..(48)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (67)..(67)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (68)..(68)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (70)..(70)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (74)..(74)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (76)..(76)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (77)..(77)
<223> OTHER INFORMATION: Xaa may be an amino acid substitution in
      comparison with SEQ ID NO.:12
<220> FEATURE:
```

```
<221> NAME/KEY: MISC_FEATURE
<222> LOCATION: (87)..(87)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (91)..(91)
<223> OTHER INFORMATION: Xaa may be an amino acid substitution in
      comparison with SEQ ID NO.:12
<220> FEATURE:
<221> NAME/KEY: MISC_FEATURE
<222> LOCATION: (123)..(123)
<223> OTHER INFORMATION: Xaa may be an amino acid substitution in
      comparison with SEQ ID NO.:12

<400> SEQUENCE: 36

Glu Ile Gln Leu Gln Gln Ser Gly Xaa Glu Xaa Xaa Xaa Pro Gly Xaa
1               5                   10                  15

Ser Val Xaa Xaa Ser Cys Lys Ala Ser Gly Tyr Thr Phe Thr Asp Tyr
            20                  25                  30

Asp Met His Trp Val Xaa Gln Xaa Pro Xaa Xaa Gly Leu Glu Trp Xaa
            35                  40                  45

Gly Thr Ile Asp Pro Glu Thr Gly Gly Thr Ala Tyr Asn Gln Lys Phe
        50                  55                  60

Lys Gly Xaa Xaa Thr Xaa Thr Ala Asp Xaa Ser Xaa Xaa Thr Ala Tyr
65                  70                  75                  80

Met Glu Leu Ser Ser Leu Xaa Ser Glu Asp Xaa Ala Val Tyr Tyr Cys
                85                  90                  95

Thr Ser Phe Tyr Tyr Thr Tyr Ser Asn Tyr Asp Val Gly Phe Ala Tyr
                100                 105                 110

Trp Gly Gln Gly Thr Leu Val Thr Val Ser Xaa
            115                 120

<210> SEQ ID NO 37
<211> LENGTH: 123
<212> TYPE: PRT
<213> ORGANISM: Artificial Sequence
<220> FEATURE:
<223> OTHER INFORMATION: Generic 25E9 heavy chain variable domain
      (consensus 2)
<220> FEATURE:
<221> NAME/KEY: MISC_FEATURE
<222> LOCATION: (9)..(9)
<223> OTHER INFORMATION: Xaa may be a semi-conservative amino acid
      substitution in comparison with SEQ ID NO.:12
<220> FEATURE:
<221> NAME/KEY: MISC_FEATURE
<222> LOCATION: (11)..(11)
<223> OTHER INFORMATION: Xaa may be a conservative amino acid
      substitution in comparison with SEQ ID NO.:12
<220> FEATURE:
<221> NAME/KEY: MISC_FEATURE
<222> LOCATION: (12)..(12)
<223> OTHER INFORMATION: Xaa may be V or K
<220> FEATURE:
<221> NAME/KEY: MISC_FEATURE
<222> LOCATION: (13)..(13)
<223> OTHER INFORMATION: Xaa may be a conservative amino acid
      substitution in comparison with SEQ ID NO.:12
<220> FEATURE:
<221> NAME/KEY: MISC_FEATURE
<222> LOCATION: (16)..(16)
<223> OTHER INFORMATION: Xaa may be a conservative amino acid
      substitution in comparison with SEQ ID NO.:12
<220> FEATURE:
<221> NAME/KEY: MISC_FEATURE
<222> LOCATION: (19)..(19)
<223> OTHER INFORMATION: Xaa may be a semi-conservative amino acid
      substitution in comparison with SEQ ID NO.:12
<220> FEATURE:
```

```
<221> NAME/KEY: MISC_FEATURE
<222> LOCATION: (20)..(20)
<223> OTHER INFORMATION: Xaa may be a conservative amino acid
      substitution in comparison with SEQ ID NO.:12
<220> FEATURE:
<221> NAME/KEY: MISC_FEATURE
<222> LOCATION: (38)..(38)
<223> OTHER INFORMATION: Xaa may be a conservative amino acid
      substitution in comparison with SEQ ID NO.:12
<220> FEATURE:
<221> NAME/KEY: MISC_FEATURE
<222> LOCATION: (40)..(40)
<223> OTHER INFORMATION: Xaa may be a conservative amino acid
      substitution in comparison with SEQ ID NO.:12
<220> FEATURE:
<221> NAME/KEY: MISC_FEATURE
<222> LOCATION: (42)..(42)
<223> OTHER INFORMATION: Xaa may be V or G
<220> FEATURE:
<221> NAME/KEY: MISC_FEATURE
<222> LOCATION: (43)..(43)
<223> OTHER INFORMATION: Xaa may be a conservative amino acid
      substitution in comparison with SEQ ID NO.:12
<220> FEATURE:
<221> NAME/KEY: MISC_FEATURE
<222> LOCATION: (48)..(48)
<223> OTHER INFORMATION: Xaa may be a conservative amino acid
      substitution in comparison with SEQ ID NO.:12
<220> FEATURE:
<221> NAME/KEY: MISC_FEATURE
<222> LOCATION: (67)..(67)
<223> OTHER INFORMATION: Xaa may be a conservative amino acid
      substitution in comparison with SEQ ID NO.:12
<220> FEATURE:
<221> NAME/KEY: MISC_FEATURE
<222> LOCATION: (68)..(68)
<223> OTHER INFORMATION: Xaa may be a semi-conservative amino acid
      substitution in comparison with SEQ ID NO.:12
<220> FEATURE:
<221> NAME/KEY: MISC_FEATURE
<222> LOCATION: (70)..(70)
<223> OTHER INFORMATION: Xaa may be a conservative amino acid
      substitution in comparison with SEQ ID NO.:12
<220> FEATURE:
<221> NAME/KEY: MISC_FEATURE
<222> LOCATION: (74)..(74)
<223> OTHER INFORMATION: Xaa may be a conservative amino acid
      substitution in comparison with SEQ ID NO.:12
<220> FEATURE:
<221> NAME/KEY: MISC_FEATURE
<222> LOCATION: (76)..(76)
<223> OTHER INFORMATION: Xaa may be a conservative amino acid
      substitution in comparison with SEQ ID NO.:12
<220> FEATURE:
<221> NAME/KEY: MISC_FEATURE
<222> LOCATION: (77)..(77)
<223> OTHER INFORMATION: Xaa may be a conservative amino acid
      substitution in comparison with SEQ ID NO.:12
<220> FEATURE:
<221> NAME/KEY: MISC_FEATURE
<222> LOCATION: (87)..(87)
<223> OTHER INFORMATION: Xaa may be T or R
<220> FEATURE:
<221> NAME/KEY: MISC_FEATURE
<222> LOCATION: (91)..(91)
<223> OTHER INFORMATION: Xaa may be a conservative amino acid
      substitution in comparison with SEQ ID NO.:12
<220> FEATURE:
<221> NAME/KEY: MISC_FEATURE
<222> LOCATION: (123)..(123)
<223> OTHER INFORMATION: Xaa may be a conservative amino acid
      substitution in comparison with SEQ ID NO.:12

<400> SEQUENCE: 37

Glu Ile Gln Leu Gln Gln Ser Gly Xaa Glu Xaa Xaa Xaa Pro Gly Xaa
1               5                   10                  15
```

```
Ser Val Xaa Xaa Ser Cys Lys Ala Ser Gly Tyr Thr Phe Thr Asp Tyr
            20                  25                  30

Asp Met His Trp Val Xaa Gln Xaa Pro Xaa Xaa Gly Leu Glu Trp Xaa
        35                  40                  45

Gly Thr Ile Asp Pro Glu Thr Gly Thr Ala Tyr Asn Gln Lys Phe
    50                  55                  60

Lys Gly Xaa Xaa Thr Xaa Thr Ala Asp Xaa Ser Xaa Xaa Thr Ala Tyr
65                  70                  75                  80

Met Glu Leu Ser Ser Leu Xaa Ser Glu Asp Xaa Ala Val Tyr Tyr Cys
                85                  90                  95

Thr Ser Phe Tyr Tyr Thr Tyr Ser Asn Tyr Asp Val Gly Phe Ala Tyr
            100                 105                 110

Trp Gly Gln Gly Thr Leu Val Thr Val Ser Xaa
        115                 120
```

<210> SEQ ID NO 38
<211> LENGTH: 123
<212> TYPE: PRT
<213> ORGANISM: Artificial Sequence
<220> FEATURE:
<223> OTHER INFORMATION: Generic 25E9 heavy chain variable domain
      (consensus 3)
<220> FEATURE:
<221> NAME/KEY: MISC_FEATURE
<222> LOCATION: (9)..(9)
<223> OTHER INFORMATION: Xaa may be a hydrophobic amino acid
<220> FEATURE:
<221> NAME/KEY: MISC_FEATURE
<222> LOCATION: (11)..(11)
<223> OTHER INFORMATION: Xaa may be a hydrophobic amino acid
<220> FEATURE:
<221> NAME/KEY: MISC_FEATURE
<222> LOCATION: (12)..(12)
<223> OTHER INFORMATION: Xaa may be V or K
<220> FEATURE:
<221> NAME/KEY: MISC_FEATURE
<222> LOCATION: (13)..(13)
<223> OTHER INFORMATION: Xaa may be a basic amino acid
<220> FEATURE:
<221> NAME/KEY: MISC_FEATURE
<222> LOCATION: (16)..(16)
<223> OTHER INFORMATION: Xaa may be A or S
<220> FEATURE:
<221> NAME/KEY: MISC_FEATURE
<222> LOCATION: (19)..(19)
<223> OTHER INFORMATION: Xaa may be T or K
<220> FEATURE:
<221> NAME/KEY: MISC_FEATURE
<222> LOCATION: (20)..(20)
<223> OTHER INFORMATION: Xaa may be a hydrophobic amino acid
<220> FEATURE:
<221> NAME/KEY: MISC_FEATURE
<222> LOCATION: (38)..(38)
<223> OTHER INFORMATION: Xaa may be a basic amino acid
<220> FEATURE:
<221> NAME/KEY: MISC_FEATURE
<222> LOCATION: (40)..(40)
<223> OTHER INFORMATION: Xaa may be T or A
<220> FEATURE:
<221> NAME/KEY: MISC_FEATURE
<222> LOCATION: (42)..(42)
<223> OTHER INFORMATION: Xaa may be V or G
<220> FEATURE:
<221> NAME/KEY: MISC_FEATURE
<222> LOCATION: (43)..(43)
<223> OTHER INFORMATION: Xaa may be a basic amino acid
<220> FEATURE:
<221> NAME/KEY: MISC_FEATURE
<222> LOCATION: (48)..(48)
<223> OTHER INFORMATION: Xaa may be a hydrophobic amino acid
<220> FEATURE:
<221> NAME/KEY: MISC_FEATURE

```
<222> LOCATION: (67)..(67)
<223> OTHER INFORMATION: Xaa may be a basic amino acid
<220> FEATURE:
<221> NAME/KEY: MISC_FEATURE
<222> LOCATION: (68)..(68)
<223> OTHER INFORMATION: Xaa may be a hydrophobic amino acid
<220> FEATURE:
<221> NAME/KEY: MISC_FEATURE
<222> LOCATION: (70)..(70)
<223> OTHER INFORMATION: Xaa may be a hydrophobic amino acid
<220> FEATURE:
<221> NAME/KEY: MISC_FEATURE
<222> LOCATION: (74)..(74)
<223> OTHER INFORMATION: Xaa may be a basic amino acid
<220> FEATURE:
<221> NAME/KEY: MISC_FEATURE
<222> LOCATION: (76)..(76)
<223> OTHER INFORMATION: Xaa may be a neutral hydrophilic amino acid
<220> FEATURE:
<221> NAME/KEY: MISC_FEATURE
<222> LOCATION: (77)..(77)
<223> OTHER INFORMATION: Xaa may be a neutral hydrophilic amino acid
<220> FEATURE:
<221> NAME/KEY: MISC_FEATURE
<222> LOCATION: (87)..(87)
<223> OTHER INFORMATION: Xaa may be T or R
<220> FEATURE:
<221> NAME/KEY: MISC_FEATURE
<222> LOCATION: (91)..(91)
<223> OTHER INFORMATION: Xaa may be a neutral hydrophilic amino acid
<220> FEATURE:
<221> NAME/KEY: MISC_FEATURE
<222> LOCATION: (123)..(123)
<223> OTHER INFORMATION: Xaa may be A or S

<400> SEQUENCE: 38

Glu Ile Gln Leu Gln Gln Ser Gly Xaa Glu Xaa Xaa Xaa Pro Gly Xaa
1               5                   10                  15

Ser Val Xaa Xaa Ser Cys Lys Ala Ser Gly Tyr Thr Phe Thr Asp Tyr
            20                  25                  30

Asp Met His Trp Val Xaa Gln Xaa Pro Xaa Xaa Gly Leu Glu Trp Xaa
        35                  40                  45

Gly Thr Ile Asp Pro Glu Thr Gly Gly Thr Ala Tyr Asn Gln Lys Phe
    50                  55                  60

Lys Gly Xaa Xaa Thr Xaa Thr Ala Asp Xaa Ser Xaa Xaa Thr Ala Tyr
65                  70                  75                  80

Met Glu Leu Ser Ser Leu Xaa Ser Glu Asp Xaa Ala Val Tyr Tyr Cys
                85                  90                  95

Thr Ser Phe Tyr Tyr Thr Tyr Ser Asn Tyr Asp Val Gly Phe Ala Tyr
                100                 105                 110

Trp Gly Gln Gly Thr Leu Val Thr Val Ser Xaa
                115                 120

<210> SEQ ID NO 39
<211> LENGTH: 112
<212> TYPE: PRT
<213> ORGANISM: Artificial Sequence
<220> FEATURE:
<223> OTHER INFORMATION: Generic 25D8 light chain variable domain
      (consensus 1)
<220> FEATURE:
<221> NAME/KEY: MISC_FEATURE
<222> LOCATION: (7)..(7)
<223> OTHER INFORMATION: Xaa may be an amino acid substitution in
      comparison with SEQ ID NO.:22
<220> FEATURE:
<221> NAME/KEY: MISC_FEATURE
<222> LOCATION: (8)..(8)
<223> OTHER INFORMATION: Xaa may be an amino acid substitution in
      comparison with SEQ ID NO.:22
```

```
<220> FEATURE:
<221> NAME/KEY: MISC_FEATURE
<222> LOCATION: (9)..(9)
<223> OTHER INFORMATION: Xaa may be an amino acid substitution in
      comparison with SEQ ID NO.:22
<220> FEATURE:
<221> NAME/KEY: MISC_FEATURE
<222> LOCATION: (11)..(11)
<223> OTHER INFORMATION: Xaa may be an amino acid substitution in
      comparison with SEQ ID NO.:22
<220> FEATURE:
<221> NAME/KEY: MISC_FEATURE
<222> LOCATION: (15)..(15)
<223> OTHER INFORMATION: Xaa may be an amino acid substitution in
      comparison with SEQ ID NO.:22
<220> FEATURE:
<221> NAME/KEY: MISC_FEATURE
<222> LOCATION: (17)..(17)
<223> OTHER INFORMATION: Xaa may be an amino acid substitution in
      comparison with SEQ ID NO.:22
<220> FEATURE:
<221> NAME/KEY: MISC_FEATURE
<222> LOCATION: (18)..(18)
<223> OTHER INFORMATION: Xaa may be an amino acid substitution in
      comparison with SEQ ID NO.:22
<220> FEATURE:
<221> NAME/KEY: MISC_FEATURE
<222> LOCATION: (69)..(69)
<223> OTHER INFORMATION: Xaa may be an amino acid substitution in
      comparison with SEQ ID NO.:22
<220> FEATURE:
<221> NAME/KEY: MISC_FEATURE
<222> LOCATION: (79)..(79)
<223> OTHER INFORMATION: Xaa may be an amino acid substitution in
      comparison with SEQ ID NO.:22
<220> FEATURE:
<221> NAME/KEY: MISC_FEATURE
<222> LOCATION: (109)..(109)
<223> OTHER INFORMATION: Xaa may be an amino acid substitution in
      comparison with SEQ ID NO.:22

<400> SEQUENCE: 39

Asp Ile Val Met Thr Gln Xaa Xaa Xaa Ser Xaa Pro Val Thr Xaa Gly
1               5                   10                  15

Xaa Xaa Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Xaa Ser Gly Ser Gly Thr Asp Phe Thr Leu Xaa Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Xaa Glu Ile Lys
            100                 105                 110

<210> SEQ ID NO 40
<211> LENGTH: 112
<212> TYPE: PRT
<213> ORGANISM: Artificial Sequence
<220> FEATURE:
<223> OTHER INFORMATION: Generic 25D8 light chain variable domain
      (consensus 2)
<220> FEATURE:
<221> NAME/KEY: MISC_FEATURE
<222> LOCATION: (7)..(7)
<223> OTHER INFORMATION: Xaa may be a conservartive amino acid
      substitution in comparison with SEQ ID NO.:22
<220> FEATURE:
<221> NAME/KEY: MISC_FEATURE
```

```
<222> LOCATION: (8)..(8)
<223> OTHER INFORMATION: Xaa may be a semi-conservartive amino acid
      substitution in comparison with SEQ ID NO.:22
<220> FEATURE:
<221> NAME/KEY: MISC_FEATURE
<222> LOCATION: (9)..(9)
<223> OTHER INFORMATION: Xaa may be a conservartive amino acid
      substitution in comparison with SEQ ID NO.:22
<220> FEATURE:
<221> NAME/KEY: MISC_FEATURE
<222> LOCATION: (11)..(11)
<223> OTHER INFORMATION: Xaa may be N or L
<220> FEATURE:
<221> NAME/KEY: MISC_FEATURE
<222> LOCATION: (15)..(15)
<223> OTHER INFORMATION: Xaa may be L or P
<220> FEATURE:
<221> NAME/KEY: MISC_FEATURE
<222> LOCATION: (17)..(17)
<223> OTHER INFORMATION: Xaa may be T or E
<220> FEATURE:
<221> NAME/KEY: MISC_FEATURE
<222> LOCATION: (18)..(18)
<223> OTHER INFORMATION: Xaa may be a semi-conservartive amino acid
      substitution in comparison with SEQ ID NO.:22
<220> FEATURE:
<221> NAME/KEY: MISC_FEATURE
<222> LOCATION: (69)..(69)
<223> OTHER INFORMATION: Xaa may be a semi-conservartive amino acid
      substitution in comparison with SEQ ID NO.:22
<220> FEATURE:
<221> NAME/KEY: MISC_FEATURE
<222> LOCATION: (79)..(79)
<223> OTHER INFORMATION: Xaa may be a conservartive amino acid
      substitution in comparison with SEQ ID NO.:22
<220> FEATURE:
<221> NAME/KEY: MISC_FEATURE
<222> LOCATION: (109)..(109)
<223> OTHER INFORMATION: Xaa may be a conservartive amino acid
      substitution in comparison with SEQ ID NO.:22

<400> SEQUENCE: 40

Asp Ile Val Met Thr Gln Xaa Xaa Xaa Ser Xaa Pro Val Thr Xaa Gly
1               5                   10                  15

Xaa Xaa Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Xaa Ser Gly Ser Gly Thr Asp Phe Thr Leu Xaa Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Xaa Glu Ile Lys
            100                 105                 110

<210> SEQ ID NO 41
<211> LENGTH: 112
<212> TYPE: PRT
<213> ORGANISM: Artificial Sequence
<220> FEATURE:
<223> OTHER INFORMATION: Generic 25D8 light chain variable domain
      (consensus 3)
<220> FEATURE:
<221> NAME/KEY: MISC_FEATURE
<222> LOCATION: (7)..(7)
<223> OTHER INFORMATION: Xaa may be A or T
<220> FEATURE:
<221> NAME/KEY: MISC_FEATURE
<222> LOCATION: (8)..(8)
```

```
<223> OTHER INFORMATION: Xaa may be A or P
<220> FEATURE:
<221> NAME/KEY: MISC_FEATURE
<222> LOCATION: (9)..(9)
<223> OTHER INFORMATION: Xaa may be F or L
<220> FEATURE:
<221> NAME/KEY: MISC_FEATURE
<222> LOCATION: (11)..(11)
<223> OTHER INFORMATION: Xaa may be N or L
<220> FEATURE:
<221> NAME/KEY: MISC_FEATURE
<222> LOCATION: (15)..(15)
<223> OTHER INFORMATION: Xaa may be L or P
<220> FEATURE:
<221> NAME/KEY: MISC_FEATURE
<222> LOCATION: (17)..(17)
<223> OTHER INFORMATION: Xaa may be T or E
<220> FEATURE:
<221> NAME/KEY: MISC_FEATURE
<222> LOCATION: (18)..(18)
<223> OTHER INFORMATION: Xaa may be S or P
<220> FEATURE:
<221> NAME/KEY: MISC_FEATURE
<222> LOCATION: (69)..(69)
<223> OTHER INFORMATION: Xaa may be S or G
<220> FEATURE:
<221> NAME/KEY: MISC_FEATURE
<222> LOCATION: (79)..(79)
<223> OTHER INFORMATION: Xaa may be a basic amino acid
<220> FEATURE:
<221> NAME/KEY: MISC_FEATURE
<222> LOCATION: (109)..(109)
<223> OTHER INFORMATION: Xaa may be a hydrophobic amino acid

<400> SEQUENCE: 41

Asp Ile Val Met Thr Gln Xaa Xaa Xaa Ser Xaa Pro Val Thr Xaa Gly
1               5                   10                  15

Xaa Xaa Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Xaa Ser Gly Ser Gly Thr Asp Phe Thr Leu Xaa Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Xaa Glu Ile Lys
            100                 105                 110

<210> SEQ ID NO 42
<211> LENGTH: 118
<212> TYPE: PRT
<213> ORGANISM: Artificial Sequence
<220> FEATURE:
<223> OTHER INFORMATION: Generic 25D8 heavy chain variable domain
      (consensus 1)
<220> FEATURE:
<221> NAME/KEY: MISC_FEATURE
<222> LOCATION: (4)..(4)
<223> OTHER INFORMATION: Xaa may be an amino acid substitution in
      comparison with SEQ ID NO.:26
<220> FEATURE:
<221> NAME/KEY: MISC_FEATURE
<222> LOCATION: (7)..(7)
<223> OTHER INFORMATION: Xaa may be an amino acid substitution in
      comparison with SEQ ID NO.:26
<220> FEATURE:
<221> NAME/KEY: MISC_FEATURE
<222> LOCATION: (11)..(11)
<223> OTHER INFORMATION: Xaa may be an amino acid substitution in
```

```
      comparison with SEQ ID NO.:26
<220> FEATURE:
<221> NAME/KEY: MISC_FEATURE
<222> LOCATION: (12)..(12)
<223> OTHER INFORMATION: Xaa may be an amino acid substitution in
      comparison with SEQ ID NO.:26
<220> FEATURE:
<221> NAME/KEY: MISC_FEATURE
<222> LOCATION: (16)..(16)
<223> OTHER INFORMATION: Xaa may be an amino acid substitution in
      comparison with SEQ ID NO.:26
<220> FEATURE:
<221> NAME/KEY: MISC_FEATURE
<222> LOCATION: (20)..(20)
<223> OTHER INFORMATION: Xaa may be an amino acid substitution in
      comparison with SEQ ID NO.:26
<220> FEATURE:
<221> NAME/KEY: MISC_FEATURE
<222> LOCATION: (38)..(38)
<223> OTHER INFORMATION: Xaa may be an amino acid substitution in
      comparison with SEQ ID NO.:26
<220> FEATURE:
<221> NAME/KEY: MISC_FEATURE
<222> LOCATION: (40)..(40)
<223> OTHER INFORMATION: Xaa may be an amino acid substitution in
      comparison with SEQ ID NO.:26
<220> FEATURE:
<221> NAME/KEY: MISC_FEATURE
<222> LOCATION: (48)..(48)
<223> OTHER INFORMATION: Xaa may be an amino acid substitution in
      comparison with SEQ ID NO.:26
<220> FEATURE:
<221> NAME/KEY: MISC_FEATURE
<222> LOCATION: (67)..(67)
<223> OTHER INFORMATION: Xaa may be an amino acid substitution in
      comparison with SEQ ID NO.:26
<220> FEATURE:
<221> NAME/KEY: MISC_FEATURE
<222> LOCATION: (68)..(68)
<223> OTHER INFORMATION: Xaa may be an amino acid substitution in
      comparison with SEQ ID NO.:26
<220> FEATURE:
<221> NAME/KEY: MISC_FEATURE
<222> LOCATION: (70)..(70)
<223> OTHER INFORMATION: Xaa may be an amino acid substitution in
      comparison with SEQ ID NO.:26
<220> FEATURE:
<221> NAME/KEY: MISC_FEATURE
<222> LOCATION: (72)..(72)
<223> OTHER INFORMATION: Xaa may be an amino acid substitution in
      comparison with SEQ ID NO.:26
<220> FEATURE:
<221> NAME/KEY: MISC_FEATURE
<222> LOCATION: (76)..(76)
<223> OTHER INFORMATION: Xaa may be an amino acid substitution in
      comparison with SEQ ID NO.:26
<220> FEATURE:
<221> NAME/KEY: MISC_FEATURE
<222> LOCATION: (82)..(82)
<223> OTHER INFORMATION: Xaa may be an amino acid substitution in
      comparison with SEQ ID NO.:26
<220> FEATURE:
<221> NAME/KEY: MISC_FEATURE
<222> LOCATION: (87)..(87)
<223> OTHER INFORMATION: Xaa may be an amino acid substitution in
      comparison with SEQ ID NO.:26
<220> FEATURE:
<221> NAME/KEY: MISC_FEATURE
<222> LOCATION: (91)..(91)
<223> OTHER INFORMATION: Xaa may be an amino acid substitution in
      comparison with SEQ ID NO.:26
<220> FEATURE:
<221> NAME/KEY: MISC_FEATURE
<222> LOCATION: (114)..(114)
<223> OTHER INFORMATION: Xaa may be an amino acid substitution in
      comparison with SEQ ID NO.:26

<400> SEQUENCE: 42
```

```
Gln Val Gln Xaa Gln Gln Xaa Gly Ala Glu Xaa Xaa Lys Pro Gly Xaa
 1               5              10                 15

Ser Val Lys Xaa Ser Cys Lys Ala Ser Gly Tyr Thr Phe Thr Ser Tyr
            20                  25                 30

Trp Met His Trp Val Xaa Gln Xaa Pro Gly Gln Gly Leu Glu Trp Xaa
            35              40                  45

Gly Leu Ile Asn Pro Ser Asn Ala Arg Thr Asn Tyr Asn Glu Lys Phe
        50              55              60

Asn Thr Xaa Xaa Thr Xaa Thr Xaa Asp Lys Ser Xaa Ser Thr Ala Tyr
65              70              75                  80

Met Xaa Leu Ser Ser Leu Xaa Ser Glu Asp Xaa Ala Val Tyr Tyr Cys
            85              90                  95

Ala Arg Gly Gly Asp Gly Asp Tyr Phe Asp Tyr Trp Gly Gln Gly Thr
           100             105             110

Thr Xaa Thr Val Ser Ser
       115
```

<210> SEQ ID NO 43
<211> LENGTH: 118
<212> TYPE: PRT
<213> ORGANISM: Artificial Sequence
<220> FEATURE:
<223> OTHER INFORMATION: Generic 25D8 heavy chain variable domain
      (consensus 2)
<220> FEATURE:
<221> NAME/KEY: MISC_FEATURE
<222> LOCATION: (4)..(4)
<223> OTHER INFORMATION: Xaa may be a conservartive amino acid
      substitution in comparison with SEQ ID NO.:26
<220> FEATURE:
<221> NAME/KEY: MISC_FEATURE
<222> LOCATION: (7)..(7)
<223> OTHER INFORMATION: Xaa may be a semi-conservartive amino acid
      substitution in comparison with SEQ ID NO.:26
<220> FEATURE:
<221> NAME/KEY: MISC_FEATURE
<222> LOCATION: (11)..(11)
<223> OTHER INFORMATION: Xaa may be a conservartive amino acid
      substitution in comparison with SEQ ID NO.:26
<220> FEATURE:
<221> NAME/KEY: MISC_FEATURE
<222> LOCATION: (12)..(12)
<223> OTHER INFORMATION: Xaa may be V or K
<220> FEATURE:
<221> NAME/KEY: MISC_FEATURE
<222> LOCATION: (16)..(16)
<223> OTHER INFORMATION: Xaa may be a conservartive amino acid
      substitution in comparison with SEQ ID NO.:26
<220> FEATURE:
<221> NAME/KEY: MISC_FEATURE
<222> LOCATION: (20)..(20)
<223> OTHER INFORMATION: Xaa may be a conservartive amino acid
      substitution in comparison with SEQ ID NO.:26
<220> FEATURE:
<221> NAME/KEY: MISC_FEATURE
<222> LOCATION: (38)..(38)
<223> OTHER INFORMATION: Xaa may be a conservartive amino acid
      substitution in comparison with SEQ ID NO.:26
<220> FEATURE:
<221> NAME/KEY: MISC_FEATURE
<222> LOCATION: (40)..(40)
<223> OTHER INFORMATION: Xaa may be R or A
<220> FEATURE:
<221> NAME/KEY: MISC_FEATURE
<222> LOCATION: (48)..(48)
<223> OTHER INFORMATION: Xaa may be a conservartive amino acid
      substitution in comparison with SEQ ID NO.:26
<220> FEATURE:
<221> NAME/KEY: MISC_FEATURE
<222> LOCATION: (67)..(67)
<223> OTHER INFORMATION: Xaa may be a conservartive amino acid

```
       substitution in comparison with SEQ ID NO.:26
<220> FEATURE:
<221> NAME/KEY: MISC_FEATURE
<222> LOCATION: (68)..(68)
<223> OTHER INFORMATION: Xaa may be a semi-conservartive amino acid
       substitution in comparison with SEQ ID NO.:26
<220> FEATURE:
<221> NAME/KEY: MISC_FEATURE
<222> LOCATION: (70)..(70)
<223> OTHER INFORMATION: Xaa may be a conservartive amino acid
       substitution in comparison with SEQ ID NO.:26
<220> FEATURE:
<221> NAME/KEY: MISC_FEATURE
<222> LOCATION: (72)..(72)
<223> OTHER INFORMATION: Xaa may be a semi-conservartive amino acid
       substitution in comparison with SEQ ID NO.:26
<220> FEATURE:
<221> NAME/KEY: MISC_FEATURE
<222> LOCATION: (76)..(76)
<223> OTHER INFORMATION: Xaa may be a conservartive amino acid
       substitution in comparison with SEQ ID NO.:26
<220> FEATURE:
<221> NAME/KEY: MISC_FEATURE
<222> LOCATION: (82)..(82)
<223> OTHER INFORMATION: Xaa may be a conservartive amino acid
       substitution in comparison with SEQ ID NO.:26
<220> FEATURE:
<221> NAME/KEY: MISC_FEATURE
<222> LOCATION: (87)..(87)
<223> OTHER INFORMATION: Xaa may be T or R
<220> FEATURE:
<221> NAME/KEY: MISC_FEATURE
<222> LOCATION: (91)..(91)
<223> OTHER INFORMATION: Xaa may be a conservartive amino acid
       substitution in comparison with SEQ ID NO.:26
<220> FEATURE:
<221> NAME/KEY: MISC_FEATURE
<222> LOCATION: (114)..(114)
<223> OTHER INFORMATION: Xaa may be a conservartive amino acid
       substitution in comparison with SEQ ID NO.:26

<400> SEQUENCE: 43

Gln Val Gln Xaa Gln Gln Xaa Gly Ala Glu Xaa Xaa Lys Pro Gly Xaa
1               5                   10                  15

Ser Val Lys Xaa Ser Cys Lys Ala Ser Gly Tyr Thr Phe Thr Ser Tyr
            20                  25                  30

Trp Met His Trp Val Xaa Gln Xaa Pro Gly Gln Gly Leu Glu Trp Xaa
        35                  40                  45

Gly Leu Ile Asn Pro Ser Asn Ala Arg Thr Asn Tyr Asn Glu Lys Phe
    50                  55                  60

Asn Thr Xaa Xaa Thr Xaa Thr Xaa Asp Lys Ser Xaa Ser Thr Ala Tyr
65                  70                  75                  80

Met Xaa Leu Ser Ser Leu Xaa Ser Glu Asp Xaa Ala Val Tyr Tyr Cys
                85                  90                  95

Ala Arg Gly Gly Asp Gly Asp Tyr Phe Asp Tyr Trp Gly Gln Gly Thr
            100                 105                 110

Thr Xaa Thr Val Ser Ser
        115

<210> SEQ ID NO 44
<211> LENGTH: 118
<212> TYPE: PRT
<213> ORGANISM: Artificial Sequence
<220> FEATURE:
<223> OTHER INFORMATION: Generic 25D8 heavy chain variable domain
       (consensus 3)
<220> FEATURE:
<221> NAME/KEY: MISC_FEATURE
<222> LOCATION: (4)..(4)
<223> OTHER INFORMATION: Xaa may be a hydrophobic amino acid
```

```
<220> FEATURE:
<221> NAME/KEY: MISC_FEATURE
<222> LOCATION: (7)..(7)
<223> OTHER INFORMATION: Xaa may be P or S
<220> FEATURE:
<221> NAME/KEY: MISC_FEATURE
<222> LOCATION: (11)..(11)
<223> OTHER INFORMATION: Xaa may be a hydrophobic amino acid
<220> FEATURE:
<221> NAME/KEY: MISC_FEATURE
<222> LOCATION: (12)..(12)
<223> OTHER INFORMATION: Xaa may be V or K
<220> FEATURE:
<221> NAME/KEY: MISC_FEATURE
<222> LOCATION: (16)..(16)
<223> OTHER INFORMATION: Xaa may be A or S
<220> FEATURE:
<221> NAME/KEY: MISC_FEATURE
<222> LOCATION: (20)..(20)
<223> OTHER INFORMATION: Xaa may be a hydrophobic amino acid
<220> FEATURE:
<221> NAME/KEY: MISC_FEATURE
<222> LOCATION: (38)..(38)
<223> OTHER INFORMATION: Xaa may be a basic amino acid
<220> FEATURE:
<221> NAME/KEY: MISC_FEATURE
<222> LOCATION: (40)..(40)
<223> OTHER INFORMATION: Xaa may be R or A
<220> FEATURE:
<221> NAME/KEY: MISC_FEATURE
<222> LOCATION: (48)..(48)
<223> OTHER INFORMATION: Xaa may be a hydrophobic amino acid
<220> FEATURE:
<221> NAME/KEY: MISC_FEATURE
<222> LOCATION: (67)..(67)
<223> OTHER INFORMATION: Xaa may be a basic amino acid
<220> FEATURE:
<221> NAME/KEY: MISC_FEATURE
<222> LOCATION: (68)..(68)
<223> OTHER INFORMATION: Xaa may be a hydrophobic amino acid
<220> FEATURE:
<221> NAME/KEY: MISC_FEATURE
<222> LOCATION: (70)..(70)
<223> OTHER INFORMATION: Xaa may be a hydrophobic amino acid
<220> FEATURE:
<221> NAME/KEY: MISC_FEATURE
<222> LOCATION: (72)..(72)
<223> OTHER INFORMATION: Xaa may be a hydrophobic amino acid
<220> FEATURE:
<221> NAME/KEY: MISC_FEATURE
<222> LOCATION: (76)..(76)
<223> OTHER INFORMATION: Xaa may be a neutral hydrophilic amino acid
<220> FEATURE:
<221> NAME/KEY: MISC_FEATURE
<222> LOCATION: (82)..(82)
<223> OTHER INFORMATION: Xaa may be Q or E
<220> FEATURE:
<221> NAME/KEY: MISC_FEATURE
<222> LOCATION: (87)..(87)
<223> OTHER INFORMATION: Xaa may be T or R
<220> FEATURE:
<221> NAME/KEY: MISC_FEATURE
<222> LOCATION: (91)..(91)
<223> OTHER INFORMATION: Xaa may be a neutral hydrophilic amino acid
<220> FEATURE:
<221> NAME/KEY: MISC_FEATURE
<222> LOCATION: (114)..(114)
<223> OTHER INFORMATION: Xaa may be a hydrophobic amino acid

<400> SEQUENCE: 44

Gln Val Gln Xaa Gln Gln Xaa Gly Ala Glu Xaa Xaa Lys Pro Gly Xaa
1               5                   10                  15

Ser Val Lys Xaa Ser Cys Lys Ala Ser Gly Tyr Thr Phe Thr Ser Tyr
            20                  25                  30

Trp Met His Trp Val Xaa Gln Xaa Pro Gly Gln Gly Leu Glu Trp Xaa
        35                  40                  45
```

```
Gly Leu Ile Asn Pro Ser Asn Ala Arg Thr Asn Tyr Asn Glu Lys Phe
        50                  55                  60

Asn Thr Xaa Xaa Thr Xaa Thr Xaa Asp Lys Ser Xaa Ser Thr Ala Tyr
 65                  70                  75                  80

Met Xaa Leu Ser Ser Leu Xaa Ser Glu Asp Xaa Ala Val Tyr Tyr Cys
                 85                  90                  95

Ala Arg Gly Gly Asp Gly Asp Tyr Phe Asp Tyr Trp Gly Gln Gly Thr
                100                 105                 110

Thr Xaa Thr Val Ser Ser
        115

<210> SEQ ID NO 45
<211> LENGTH: 467
<212> TYPE: PRT
<213> ORGANISM: Artificial Sequence
<220> FEATURE:
<223> OTHER INFORMATION: Chimeric 25D8 heavy chain (IgG1)

<400> SEQUENCE: 45

Met Asp Trp Thr Trp Arg Ile Leu Phe Leu Val Ala Ala Thr Gly
 1               5                  10                  15

Thr His Ala Gln Val Gln Val Gln Pro Gly Ala Glu Leu Val Lys
                 20                  25                  30

Pro Gly Ala Ser Val Lys Leu Ser Cys Lys Ala Ser Gly Tyr Thr Phe
                 35                  40                  45

Thr Ser Tyr Trp Met His Trp Val Lys Gln Arg Pro Gly Gln Gly Leu
        50                  55                  60

Glu Trp Ile Gly Leu Ile Asn Pro Ser Asn Ala Arg Thr Asn Tyr Asn
 65                  70                  75                  80

Glu Lys Phe Asn Thr Lys Ala Thr Leu Thr Val Asp Lys Ser Ser Ser
                 85                  90                  95

Thr Ala Tyr Met Gln Leu Ser Ser Leu Thr Ser Glu Asp Ser Ala Val
                100                 105                 110

Tyr Tyr Cys Ala Arg Gly Gly Asp Gly Asp Tyr Phe Asp Tyr Trp Gly
            115                 120                 125

Gln Gly Thr Thr Leu Thr Val Ser Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
        210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
            275                 280                 285
```

```
Glu Asp Pro Glu Val Lys Phe Asn Trp Tyr Val Asp Gly Val Glu Val
            290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 46
<211> LENGTH: 467
<212> TYPE: PRT
<213> ORGANISM: Artificial Sequence
<220> FEATURE:
<223> OTHER INFORMATION: Humanized 25D8 heavy chain (IgG1)

<400> SEQUENCE: 46

Met Asp Trp Thr Trp Arg Ile Leu Phe Leu Val Ala Ala Thr Gly
1               5                   10                  15

Thr His Ala Gln Val Gln Leu Gln Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Ser Tyr Trp Met His Trp Val Arg Gln Ala Pro Gly Gln Gly Leu
    50                  55                  60

Glu Trp Met Gly Leu Ile Asn Pro Ser Asn Ala Arg Thr Asn Tyr Asn
65                  70                  75                  80

Glu Lys Phe Asn Thr Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Gly Asp Gly Asp Tyr Phe Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175
```

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
    450                 455                 460

Pro Gly Lys
465

<210> SEQ ID NO 47
<211> LENGTH: 16
<212> TYPE: PRT
<213> ORGANISM: Artificial Sequence
<220> FEATURE:
<223> OTHER INFORMATION: CDR1 of the 25E9 light chain mouse variable
      domain

<400> SEQUENCE: 47

Arg Ser Thr Lys Ser Leu Leu His Ser Asn Gly Asn Thr Tyr Leu Tyr
1               5                   10                  15

<210> SEQ ID NO 48
<211> LENGTH: 7
<212> TYPE: PRT
<213> ORGANISM: Artificial Sequence
<220> FEATURE:
<223> OTHER INFORMATION: CDR2 of the 25E9 light chain mouse variable -continued

```
                                           domain

<400> SEQUENCE: 48

Arg Met Ser Asn Leu Ala Ser
1               5

<210> SEQ ID NO 49
<211> LENGTH: 9
<212> TYPE: PRT
<213> ORGANISM: Artificial Sequence
<220> FEATURE:
<223> OTHER INFORMATION: CDR3 of the 25E9 light chain mouse variable
      domain

<400> SEQUENCE: 49

Met Gln His Leu Glu Tyr Pro Phe Thr
1               5

<210> SEQ ID NO 50
<211> LENGTH: 10
<212> TYPE: PRT
<213> ORGANISM: Artificial Sequence
<220> FEATURE:
<223> OTHER INFORMATION: CDR1 of the 25E9 heavy chain mouse variable
      domain

<400> SEQUENCE: 50

Gly Tyr Thr Phe Thr Asp Tyr Asp Met His
1               5                   10

<210> SEQ ID NO 51
<211> LENGTH: 17
<212> TYPE: PRT
<213> ORGANISM: Artificial Sequence
<220> FEATURE:
<223> OTHER INFORMATION: CDR2 of the 25E9 heavy chain mouse variable
      domain

<400> SEQUENCE: 51

Thr Ile Asp Pro Glu Thr Gly Gly Thr Ala Tyr Asn Gln Lys Phe Lys
1               5                   10                  15
Gly

<210> SEQ ID NO 52
<211> LENGTH: 14
<212> TYPE: PRT
<213> ORGANISM: Artificial Sequence
<220> FEATURE:
<223> OTHER INFORMATION: CDR3 of the 25E9 heavy chain mouse variable
      domain

<400> SEQUENCE: 52

Phe Tyr Tyr Thr Tyr Ser Asn Tyr Asp Val Gly Phe Ala Tyr
1               5                   10

<210> SEQ ID NO 53
<211> LENGTH: 16
<212> TYPE: PRT
<213> ORGANISM: Artificial Sequence
<220> FEATURE:
<223> OTHER INFORMATION: CDR1 of the 25D8 light chain mouse variable
      domain

<400> SEQUENCE: 53

Arg Ser Ser Lys Ser Leu Leu His Ser Asn Gly Ile Thr Tyr Leu Tyr
1               5                   10                  15
```

```
<210> SEQ ID NO 54
<211> LENGTH: 8
<212> TYPE: PRT
<213> ORGANISM: Artificial Sequence
<220> FEATURE:
<223> OTHER INFORMATION: CDR2 of the 25D8 light chain mouse variable
      domain

<400> SEQUENCE: 54

Gln Met Ser Asn Leu Ala Ser Gly
1               5

<210> SEQ ID NO 55
<211> LENGTH: 9
<212> TYPE: PRT
<213> ORGANISM: Artificial Sequence
<220> FEATURE:
<223> OTHER INFORMATION: CDR3 of the 25D8 light chain mouse variable
      domain

<400> SEQUENCE: 55

Ala Gln Asn Leu Glu Leu Pro Tyr Thr
1               5

<210> SEQ ID NO 56
<211> LENGTH: 10
<212> TYPE: PRT
<213> ORGANISM: Artificial Sequence
<220> FEATURE:
<223> OTHER INFORMATION: CDR1 of the 25D8 heavy chain mouse variable
      domain

<400> SEQUENCE: 56

Gly Tyr Thr Phe Thr Ser Tyr Trp Met His
1               5                   10

<210> SEQ ID NO 57
<211> LENGTH: 17
<212> TYPE: PRT
<213> ORGANISM: Artificial Sequence
<220> FEATURE:
<223> OTHER INFORMATION: CDR2 of the 25D8 heavy chain mouse variable
      domain

<400> SEQUENCE: 57

Leu Ile Asn Pro Ser Asn Ala Arg Thr Asn Tyr Asn Glu Lys Phe Asn
1               5                   10                  15

Thr

<210> SEQ ID NO 58
<211> LENGTH: 9
<212> TYPE: PRT
<213> ORGANISM: Artificial Sequence
<220> FEATURE:
<223> OTHER INFORMATION: CDR3 of the 25D8 heavy chain mouse variable
      domain

<400> SEQUENCE: 58

Gly Gly Asp Gly Asp Tyr Phe Asp Tyr
1               5

<210> SEQ ID NO 59
<211> LENGTH: 468
<212> TYPE: PRT
<213> ORGANISM: Artificial Sequence
<220> FEATURE:
<223> OTHER INFORMATION: 25E9 heavy chain (IgG2) humanized variant 2
```

<400> SEQUENCE: 59

```
Met Asp Trp Thr Trp Arg Ile Leu Phe Leu Val Ala Ala Thr Gly
1               5                   10                  15

Thr His Ala Glu Ile Gln Leu Gln Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asp Tyr Asp Met His Trp Val Arg Gln Ala Pro Gly Gln Gly Leu
    50                  55                  60

Glu Trp Ile Gly Thr Ile Asp Pro Glu Thr Gly Gly Thr Ala Tyr Asn
65                  70                  75                  80

Gln Lys Phe Lys Gly Arg Ala Thr Leu Thr Ala Asp Arg Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Ser Phe Tyr Tyr Thr Tyr Ser Asn Tyr Asp Val Gly
        115                 120                 125

Phe Ala Tyr Trp Gly Gln Gly Thr Leu Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
                325                 330                 335

Gly Lys Glu Tyr Lys Cys Lys Val Ser Asn Lys Gly Leu Pro Ala Pro
            340                 345                 350

Ile Glu Lys Thr Ile Ser Lys Thr Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400
```

```
Glu Trp Glu Ser Asn Gly Gln Pro Glu Asn Asn Tyr Lys Thr Thr Pro
            405                 410                 415

Pro Met Leu Asp Ser Asp Gly Ser Phe Phe Leu Tyr Ser Lys Leu Thr
        420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 60
<211> LENGTH: 468
<212> TYPE: PRT
<213> ORGANISM: Artificial Sequence
<220> FEATURE:
<223> OTHER INFORMATION: 25E9 heavy chain (IgG2) humanized variant 3

<400> SEQUENCE: 60

Met Asp Trp Thr Trp Arg Ile Leu Phe Leu Val Ala Ala Thr Gly
1               5                   10                  15

Thr His Ala Glu Ile Gln Leu Gln Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asp Tyr Asp Met His Trp Val Lys Gln Ala Pro Gly Gln Gly Leu
    50                  55                  60

Glu Trp Ile Gly Thr Ile Asp Pro Glu Thr Gly Thr Ala Tyr Asn
65                  70                  75                  80

Gln Lys Phe Lys Gly Lys Ala Thr Leu Thr Ala Asp Arg Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Ser Phe Tyr Tyr Thr Tyr Ser Asn Tyr Asp Val Gly
        115                 120                 125

Phe Ala Tyr Trp Gly Gln Gly Thr Leu Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285
```

```
His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
                325                 330                 335

Gly Lys Glu Tyr Lys Cys Lys Val Ser Asn Lys Gly Leu Pro Ala Pro
            340                 345                 350

Ile Glu Lys Thr Ile Ser Lys Thr Lys Gly Gln Pro Arg Glu Pro Gln
        355                 360                 365

Val Tyr Thr Leu Pro Pro Ser Arg Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 61
<211> LENGTH: 468
<212> TYPE: PRT
<213> ORGANISM: Artificial Sequence
<220> FEATURE:
<223> OTHER INFORMATION: 25E9 heavy chain (IgG2) humanized variant 4

<400> SEQUENCE: 61

Met Asp Trp Thr Trp Arg Ile Leu Phe Leu Val Ala Ala Ala Thr Gly
1               5                   10                  15

Thr His Ala Glu Ile Gln Leu Gln Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asp Tyr Asp Met His Trp Val Lys Gln Ala Pro Gly His Gly Leu
    50                  55                  60

Glu Trp Ile Gly Thr Ile Asp Pro Glu Thr Gly Gly Thr Ala Tyr Asn
65                  70                  75                  80

Gln Lys Phe Lys Gly Lys Ala Thr Leu Thr Ala Asp Arg Ser Thr Ser
                85                  90                  95

Thr Ala Tyr Met Glu Leu Ser Ser Leu Thr Ser Glu Asp Thr Ala Val
            100                 105                 110

Tyr Tyr Cys Thr Ser Phe Tyr Tyr Thr Tyr Ser Asn Tyr Asp Val Gly
        115                 120                 125

Phe Ala Tyr Trp Gly Gln Gly Thr Leu Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175
```

```
Glu Pro Val Thr Val Ser Trp Asn Ser Gly Ala Leu Thr Ser Gly Val
            180                 185                 190
His Thr Phe Pro Ala Val Leu Gln Ser Ser Gly Leu Tyr Ser Leu Ser
        195                 200                 205
Ser Val Val Thr Val Pro Ser Ser Asn Phe Gly Thr Gln Thr Tyr Thr
210                 215                 220
Cys Asn Val Asp His Lys Pro Ser Asn Thr Lys Val Asp Lys Thr Val
225                 230                 235                 240
Glu Arg Lys Cys Cys Val Glu Cys Pro Pro Cys Pro Ala Pro Pro Val
            245                 250                 255
Ala Gly Pro Ser Val Phe Leu Phe Pro Pro Lys Pro Lys Asp Thr Leu
        260                 265                 270
Met Ile Ser Arg Thr Pro Glu Val Thr Cys Val Val Val Asp Val Ser
    275                 280                 285
His Glu Asp Pro Glu Val Gln Phe Asn Trp Tyr Val Asp Gly Val Glu
290                 295                 300
Val His Asn Ala Lys Thr Lys Pro Arg Glu Glu Gln Phe Asn Ser Thr
305                 310                 315                 320
Phe Arg Val Val Ser Val Leu Thr Val Val His Gln Asp Trp Leu Asn
            325                 330                 335
Gly Lys Glu Tyr Lys Cys Lys Val Ser Asn Lys Gly Leu Pro Ala Pro
        340                 345                 350
Ile Glu Lys Thr Ile Ser Lys Thr Lys Gly Gln Pro Arg Glu Pro Gln
    355                 360                 365
Val Tyr Thr Leu Pro Pro Ser Arg Glu Glu Met Thr Lys Asn Gln Val
370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
            405                 410                 415
Pro Met Leu Asp Ser Asp Gly Ser Phe Phe Leu Tyr Ser Lys Leu Thr
        420                 425                 430
Val Asp Lys Ser Arg Trp Gln Gln Gly Asn Val Phe Ser Cys Ser Val
    435                 440                 445
Met His Glu Ala Leu His Asn His Tyr Thr Gln Lys Ser Leu Ser Leu
450                 455                 460
Ser Pro Gly Lys
465

<210> SEQ ID NO 62
<211> LENGTH: 336
<212> TYPE: DNA
<213> ORGANISM: Artificial Sequence
<220> FEATURE:
<223> OTHER INFORMATION: 25E9 light chain mouse variable domain

<400> SEQUENCE: 62
gatattgtga tgacccaggc tgcaccctct gtacctgtca ctcctggaga gtcagtatcc      60
atctcctgca ggtctactaa gagtctcctg catagtaatg caacacttta cttgtattgg     120
ttcctgcaga ggccaggcca gtctcctcag ctcctgtatt atcggatgtc caaccttgcc     180
tcaggagtcc cagacaggtt cagtggcagt gggtcaggaa ctgctttcac actgagaatc     240
agtagagtgg aggctgagga tgtgggtgtt tattactgta tgcaacatct agaatatcct     300
ttcacgttcg gagggggac caagctggaa ataaaa                                336
```

<210> SEQ ID NO 63
<211> LENGTH: 369
<212> TYPE: DNA
<213> ORGANISM: Artificial Sequence
<220> FEATURE:
<223> OTHER INFORMATION: 25E9 heavy chain mouse variable domain

<400> SEQUENCE: 63

| gagatccagc tgcagcagtc tggagttgag ctggtgaggc ctggggcttc agtgacgctg | 60 |
| tcctgcaagg cttcgggcta cacatttact gactatgaca tgcactgggt gaagcagaca | 120 |
| cctgttcatg gcctggaatg gattggaact attgatcctg aaactggtgg tactgcctac | 180 |
| aatcagaagt tcaagggcaa ggccacactg actgcgaca gatcctccac cacagcctac | 240 |
| atggagctca gcagcctgac atctgaggac tctgccgtct attactgtac aagtttctac | 300 |
| tatacttact ctaattacga cgtggggttt gcttactggg ccaagggac tctggtcact | 360 |
| gtctctgca | 369 |

<210> SEQ ID NO 64
<211> LENGTH: 336
<212> TYPE: DNA
<213> ORGANISM: Artificial Sequence
<220> FEATURE:
<223> OTHER INFORMATION: humanized 25E9 light chain variable domain
      variant 1

<400> SEQUENCE: 64

| gacatcgtga tgacccagtc ccccctgtcc ctgcctgtga cacctggcga gcccgcctcc | 60 |
| atctcctgcc ggtccaccaa gtccctgctg cactccaacg gcaacaccta cctgtactgg | 120 |
| tatctgcaga agcccggcca gtcccctcag ctgctgatct accggatgtc caacctggcc | 180 |
| tccggcgtgc ccgacagatt ctccggctct ggctccggca ccgacttcac cctgaagatc | 240 |
| tcccgggtgg aagccgagga cgtgggcgtg tactactgca tgcagcacct ggataccccc | 300 |
| ttcaccttcg gcggaggcac caaggtggaa atcaag | 336 |

<210> SEQ ID NO 65
<211> LENGTH: 369
<212> TYPE: DNA
<213> ORGANISM: Artificial Sequence
<220> FEATURE:
<223> OTHER INFORMATION: humanized 25E9 heavy chain variable domain
      variant 1

<400> SEQUENCE: 65

| gagattcagc tgcagcagtc aggagccgaa gtgaagaaac ccggctccag cgtcaaggtg | 60 |
| agttgcaagg cctccggata cactttcacc gactatgata tgcactgggt gagacaggca | 120 |
| cctgggcagg gtctggagtg gatggggacc atcgatccag aaaccggcgg aacagcctac | 180 |
| aaccagaagt ttaaaggtcg agtgacaatt actgctgaca gtccaccag cacagcatat | 240 |
| atggagctgt ctagtctgcg ttctgaagat acagccgtct actattgcac ttctttctac | 300 |
| tacacctaca gtaactacga cgtggggttt gcttactggg ccagggaac tctggtcacc | 360 |
| gtgtcatcc | 369 |

<210> SEQ ID NO 66
<211> LENGTH: 112
<212> TYPE: PRT
<213> ORGANISM: Artificial Sequence
<220> FEATURE:
<223> OTHER INFORMATION: candidate human model for the 25D8 light chain variable domain

<400> SEQUENCE: 66

```
Asp Ile Val Met Thr Gln Thr Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
Asn Gly Tyr Asn Tyr Leu Asp Trp Tyr Leu Gln Lys Pro Gly Gln Ser
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Gly
                85                  90                  95
Leu Gln Thr Pro Leu Thr Phe Gly Gly Gly Thr Lys Val Glu Ile Lys
            100                 105                 110
```

<210> SEQ ID NO 67
<211> LENGTH: 112
<212> TYPE: PRT
<213> ORGANISM: Artificial Sequence
<220> FEATURE:
<223> OTHER INFORMATION: candidate human model for the 25D8 light chain variable domain

<400> SEQUENCE: 67

```
Asp Ile Val Met Thr Gln Thr Pro Leu Ser Leu Pro Val Thr Pro Gly
1               5                   10                  15
Glu Pro Ala Ser Ile Ser Cys Arg Ala Ser Gln Ser Leu Leu His Ser
            20                  25                  30
Asn Gly Tyr Asn Tyr Leu Asp Trp Tyr Leu Gln Lys Pro Gly Gln Ser
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Arg Ile
65                  70                  75                  80
Ser Arg Val Glu Ala Glu Asp Val Gly Val Tyr Tyr Cys Met Gln Gly
                85                  90                  95
Leu Gln Thr Pro Leu Thr Phe Gly Gly Gly Thr Lys Val Glu Ile Lys
            100                 105                 110
```

<210> SEQ ID NO 68
<211> LENGTH: 112
<212> TYPE: PRT
<213> ORGANISM: Artificial Sequence
<220> FEATURE:
<223> OTHER INFORMATION: candidate human model for the 25D8 light chain variable domain

<400> SEQUENCE: 68

```
Asp Ile Val Met Thr Gln Ser Pro Leu Ser Leu Ser Val Thr Pro Gly
1               5                   10                  15
Gln Pro Ala Ser Ile Ser Cys Lys Ser Ser Gln Ser Leu Leu His Ser
            20                  25                  30
Asp Gly Lys Thr Tyr Leu Tyr Trp Tyr Leu Gln Lys Pro Gly Gln Pro
        35                  40                  45
Pro Gln Leu Leu Ile Tyr Glu Val Ser Asn Arg Phe Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Tyr Thr Phe Gly Gln Gly Thr Lys Leu Glu Ile Lys
            100                 105                 110
```

<210> SEQ ID NO 69
<211> LENGTH: 98
<212> TYPE: PRT
<213> ORGANISM: Artificial Sequence
<220> FEATURE:
<223> OTHER INFORMATION: candidate human model for the 25D8 light chain
      variable domain

<400> SEQUENCE: 69

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln
```

<210> SEQ ID NO 70
<211> LENGTH: 98
<212> TYPE: PRT
<213> ORGANISM: Artificial Sequence
<220> FEATURE:
<223> OTHER INFORMATION: candidate human model for the 25D8 light chain
      variable domain

<400> SEQUENCE: 70

```
Asp Ile Val Met Thr Gln Pro Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln
```

<210> SEQ ID NO 71
<211> LENGTH: 99
<212> TYPE: PRT
<213> ORGANISM: Artificial Sequence
<220> FEATURE:
<223> OTHER INFORMATION: candidate human model for the 25D8 light chain -continued variable domain

<400> SEQUENCE: 71

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu

<210> SEQ ID NO 72
<211> LENGTH: 112
<212> TYPE: PRT
<213> ORGANISM: Artificial Sequence
<220> FEATURE:
<223> OTHER INFORMATION: candidate human model for the 25D8 light chain
      variable domain
<220> FEATURE:
<221> NAME/KEY: misc_feature
<222> LOCATION: (101)..(101)
<223> OTHER INFORMATION: Xaa can be any naturally occurring amino acid

<400> SEQUENCE: 72

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Asn Asn Tyr Leu Asn Trp Tyr Leu Gln Lys Pro Gly Gln Ser
        35                  40                  45

Pro Gln Leu Leu Ile Tyr Leu Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Pro Arg Xaa Thr Phe Gly Gln Gly Thr Lys Val Glu Ile Lys
            100                 105                 110

<210> SEQ ID NO 73
<211> LENGTH: 119
<212> TYPE: PRT
<213> ORGANISM: Artificial Sequence
<220> FEATURE:
<223> OTHER INFORMATION: candidate human model for the 25D8 heavy chain
      variable domain

<400> SEQUENCE: 73

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Gly Ser Tyr
            20                  25                  30

Ala Ile Ser Trp Val Arg Gln Ala Pro Gly Gln Gly Leu Glu Trp Met
        35                  40                  45

```
Gly Arg Ile Ile Pro Ile Leu Gly Ile Ala Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Gly Lys Gly Glu Phe Glu Gly Met Asp Val Trp Gly Gln Gly
            100                 105                 110

Thr Thr Val Thr Val Ser Ser
            115

<210> SEQ ID NO 74
<211> LENGTH: 119
<212> TYPE: PRT
<213> ORGANISM: Artificial Sequence
<220> FEATURE:
<223> OTHER INFORMATION: candidate human model for the 25D8 heavy chain
      variable domain

<400> SEQUENCE: 74

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr His Ser Trp Phe Ala Phe Asp Ile Trp Gly Gln Gly
            100                 105                 110

Thr Met Val Thr Val Ser Ser
            115

<210> SEQ ID NO 75
<211> LENGTH: 118
<212> TYPE: PRT
<213> ORGANISM: Artificial Sequence
<220> FEATURE:
<223> OTHER INFORMATION: candidate human model for the 25D8 heavy chain
      variable domain

<400> SEQUENCE: 75

Glu Val Gln Leu Val Gln Ser Gly Ala Glu Met Lys Lys Pro Gly Ala
1               5                   10                  15

Ser Val Lys Val Ser Cys Lys Ala Ser Gly Tyr Ser Phe Ser Ile Tyr
            20                  25                  30

Asn Ile His Trp Val Arg Gln Ala Pro Gly Gln Gly Leu Glu Trp Met
        35                  40                  45

Gly Trp Ile His Ala Gly Thr Gly Asn Arg Lys Tyr Ser Gln Val Phe
    50                  55                  60

Gln Asp Arg Val Thr Ile Thr Arg Asp Thr Ser Ala Ser Thr Ser Tyr
65                  70                  75                  80

Met Glu Leu Ser Ser Leu Thr Ser Glu Asp Thr Ala Val Tyr Tyr Cys
                85                  90                  95
```

Ala Arg Asp Pro Asn Phe Gly Asp Phe Asp Ser Trp Gly Gln Gly Thr
            100                 105                 110

Leu Val Thr Val Ser Ser
        115

<210> SEQ ID NO 76
<211> LENGTH: 118
<212> TYPE: PRT
<213> ORGANISM: Artificial Sequence
<220> FEATURE:
<223> OTHER INFORMATION: candidate human model for the 25D8 heavy chain
      variable domain

<400> SEQUENCE: 76

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Tyr Asn Trp Asn Phe Phe Asp Tyr Trp Gly Gln Gly Thr
            100                 105                 110

Leu Val Thr Val Ser Ser
        115

<210> SEQ ID NO 77
<211> LENGTH: 120
<212> TYPE: PRT
<213> ORGANISM: Artificial Sequence
<220> FEATURE:
<223> OTHER INFORMATION: candidate human model for the 25D8 heavy chain
      variable domain

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Asp Gly Tyr Ile Gln Ala Phe Asp Tyr Trp Gly Gln
            100                 105                 110

Gly Thr Leu Val Thr Val Ser Ser
        115                 120

<210> SEQ ID NO 78

```
<211> LENGTH: 98
<212> TYPE: PRT
<213> ORGANISM: Artificial Sequence
<220> FEATURE:
<223> OTHER INFORMATION: candidate human model for the 25D8 heavy chain
      variable domain

<400> SEQUENCE: 78
```

| Gln | Val | Gln | Leu | Val | Gln | Ser | Gly | Ala | Glu | Val | Lys | Lys | Pro | Gly | Ser |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Gly | Thr | Phe | Ser | Ser | Tyr |
|---|---|---|---|---|---|---|---|---|---|---|---|---|---|---|---|
| | | | 20 | | | | | 25 | | | | | 30 | | |

| Ala | Ile | Ser | Trp | Val | Arg | Gln | Ala | Pro | Gly | Gln | Gly | Leu | Glu | Trp | Met |
|---|---|---|---|---|---|---|---|---|---|---|---|---|---|---|---|
| | | 35 | | | | | 40 | | | | | 45 | | | |

| Gly | Gly | Ile | Ile | Pro | Ile | Phe | Gly | Thr | Ala | Asn | Tyr | Ala | Gln | Lys | Phe |
|---|---|---|---|---|---|---|---|---|---|---|---|---|---|---|---|
| | 50 | | | | | 55 | | | | | 60 | | | | |

| Gln | Gly | Arg | Val | Thr | Ile | Thr | Ala | Asp | Lys | Ser | Thr | Ser | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Ser | Ser | Leu | Arg | Ser | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

Ala Arg

```
<210> SEQ ID NO 79
<211> LENGTH: 98
<212> TYPE: PRT
<213> ORGANISM: Artificial Sequence
<220> FEATURE:
<223> OTHER INFORMATION: candidate human model for the 25D8 heavy chain
      variable domain

<400> SEQUENCE: 79
```

| Gln | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Ser | Tyr |
|---|---|---|---|---|---|---|---|---|---|---|---|---|---|---|---|
| | | | 20 | | | | | 25 | | | | | 30 | | |

| Tyr | Met | His | Trp | Val | Arg | Gln | Ala | Pro | Gly | Gln | Gly | Leu | Glu | Trp | Met |
|---|---|---|---|---|---|---|---|---|---|---|---|---|---|---|---|
| | | 35 | | | | | 40 | | | | | 45 | | | |

| Gly | Ile | Ile | Asn | Pro | Ser | Gly | Gly | Ser | Thr | Ser | Tyr | Ala | Gln | Lys | Phe |
|---|---|---|---|---|---|---|---|---|---|---|---|---|---|---|---|
| | 50 | | | | | 55 | | | | | 60 | | | | |

| Gln | Gly | Arg | Val | Thr | Met | Thr | Arg | Asp | Thr | Ser | Thr | Ser | Thr | Val | Tyr |
|---|---|---|---|---|---|---|---|---|---|---|---|---|---|---|---|
| 65 | | | | | 70 | | | | | 75 | | | | | 80 |

| Met | Glu | Leu | Ser | Ser | Leu | Arg | Ser | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

Ala Arg

```
<210> SEQ ID NO 80
<211> LENGTH: 118
<212> TYPE: PRT
<213> ORGANISM: Artificial Sequence
<220> FEATURE:
<223> OTHER INFORMATION: candidate human model for the 25D8 heavy chain
      variable domain

<400> SEQUENCE: 80
```

| Gln | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Ser | Tyr |
|---|---|---|---|---|---|---|---|---|---|---|---|---|---|---|---|
| | | | 20 | | | | | 25 | | | | | 30 | | |

| Ala | Ile | Ser | Trp | Val | Arg | Gln | Ala | Pro | Gly | Gln | Gly | Leu | Glu | Trp | Met |
|---|---|---|---|---|---|---|---|---|---|---|---|---|---|---|---|
| | | 35 | | | | | 40 | | | | | 45 | | | |

Gly Trp Ile Asn Pro Gly Asn Gly Asp Thr Asn Tyr Ala Gln Lys Phe
            50                  55                  60

Gln Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Gly Arg Gly Asp Tyr Phe Asp Tyr Trp Gly Gln Gly Thr
            100                 105                 110

Leu Val Thr Val Ser Ser
            115

<210> SEQ ID NO 81
<211> LENGTH: 112
<212> TYPE: PRT
<213> ORGANISM: Artificial Sequence
<220> FEATURE:
<223> OTHER INFORMATION: candidate human model for the 25E9 light chain
      variable domain

<400> SEQUENCE: 81

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Phe
                85                  90                  95

Leu Gln Thr Pro Leu Thr Phe Gly Gly Gly Thr Lys Val Glu Ile Lys
            100                 105                 110

<210> SEQ ID NO 82
<211> LENGTH: 112
<212> TYPE: PRT
<213> ORGANISM: Artificial Sequence
<220> FEATURE:
<223> OTHER INFORMATION: candidate human model for the 25E9 light chain
      variable domain

<400> SEQUENCE: 82

Asp Ile Val Met Thr Gln Thr Pro Leu Ser Leu Pro Val Thr Pro Gly
1               5                   10                  15

Glu Pro Ala Ser Ile Ser Cys Arg Ala Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Met Gln Gly
                85                  90                  95

Leu Gln Thr Pro Leu Thr Phe Gly Gly Gly Thr Lys Val Glu Ile Lys
            100                 105                 110

<210> SEQ ID NO 83
<211> LENGTH: 98
<212> TYPE: PRT
<213> ORGANISM: Artificial Sequence
<220> FEATURE:
<223> OTHER INFORMATION: candidate human model for the 25E9 light chain
      variable domain

<400> SEQUENCE: 83

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln

<210> SEQ ID NO 84
<211> LENGTH: 98
<212> TYPE: PRT
<213> ORGANISM: Artificial Sequence
<220> FEATURE:
<223> OTHER INFORMATION: candidate human model for the 25E9 light chain
      variable domain

<400> SEQUENCE: 84

Asp Ile Val Met Thr Gln Pro Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln

<210> SEQ ID NO 85
<211> LENGTH: 112
<212> TYPE: PRT
<213> ORGANISM: Artificial Sequence
<220> FEATURE:
<223> OTHER INFORMATION: candidate human model for the 25E9 light chain
      variable domain
<220> FEATURE:
<221> NAME/KEY: misc_feature
<222> LOCATION: (101)..(101)
<223> OTHER INFORMATION: Xaa can be any naturally occurring amino acid

<400> SEQUENCE: 85

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Asn Asn Tyr Leu Asn Trp Tyr Leu Gln Lys Pro Gly Gln Ser
        35                  40                  45

Pro Gln Leu Leu Ile Tyr Leu Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Pro Arg Xaa Thr Phe Gly Gln Gly Thr Lys Val Glu Ile Lys
            100                 105                 110
```

<210> SEQ ID NO 86
<211> LENGTH: 119
<212> TYPE: PRT
<213> ORGANISM: Artificial Sequence
<220> FEATURE:
<223> OTHER INFORMATION: candidate human model for the 25E9 heavy chain
      variable domain

<400> SEQUENCE: 86

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Ser Ile Ser Trp Val Arg Gln Ala Pro Gly His Gly Leu Glu Trp Met
        35                  40                  45

Gly Arg Ile Phe Pro Leu Leu Gly Val Ala Lys Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Val Pro Arg Ser Ser Ser Tyr Trp Phe Asp Pro Trp Gly Gln Gly
            100                 105                 110

Thr Leu Val Thr Val Ser Ser
        115
```

<210> SEQ ID NO 87
<211> LENGTH: 123
<212> TYPE: PRT
<213> ORGANISM: Artificial Sequence
<220> FEATURE:
<223> OTHER INFORMATION: candidate human model for the 25E9 heavy chain
      variable domain

<400> SEQUENCE: 87

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60
```

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Asn Tyr Asp Ser Ser Gly Tyr Asp Asp Ala Phe Asp Ile
            100                 105                 110

Trp Gly Gln Gly Thr Met Val Thr Val Ser Ser
            115                 120
```

<210> SEQ ID NO 88
<211> LENGTH: 123
<212> TYPE: PRT
<213> ORGANISM: Artificial Sequence
<220> FEATURE:
<223> OTHER INFORMATION: candidate human model for the 25E9 heavy chain
      variable domain

<400> SEQUENCE: 88

```
Glu Val Gln Leu Val Gln Ser Gly Ala Glu Val Lys Lys Pro Gly Ser
1               5                   10                  15

Ser Val Lys Leu Ser Cys Lys Ala Ser Gly Asp Thr Phe Ser Ser Arg
                20                  25                  30

Pro Val Ser Trp Val Arg Gln Ala Pro Gly Gln Gly Leu Glu Trp Met
            35                  40                  45

Gly Gly Ile Ile Pro Ile Phe Arg Thr Thr Asn Tyr Ala Gln Lys Phe
    50                  55                  60

Gln Gly Arg Val Thr Ile Thr Ala Asp Glu Ser Met Thr Thr Ala Tyr
 65                 70                  75                  80

Leu Glu Leu Arg Gly Leu Thr Ser Asp Thr Ala Val Tyr Tyr Cys
                85                  90                  95

Ala Thr Thr Arg Met Lys Ile Thr Val Phe Ala Ser Thr Phe Asp Tyr
            100                 105                 110

Trp Gly Gln Gly Thr Leu Val Thr Val Ser Ser
            115                 120
```

<210> SEQ ID NO 89
<211> LENGTH: 96
<212> TYPE: PRT
<213> ORGANISM: Artificial Sequence
<220> FEATURE:
<223> OTHER INFORMATION: candidate human model for the 25E9 heavy chain
      variable domain

<400> SEQUENCE: 89

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
 65                 70                  75                  80

Met Glu Leu Ser Ser Leu Arg Ser Glu Asp Thr Ala Val Tyr Tyr Cys
                85                  90                  95
```

<210> SEQ ID NO 90
<211> LENGTH: 96

```
<212> TYPE: PRT
<213> ORGANISM: Artificial Sequence
<220> FEATURE:
<223> OTHER INFORMATION: candidate human model for the 25E9 heavy chain
      variable domain

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

<210> SEQ ID NO 91
<211> LENGTH: 98
<212> TYPE: PRT
<213> ORGANISM: Artificial Sequence
<220> FEATURE:
<223> OTHER INFORMATION: candidate human model for the 25E9 heavy chain
      variable domain

<400> SEQUENCE: 91

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 92
<211> LENGTH: 123
<212> TYPE: PRT
<213> ORGANISM: Artificial Sequence
<220> FEATURE:
<223> OTHER INFORMATION: candidate human model for the 25E9 heavy chain
      variable domain
<220> FEATURE:
<221> NAME/KEY: misc_feature
<222> LOCATION: (109)..(109)
<223> OTHER INFORMATION: Xaa can be any naturally occurring amino acid

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

-continued

```
Ala Ile Ser Trp Val Arg Gln Ala Pro Gly Gln Gly Leu Glu Trp Met
        35                  40                  45

Gly Trp Ile Asn Pro Gly Asn Gly Asp Thr Asn Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ala Pro Gly Tyr Gly Ser Arg Gly Asp Tyr Xaa Phe Asp Tyr
            100                 105                 110

Trp Gly Gln Gly Thr Leu Val Thr Val Ser Ser
        115                 120
```